US011746383B2

(12) United States Patent
Tao et al.

(10) Patent No.: US 11,746,383 B2
(45) Date of Patent: Sep. 5, 2023

(54) BIOMARKER DLEC1 FOR CANCER

(71) Applicant: The Chinese University of Hong Kong, Hong Kong (CN)

(72) Inventors: Qian Tao, Hong Kong (CN); Lili Li, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 489 days.

(21) Appl. No.: 16/530,416

(22) Filed: Aug. 2, 2019

(65) Prior Publication Data

US 2020/0131584 A1   Apr. 30, 2020

Related U.S. Application Data

(60) Provisional application No. 62/714,506, filed on Aug. 3, 2018.

(51) Int. Cl.
| | | |
|---|---|---|
| *C12Q 1/68* | (2018.01) | |
| *C12Q 1/6886* | (2018.01) | |
| *C12Q 1/6806* | (2018.01) | |
| *C12N 5/09* | (2010.01) | |
| *C12N 15/11* | (2006.01) | |

(52) U.S. Cl.
CPC ......... *C12Q 1/6886* (2013.01); *C12N 5/0693* (2013.01); *C12N 15/11* (2013.01); *C12Q 1/6806* (2013.01); *C12Q 2600/112* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

PUBLICATIONS

Ku et al., "Methylation-Specific PCR", (2011) Epigenetics Protocols: Second Ed., Methods Mole Biol 791: pp. 24 (Year: 2011).*
Harrison et al., "DNA methylation: A timeline of methods and applications", (2011) Front Genet 2 (Year: 2011).*
Wang et al., "Epigenetic silencing of the 3p22 tumor suppressor DLEC1 by promoter CpG methylation in non-Hodgkin and Hodgkin lymphomas", (2012) J Trans Med 10(209): 1-7 (Year: 2012).*
Tang et al., "SEMA3B improves the survival of patients with esophageal squamous cell carcinoma by upregulating p52 and p21", (2016) Oncol Reports 36: 900-908 (Year: 2016).*
Li et al., "Epigenomic characterization of a p53-regulated 3p22.2 tumor suppressor that inhibits STAT3 phosphorylation via protein docking and is frequently methylated in esophageal and other carcinomas", (2018) Theranostics 8(1): 61-77 (Year: 2018).*
Agathanggelou, et al. "Epigenetic inactivation of the candidate 3p21. 3 suppressor gene BLU in human cancers." Oncogene 22, No. 10 (2003): 1580.
Bocchini, et al. "Contribution of chaperones to STAT pathway signaling." Jak-stat 3, No. 3 (2014): e970459.

Bromberg, et al. "Stat3 as an oncogene." Cell 98, No. 3 (1999): 295-303.
Chan, et al. "Transcriptional repression of DLEC1 associates with the depth of tumor invasion in oral squamous cell carcinoma." Oral oncology 46, No. 12 (2010): 874-879.
Chen, et al. "Acylglycerol kinase augments JAK2/STAT3 signaling in esophageal squamous cells." The Journal of clinical investigation 123, No. 6 (2013): 2576-2589.
Chen, et al. "A positive autoregulatory loop of LMP1 expression and STAT activation in epithelial cells latently infected with Epstein-Barr virus." Journal of virology 77, No. 7 (2003): 4139-4148.
Chow, et al. "RASSF1A is a target tumor suppressor from 3p21. 3 in nasopharyngeal carcinoma." International journal of cancer 109, No. 6 (2004): 839-847.
Daigo, et al. "Molecular cloning of a candidate tumor suppressor gene, DLC1, from chromosome 3p21. 3." Cancer research 59, No. 8 (1999): 1966-1972.
Dammann, et al. "Epigenetic inactivation of a RAS association domain family protein from the lung tumour suppressor locus 3p21. 3." Nature genetics 25, No. 3 (2000): 315.
Gao, et al. "Mutations in the EGFR kinase domain mediate STAT3 activation via IL-6 production in human lung adenocarcinomas." The Journal of clinical investigation 117, No. 12 (2007): 3846-3856.
Harada, et al. "The role of STAT3 in non-small cell lung cancer." Cancers 6, No. 2 (2014): 708-722.
Hesson, et al. "Evaluation of the 3p21. 3 tumour-suppressor gene cluster." Oncogene 26, No. 52 (2007): 7283.
Ho, et al. "STAT3 as a therapeutic target for Epstein-Barr virus (EBV)-associated nasopharyngeal carcinoma." Cancer letters 330, No. 2 (2013): 141-149.
Hu, et al. "Phospholipase C delta 1 is a novel 3p22. 3 tumor suppressor involved in cytoskeleton organization, with its epigenetic silencing correlated with high-stage gastric cancer." Oncogene 28, No. 26 (2009): 2466.
Huang, et al. "Loss of heterozygosity on the short arm of chromosome 3 in nasopharyngeal carcinoma." Cancer genetics and cytogenetics 54, No. 1 (1991): 91-99.
Jin, et al. "Epigenetic silencing of a Ca2+-regulated Ras GTPase-activating protein RASAL defines a new mechanism of Ras activation in human cancers." Proceedings of the National Academy of Sciences 104, No. 30 (2007): 12353-12358.
Kashuba, et al. "RBSP3 (HYA22) is a tumor suppressor gene implicated in major epithelial malignancies." Proceedings of the National Academy of Sciences 101, No. 14 (2004): 4906-4911.

(Continued)

*Primary Examiner* — Jehanne S Sitton
(74) *Attorney, Agent, or Firm* — Kilpatrick Townsend & Stockton LLP

(57) ABSTRACT

The present invention provides a method for diagnosing and determining prognosis of certain cancers (e.g., esophageal squamous cell carcinoma or ESCC) in a subject by detecting suppressed expression of the DLEC1 gene, which in some cases is due to elevated methylation level in the genomic sequence of this gene. A kit and device useful for such a method are also provided. In addition, the present invention provides a method for treating cancer by increasing DLEC1 gene expression or activity.

6 Claims, 51 Drawing Sheets
(37 of 51 Drawing Sheet(s) Filed in Color)
Specification includes a Sequence Listing.

(56) References Cited

PUBLICATIONS

Kovacs, et al. "Consistent chromosome 3p deletion and loss of heterozygosity in renal cell carcinoma." Proceedings of the National Academy of Sciences 85, No. 5 (1988): 1571-1575.

Kwong, et al. "Epigenetic inactivation of the deleted in lung and esophageal cancer 1 gene in nasopharyngeal carcinoma." Genes, Chromosomes and Cancer 46, No. 2 (2007): 171-180.

Kwong, et al. "Candidate tumor-suppressor gene DLEC1 is frequently downregulated by promoter hypermethylation and histone hypoacetylation in human epithelial ovarian cancer." Neoplasia (New York, NY) 8, No. 4 (2006): 268.

Li, et al. "Functional characterization of the candidate tumor suppressor gene NPRL2/G21 located in 3p21. 3C." Cancer research 64, No. 18 (2004): 6438-6443.

Li, et al. "The tumor suppressor UCHL1 forms a complex with p53/MDM2/ARF to promote p53 signaling and is frequently silenced in nasopharyngeal carcinoma." Clinical Cancer Research 16, No. 11 (2010): 2949-2958.

Li, et al. "Epigenetic identification of receptor tyrosine kinase-like orphan receptor 2 as a functional tumor suppressor inhibiting β-catenin and AKT signaling but frequently methylated in common carcinomas." Cellular and molecular life sciences 71, No. 11 (2014): 2179-2192.

Li, et al. "Epigenetic inactivation of the CpG demethylase TET1 as a DNA methylation feedback loop in human cancers." Scientific reports 6 (2016): 26591.

Li, et al. "Characterization of the nasopharyngeal carcinoma methylome identifies aberrant disruption of key signaling pathways and methylated tumor suppressor genes." Epigenomics 0 (2015): 155-173.

Naylor, et al. "Loss of heterozygosity of chromosome 3p markers in small-cell lung cancer." Nature 329, No. 6138 (1987): 451.

Ogasawara, et al. "Frequent microsatellite alterations on chromosome 3p in esophageal squamous cell carcinoma." Cancer research 55, No. 4 (1995): 891-894.

Pastuszak-Lewandoska, et al. "Quantitative analysis of mRNA expression levels and DNA methylation profiles of three neighboring genes: FUS1, NPRL2/G21 and RASSF1A in non-small cell lung cancer patients." Respiratory research 16, No. 1 (2015): 76.

Pierce, et al. "ZDOCK server: interactive docking prediction of protein-protein complexes and symmetric multimers." Bioinformatics 30, No. 12 (2014): 1771-1773.

Qiu, et al. "The candidate tumor suppressor gene BLU, located at the commonly deleted region 3p21.3, is an E2F-regulated, stress-responsive gene and inactivated by both epigenetic and genetic mechanisms in nasopharyngeal carcinoma." Oncogene 23, No. 27 (2004): 4793.

Qiu, et al. "The tumor suppressor gene DLEC1 is frequently silenced by DNA methylation in hepatocellular carcinoma and induces G1 arrest in cell cycle." Journal of hepatology 48, No. 3 (2008): 433-441.

Rauch, et al. "MIRA-assisted microarray analysis, a new technology for the determination of DNA methylation patterns, identifies frequent methylation of homeodomain-containing genes in lung cancer cells." Cancer research 66, No. 16 (2006): 7939-7947.

Sarakbi, et al. "Evidence of a tumour suppressor function for DLEC1 in human breast cancer." Anticancer research 30, No. 4 (2010): 1079-1082.

Sasaki, et al. "Methylation of the DLEC1 gene correlates with poor prognosis in Japanese lung cancer patients." Oncology letters 1, No. 2 (2010): 283-287.

Sato, et al. "Accumulation of genetic alterations and progression of primary breast cancer." Cancer Research 51, No. 21 (1991): 5794-5799.

Sehgal, "Plasma membrane rafts and chaperones in cytokine/STAT signaling." Acta Biochim Pol 50, No. 3 (2003): 583-94.

Seng, et al. "DLEC1 and MLH1 promoter methylation are associated with poor prognosis in non-small cell lung carcinoma." British journal of cancer 99, No. 2 (2008): 375.

Stahl, et al. "Choice of STATs and other substrates specified by modular tyrosine-based motifs in cytokine receptors." Science 267, No. 5202 (1995): 1349-1353.

Tan, et al. "Epigenomic analysis of lung adenocarcinoma reveals novel DNA methylation patterns associated with smoking." OncoTargets and therapy 6 (2013): 1471.

Timme, et al. "STAT3 expression, activity and functional consequences of STAT3 inhibition in esophageal squamous cell carcinomas and Barrett's adenocarcinomas." Oncogene 33, No. 25 (2014): 3256.

Wang, et al. "Epigenetic silencing of the 3p22 tumor suppressor DLEC1 by promoter CpG methylation in non-Hodgkin and Hodgkin lymphomas." Journal of translational medicine 10, No. 1 (2012): 209.

Ye, et al. "Methylation of DLEC1 promoter is a predictor for recurrence in Chinese patients with gastric cancer." Disease markers 2014 (2014).

Ying, et al. "DLEC1 is a functional 3p22. 3 tumour suppressor silenced by promoter CpG methylation in colon and gastric cancers." British journal of cancer 100, No. 4 (2009): 663.

Ying, et al. "Genome-wide screening for genetic alterations in esophageal cancer by aCGH identifies 11q13 amplification oncogenes associated with nodal metastasis." PloS one 7, No. 6 (2012): e39797.

Ying, et al. "Functional epigenetics identifies a protocadherin PCDH10 as a candidate tumor suppressor for nasopharyngeal, esophageal and multiple other carcinomas with frequent methylation." Oncogene 25, No. 7 (2006): 1070.

Yu, et al. "Revisiting STAT3 signalling in cancer: new and unexpected biological functions." Nature reviews Cancer 14, No. 11 (2014): 736.

Yue, et al. "Targeting STAT3 in cancer: how successful are we?." Expert opinion on investigational drugs 18, No. 1 (2009): 45-56.

Zabarovsky, et al. "Tumor suppressor genes on chromosome 3p involved in the pathogenesis of lung and other cancers." Oncogene 21, No. 45 (2002): 6915.

Zhang, et al. "DLEC1, a 3p tumor suppressor, represses NF-κB signaling and is methylated in prostate cancer." Journal of molecular medicine 93, No. 6 (2015): 691-701.

Zhang, et al. "Aberrant promoter methylation of DLEC1, a critical 3p22 tumor suppressor for renal cell carcinoma, is associated with more advanced tumor stage." The Journal of urology 184, No. 2 (2010): 731-737.

Zhang, et al. "Enhanced IL-6/IL-6R signaling promotes growth and malignant properties in EBV-infected premalignant and cancerous nasopharyngeal epithelial cells." PloS one 8, No. 5 (2013): e62284.

\* cited by examiner

A

B

SEQUENCE LISTING

```
<160> NUMBER OF SEQ ID NOS: 54

<210> SEQ ID NO 1
<211> LENGTH: 86021
<212> TYPE: DNA
<213> ORGANISM: Homo sapiens

<400> SEQUENCE: 1
tagtactgca ttgtggtttt aatttccact tctttgatga ctaatgatgt tcagtctact      60
ccttctttga aatctctgct tggttttcat ttgttccaag aagtaatcgc tccttctaca     120
gactaagttc ctgtcctcct ttgtagttcc atgacaacca atatttatct ccaccttggc     180
```

```
cttaacccac taaagtacag ttgttttact tttacctcca cacccaccgc catcatcaca    240
aacacacaca tacacgactg tgcacttcct gaaggcagaa gcagcatcat acttctttgg    300
tatcttcagc aatcagcaca gacctgaaac acaatcttta cacaataaat atgatgagtg    360
aatgaacagt tgcttaacaa attaaagaat ggatgaaggt aggtagttag gtacaaggtt    420
ttgcagatag gcctggctgt gtcaattaaa cctttcttca tgggtcctca cacttagtaa    480
gctcactttt aaaaggacaa tgctgaagac acaaatgttt acaatgacca cagcgatgac    540
gggatccgag agaaaggcaa ggcggaaggg gtgaggccgg aagccgaagt gccgcaggga    600
gttagcggcg tctcggttgc catggagacc aggagctcca aaacgcggag gtctttagcg    660
tcccggacca acgagtgcca ggggacaatg tgggcgccaa cttcgccacc agccgggtcc    720
agcagcccca gccagcccac ctggaagtcc tccttgtatt cctccctcgc ctactctgag    780
gccttccact acagcttcgc agcccggccc cgccgcctca cgcagcttgc gctggcgcag    840
cgtcccgagc ctcagctgct tcgtctgcgc ccctcctcgc tgcgcaccca agatatctcg    900
cacttgctca ccggcgtctt ccgcaacttg tactcagccg aggtcatcgg cgacgaagtg    960
agcgcaagct tgatcaaggc ccgcggcagc gagaatgagc gccacgagga gttcgtggac    1020
cagctgcagc aggtaacgtg gcggtggcgt cgcgtctgcg gacggtgccg gggtctcagc    1080
gctcggcacg cgtcagcacc tgccaggtgc caggcgctgt tccaggatct ggggctgcag    1140
ttgagaaaca gcccatcatg ccgaagtggg cccgacattc tagtggaagg acgctctatc    1200
catacacaca catgcgcaaa taccacacat accacacaac gtgcggcata tatctgtagc    1260
acctgtctat atttctctag acacatacgt tatatattgc atatatcaat gaacgactgc    1320
ggcagaccgc tgaatagttg ttccatggag aggataaagc caaaagtcac ccggctttgg    1380
ggtgcctttg tatcacaaac cacaatcttg actgggccat tcatgcgcag attttaggaa    1440
gcgtgtctag cctctagaac agcaactctg cttcctcatc tgtacaagga gaaaaccagc    1500
tgactcgcgg cctctgtgct gagtcggcct ctgctggcca cactactgaa gactccctta    1560
aacttgtggg cactcctccc atacccgatc ctttaccccg gtgtgcttcc tgcctctcag    1620
atcttcttct tctcctttct gttctgtcct ctacctgccc cttaagtgac atgcatccca    1680
cgtcgttagc ttcagtcatt ccttcactta acacatttgt tgaatgtctg ctgggtgtca    1740
tactctgttc taggcagtgg ggattcagca gtgaataaaa acgccagtgt tcgggcacac    1800
ccacactcac acacgcaacc tgtcctctgt agctttcaac ctaactgagg tagatagaca    1860
ttaacaaaat gaatacctat acagtatgtg agatacttac aggaccagtc tcgccgcctc    1920
cacgggttat aggcttctta aagtgcagcc agagccctg gctgggatcc tgtactctgt    1980
gattcgtggg tcaccacatt cactctgcta agacttcagc ctaccagcc agaccttgcc    2040 cttgaacttc agactcacat ccctgtcatt cacatgagcc agaatatatg gagcattata    2100
aacctataaa ccccatgacc agtcacccag ttcactggat tctatcttct cagtatctgt    2160
cccataagta gccactatac cagagtctga attggcaaat agtgatccct ttttttgaag    2220
aaaaaaagta atacatatta caaattttt ttttgacag agtctggctc tgttgcccag    2280
gctggagtgc agtgatgtga tcacagctca ctgcagcctt aacatcaggg gctcaactga    2340 tcctcctcc tcagcatctg gagtagctag gaccacaggt gtgcaccagt atgcccagct    2400
tatttattta tttatttatt tatttgagat ggagtctcac tctgtcaccc aggctggagt    2460
gcatggcgca atctcagctc actgcaagct ccacctccca cattcatgcc attctcctgc    2520
ctcagccttc tgagtagctg gcgcctgcca ccacacctgg ctaatttttt tgtattttta    2580
```

```
gtagagacag ggtttcactg tgttagccag gatggtctcg atctcctgac ctcgtgatct    2640
gcccaccttg gcctcccaaa gtgttgggat tacaggcatg agccaccaca tctggcctaa    2700
atttttattt tttaaaaatt gtgagatggg gtcccactat gttgcccagg ctggtctcaa    2760
atttctggcc tcaattgatc cttccacctc agcctctcca gatgccggta ttacaggtgt    2820
gagccactgt gcctggccca cattataaaa atcttaattt agaagctgaa atttaattta    2880
aacatttgaa gttttaaaat tgcagaaatt tcagaatgca gaaaagttta aagagtgatc    2940
ccctatagaa atacaactat gcggccgggc gtggtggctc acgcctataa tcccagcact    3000
ttgggaggcc gaggcgggca gatcacgagg tcagaagttt gagtccagtc tgaccaacat    3060
agtgaaaccc tgtctgtact aaaaatacca aaaattagcc gggcgtggtg gtgtgtgact    3120
gtaatcccag gtactcggga ggctgagaca ggagaattgc atgaacccag gaggcggagg    3180
ttgcaatgag ccaagactgc accactgcac tccagcctgg gcgacagaac gagactccgt    3240
ttcaaaaaaa aaaaaaaaaa aagaaataca actatgcaaa gataagttga ctttataaat    3300
tatggtatat tcacactatg gaatactaca aagttgttaa aaagaatgaa ttatacctgc    3360
attgtagaca aacacagctg ccatttattt atttatttat ttttttgagg cagagtctcg    3420
ctctgttgcc cagtctggag tgcagtgcca cgatcttggc tcactacaac ttccgtctcc    3480
tgggttcaag cgattctcct gcctcagcct cctgagtagc tgggattaca gacatgcacc    3540
accatgcctg gctaattttt gtattttag tagagatggg gtttcaccat gttggccagg    3600
ctggtctcca actcctgacc tcaagtgatc tgcccgcctc agcatcccaa agtgctagga    3660
ttacaagagt gtgccactgc gcctggcccg ccatttatta atttagcaaa aaagccatag    3720
aacaatgtta ggataattta atttttata atatatatgc atgggaaaaa agctgaaaac    3780
tttcacaaca aaatgttaac aatattctta tgggacattt aacttttcct ttgcacattt    3840
ctatattgtc tgaattttgc aatgtacacg aattaatttt gtaattacaa aaaagaaac    3900 tttgaaaaga gcaggcatct gttattccac ttctgtaatg ttgctggctt tttttttttt    3960 ttttttttg agacagagtc ttgcactgtt gcctgggcta gagtgcagtg gcacgatctc    4020
agctcactgc aacccctgcc tcccgggttc atgtgattct cctgcctcag cctcccaagt    4080
agctgggatt acaggcacac accaccacac caggctaatt ttttgtattt ttagtaaaga    4140
cagggtttca ctatgttggc cagactggtc ttgaactcct gacctcgtga tccacccgcc    4200
tcggcctccc aaagtgctgg gattacagac gtgagacact gcgcccagca atgttgctgt    4260
tcttatacct atattcctct ccctctttcc tttttcgtca tctgttcttt gcttttcctc    4320
actcgtctct agatgtcact gccatgtgac catctgtaca ggactcagat tcattctccc    4380
tgggaggagc aataatcact attccgtatg agtgtctgca ttgcctgagt ttttccctca    4440
gataaccccg ttggcagctg atcttcccca agcccaccta tagaaatatc tcatggtcta    4500
atgattgaga gcaaatgctc tggaaccata caccctgggt tcaagtcctg gctcctacac    4560
ataccatcta taggaccttg ggtgatattt acttctataa gcctcagttt ccttatctgt    4620
aaaatgcaga taataataat attcaccca taggttggtt gttttgagga ttaaatgagt    4680
caatacagta aagcatttac aatattgagc atttacaaca tggtaagccc tcagtaagtg    4740
atagttggtc ttgttatttg gactagatgc taattcctac atccagaaat tagggtcaga    4800
gattgtcagc agacccaaat agtaagacac ataacacaga acatagtact ttatatttga    4860
ggaactgtcc caggccactg tctcctgaaa aacatttcct gactccaaga agatttagtt    4920
```

```
acttcttctt agccttccat atatcctcat tcatatgcta ttatagcgct tttaagagtt    4980
gatttcacct atttgtatcc ttgccaggcc cctcctgcta aactgtaaac tctttaagag    5040
cagaaaccat atctgattca tttccccaaa tgtaaatggt aattacacaa taaatctttt    5100
tttttaaga tggggttttg ctcctgttgc ccaggctgca gtgcaatggc acaatctcaa    5160
ctcactgtaa tctctgcctc ctgggttcaa gtgattctcc cgcctcagcc taccgaatag    5220
ctgggattac aagtgcctgc caccacgcct gggtacacaa taaatcttta ttaaaagaat    5280
gactaaataa atctttgcga tcccaccaac tttaggaata caataaggaa cactgtcttc    5340
ctacataaac tgtttttttt tttctttaaa agaaatgggg ttagctgggc atggtggctt    5400
gtgcctgtaa tcccagcact taggaggct gagatgagag gattacttga gtccaggagt     5460
ttgagacccc atctctacaa aaaatttaa aaattagctg gatatggtgg tgtatgcctg     5520
taatcccagc tacttggagg ctgaggcagg aggatcccctt gaccccagga atagcaggca   5580
ggagtgagct gtgattgcgc cactgtactc caggctaagc cacaaagcaa gactccagtt    5640
ctaaaaaata aataaataag aaaggaaaat aagactgggc gcagtggctc ataactgcaa    5700
tcccagcgct ttgggaggct gaggtgagta gatcatctga ggtcaggagt tcaagaccag    5760
cctggccaac atggtgaaac cccatctcta ctaaaaaata tacaaaaaat tagctgggca    5820
tcatggcggg cacctgtaat cccagctgct tcagaggctg aggcaggaga atcacttgaa    5880
cccgggaggc agaggtttca gtgagccaag gccatgccat tgcactccag cctgggcaac    5940
aagagcaaaa ctctgtctca aaaagaaaa aaaagaaag aaggaaaag aaagaaacag      6000
ggtctcactg tgttgcccag gctgatcttg cactcctagg ctcaagcgat tctcttgcct    6060
gccaagtagc tgggactaca ggtgcacacc accatgcctg gctaatgcaa actatctttc    6120
atattcctg taccagtgag ctctctgctt cttgcctcga gaagtctgaa ccagaaaata     6180
tggatcagaa gtttggctgg ttgaatagtc aatcagtaat tagtcttgag gagtatgttg    6240
ggcatccaag tggactctct gggcgcaagt actgtgacag agtttgggct acaggtgttt    6300
gttagctatc aacacctgtg aggggagggg aatgaaagaa ggagtgagcc acggaagaag    6360
ctgaactgtg atgggggccc aacaagcctt gacaaatgca gcatgttgct ctgaagagag    6420
tattgcctgt caaagtttct ctctttgggt caaaatggcc aggtctttat accctgcct     6480
ctctcagtca caggatgtgg gtgctgcaga aaggacatgg tctcaggtga ctcctttca     6540
gcagcttagg tagactgtga aggggctgtc tgctgacgac gttccctgta gctagggagc    6600
aagtccttcc ttgaacgtgg atctgggtgg caccacagga agtgtgctaa cttgtatttg    6660
gtatttcact gtttggatgg cagctctctt tattgtgaag ccaggagaca ggtaaccaag    6720
ctcaagtctg ttactggcct tactatggaa acctttaaac cattccctc tatgggtctc     6780
agttttcaga tctagtagtt cagaccagat ggttggaata gttctctgac tattctatgc    6840
ttcactggaa gccctgatcc tggggtaggg ctgagtaaag ctaagtaatg gtaagtaatc    6900
tcaccatatt tctgtgcatt tgatcatccc cctgccagat tcgggagctc tataagcagc    6960
ggctggatga gtttgaaatg ttggagagac atatcactca ggcccaagca cgggctattg    7020
cggaaaatga gcgggtcatg agccaggctg gagtacagga cctcgagagc cttgtcaggt    7080
tgcctccagg tgtgtataaa gaactcccac atgcctgccc aattcccggg ctgttgatat    7140
ttcactgtgt ttgctccatt gcccactctc taggcttttt ctggatattt ggagagcaag    7200
tcgcagacat gataatatga atattaccac aaaagaaat ttcattacca caaaacactt     7260
ctgtatgtgt atcttcaaaa caaggacgct ctcctacata accagcatat aaccccccaca   7320
```

```
acctggaaat cagtttctgt gcaacactaa cctctgaccc acagatactt gtcaacctaa   7380
atagcagaga gagactctct aaaagaaaat gatggacact gcaatgggaa tacatgtgcc   7440
attgtaaact gtgtgcatat tcagggaggt aaaggaagac aaaggttttt aaaggaaaag   7500
tgaggaggat tacacaatgg ttttgaagta attatccttg gctgaaaaat cattaacaag   7560
agtagtacca gtctgagatt aaacaggcgg ttgctgggca gatttgtgtg tgtgtgtagg   7620
gttgcaatga cctttgtgtg aggttgtgat ttttgtggcg tgatatggtt tgtctgcatc   7680
cccacccaaa tctcaccttg aattgtagct cccgtaatcc ccacgtgtca tgggagggac   7740
ctggtggaag gtattgaatc atgggggcag gttttccct tgctattctc atgatagtga    7800
gtaagtctga tgagatctga tggttttata aagggcaatt ctcctgcaca cactctcttg   7860
ccttcgctca tgtaagacat gcctttgctc tccttcacc ttctaccatg attgtgaggc    7920
ctccccagcc atgtggaact gtgagtccat taaacctctt tttctttata aattacacag   7980
tctcgggtat ttattcatag cagtatgaaa atggactaat acaaggcatc ttttgtgata   8040
attcttgtta tcaggcactt atgcatggcc ttccccagca ccatttgtca gggtttttta   8100
acacaagtga ctccattttg attcagacaa cttttacatc ccattcaaat tttactgact   8160
gtcctactgt ggcttttttcc cccctcagg cccaggatcc tgtccaggaa gtcatgtcac    8220
atgcaattgt catgtctctt tttgagatgc cttcatttgg aacaattcct tgatcttttc   8280
ttgtctttca tcttcctgac agttcttgac cagacttata ttctgtagga tggggatggt   8340
tctgtctgat gcttccccat gaccagactt aggcaaacat tctgggcaac aggaccacat   8400
aaagttattc cttgttcatc tcactgcagc acagcaggag ggtcacgtga tgttaacctc   8460
catcccctga gtaggttggt gtctgccagg attttctgca ttaaattctc caaatcaaat   8520
tataattgat tagcatttta tagagaggta ttctcagatt acaccaatat cttgttcctc   8580
atcaaagctc catcgccata ccaccagcat tcactgaaaa ttcttttctt aatgcagaag   8640
tttaaagagt gatcctttag aaatacaact atgcaaagat aagttgactt tattaattat   8700
ggtatatcca cactatggaa tactgcaaag ttgtttaaaa gaatgaatta tacctgtgtt   8760
gtagatatag atggctgtct gctatttatt aatttagcaa aaaagtcaca gaacaatgtt   8820
aggataatcc cattttttata gtatagatgc atgaaaaaaa gctgaaaatt tgtatatcag   8880
aatgttaata atgttcttag ggggcaatta actacctata atcaaaattg ggttgttttt   8940
cctatggact tgtccatagt ctggatttta ctgatatcag catcatggtg tcatttaacc   9000
tgttcttcct tgtatttcct ataaatctgt aattagttct agagacttta tgaggttag    9060 gttcaatgat ggtcaggtgg tggggaaaga gcacttcata ggtgatgctg tgtgtttccc   9120
tcaggaggta catgatatgt ggttgctatc tctccttttca tgatgctggc agcctttta   9180 ttttattatt ttattagggg ttacaaatta taatgaaatg ctaatggtaa taataattct   9240
atctttattt atttgtcagc tgaactactt ctataaagac aaactttca gaaactactt    9300 tgattacccc aaagtatggg cagcattaat tctttcccct tatttgccag tgtttaaaat   9360
agtgagttgg ttcccctaac atctgccaaa ggtgactaat gaggtttgtt tggttgtttt   9420
agtatcattg tgcacgcttg gatttcatga ctgcaaatta tttattatcc ttttggtgct   9480
caaattgttc catctttggc agagagcctt ttccagttga ctgctgattc atttgacaat   9540
cagctgtctt tgataacttc cttgctttct gagctggtga gatgttccag gccatcttgg   9600
gtatttctgg ccccagatct ggaatcagcc atttcttcaa gaaacgctga ttccttttat   9660
```

```
tccctccacc actccccaca aagaccttga cctgttctcc tgaattcttg aaaatcttga    9720
aaattcttga aaattatcat tttccagtgc agtagacaga aaagacagta tatttaggag    9780
acctgttata tctatggcct agagggaaag atctaaggga ggaagaagtg aagatacag    9840
tgccttaaaa ggcatttaaa cttatgagga cctactaggg cccagatgct aatatgcttt    9900
gcataggtta tcccactaaa tcctcccgac aaccctgtaa ggtaggtttt ctttctatct    9960
tacaggtgta ggaactaaac ttagatgatc aaacgacttc cctgaagccc acagcttgg    10020
aagggggtgg gacttagatt tgaacttggg tgtgtctgct gtcaaaaccc atggctttct   10080
tctatcggga ggaggaagga ttgttgatga gccatggtgt ctcaggagtg ttgatgactt   10140
ctcttagagt gtggctctga gcagcagaag ccctatcctt catcaggcct gccagacctc   10200
tgagactcaa gtcccattaa acagtaacac tcaggcacag gttctgtatc tcttcctgtt   10260
tcccccctcca ccacagcaca gtgtagctgc aaggacccct ccctcaatgg tggcccagat  10320
aatgtggatt ttgcagaaat tattggtagc aaatgtccag agtctttact ggttgcctga   10380
tgttccctga atcctgggag tcagctactg tcccttttt gttgttgttg ctagagatt    10440
agggagatt aaataattaa ctatttgggt tttttttt aatgaaagtg aaataaaaca     10500
ttgagaacca ggagacaaat gtcagtttgg agaatttttc aatgactttc attttatttt   10560
tacccaagaa tgatattaag ttctaatcag ccattatctg tcctggtttc tcaggtctct   10620
gctggtgatg tgtcttttctt ttaagaagtg aagaagtaga cacactaatc cagttccatg  10680
gatacccctc tggtgtgtct gcttctcaga gaagggtgag gtaactttt tttataactc    10740
agataactgg caatgaggac attcccctaa agtttctta tttgaggcat agaggcaacc    10800
tttctgtgtt tgctaataaa aatgtgacaa agtggcaagc acatgtaaat tctccaaagt   10860
gagggagaaa gatcagaatg ctgcagaaca tcttgtgctt tcattcttgt cccttgctgg   10920
aaacttgtcc acattatcca agacctcgca gagccatgcc caggagccac agtgttagta   10980
taggaagccc acccttccca ggggagaaga gatggtcaca aggccagagc aggcttttcc   11040
aaggctcggg gtacatgccc aggcctgaca gctcctgcag acacagcacc tagccaccca   11100
taacctgggg caggactgtg gaaagaattg tatcagaaga gagaggatac atctcttgtc   11160
acatggcctt tatcctttgt atagaagtct tatctttga tattttaaat aggccatcac    11220
caaagtcctt gggaactggg ctagtttgtg tcaacttggc attgctgtta ccgcctgcta   11280
aagtctctgt tgccaaggag agaccaggga gtacatttcc cagaaggcac ctcccacttg   11340
tgcttccagg ataggtcagc tgatgagaag cccttggtga gttttggaaa ggaaggccat   11400
ttatttcaaa aagcagtagt aggcagatga ttgagtggct gtgagtttga aaacaacttc   11460
cagataactt ttttttttt tcaagacagg gtctcgcttc atcacccagg ctggagtgca   11520
gtggtgcaat cttagctcac tgcaacccct gactcctggg ctcaagtaat cctcccacct   11580
cagcctccct agtagctggg accacaggca cataccacca cacccggcta gttttttgta   11640
tttttagtag agacagggtc ttgccatgtt gcccaggctg agtttccaga taacgtctta   11700
agaaagccct gcttcagtgc tactggctga agttgttaat gatgatgtct tagttcattt   11760
gtgttgctgt aaaggaatac ctgaggctgg gtaatttata aagaaaagag attgatttgg   11820
ctcatgattc tgcaggctgg aatactgggc atctggtgaa agcctcagtc tgcttccact   11880
catgggggaa ggcaaagggg agccacgcag atatcacatg gcgagaaagc aagtgagagt   11940
gggggttttg gggggccag gtgagctaat atagtgagga ctcactccct gcctgccccc     12000
acctagggca ttcatctaca catgaggggt ccactcccat gacccaacac ttcccattgg   12060
```

```
gccccacctc caactttagg aaaaaatttc agtataagat ttgagggaac aaactcctaa    12120
actatagcag atggcttccc tgacattatt tccctcagtc ttcaatcctt tgtattaaaa    12180
cctttaatat ttgatataca tagattagtt tctgttttcc tgatggaact ctcaatgaac    12240
atatgtgatg ggggaatgca tgtcttcact gataggttgg ttataggaga cctccaaaag    12300
gaaagaccat tcaaaggcac catgtctctc tctctctttt ttttttttgc tggagggcat    12360 tggcccata ctggctcact gcaacctcca cctcccaagg gatcctccca cctcagcctc     12420
cagagtagct ggaaccacag acgggcacca ccacacccac taattttgt atttttgta     12480 gagatggggt ttcactgtgt tgcccaggct ggtcttgaac tcctgggctc aagcaatccg    12540
cccacctcag cctcccacag tgctgggatt acaggcgtga gctacctcac ctggctggca    12600
acatgtctta agataatgtt ggctaatgga gcaaacaaca aagtttgaaa acttccaaca    12660
agtcttctgt tcgggcgctg gtgacagccg ggactgatcg ctcagcggca gtggcgcaga    12720
ggcctcctcc ctggtccacc gcggtcccca cccaacccca cctgtccctg ctgcctgctg    12780
ccgtagcagg agctggaggc tgctgctgcc agagggcaat gagttccagt ggtgcttctc    12840
ccaagtcaat ggggccatcg aggaggacat ggctgaagat ctgccacagg ggagaggcca    12900
gaagaggctt tgacgaccat cagtgagtga ccagggggct acacagcctc actctgcagc    12960
agatatcatt tccactgttg agtttaatta ctctggagat cctgtggcag agacaagga    13020 cggtggagtc gttttcagc agagctagag aataaaagcc gccctcattc tagggggagaa   13080 tataatgttt acagtacctt taaaggtcat gaaccagggt ttggctatta gaaaagtcta    13140
gaaattgagc aaaaaataaa attaggtggt tacaacagaa cactgctcat tttctactct    13200
ctacaaatga taaaactata aaattatgga aagaagcgg atgagataaa agagcagaaa    13260
gttataactt gaatgatgaa gatggatgac ttcaagattc atttagaatt acagcactat    13320
caatgacctg aggattaatt tatgacactt agaaatcaca catagacatt ttgacgtggt    13380
agacatcaaa cctgctaacc tggagcagct gacagaagtc attgtggcag ccaagttcca    13440
ctcataccag tgcaatgtgc ttgtctacag tagtagcaaa ggaaccattg actaagcagc    13500
atgggctcct cgaccctgtg caacagacac tccaagtttt ttgaagagcc tcaagatccc    13560
agcagtaggt ccttcttctc agaaataatt tcatccatac ccaatgtaaa atgtagccat    13620
agtgggcagt acctgatgac cagagactcc ctgttggtga aggtgtggga cctcaacata    13680
gagagcaggc tgggaccaca ccgggaccac gagtacctgc acagcaagct ctgctttctc    13740
tatgagaatg actgcatctt tgatagcttt gaatgttgct ggaatggttc ggataggtgc    13800
atagttgaac cacaaataag caagggaaat ctcccaacag ccagaaacga agagggagct    13860
gaaaccagaa ccgtagcctc taaagacgtt tattgcgaga gaagcccac accctggct     13920 ggccttgggt gcatcagcca atagcaggaa ccgctgcctc ctgtgaacag caagttgtgg    13980
cgcagagctg aagccttgga ccatgagtg tggagttgga actgcgccct caaagatgat    14040
gaggtctccg tccactggag tccagaggga agtttatctg agatcttgca ttgggggtggc    14100 caaagctccc ctgagatgtg taagcatagc ttcccattac aagggtttga agtccctctc    14160
tctccctccc cctccgcctc ctcctccccc tctccctctc actggtctcc ctctgatgcc    14220
accaaagttg tgaaagccga ggctggactg tactgccgcc atctcggctc actgcaacct    14280
ccctgcctga ttctcctgcc tcagcctgcc gagtgcctga gattgcaggg gcgcgccgcc    14340
acgcctgact ggttttcgta ttttttttggt ggagacgggg tttcgctgtg ttggccgggc    14400
```

```
tggtctccag ctcctaaccg cgagtgatct gccagcctcg gcctctcgag gtgccgggat  14460
tgtagacgga gtctcgttca ctcagtgctc aatgttgccc aggctggagt gcagtggcgt  14520
gatctcggct cgctacaacc tccacctccc agccgcctgc cttggcctcc caaagtgccg  14580
agattgcagc ctctgcccag cggccacccc atctgggaag tgaggagcgt ctctgcctgg  14640
ccgcccatcg tctgggatgt gaggagcccc tctgcccggc cgcccagtct gggaagtgag  14700
gagcgcctct tcccggccgc catcccatct aggaagtgag gagcgtctct gcccggccgc  14760
ccattgtctg agatgtgggg agtgcctctg ccccgccgct ccgtctggga tgtgaggagc  14820
gcctctgccc ggccgcgacc ccgtctggga ggtgaggagc atctctgccc agccgccctg  14880
tctgagaagt gaggagcccc tccgcccggc agccgccccg tctgggaagt gaggagcgtc  14940
tccacccggc agctgccccg tccggaggt gggggcagc cccgcccgg ccagccgccc  15000
```

```
agactgagag tagactttat agcagccaca gtgggagccg aagccatgt gatacagtga    16860 gtgtgacttg ggactcttca ccatcagctt agaatcaggc attgaaatag atggttgttc    16920
aagaatctgc ttatggtaaa ggcatttcca gatgggaaac agaatttatc acaacaggaa    16980
actcaggaga gtgagactca aggaactcac tgaagaacgt acttccagca gaaggagagt    17040
ggtcctggag aaagggtgtg attctgagat aggcagatga acagagcagt cagtgaagac    17100
gtgagcaacg gaaagcaacg tggactctaa agctctgtta actgggtgac cctggttatc    17160
tgggttgcgg ggagaaaaat tagagccctc accaacacca cacagcaaat aagctctgaa    17220
tgttttaaag cctagaagac gctatgggag agcatcttca tggctctgga gatgaaaggc    17280
cttctttaac aaggtcctaa atgcccagtg aaggaaaaca ttaagaaatt caggctgatc    17340
gtgctggctc aagcctgtaa tcccagcact tcgggagacc gagttgggtg atcacttga    17400 gcccaggagt ttgagaccag cctgggcaaa atggtgaaat ctgatctcta caaaaaatac    17460
acacacacac acacacacac acacacacac acacacacac acacacacac acaaatagct    17520
gagtgtggtg gcatgcgcct cccagctact tgggaggctg agatgggagg atcacctgag    17580
ctagggaggt ggaggttgca ataagctgag atcgtgccat cacactccag cctgggtgat    17640
agaatgagac cctgtctcaa aaaaaaacaa tactgtagtt aaatttagtg gttttggtt    17700 ttttggttt gtttttgttt tttgagacag agtcttgctg tgttcccag gctggagtgt    17760 agtggctcaa tctagatcca ctgcaacctc tctctcctgg gttcaagtga ttctcctgcc    17820
tcagcctcct gagtagctgg gattacaggc atgtgccacg aggcctggct gattttgta    17880 tttttaatag atggggtt ttaccatgtt ggccaggctg gtcttgaact cttgacctca    17940
agtgatctgc ccacctcggc ctcccaaagt gctgggatta caggcgtgag ccaccatgcc    18000
cggccaacta cattaaattt taaacttctt tattttgaaa taaaaagtaa aaacaggctg    18060
ctctgcctat ggagtagcca ttcttttatt cctttacttt gttaataaac tagctttcat    18120
cttaaaaaaa aagtgaaaac aaaatccaca aaagcaaata taacgaacag attcagtatc    18180
caaaatatgt aaagaattag gagtcaacaa gaaggtggca aacagctcac ttaggaaaga    18240
gcaaaaacca tgactgggaa tttgcagaaa tggaaaaata aataaaatg ctcattctta    18300 gtgatcagca aattagagcc agagggatgt cctttcacac ccatcagaat gatgatgatg    18360
atgtcaggga aaggaatgaa ggccagtggg cgagaccact gccttttgt gggcctcctt    18420 ggtggcagca agtccagttg ggagcttctt gtatgtacag acaagaaaat gtattcagaa    18480
gcttgaaata gcaaacacct ggagacagct caggggtgca tcattagggg aatggatagg    18540
taggttgttg tctatcatat gctaaaaagc agtaagaatc aattatttga actacatgga    18600
tcacagctgg gcacagtggc tcacgcctgt aatcccagta ctttgggagg ccaaggcggg    18660
cagatcacct gaggtcagga gtttgagacc agcctggcca acatggtgaa accccgtctc    18720
tactaaaaat acaaaacatt agctgggcgt ggtggcacga gcctgtagtc ccagctactc    18780
aggcagctga ggtaggagaa gcgcttgaac ccaggaagca gaagttgcag tgagctgaga    18840
tcatgccact gcactccagc ctggatgaca gagcgagact gtgtctcaaa aaaaaaaga    18900 actacatgga tcacataggt ggatctcaca aagataaaga taatccgcaa agaaagaaaa    18960
ttcaggcgga acacatacag tgtgatgaca tttgacatgt tatatttaag gcatgcagaa    19020
gttttatttg ttttttaagaa tctgtaacta ttcaaaaata taaacgtgca tggggatgat    19080
acatacgtac tctagtgagt gatttcccca gctggggaca ggattggaga tgatcttcct    19140
```

```
agagtgggac atggtggagg ttaactgtct tagcaatgac ttatgggtac ttggatactc    19200
actgtattat tccttttttt tttttttttt gagacagagt ctcgctctgt tgcccaggct    19260
ggagtgcagt ggcgcaatct cggctcactg caaactccac ctcctgggtt cacgccattc    19320
tcctgcctca gcctcctgag tagctgggac tataggcgcc cgccaccaca cctggctaat    19380
ttttgtattt tcagtagaga cggggtttca ccgtggtctc gatctcctga cctcgtgatc    19440
cgcctgcctc agcctcccaa agtggtggga ttacagcatg agccaccgtg cccggcccac    19500
tgtattattc tttgttcctc ttgatatatc tgaaatattg tgaagtatac ttaaattaca    19560
catccctaag aatatccaaa agctctcctg gtaatatttg cttactccat tcactcttac    19620
aaacactccc atatcttctt gcctggaaac atctgttgag ggatgggatg aaggggaatg    19680 agattttttca gtgctctctc tgcccagtcc tgatcccctg tgtgacacca ctttctggtg    19740
ctctaggttg ccccgcaaaa ccagacatag ccgcttgctc ttgagtgtgt ctgcactgtc    19800
cctacctcag gccagcaccg atgcaggcgg ctaggcggct gtcttgttta cagtgtggaa    19860
atgcccactc ccaggccagc attgcctatc aataattgac aagtgataat aaaactgtat    19920
aaaagctgaa aaagtcttat attcttcctg ttttttcttt aattttttatc aaagtaataa    19980 atatatatgg ttttaaaaa tcaaatagtt tagaagaact tctaatgaag aataaaaagc    20040
ctccacctgt acattataaa tttgtacaaa tgcacagaat gtacaccacc aagagtgacc    20100
tgtaatgtaa acatggactt tgggtgataa taatgtgtct atgtaggttc ttcagtagta    20160
acaaatgtat ctctctagtg ggggacgttg ataatggtgg aggctgtgca tgcaggggct    20220
gtatggggaa tctttgtacc ttcctctcaa ttttgctgca aacctataac tggtctaaaa    20280
ataaagtcta tttttaaaaa agccttttcc acctcacctc tcccaacctc agtccacttg    20340
ccaaaggtag ccattgctag ttttaattct ttggaatacc tataaataat gttatttata    20400
tgttatataa ataataatgt gtttgctact atttctgggc tcatcaccca tagacgttaa    20460
ttatcacctt tcctctcttg agattttctc tctcctgtat ctgcaggtca gtggggaatt    20520
ggccgagctg gctgggcttg gctggctgga ctggctccaa gctgtgggtc cagctaggca    20580
tgtctccttc gtaggtcagg ctcaggtctg ctctggattc cccctggggt ctaagatgaa    20640
gggacaggga agctcttgtc acaataatgg caaagccaca agagggaagg ctcagctgca    20700
caagtgcatt tcaaaccttt gctaacatct cattggccaa agcacgtcac atggccacag    20760
tcaggagtga agaagtgcac tgtctctagt agcaggcact gcaaagtcac atagtcaagg    20820
gcctggatat agacagaagt gaagaactgg gaccttttat tcaatctacc atatttctca    20880
taattctgtt ttcttataga cttctctgta acagtatttt agctcaaata atacaacaca    20940
gctttgccca atggttggcc tcttttaagt ggctgataga tacttgatga gtttcttaaa    21000
tctcaacatt cccacaggtt tctgagaagg aattttgtta gatagtttag gcttggcgga    21060
tgaagaaagt ttgggtgtgg gttcttcaaa gtcagtctgg ctggaaacac cttgttctcc    21120
ccttcccttc tatgaagtga agagtgtctc cagatggtgt atagacagcg agttgctacg    21180
gaaacatcat ttgatctccc cagaagatta ctacaccgat acagtgccgt ttcactctgc    21240
acctaaaggt aatgcttctg tgctctcaag gcctctgata ccatttgggg gaagttcagt    21300
agggccacgt tggccacctc tgctgccatt tccttgctca gaggtttttt tcacctttc    21360 tttaatttcg atggtgactg ttgggaaagt caaatctgag catctgagca tgccaatttc    21420
ttgctagtgc tcccccgcct gtatgactga agtccaggct tctccatgtg gactatgatg    21480
cccacatctg ctgcccaata ccaagaatta tgtaagtgct tggagttgca gttgaaccaa    21540
```

```
gagaaggaaa aactgaagac atagaaaagc aagggagcgt gtacctgatg agttggagca   21600
gggacttatg ggttttccca tgcaggaaaa gagcagcttc tcatcctttc agaatggagg   21660
gaagcctggg tagagaggca gagagggtgt gtacatgtat gtgacattgg gccagtttcc   21720
tgtgatatgg gaggcaagat attctgagaa tgagtggggt gggaggctgt gatgtgggct   21780
taagcagcga gttagactta tggaagagtc cacacgtgga cagggagaag tccctgtgtg   21840
gattctgtgg ccagttatcg ggattgccta gcatgctggg ctcagaagac aagctctccc   21900
atagctccag ttgagggact gttttgattct ctggggcttg ggagctgaga aggtgtttgg   21960
ggtgggagga ttgggatcta gaaaattgag ggtgctcctg gggagagttc cactgatggt   22020
ctgagctacg tagggaagta aggcaagaaa gaggtagcag aatcaagtgt catggagtac   22080
taagccactt agtatttttt ttttttttgag gcagagtttc acttttgttg tccaggctag   22140
agtgcaatgg cacgatcttg gctcaccaca acctccatct cccaggttca gcaattctc    22200
cttcctcagc ctcccaagta gctgggatta caggcgtgtg ccaccacacc tggctaattt   22260
tgtattttta gtagagaggg ggtttctcca tgttggtctc aaactcctga cctcaggtga   22320
tccacccacc tcagcctccc aaagtgctgg gattacaggc atgagccacc gcacccggcc   22380
accacttagt attttaaagt tagttggaaa ctcagtatct tatgcaggtc aataagaatg   22440
gggctaacat gtattgagag ttaaccaggc attgtgctaa gagatttgtg atggtatcca   22500
tttgattgca ttcttgctag caatgaatgt tctcatttaa cctttggagg gatggttttc   22560
ttgtttgttt gtttgtttgt ttgttttttc ttgagacaga gtctcgcttt gtcacccagg   22620
ccagagtaca gtggtgtgat ctactgcaac ctctgcctcc tgggttcaag cgtttctcct   22680
gcttcagcct cagcctcctg agtagctggg attaaaggcg cctgccatca tgcctggata   22740
attttttgt attttagta gagacagggt ttcaccatgt tggccaggct ggtttccaac    22800
tcctgacctc aagtgatccg ccggcctcag cctcccaaat tgccaggatt acaggcatga   22860
gccactgcgc ttggccaggg ggtgggggat gatcttaaca gtgtaaaaag ctcatacaaa   22920
cttcattcc ttctgtgagc tcttcagaaa gcatgctcat gtatgggta tgtgtacagg     22980
catgtgtgtg tgacagtggt ctactcatgt tctttgacca tgttggaaaa tattttaaca   23040
ctctagtcct aaattttgtt gttgtttgtt tgtttgtttt tgagaccggg tcttgctttg   23100
ttgcccaggc tggagtgcag aagcacaacc ataactcact acaaccttga cctcctgtgc   23160
tgaagtaatt ctccccactc agcctcctga gcatctggga ccacaggcat gcactaccac   23220
acccagcaaa ttttttaaatt tatttttttgt agagataggg tctcactctc actatgttgc   23280
caaggctggt gtcaactcct gggcttaagt gatgctccca ccttggcctc ccaaagtgct   23340
gggatgatag gtgtgagcca ccacacatgg ccattttgaa tacatagaat aagttccagg   23400
agtaattcat atgttgaaga gcaattatag ctggtgtggt aaatatgaaa gtttaggaga   23460
aagatcaagc taactgtggc tttggtggtt ttatttggtc atcttaggaa tgcccacctc   23520
ctcaccttgt tgcagtgatt cagtttgttt ccttgatgct gtaggcatct ccctacctgg   23580
atgttcaaaa ctgacattta gctgtgagaa gcgttccgtc cagaagaaag agctgaacaa   23640
gaagcttgaa gattcatgca ggaagaagct tgctgagttc aagatgagt tagaccacac    23700
tgtggacagc ctgacatgga atttaactcc taaggccaaa gaaaggacca gagaacctct   23760
caaggtcagt ttgaaaggct gtgcagagca gtgtttgggg ggacagagag gcagtgaagg   23820
ggaaggcatt cagatgacat gagaagctgt gatgaatcca tcgcaaaata gagtagagct   23880
```

```
tgtgttggcc atctatgggt catgcagttg gtcaagatgt caacaagcac aatccctttg   23940
cctgtcattg actctatgct tttgtatgtt tcaaagaaag caagtcaacc aaggaataaa   24000
aactggatga accacttacg tgtgccacag agagagctag acagacttct gcttgccaga   24060
atggagagtc ggaaccactt cctaaaaaat ccccgttttt ttcctcctaa cactcgatat   24120
ggaggcaagt ctcttgtttt tcctccaaag aagccagcac cgataggaga attccagagt   24180
acagagccag aacagaggta tgtctttctc tggcttgaac tctcagaaaa cctggcccat   24240
gagagttaac ctagatggtc ctccgtttgg tctggctgta gaggtcccta gacttgtggg   24300
gcagggtagc agtatcagaa cagagcaggg ctgcagggtc acccactggt gtggcctttg   24360
aaccttcccc agagtcctgg gtttatgctt ttctgacctg ccagggtct tgagaaatag    24420 gggttggtgt tggcccttta tttacattgg agcaatctgg gtcaaatgga agcaatcccg   24480
ttagagacat aggtcttgag taataacagc atttgaaatt tgattgatta taaataatta   24540
gtgtaaactg tgattttct ttaagagtgc ctttgcctat atatcagtaa ctgtccttat    24600
gaaagtaatg agttgcttca tgggttcata attttagtaa gcctaaaact attaacattt   24660
ctttattaga caactaatat tttttattaa gaaaaattag atacaaaaac tagctgggta   24720
tggtggcatg cacctgtgat cccagccact gggaggcgg aagtggaagg atcacctgag    24780
cacaggggtg tcgaggctgc agtgagccaa gattgtgcca ctgcactcca gcctaggtga   24840
cagagtgaga ccctgtcaaa agaaaatag aagagaagag aagagaggag gagaaaagag    24900
aaagaaaaga aagaaagatt agaaaagact aatatttgag atacctatat taaaaaccca   24960
cttacttatt ggtgtttaaa catgtagagt ttttcctatg catattgaaa atgaaatatg   25020
tagctactta tgtcttcaca aagattggat catactgtaa aattatttta taacctgcat   25080
taacaataag atccaaaaac cccccaacaa atggtatatt gtgaatatct ttgatggtct   25140
ttatgtattt attttacat taatcagtca ctgcctacta tttcattgta tggatgaaac    25200
taacagcctt tctcccccctc tttttcatc ccacagttgt gctgatactc cagtgtttct   25260
agctaagcca ccaattgggt ttttcacaga ttatgaaatt ggtccagttt atgaggtaga   25320
catcttgttt ctttacagct cccaccccat ctgctttctt attttaaaa agtctttatt   25380 atggaaattt tcttttttt ttcttttttt tttttttttt agtatttatt gatcattctt   25440
gggtgtttct cggagagggg gatttggcag ggtctaggac aatagtgaag ggaaggtcag   25500
cagataaaca tgtgaacaaa ggtctctggt tttcctaggc agagggccct gccgccttcc   25560
gcagtgtttg tgtccctggg tacttgagat tagggagtgg tgatgactct taacgagcat   25620
gctgccttca agcatctgtt taacaaagca catcttgcac cgcccttaat tcatttaacc   25680
ctgagtggac agagcacatg tttcagagag cacggggttg ggggtaaggt tatagattaa   25740
caccatccca aggcagaaga attttcttta gtacagaaca aaatggagtc tcctatgtct   25800
acttctttct atacagacac agtaaaaatc tgatctctct ttcttttccc cacatttccc   25860 cctttctat ttgacaaaac cgccatcggc atcatggccc gttctccatg agctattggg    25920
tacacctccc agacggggtg gcggccgggc agagggctc ctcacttccc ggacggggcg    25980
gccgggcaga ggctccccca ccacctcccg gaagggcgg ctagccggc ggggctgcc     26040 ccccacctcc cggacggggt ggctgcgggg cagagacact cctcagttcc cagacggggt   26100
cgcggccggg cagaggcgct cctcacatct cagacggggc ggcggggcag aggcgctccc   26160
cacatcccag acgatgggcg gccgggcaga gacgctcctc acttcctaga tgggatgacg   26220
gccaggaaga ggcgctcctc acttcccaga ctgggcggcc gggcagaggg gctcctcaca   26280
```

```
tcccagacga tgggcggcca ggcagagacg ctcctcactt cctagatggg gtggcggccg   26340
ggcagaggct gcaaactcag cactttggga ggccaaggca ggcggctggg aggtggaggt   26400
tgtagcgagc cgagatcatg ccactgcact ccagcctggg caacattgag cactgagtga   26460
gcgagactcc gtctgcaatc ccggcacctc gggaggctga ggctggcaga tcactcgtgg   26520
tcaggagctg gagaccagcc cggccagcac agcgaaaccc cgtctccacc aaaaaacacg   26580
aaaaccagtc atgcgtggcg gcgcacgcct gcaatcgcag gcactcggca ggctgaggca   26640
ggagaatcag gcagggaggt tgtagtgagt cgagatggcg gcagtacagt ccagcctccg   26700
ctcggcatca gagggagacc gtgcagaggg agagggagag ggaggagagg gagactgtgc   26760
agagggagag ggagagggag agggaggaga ggaagaccgt gcagagggaa agggagaggg   26820
agagggcgga aattttttaac tgtacacaaa actaggaaaa agactataac tactcctcat   26880
gtgcccaata tgcagcttca acagttatct acattttgcc aatctggttt tgtctattac   26940
tcctacaacc tcttcatgta cacatctata tgcacatgta tgtgctggag tcatagaagg   27000
aaaatatgat atcatgtcat tcttcagtta atacatcaat tagtatctct aacagataag   27060
ggttttaaaa agtaaccata gtaccactgt cacacccagc catattaata atgattcctt   27120
aatatcaact aatacccatc tatgtctgat cttcatttgt tttaaaaaaa agtccattta   27180
tatttggttt ctttgcatca gaatctaaac attgcatttg attaaagtat ctcttaattc   27240
tcctttagtt gataataatt cctctcccac ctcctgcttt ttaaaaatgc catttatttg   27300
ttgaagaaac tgcaatttcg tacaccctgg atttggctaa ttgcgttatt gtggtgacat   27360
taaacgtgtt cttttatctt ccatattttc cacaaactgg tcattagata tagagatttg   27420
atgagattca agttccattt ttcctctttt ttgacaagaa tacttccttg gtggtactgt   27480
gtatttctta ttgcaatcca tcaggaggaa gcatgggatc tgggtttccc atgatcagtt   27540
atgaatggca tcaggtgttg aaattctgat tcattctcta taaagttctt atcaaacttt   27600
cacttaatag ttaacagcct agatgactgc cagatgacta ttgtccagat ccatttttc    27660 ttcaatcagg gcttacaaaa tggtaatttc taattctatt attccatcta catttattag   27720
cttgattttc catttaaaaa acagaataaa actttccctc taactttgat tcctgcctcc   27780
tcctctttct tgtactctcc tgatatctat aggtaactat ttctattagt ttgcattctt   27840
ccattgtttc ttttttgaacc ataagcaaat atgtatatat agttgaaccc cctttccttc   27900
ttactgtcct ctacatctta acagtatatc cagtaattcc tgcaagagca gaggctttcc   27960
tcattccttt ttcccagctt cttcttttta gaagcttccc accttcttgg ggaatcaggt   28020
caagaccaag cttagcagtc accaactctg ctcaccaggt acaaagacaa ctaggcctaa   28080
tgatagcaat cccttcacat gcacatggat tgcattttat agtttaaaga gcacttgcct   28140
atccataatt cttgaggaat gtctcaacca ctcatggcaa aaagcagacc aatatggtag   28200
ctctatatgc tgaacattag aggaagcatt ttgcttactc cctggactta acagtaatgt   28260
gttgtctttt gtacttctgt gtctgggact tctgtgtctg gccatcacgt tttaaggaca   28320
gttgtagaag ctggcaaaca cccagaggaa aggagctaaa atcatgtcag ttagggaata   28380
gaatagggaa aagggagagc tgctgatgga cttatggaag atattcttct tcagggcttt   28440
cagatgcctg ctgtggaagc ctgtgctcag agcctggaga tcctgaggct gtagatgagg   28500
tagacataga ctgctatgga acagtctttc ctctgatctt tgcctacttg tctaattctc   28560 atcccttga tgttcataac agttgtttac ccggctaaac tataaagtgt aaggataaaa   28620
```

```
acagttcaaa ttttcagtct ttaaaaattt atgtcccatg tacccttttct ctgaaacctc   28680 ccagggaaca tgcttctttta atagaaatga ggaaaccaat gaagaggaag catggaatg    28740 tggtaccaag agatccaaca taggggagag gtgaaggaaa tctccaggtt aataactctt   28800
aagagatttt gcagttaata ttgctgcaaa gcaaaatttc ccaaagctca gcaacttaaa   28860
acaatcattt tatcatgctt acaaattctt tgggtgaaaa attcagagag agcacaatgg   28920
gaatgacttg ttccacaatg tctgaggcca ttgctggaaa gagtcagtgc ttaggggtga   28980
cataaaagtt ggggttgatg ctgttgatgc tgttgtagat agagagctga ggctgtctac   29040
cagaatgtct acaccacata gcttctctat gtgggctgtg cttccttaca gtatggcaat   29100
ctcaggttaa tcagactttt acatgacaat gcaagtgagt atctgcactt tttttttttt   29160 tttttttgaga tggaatcttg ctctattacc caagctggag tgcagttgca ggatcttggc   29220
tcactgcaac ctctgcctct tgggttcaag caattctccc acttcagcct cctgtgtaac   29280
tgggattaca ggtacgcacc accacgcctg gctaatttttt tataatttttg gtagagagag   29340 ggttttgcca tgttggccat gctggtctcg aactcctgac ctcagatgat tcactcgcct   29400
tggcctccca aagtcctggg attacaggcg tgagccattg tacctggcca agtatctgca   29460
cttctaagtg agtatcctag caagcaagaa ggagattgca tcacatttta tgacctaatc   29520
ttgtaagttg cacagcacta catcctctgc atgccgtaga ttacaaacaa gtcactaagg   29580
ttcatccaga ttcaagggaa gatatgtaga cttcatttct ttttttttaa aaccttttttt  29640 tttgaaataa ggtctggctc tgtcgcccag gctggagtgc agtggcatga tcttggctca   29700
ctgcaacctc tgcctcctgg gctcaagcaa ctcctcccaa ctcagcttcc caagaagctg   29760
gggctacagg tgcaggccac cacacctggc taatttttgt atttttttgta tagacgggtt   29820 tttgctatgt tgcccaggct ggtttcaaac tcctgagctc aagcaaccca cccgcctcgg   29880
cttcctaaag tgctaggatt acaggcgtga gccagtgtcc agcctagact tcatctctaa   29940
tgagaacagt gtcaaagaac ttatggatgt gtcttaaaac tgctctagga gttatcctat   30000
atgatagcag taggtgtagt gggcaactag cccagattag aagaggccag aaagctctag   30060
gagaggttga tttatggaga tgacattgag aagagtccct gatacacctg gacatatggg   30120
ggagagattt gtagggtggt ggagaaggat tgaattattg ataagcacaa agcaaacaaa   30180
ataattagtt gattattcac tccaggaaaa ccaaaaattg tacaaggcag ggaaaggaat   30240
cacctcatgc tcagctgtga atagcaatta cttagtaact tgaatataac atgaattact   30300
aatctaacca gtagtatgat ataactatat tggaaacatg ggggatagga agggcgtgtc   30360
atatggtgag tcagatatgg gagagggaag agggaatatc catatcctcc atctataatt   30420
aatacctaaa actgaacaaa agtagtatac tatttggaga catggaaata aataccaaaa   30480
taatcagcta aaggatgaaa aagtgtttat ctttggggag tgggaaatgg caggatgggg   30540
ccaggggaag agggcagtat tctattttca aaaccttgtc gaactctgac tctttaaacc   30600
atgtggctgt ccaacttaga agaaaacaat ttaaaaaaac ccaaaacttt ccacaaaaag   30660
aaacaccagg cccagatcat tttgcaggca cagattatga acattcgag ctattcccta    30720 ttttatgaaa ctatttcaga gactagaaaa agagggaatg taccatcatt attaggtaat   30780
aagcctaatt accttgacac caaataaaaa tatataccag tcttaagaac ataggtgcag   30840
aaatactagg taaaaaacag caaaccaaac caaacagtaa ggaacaacac acacacacac   30900
acacgcagcc aattctttga aacccaggaa cgcagggaat gtcttcacag caggccttga   30960
gttggcagtt ggctctgctg agcctattat ttttttcctc caaagcttcc agtgctgtta   31020
```

```
aggaaagcca gtccatgcca cagtccttat aatgatcact atcccaaacc ttgcagccac    31080
cacagctacc atgtttcact ccctggcctt ccacctgcac ctcatttcag ttgaccacta    31140
gtgaaagcct tggtaattgt gacaatacca tcccatggtg ctcacaccct agttcccacc    31200
agctgtttca cagatggatt ggtgtaatat gtagtgttgg ccaaaaattg atgtaaatgc    31260
tgatttagga atacaaatct ataaataaaa ataggaagac atacttcata tttatgtcaa    31320
tttttatctg gtgggggggct ggtagaggat ttcaacttta tctgtaatgt tttatttctt    31380
aagctgggtg atggaaacat ggcttctgtc atgttataat ttatacattg ttttctagtg    31440
taacatttca caaatatta acaaaagatg tgtacctgta ttgatgtgct acacactgtg    31500
ctgggtgcag ttggaggatt aggtctagac cttgcccttg ggggtctccc aatctggggt    31560
ggcagaaaag aaagtggggc ttaaaggggg tgagtgggtt gcgtaagagg cccaattaca    31620
tcctgacata gaggtgccat aacactcttt gtgtccatgg aagaatggt tcagagatac    31680 gtgttgagga agacagtaag taagaggtga ggtgagcaaa actttgaaac cagatatcct    31740
aggctcaaac ctaactggtg cctctttgaa ctccagtttc ttcagctgtg agatagaaac    31800
agttcccacc tttcctggtt gttgcgaggt tgaggaggta cagagcagat gctcataaat    31860
agtaattgtt attttaaaca ataggtcagt ttcatgcacg tccgtgtgaa gagactgcta    31920
aacaagcttt gtgtgagcaa taaaagcttt taatcacctg ggtgcaggcg agctgcgtcc    31980
acaaagagag tcagtgaaaa gagatggggt gggtccattt tataagattt gggtgggtaa    32040
aggaaaattg cagtcaaagg gggtttgttc tctggcgggc aggagtggga gtcgcaaggt    32100
gctcagtggg ggagctttt gagccaggaa aaggactttc acaaggtaat gtcatcactt    32160
aaggcaagga ccggccattt tcacttcttt tgtggtggaa tgtcatcagt taaggcgggg    32220
cagggcattt tcacttcttt tgtgattctt tagttacttc aggccatctg gcatatagg    32280 tgcaagtcac aggagatgcg atggcttgcc ttgggctcag aggcctgaca ttcctgcctt    32340
cttatattaa taagaaaaat gaaacaaaat agtgttgaag tgttgggtg gcgaaaattt    32400 ttggggatg gtatggagag agagaatggg cgatgtttct tagggctgct tcaagcggga    32460
ttggggcagc gtgggaacct agagtgggag agagaaagct gaaggagat cttgtggtaa    32520 gtggtgatat cgtgggggttg ttagaagaaa catttgttgt atagaatgat tggtgatggc    32580
ctggatatgg ttttgatga attgagaaac taaacgaaag atacaaggtc tgaataaaag    32640
aaggagaaaa atgggtatta aaggactaag aattgggagg acctaggata tttaattaga    32700
gagtgcctaa gggggttcag cgcaattact tgcttggttt agaagtgatc tccttgagga    32760
tagatttcca tgatggaaag gaaatgagag gttctaagag acgggctagc ggcttgtaac    32820
ctacatggaa gaggttatga atgacgaca gaatagaatg ggcctgtgag gctggaagga    32880
ggtattttcc ttggtctaag aactatttgc cttgtgtggg aagagattga taggtggaaa    32940
tttcagcggg gaagtaggtg ggagtgaccg atgtgaagga gaaaactgg ccctgaggga    33000 cagaagttgg agagctagct gcttgtctag ccaccttatc agcataagcg ttgcttagag    33060
caatgggatc tgacgccttt tgatgcctct tgcagtgaat gaccttagcc tccttttgaa    33120
gtaaaggggc cttgagtaga gtttttatta aagaggcatt aatgatgag gacccttgtg    33180 tagtgaggga gcctctttca gcctatatga ccacatggtg gtgcagaata tgaaaggcat    33240
atttagaatc agtgtagata ttgacgcata gtccttttcc aagagtgagg gcttgagtta    33300
aggcaactag tctggcttgc tgagaggtag tggagggggg cagagtggta gcctcaatga    33360
```

```
tagatgtgga agatactata gcatagcctg cctttgctgg tgagtggcaa ttaggcctgg    33420
tggaactgcc atcaataaac caagtgtgat tagggtgaga acaaggaag aaggaaatgt    33480 ggggaaatgg ggtgaacatc aggtggatca gagagatgca gtcatgaggg tcaggtgtgg    33540
tatctggaat aatgtgggag gccagattga agtccaggcc aggaacaatg gtaactgtgg    33600
gagattcaac gaagagtgag tgtagctgaa ggagccgggg agcagaaagt atatgcgtca    33660
ggtgtgagga agaaaataga ttttggaaat tatgagagct gtagagagtg agttgagcat    33720
agtttgtgat tttgagggcc tctaaaagta ttagggcggc agcagccact gcacggagac    33780
atgatggcca gcctaaaaca gtaaggtcaa gttgtttgga caaaaaggct acaggacgcg    33840
atcctggtcc ttgtgtaaga attctgactg cacagccctg cacttcggct gtgtgtaatg    33900
aaaagagttg ggatgagtca gggagagcta gagtgggggc agtctctaaa gctgtcttca    33960
aggaacagaa agaggagtgg ggaaaggatt taggatctat ggggtcaact aggtttcctt    34020
ttgtgagttt atataatggt tttgttagga tggcaaaacc aggtatctaa aggcgaaaat    34080
atctaaccat gcctaggaag gaaaggagtt gttgttttgt agaaggggtt gggtttgag    34140 agattagtcg ggcacgattg gcagggagag cacgtgtgtt tttatgaaga attatgccga    34200
ggtaggtaat ggatgagaa gacatttgag ttttggaggg agatacctga tatcctttgg    34260
agaataaatg ttgaaggagc agaagtgtgt cttgttgaga agattcaaag gaggggctac    34320
aaagaagaag gtcatcaata tattgaataa ggtgagaagc ggaggggtgg aaagaaagta    34380
aatcacgaga aagagcttgg ctgaagtaat gagggctgtc cctgaaacct gcggcagca    34440 cagcccaggt aagctgctgg gactgatggg tgacagggtc agtccaggtg aaagcaaaga    34500
gaggctggga tgaggagtgc aggggaatag tgaaaaaagc atctttaaga tcgagaacag    34560
aacactgagt tgtggaggaa ggtattgagg acaaagagt gtatgggttg ggcaccacag    34620
gatggatggc aaaacaattt ggttgataag gtgcagatcc tgaactaatc tgtaagactt    34680
gtctggtttt tggacaggta aagtggggga attgtaagga gagttttttag gttttagaag    34740 cccatgctgt agcaggcgag tgataacagg ctttaatcct tttaaagtgt gctgtgggat    34800
gggatattgg cattgagtgg ggtaagggtg attaggtttt aatggatgg taataggcat    34860 gtgatcagtt gccagggaag gagtagagat gtcttatact tgtgggttaa ggtgggggga    34920
tacgagagga agacacaaag gaggcttttgg gttggggaga agagcggcaa tgagatgcgg    34980
ctatagtagt cagggaagca gataatttgg ttaaaatatc tcggcctaat aagggaactg    35040
ggcaggtggg gataactgaa aaagagtgca taaagagtg ttgcccaagt tggcaccaga    35100 gtggggggagt tttcagggggt tttgaagctt ggccgtcagt acctacaaca gttattgggg    35160
ctagggaaac aggcctttga aaagaaggca acatggagtg ggtagcccct gtgtcgatta    35220 aacagggggat ggacttactc tccactgtga gagttacctg aagctcagca tctgtgatgg    35280 tctagggggga ttctgaggtg atcgggcagc atcaatcttc agtcgctaag ctgagcagat    35340
ctgggaagga gtcggtcaga gagccttggg ctagagcttt aggggctcta ggagtggctg    35400
ctgggcgagc tgggcagtct gccttccagt gggtccttac acagatggga catggcttgg    35460
aaggaatcct gggctgcagg cattccttgg cctagtggcc agatttctgg cacttgaagc    35520
aggatcctga tggaggaagt cttgtaggaa tgcttgactg ctgcagctta ggcatttga    35580 agttcttgta tgctggaggt gtggctgagt tttgtctcac agcagaggca agtaattgta    35640
actcagaaat gcgttgccat ctggctgctt cctctctatt attgtacacc ttgaaggtga    35700
ggttgattaa ttcctgtttg tggggtttga gggccagatt ctaatttttg aagttttttc    35760
```

```
ctaatgtcag gagtggattg ggtgataaaa tgcatattga gaataaggcg gccttctggc   35820
ccctctgggt ctagggcggt aaagcgtcta agggttgctg cttaagcggg ccatgaactg   35880
ggctgggttt tcgtctttac cttgggtagt ttctttaagc ttgtcagaat taacagcttt   35940
gtaagctgcc tttttaagcc tttcaactag gcaggaaatc atgtaatctt gcctagctat   36000
acctggggaa tttgtctggt agttccattg gggatcctct tggggaactg ctctaatgcc   36060
ttcctggagg tcaggttcat gaagccggcg gttatcagca tgagattggg ctagagaaaa   36120
aactctttcc tgttcatctg gggagagggt agaagtcagg atgacattta agtcactcca   36180
ggttaaattg taggacagag ttagatatca gaattcctgt atatatttag tggggtctga   36240
tgagaaagag cctaaacgct gactgatttg agagaggtct gatagagaaa aaggtacatg   36300
taccctgact atgcctttag ctccagccac ctctctaaga ggaaattgtt gggcgggtgg   36360
ggaaaagcta gtcgcagaac taaactgtaa gccggaccgg gtgtgaggag gggaggtggt   36420
agaaggatta taggatggaa gagcggaggc tgaggaagaa ttgggactta gctcaacctg   36480
gccatgagca gcctgaggag gaggggaaag gtcagatggg cctgtagaag gaagactgga   36540
aagattcaac gacgctttggg gttgggactg aggggggcagg cggaaggaa agaaggagga   36600 tttgggagga atcgcattgg gaacagagac tagggaggga acaaagtgtg aaaagtgcct   36660
ggacgtaagg cacctcagac catttgccta tttttttgaca aaaattattt aggtcttgta   36720
ggatggagaa attgaaagtg ccattttctg gccatttaga gccattgtca gtttgtatt    36780 ggggccaagc agtgttgcag aagaaaataa ggcatttagg ttttaggtca gatgtgagtt   36840
gaagaggttt taagttcttg agaacacagg ctaagggaga agaaggagga atggagggtg   36900
gaaggttgcc catagtgaag gaggcaagcc cagagaaaag agagagtaga gacacggagg   36960
gaaggggttc gggggttctt accctccaga aaagtgggaa aggggtcggg gcgtggaaat   37020
aaggggttgg ggcacagaga taagaggtca gggcatggaa ataagggatc gggtgcaga   37080 gataagaggt cggggcacag aaataaggga ttggggcaca gggataagag gttgggcat    37140 ggaaataagg gattgggggt tcttgccccc tagaaaagcg ggacttgcca ctaagggtga   37200
aggagaaggg gttgaggggt tcttgcctct ccccctagaaa agcagagaag gggtagagac   37260
tcagagagaa ggggttgggg tacttgcccc tcccctagaa aagcgggact tgccactaag   37320
ggtgaaagac caaggcaggt gtccttgtgt ggtctgacac ctctgaaacg tgggtgaata   37380
atcagagagg catccctgca atgattaaac atcaagggaa ggctgccttc ctagtctgtg   37440
accggcaccg gagttttggg tccacggata aaacatgtct cctttgtctc taccagaaaa   37500
tgaaaggaat tgaaattaag agaagggaga gattgaaggg tggcgccaag attgaaagga   37560
gaaagaggtt gagggatagt gagggaggtt ggagaagaga gtaaaaagag gccgcttacc   37620
agatttgaaa ttggtgagat gtttcttggg ctcatcggtc tgaggacctg aggtcgtagg   37680
tggtttcatg tgcgtccgtg tgaagagacc accaaacagg ctttgtgtga gcaataaagc   37740
tgtttatttc acctgggtac aagtgggctg agtctgaaaa gagagtcagt gaagggagat   37800
ggggtggggc tgttttataa gatttgggtg ggtaaaggaa aattacagtc aaaggggggtt   37860 tgttctctgg caggcaggag tggggtcgc aaagtactca gtgggggagc ttttttgagcc   37920 aggatgagcc aggaaaagga ctttcacaag gtaatgtcat cactcaaggc aaggaccggc   37980
catttacact tcttttgtgg tggaatgtca tcagttaagg tggggcaggg catattcact   38040
tcttttgtga ttcttcagtt acttcaggcc atctgggcat atacatgcaa gtcacagggg   38100
```

```
atgcaatgtc ttggcttggg ctcagaggcc tgacattcct gccttcttat attaataaga   38160
aaaataaaac aaaatagtgg taaagtgttg ggacagcaaa aattttgggg gatggtatgg   38220
agcgataatg ggcgatgttt ctcagggctg ctttgatcag gattaggggc agcgtgggaa   38280
cctagagtgg gagagattaa gctgaaggaa gattctgtgg taaggggtga tattgtgggg   38340
ttgttagaag aaacatttgt tgtgtagaat tattggtgat ggcctggata cagttttgta   38400
tgaattgaaa aactaaatgg aataagagaa ggagaaaaac agatataaaa ggtctaagaa   38460
ctgggaggac ctaggacatc tgattagaga gtgcctaagg agattcagca tagtcctgcc   38520
agcaaagatt atttatttac ttcaagagtt aagaatggca gtttgggggat agcacgagga   38580 gatatcagct gtgatggctt ggagaaacag tgtaaaccgg cagtgtaaac aagagcaggg   38640
catgtatgag tagttgagaa tggagaatag gagtatgact agacagaaaa tagtagggat   38700
gacaagtgtt tttggggcac agtctaagtt ggtccagtgt ctggaatgag actgggacct   38760
aataaaaagg agctcaaatg ggctgtacct tgtagcattc cgaggacagg tctgatttct   38820
gagaagggaa agtggtgaaa gtattgtcca gtccttttta agttggtggc tgagcttggt   38880
gaggtttgtt tttaaaagac ctttagtctg ttctactttt cttgaagaca gaggaccgta   38940
agggatataa aggtttcctg aaaaactgct tggctgattt gacaaataaa ggctggtctg   39000
ttatcagatt gtatagaggt gggaaggcta aactgaggaa ttatgtctga cagaagggaa   39060
gaaattactg ggatggcctt ctcagaccct gtaggaaagg cctctactta tctagtgaaa   39120
gtgtctactt agactaagag gtattttagt tatctgactc agggcatgtt gagtaaagct   39180
aatttgccag tcctgggtgg gggcaaatct tcaagcttga tgtgtaggga agggaggggg   39240
cctgaataat ccctgaggag tagtagaata gcagatggaa cactgagaag ttatttcctc   39300
gaggatagat ttccacaatg gaaaggaaat gagaggttct aagaggcggg ctagtggctt   39360
gtactatagc atagcctgcc tttgctggtg tgtggcgatt aggcctggtg gaactgccat   39420
caataaatca agcatgatca gggtgaggga caggaaagaa ggaaatatgg ggaaatgggg   39480
tgaatgtcag gtggatcaga gagatacagt catgggggtc aggtgtgtta tcaggaataa   39540
tgtgagaggc cagattgagg tccgggccag gaacaatggt aactgtggga cttaacaaag   39600
agtgagtaca gctgaaggag ccggggagca gaaagtatat gcgtcaggta tgaggaagaa   39660
aatagatttt ggaagttatg agaaatgtag agagtgagtt gagcataatt tgtgattttt   39720
agggcttcta aaagtattaa agcagcagca gccgctgcac gcagacatga gggctaggct   39780
aaaacagtaa ggtcaagttg tttggacaga aaggctacag ggtgcggtcc tggctcttgt   39840
gtaagaaatc cgactgcact aaccatgcct aggaaggaaa ggagttgttg ttttgtaaca   39900
gattgaggtt tgggagatta attgggcaca atcagcaggg agagcacgtg tgtttttatg   39960
agaattatgc cgagataggt aacagatgag gacgaaattt gggcttgact gaagtaatgg   40020
ggtctatctg tgaagtcttg cggcagtaca gcccaggtaa tttgctgagc ctaatgggtg   40080
tcagggtcag tctaagtgaa agcaaagaga ggctgggatg aagggtgcaa aggaatagta   40140
aagaaagcat gtttgagatc cagaacagaa taatgggtag tagagggagg tattgaggac   40200
aggagagtat atgggtttga caccatgggg tggataggca aaacaatttg gttgataagg   40260
catagatcct gaactaactt gtaaggcttg tctggtttta ggacaggtaa aatggaggaa   40320
ttgtaaggag agtttatagg ctttaaaagg ccatgctgta gcaggcgagt gataacaggc   40380
tttaatcctt tcaaaacatg ctgtgggatg ggatattggc attgagcggg gtaagggtga   40440
ttaggtttta atgagatggt aaggggtgca tgatcggtcg ccaaggaggg agtagaggta   40500
```

```
tcttatactt gtgggttaag gtgggggaat acaagaggag ggcccaaagg aggctttgga   40560
ttgggaagaa gggcagcaat gagatgtagc tgtaatccag gaatagtcag ggaagcagat   40620
aatttagtta aagtgtctcg gcctaataag ggaactgggc aggtggggat aactaaaagg   40680
agtgcttaaa agagtattgt ctaagttagc accagagttg gggagtttta agaggtttag   40740
aagcctggct gtcaataccc acaacagtta tggaggcaag ggaaacaggc ccttgaaaat   40800
aaggtaatgt ggagtgggta gcctccgtat tgattaagaa ggggacagac ttaccttcca   40860
ctgtgagagt tacccaaagc tcggtgtccg tgatggtcta gggggctttg gaggcgatcg   40920
ggcagcatca gtcttcaggc actaagccaa aagacctgg gaaggagtca gtcagagagc    40980
cttgggccag agttccaggg gctctgggag tggctgccag gtgagttgga cagtccgatt   41040
tccagtgggg tcccacacag atgggacgtg gcttaggaga aatcccgggt tgcaggcatt   41100
ccttggcctg gtggtcagat ttctggcact cgtagcaagc tcctggggga ggaggttctg   41160
gaggaatgcc tggctgctgc ggttcaggcg tttggaagtt ctcgtgtgct ggagatgtgg   41220
ctggggtttg tctcacagtg gaggcaagga attgcaactt ttttctatta ttgtacacct   41280
tgaaggtgag gctaattaag tcctgttgtg gggtttgagg gctggaattt aattttttgga  41340 gttgtattta atgtcaggag cggattgggt aataaaatgt atattgagaa taagatagcc   41400
ctttgacctt ttagggtcta gggctgtaaa gcgtctcagg gttgctgctg aaggagccat   41460
gaactgggct gggttttat atttgatgaa aaagcctaaa tgctgtctga tttgggataa   41520
agaaaaagga gcattaacct tgactatgcc tttagctcca gccacctttt taagagtaaa   41580
ttgctgggca ggtgggggag ggctagtcac ggaacgaaac tgtaagccgg accaggtgtg   41640
aggaggggag gtgataaaag gattataggg tggaggagca gaggctgaag aagaattggg   41700
acctagcttg gcctggtgag gagggggagag gtcagatggg tctgtagaaa aggaagatta   41760
gaaagactca atgatgcttg gggttgggac tgaggggaca ggcggagggg aaagaaggaa   41820
gatttgggac gagttgcatt gggcacagag actaggaagg gactgatgtg taaaagaatg   41880
cctggacatc aggcacctca gaccgttttgc ctattttatg acaattattt agatcttgta   41940
ggatggaaaa attgaaagtg ccgttttcca gctatttgga actactgtcg agtttgtatt   42000
ggggccaagc ggtgttgcag aagaaaacaa ggcatttagg ttttaggtca ggtgtgagtt   42060 gaaagagcttt taagttcttg agaacacagg ctaaggagg agaaggagga atggagggtg   42120
gaaggttgcc catagtgaag gaggcaaaca cagagagaag agagcgtaga gacacggagg   42180 gaagggggttc gggtgttctt ttttttttttt tttttttttaa tttatttttt attgataatt   42240
cttgggtgtt tctcacagag ggggatttgg cagggtcatg ggacaatagt ggagggaagg   42300
tcagcagata aacaagtgaa caaaggtctc tggttttcct aggcagagga ccctgcggcc   42360
ttccgcagtg tttgtgtccc tgattacttg agattaggga ttggtgatga ctcttaacga   42420
gcatgctgcc ttcaagcgtc tgtttaacaa agcacatctt gcaccgccct taatccattt   42480
aaccctgagt ggacacagca catgtttcag agagcacagg gttgggggca aggtcacaga   42540
tcaacaggat cccaaggcag aggaattttt cttagtgcag aacaaaatga aagtctccc    42600 atgtctactt ctttctacac agacacggca accatccgat ttctcaatct tttccccacc   42660
tttcccgcct ttctattcca caaagcagcc attgtcatcc tggcccgttc tcaatgagct   42720
gttgggcaca cctcccagac gggtggtgg ccgggcagag gggctcctca cttcccagta    42780
ggggcggccg ggcagaggcg cccctcacct cccggacggg gcggctggcc gggcgggggg   42840
```

```
ctgaccccc  aacctccctc  ccggacgggg  cggctggccg  ggcagagggg  ctcctcactt   42900
cccagtaggg  gcggccgggc  agaggcgccc  ctcacctccc  ggatggggcg  gctggccggg   42960 caggggctg   agccctcac   ctcccggacg  gggcggctgg  ccgggcggag  ggctgacccc   43020
cccacctccc  tcccggacgg  ggcggctggc  cgggtggggg  ggctgacccc  ccatctccc   43080 tcccggacgg  ggtggctggc  cgggctgagg  ggctcctcac  ttcccagtag  gggcggccgg   43140
gcagaggcgc  ccctcacctc  ccggacgggg  cggctggccg  ggcggggggc  tgaccccccc   43200
acctccctcc  cggacggcac  ggctggccag  gcggggggct  gaccccccca  cctccctccc   43260
ggatggggcg  gctggccggg  cggggggctg  acccccccc   acctccctcc  ggacggggt    43320 ggctgccggg  cggagatgct  cctcacttcc  cagatggggt  ggctgccggg  cggagaggct   43380
cctcacttct  cagacgggc   agctgccggg  cggaggggct  cctcacttct  cagacggggt   43440
ggttgccagg  cagagggtct  cctcacttct  cagacggggc  ggccgggcag  agaccctcct   43500
cacctcccag  acggggtctc  ggccaggcag  aggcgctcct  cacatcccag  atggggcggc   43560
ggggcagagg  cgctccccac  atctcagacg  atggcggcc   gggcagagac  gctcctcact   43620
tcctagatgt  gatggcggct  gggaagaggc  tctcctcact  tcctagatgg  gatggcggcc   43680
gggcggagac  gctcctcact  ttccagactg  ggcagccagg  cagaggggct  cctcacatcc   43740
cagacgatgg  gcggccaggc  agagacactc  ctcacttccc  agacggggtg  gcggccgggc   43800
agaggctgca  atctcggcac  tttgggaggc  caaggcaggc  ggctgctcct  tgccctcggg   43860
ccccgcgggg  cccgtcccgg  ttcgggtgtt  cttaaccctc  cagaaaagtg  ggaaaggggt   43920
cagggcacgg  aaataaggga  ttggggcaca  gagataagag  gttggggtgt  ggaaataagg   43980 gattggggt   tcttgccccc  tagaaaagcg  ggacttgccg  ctaagggtga  aggagaaggg   44040 gttgagggt   acttgcccct  cccccagaaa  agcagagaag  gggtagagac  tcagaagggg   44100
ttggggtact  tgcccctccc  ccagaaaagc  agagaagggg  tagagacatg  gagagaaggg   44160 gttgggtac   ttgcccctcc  cccagaaaag  cgggacttgc  cgctaagggt  gaaggaccaa   44220
ggcaggcctc  cctgcgtggt  ctgacacctt  tgaaacgtgg  gtgaatgatc  agagaggtgt   44280
ccctgcaatg  attaaacact  acgggaaggc  tgccttccca  gtccgtgacc  ggcgccgag    44340 ttttgggtcc  acaaataaaa  cgtgtctcct  ttgtctctac  cagaaaatga  aggaattga    44400 aattaagaga  agggagagat  tgaagggtgg  caccaagatt  gaaaggagaa  agaggttgag   44460
ggatagtgag  ggaggttgga  gaagagagta  aaaagaggcc  gcttaccgga  tttgaaattg   44520
gtgagatgtt  tcttgggctc  atcggtctga  ggacctgagg  tcgtaggtgg  tttcatgtgc   44580
gtccgtgtga  agagaccacc  aaacaggctt  tgtgtgagca  ataaagctgt  ttatttcacc   44640
tgggtacaag  tgggctgagt  ctgaaaagag  agtcagcgaa  gggagatggg  gtggggctgt   44700
tttataagat  ttgggtgggt  aaaggaaaat  tacagtcaaa  gggggtttgt  tctctggcag   44760
gcaggagtgg  ggggttgcaaa gtactcagtg  ggggagcttt  ttgagccagg  attggccagg   44820
aaaaggactt  tcataaggtc  acatcatcac  ttaaggcaag  gatgggccat  tttcacttct   44880
tttgtggtgg  aatgtcatca  gttaaggcaa  ggaccagcca  tttacacttc  ttttgtggtg   44940
gaatgtcatc  agttaaggca  aggaccagcc  atttacactt  cttttgtggt  ggaatgtcat   45000
cagttaaggt  ggggcagggc  atttttcactt cttttgtgat  tcttcagtta  cttcaggcca   45060
tctgggcata  tacctgcaag  tcacagggga  tgcaatggct  tagcttaggc  tcagagttct   45120
gacagatcta  ttcctgcctt  catttttacc  ttgtatttta  tttatttgtt  tttaaatttt   45180
taaactaatt  tttttgtttt  ttttttttggt agagagagtc  tcttcatgtt  gtccaggcag   45240
```

```
gtctcaaact tctgacctca agtgatccgc ctgccccagc ctcccaaagt gccgggatta   45300
caggcgtgag ccaccacacc tggcctgtat tttatttttt actatggaaa cttcccaaaa   45360
caaacaaaag tacataggat ggcataatga atccccatgt accccctcagc cagcttcgac   45420 agttaccaac atgtggccaa gcctatttca tttctacctc taccccttc tcatattaga    45480 gtaaatcctg gacatcgtat catttcgtct ataagtgttg ctgtctaaaa gagatcatct   45540 taccttcaa cagatggtaa ttgcgctgca gaacaccacc acgaccagcc gctacctgcg    45600
agtcctcccg ccttccacgc catacttcgc tctgggactg gtaagttca gtatttgtaa    45660 gttcattagt agtagtggta atagtagtgg tggtattagt agtaatagta gtagtggtgg   45720
tagtaatggt agcaatgata gtagtagtgg tggtggtagt agtagtagtg atggtggtag   45780
tagtggtagt agtagtagtg gtggtggtag tagtagtggt agtagtagta gtggtggtgg   45840
tggtggtggt agtagtaata gtagtggtgg tggtggtagt agtggtggta gtagtagtgg   45900
tagtagtagt agtggtagta gtagtagtgg tggtggtagt agtagtggta gtagtagtgg   45960
tagtagtagt agtgggggggg tggtagtagt agtagtagca gtagcagtag cagtactgct  46020
actactttga ggattgcctc aaagtcactt gctgggcttg ctgccagttg ctgactcccg   46080
ccctgagtct acagcctggg cctggactcc ccccatcagc agtccttgag ggctcctcat   46140
gctccaccag caatgtgtcc tcagagcctt gacagtcct ttctcctgac cgcctccacc    46200
caggcactgg tcctgctatc tccccactcc tcgtgctgcc attctcctca atcaggccct   46260
ctctattcct cacttaagcc tcagcagcag ccccccagcc agccttccta ctttagtgtc   46320
acagtatttg tcttaagaac aactctgatc atgtcacccc gttcagaaat ctcaaaagtt   46380
tctctgctat ccaccaaaga aattctaagc catagggcca ggcatggccc cacctgacct   46440
ttctggatgg atggtgtcat ttccccccag gctctggcat gcttacctgg agtcgccacc   46500
cttgcagcct gctcccctcg catgcccttt tcctgccatc agcgtggctt tggcccagaa   46560
ggcacttaca gagccagccc tggcagggct ggggtctgta ccagctgagc tcaagccctg   46620
gtggctggct gctcccagga tcctcacttg tcacttttgt catgcacagg gatgttccca   46680
ggaaaaggtg gaatggtggc tcctggaatg acctgccagt acattgtcca gttttttccc   46740
gactgccttg gggattttga tgattttatt ttagtggaga cccagtcagc ccacacactt   46800
ctgatccccc tgcaggcccg gaggccgccc ccgtgctga catgtgagtg tgcaccgtag    46860
cttcccacag attcagttaa ggttggagag tccccataag gactgcctgc ctctcaggtt   46920
ccctttgtat cagcacacag cttggctctc ttgggcaggg gccgtgggtc ctgcagagga   46980
aactgctagc agcttctgta gccatccaca gtgtcaagcc atgattgttc tgcttgcttt   47040
tgggttttct cagtggaggt tgactcacag caggggatga ggccaacagt ccagctaacc   47100
ccaccatagg ttttgctggc ttatgaacat ccctgagggg acctgtgcca cagtgggcaa   47160
ggaagaagtg cctgtgcacc ctgaggagtc ctaacaggtc gtcgttgtcc tcgtggctgt   47220 ggggggtagga gtccttagca aagctggctt cagctgggct ccctcagcga caagcttcta  47280
cagctgggca taggctggaa tttgggaccg tgatccccct tacttctgcc atagccccca   47340
aggaccatgc tgggtggccc tggctgagca tgaatccaca atgggcactg acttctgctg   47400
ctctagccag gagtgaatag agtcccatgg cactattgcc atgtggccag cagcagcctg   47460
ggcagagccc aagtgggtgt agggtcagga catgtcccca ctcatcctct ctgcataggg   47520
tgctgggctg ggaccagctg tcctgatctc tggctgtacc tcaggagaag catgacagta   47580
```

```
gggcctatta agagtgacct gttgtttctc ttgcacatgt tctcctgtgg ctacagtgtc   47640
accggtgttg gactgtggtt actgcctcat tgggggagtc aagatgacca gattcatctg   47700
caaaaatgtg ggtttcagtg ttggcaggtt ctgcattatg cccaaaacaa gctggccacc   47760
actaagtttc aaggtgagtg atcacaggtt gctaactgga aaattacaa gtccatcaaa    47820 ggaaataacc cccagaggaa cttactagag tatacctatg attggaaaca cacagaacgc   47880
agagtgttgt aaactctcta tgcaactgcc acaacccgaa tgagaatgga tgtataaggg   47940
tccagtgttg tagttctggt tatgtcacta ataccctgtac catgctgggc aagcggtatc   48000
acctctctta tccttcaagc cctggctcaa atgtgactgc attcactcat tcagtccttc   48060
tttattgtag caaatgactg aatagttcag aggttacaaa ttggctgccc tttggccaaa   48120
ttctgctggt atttgtttgg cacagcactt aacattttct gagccaacat ttaaaaataa   48180
ggagatttgg ccaggcgcag tggctcacac atgtaatccc agcactttgg gaggctgagg   48240
caggcagatt acctgaggtc aggggtttga gaccagcctg gccaatatga tgaaacaccg   48300
tctctactaa aaataaaaaa ttagccgggt gtggtggcat gtgcctgtag tcccagctac   48360
tcaggaggct gaggaaggag aatcacttga acccgggagg tggaggttgc agtgagccga   48420
gatcgcacca ctacactcca gcctgggcga cagagtgaga ctccatctca aaaaaaaaa    48480 aaaaatggag attttatata aagttctaca tttccagtcc tttgaaaaac tggaagatat   48540
gaaggccagg gccaggattc actgtgagcc tgttggccag ggctgggggc aggccctgtg   48600
taccttgtcc tgagtgccca gctccaccag tcccaagagc atcccagcac tgacaccatc   48660
catcagcatg ctcacaccat ccatcagcac tgacaccatc catcagcact gacaccatcc   48720
atcagcatgc tcacaccatc catcagcact gacaccatcc atcagcactg acaccatcca   48780
tcagcatgct cacaccatcc atcagcactg acaccatcca ttagcactga caccatccat   48840
cagcatgctc acaccatcca tcagcactga caccatccat cagcatgctc acaccatcca   48900
tcagcactga caccatccat cagcactgac accatccatc agcatgctca ccatccat    48960 cagcactgac accatccatc agcatgctca ccatccat cagcactgac accatccatt     49020
agcatgctca ccattatt tttctcatag caaagatatt tatttgtacc cagaaaacaa     49080
gggatacatc tagaggatga catttcaaga tgttccaaga aagacatttc actcatttct   49140
gttactgacc agggtcttgt aggcatgggt ttgtgtccct ggcatgctaa gtgacttctt   49200
gtgtaggcac tggggctgca gctctcgtgc ctcaggagct tgtagccagg ggtgggtcag   49260
ggttggaggc agacacatat gctagcacct gtgacactgg gtgttactgt aggaaaagga   49320
caatgtgctt tgggagccca ggggagggcc cactcagctc acctcctgag tgagaccttc   49380
tcacacgctt gtcactttgt gtcccaatca cttggtgatg gtgttccttg tacctcctgt   49440
cagtagtcag ctcttcacag atgttctaag acttactctc cttaaccttc agaacctcac   49500
ctggtacctg gtgatggctg agtaaatgcc tgctgaatga ataagcctca gttttttcat   49560
taccatgtga ctggatgatc cttaagttcc ttcacattgc aaaatggatg tttgaaggag   49620
agaagtttgc aatctgaata ctggctttta caatgtcttc cacactgttg ggtaatctgc   49680
ttttctttaa ggccattgca accgtcggct ttgttgaaca acctccttttt ggaatcctgc   49740 cttcggtgtt tgagctggcc ccgggacatg ctatattagt ggaggtaggt aatcagacat   49800
tggcatgtat ttcctcaact gcttgcatgc ttgcatttgt ctctgtttc atgactcaag    49860 tgtccagtcc catcccatat cacagcctta gtgacttctg ggtagacgca tattcttgca   49920
ttctgtaggg tgatgtcaga tgtcatttga ctgtcttatg agcattttca caaagcaaat   49980
```

```
gcagatagcc ctagcatcac atcacaaacc tgagccttgc tagtccacac ctttagtctg   50040
ggagctacct ccaccaatgt ccaagctgcc tccaagatct tcgcttggtt cttcagtctc   50100
tcttgggtct tccctccccc aggcccctct atcatctggt acctgattat tgcggttatt   50160
gtggctttgt tctcactttc ctgcttcatc ctcagtttgt atagtcagca aggcccaact   50220
ccgttacgcc tcatcctgaa cctctgcaga agctctcagt ggtctgcccc tggctgtggg   50280
cgtctccttt cctaactggc cccttttgct gcccccttca gctgatcaca cctgcttgct   50340
ggtccccaga ggtgcccatg agaaatggtg atacttcctg tccctgttgc agcacactgc   50400
cactctcccc gactcctggt ctaggagtct gactccactt catgtgactg ggtgtgggct   50460
gctacagaca tgcttggcct ttcacactag cctgccgagg gaggcccctg acattcagga   50520
gcaaaaaccg tctggcttct gggggtggat ttggcctgtg ccatatcacc aggtagtgag   50580
atccagcagc ccttattctt aaactcagct gcacattgca atcacctgag agacctggaa   50640
acaacaccaa ggccctatcc ctgaggttct gagttcacta gactgggctg tggcctgggt   50700
gccggacttc taaagtcccc cagggaatgc tggtgtgcag ccaagttgga gttcaactgc   50760
cacagcgact ctgccatgct gtcaggaagg gcttcctctt atcagctgct ttctagtttc   50820
aagtgcccag taggttctgc agccctagga tgtggctctc ttattcatgt ccctgctcat   50880
ctgatccctg atgagaaact agttcttggg attgagactg agccagttca ggggctttgt   50940
caggcctcat ctactgctga ggggcaggtt gggtctacaa ggcccataca caggccaggt   51000
tctctgttct cttggtgtag tccaggactt gtcacaggct catcgaagct ttaaggaatt   51060
ggagctgctc tgccctggac atcccctca tcccatcctc ctgggatctc caagtaaagg   51120
aagagggtag cagcaggact cttaggggag cagtgaggga gctggggaag gctttcccct   51180
tggcatttct tgcgtatttt gtttactgat tgtttggggg tttgtctgtt ccaaaatgta   51240
ttcatagttc caaataagaa atacatttgc atgattaaaa attcaaaaga gagactgggt   51300
gcagtggctc aggtctgtac tcctagcact ttgggaggct aaagcaagag aactgctgag   51360
tctgggagtt aaagaccagc ctgggcaaca tagtgatata ctgtctgtat agacaatttt   51420
taaagtaaaa aataaattca aaagagccag gtgtagtggc tcacacctat aatctcaaca   51480
ctttgggagg tcaagatagg aggatcactt gaggccagga gtttgagttt acagtgaact   51540
gtgattgagc cactgtactc cagcctgggc aacagagtga aaccctgtcc taaaaataaa   51600
taaataaaaa taaaacattc aaaagatgta aacaggtaaa cagtgaaatg ctcccttcca   51660
ccccagttcc tcagccatcc agaggccata cctggccagt tttctgaatg cccttccaga   51720
gatagtctat gcccaaataa gcaactgcac atgttttac ccccattttt ttcttcacac   51780
acaaagttgc ccactctata ctctgttctt gccttgtgt tttctactta actctatatc   51840
ttagagatca ttctcatatg ttttagtaac tgcatagtat cctactgtgt gaatggacca   51900
taatttagtt cagcagtctc ctgctgattg acctgaagat tttttctga tctctggcta   51960 caaattatgt ataaattata catacatcac tctgtccaag gatgagtcta cccacaggat   52020
acagtccttg aagtagattt gctgatccag cgctttgtgc cctcataatt gtaaggcatg   52080
ttgccaaaat ccttaccatg cggattgtac caattttatc tttcaacagc agtatgtaag   52140
ggtgtctgtt tctttacacc tttgccaata cagtatatta taaaacttag aaactgttca   52200
tggacgttgt atataaaaac atatacaaaa atagagagaa taatgatcat ccatgtattc   52260
attactcatc ttcaacaatt atcaaccctt ggccaatctt attacatcta taccccctcca  52320
```

```
tttccctcag acattcccca ccctgctctt ctagattatt ttgaacaaaa tcaagacaaa    52380
atatcattgc atttaacaga atgaaactag acctgtgtct ctcaccatat acaaaaatta    52440
acttattaat aaaatggatt aaagatttaa atataagact tgaaaatgta aaactactag    52500
aagaaaatgg tggaaatctg tatgacattg gtctgggcaa tgattttttg catatgatct    52560
caaaagcact ggcaacaaaa gtgaaaatag gggccaggtg cggtggctca gcactttggg    52620
aggctgaggt gggaggattt cttgagccca ggagtttgag accagcctgg gcaacataag    52680
gagaccccat ctctataaaa aatttaaaaa actagccggg tgtggtggca tgcacctgtg    52740
gtctcagcta cttgggagct gaagtgggag gatcgcttga gctcaggtgt tagaggctgc    52800
agtgagaaat gatcacacca ctgcactcca gcctgggtga cagagcaaga tcctgtctca    52860
aaaagcaaaa caaacaaatg aacaaacaaa aaacaaaca tgaatagaca aatgggatta    52920
cctcaaacga aaaagcttct acacagcaaa ggaaacaagc aacagagtga agagacaatc    52980
tgtgaaatgg gagaaaatac tatcacatct gaggaggggt taactccaaa aatatataag    53040
gaacttaatg caatagcaag aaaacaacct gcttttttta atgggccaaa gaccaattag    53100
acattcctca aaagaagaca tataaatggt caatgagtat atgaaaacat tctcaacatc    53160
attaatcatc agggaaatgc aaattaaaac cacagtgagc tcccacctga cacccgttag    53220
aatggctatt atcagaaaga tgaaaggtaa gtgttggcga ggatgtagag aaaagggaat    53280
ccttgcccgc tgttgatggg aatgtaaatt actacagccg ttatgaaaaa taatatggag    53340
ttccttcaaa aaattaaaaa tggaactacc atatgattca gcagtcctac tactaggtat    53400
atatacaaat gaaatctggc tggagtgcag tgatgtgatc attgctcact gcatcctcta    53460
actcctgggc tcaaaagata ccatttaaaa gatatccgca ctcttatgtt cattgtgtca    53520
ttcacaatag gcaagctatg gaatcaccct aagtgtctat tgatagagga taagaaaat    53580 gaggtatatg tacacaatgg aataacagcc ctgcaaaaga aggaaatcct gtcgtttgcg    53640
acaacatgga taagtctgga ggacattatg tgaagccaag cacagaaaga caaatactgc    53700
atgattgcac ctatatgttg gaccttaaat aattgaactc ataaaagcag agaatagaat    53760
ggtgattacc agggttgggg gttgggggaa ttggggaaaa aatagaaaac aaatcattgc    53820 attttatgaca gctcaccttc tgctctttgc cagtatgagt ggtaaaaagc cgttcttctg    53880
gatggttttc attgacattt ctcttattat gaatgagggt atgtgttgtc attcatttaa    53940
gggccatttg tattttggtc tctgtgaact ttatcttcat atcctttag cttgctccct    54000 gcttttctct ggggtggagc tagggtaaaa cacttggcct taggagtaag gtgggaggtg    54060
gcagggaggg gaacagagag tgaagagcaa agaaagggt gtgtgtccga gaggaggagg    54120
gtgggaggcg gggagggtgg aagcccttta atgggaggta acggaacaac ccttctctcc    54180
cccaggtctt gttttcccca aagagcctag gaaaggcaga gcagaccttc atcatcatgt    54240
gcgacaactg ccagataaag gagctggtga ccataggtgg gcttgagtgt actcccaggg    54300
gcaaggctgg agaggctgcc ccagctccag gggccactga ccacagtagc attagcggca    54360
gcccacctgt ttcctgtgtg tgtcaggagc gcacattaag aatgctgcag cctccaggtg    54420
ccagagtctc gtttcaggcc cattgctctg gtctgacttt ggagaccaag ccagtgtggc    54480
ctccaagaca gtccaaggag ccttctagca agagacagct ggaaacctgg ggtgaaatct    54540
ttcattgttt cattttgaaa ctcactttga tctccttttgg ggaattgcca gtggctcaca    54600
cataaacagc cagagccacc tctagatttc tgcagggtta aagaggcat cctaggaatc    54660 gtgacaagat gccctggcc gccctccct ctcttcctcc ctccctcctt ccttccctct    54720
```

| | | | | |
|---|---|---|---|---|
| tttcctcctt | ccctccctcc | ttttctccct | tcttctctcc | cttcctcatt aattgagtgt | 54780 |
| ctgctatatg | ctaggttctc | aaaatcacct | ccttttggtc | ttcaaagatg tgagaacatt | 54840 |
| aacctgtggg | cggatatccc | ccttttccct | ccagtgtgag | cttgcaggaa tcatggtcaa | 54900 |
| ggccagctgc | atgtgatgg | cggcatgggt | cctgcagcag | ccttggcctg atttcagccc | 54960 |
| tagtgagcct | tcactgactt | cacttactct | actttggcag | gaattgggca gctgattgct | 55020 |
| ttggatctga | tctatatttc | tggtgaaaaa | agccagccag | accctggaga gctcacagac | 55080 |
| ttaacagccc | agcacttcat | acgatttgag | cctgaaaacc | ttcggtccac ggctaggaag | 55140 |
| cagctgatta | ttagaaatgc | tacgtgggta | acccctgtgt | gtgccccaat acccaaccct | 55200 |
| tcttcttgct | tacctggccc | tcagtcccag | tgagacagga | ggtccttcca agggcctggg | 55260 |
| gaagactggg | cacagaatgg | atatccaaat | tcaattgagg | gatccagatt gacccagtct | 55320 |
| atcatggaaa | ccagtagcca | ctcttggcta | cttaaattta | aatcaattaa cattaaatta | 55380 |
| agagctcact | tcctcagtgg | caccagccac | atgtagctag | tggctgtcat attggacagt | 55440 |
| gcagatctgt | aagatctcca | tcccttcagg | aagttatgtt | agatagtgct gccccaaatc | 55500 |
| atcctggacc | atccctagcc | agccccagct | ttccagagag | gacataccat gcctgtgtag | 55560 |
| gggaagccat | ccaagtccca | ggggcagaca | gactatagtc | tgtgggtttc attctccttg | 55620 |
| ccatttattt | cctgacccgc | ctctgagcac | taccatgaaa | ccaggacaaa tctcagggag | 55680 |
| cctcccaacc | agggctgccc | tggggacccc | agacattaca | caggactctg tcatctctcc | 55740 |
| cccgggatag | ctgcaagtcc | tgcccctcct | atgctatgga | gttgccactg ttcctgttgg | 55800 |
| cagccagtag | gcacatatct | ttctggacac | agctctcctg | ggagcccata acaggaaagg | 55860 |
| cagagggcag | gaatggggtt | gatgtggcaa | accttggaaa | ctcatgtggt gagagacact | 55920 |
| gcagaagatc | ttcccaatat | tagggggtga | tgtatagcct | cttccacttt aatgattgga | 55980 |
| acatgagttc | ctgacttacc | atgtcccctg | agtcatggta | ggtccaacct ccagctgcca | 56040 |
| tggctgggaa | gcgaggagct | ctcttacata | gtctctgtct | tagactccct cgcccacttg | 56100 |
| ctgcccctcc | tccattggag | ggtcctccat | tggaagggtg | tgaaggctga cctggttct | 56160 |
| tcctgttcct | aggtcctttc | ctgctccctc | ttggagcagg | gcaggaggc atggggtgga | 56220 |
| gggacctggt | cccagcagaa | ctgggacatg | gccttggatg | cgttgccccc acaggcacgt | 56280 |
| ggagctggcc | ttctactggc | agatcatgaa | gcccaacctg | cagcccctca tgcctggaga | 56340 |
| aaccttcagc | atggacagca | tcaagtgcta | ccccgacaag | gagactgcct tctccatcat | 56400 |
| gcccagaaag | ggggttctaa | gcccccacac | agaccacgag | ttcatcctga gcttttctcc | 56460 |
| tcatgaggtt | cagatggtgt | catctcagta | gccacacatg | gttggatcat gtatttagac | 56520 |
| cccccaacctg | tgttcctcaa | tcacactgaa | gccacagctg | ggcccaccga ggtgctatcc | 56580 |
| tgcccaggcc | agcacttggc | tgagttgggt | tggagtacac | acctggtgtg cagggtgaag | 56640 |
| cagctcattt | tgtctggtcc | tgatcccaga | ctcaccccat | ctgcagcaag cccttggct | 56700 |
| ggcttcctcc | gctctgggtg | tctcccacat | gtctactatg | gcaaaaaaca ttaccatccc | 56760 |
| cacccatacc | acagcatccc | ctagagagag | tgaggtgcag | ggacccgagg gccaggttag | 56820 |
| cacagcgctg | gccccagcat | ggaggaagc | cctgtgggcc | acgtaggct agaagggaat | 56880 |
| tcgagctggg | catgaaaagg | atgctccggg | gccattgtta | gtgggtttgg ggctgagatg | 56940 |
| agtgatcctg | cctctggtcc | cagcatccag | ctgcctcgtt | gtctatcctg ggagggtgtg | 57000 |
| gtgcttcgga | cacgttgagg | ggctttgtca | gcatcaggaa | ggcctttgct tcttgcaccc | 57060 |

```
aggcccagct gagacaggcc cctgagtcct ggctcatgtt ctggcagcaa cttcactttt    57120
cctaaggagg ggaggaggca gcagggaagc aaccctgggt tttcagaagg tccttctgat    57180
ggctaggcta aggggaggaa gaattcctgc catgccccag ccttctccag gacaacctgc    57240
tggaacgcag tggtgttttc agggcactgt gtttgccttg cagctgaggg attttcacag    57300
tgtgctccag atggtgctag aggaagtccc agagcctgta aggtgagaga aactgggccc    57360
tggatgagaa gtgggcagct gggccttccc ccaccttggg ggttctcctg gggaaggtat    57420
caggtgaggg ggagtgggca gcctggtccc cgcaggcttt ggggagtgag agcatttttt    57480
ttgccttgcc ctggcaaccc agccctgcaa tgggctgagc acactaagct cgctaaactc    57540
actatgaggc caccccagga actttggagc tgtgccccag gcccattgtt gctcttgggg    57600
agccaaactg gggggccctc ggtggtggtg agtgtggagg aaaagctttg cccccatggt    57660
gtaaaccttc aggctggggc tccaggcagc ccagtgcaga gatcccaggc tggagggctg    57720
cagatggtcc ctggaggcag cagggcaatg ccccgtccca gtccttatgc taaaccactg    57780
tcacagccat cggtgcttat cacctttcag gcactggcta atgcctttga tttaggggc    57840 tcaggagctg tgggttaggc agtgtttttt ttttcacaag gccaaacgtg ggacagaggc    57900
agggacactc taggatgtgc ttccaggtgt gccggctcct agctaacggt gggtttgtgt    57960
ttagttcaga agcggagagc ctggggcact cctcctactc tgtggatgat gtgattgtcc    58020
tggaaatcga ggtgaaaggc tcagtagaac cttttccaggt tctcttagag ccatatgccc    58080
tcatcatccc aggggagaac tacattggga taaatgtgaa gaaggctttt aaggtaggtc    58140
attgtctctc ccctgcctag gctggccgag gcagtgttga catgagtgca agtgtaggga    58200
ggatatagca ggaggggcag atggtagcag ccactgcatg gaggctgagg ccattcccag    58260
ggctttgaac ccaacttgac ttgcacagat gcataggcca ggcatggctg tcttctttta    58320
tcagcctccc agaatcctct gaaagttagg gctatggaac ctattcccgt ccttggcaga    58380
gtatgtcagc cacaggcact gcagtgtgga gggagggtgc ttttggggttg ggaggcccat    58440 ggctttgggt ggccaggaat tagccgggaa gtgtcatatg gactctttac gagcccacaa    58500
tcctacagtc cttcagcagg tacagaattg acatgaaggg gcagtaaatg ggcagcctgg    58560
tctcgggtgt cttttcagatg tggaacaaca gcaagtcacc catcagatac ctgtggggga    58620
agatcagcga ctgccacatc attgaagtgg agcccggcac aggggtcata ggtaccttgg    58680
ggactgcagg agggggttgtg acctgcctgg ggctggctca ggaagaaatc ttcagagtta    58740
aaggggctta tgcagggctc ttggtgtcct gtgactgctc tggctgaggc ctgggatgtg    58800
agggagatga gaagtctgtg caagccagat gtctgggccc aatcatagga ggaaactgcc    58860
tctgcttctc ctctccacct ctcccttttcc ctctcttctc agagcccagt gaggtcgggg    58920
attttgagtt gaactttact gggggtgtcc ctggccccac aagccaggac ctgctgtgtg    58980
aaatcgaaga ctcgcccctcg ccagtggtgt tacacattga ggctgtcttt aaggtgctgc    59040
aggtggagct gggcagtggg gtgggcccag agaggtggca gggctgggac actgagccat    59100
ccccaggtgg cccagtgaca ggccctctgg gtgtctcagg ggcctgccct catcatcaac    59160
gtctcagccc ttcagtttgg tctgctccgc ctggggcaga aagccacaaa ctccatccag    59220
atccggaacg tcagccagct cccagccaca tggcgcatga aggagagccc agtctccctc    59280
caggaaaggc ctgaggatgt aagtcaggca ctgctggttc ctctggtgcc cccacaatga    59340
gcccgtttag cttgccctgg tgaaacttgc cctggtgtgt ttagatcaga gcttcgaggc    59400
tggtggagga aaagcctgcc tggtgacttc ggcctggcgg tgcctcctgt tctccccatc    59460
```

```
gctgaggcag ctcagctcct ctctacagcc aaatgtaatc ccccatcagc atttcctgtg    59520
cctttcacta ccatcggatt tagaaatagg gcgtgggttt ctccctcaga gccgtctgag    59580
gcaggaagag atgggcagct aggttgggca ggaagcctcc aaggctgctg ctgctccagc    59640
cgcattccca cctcctcccc actctctgga aggttcagat cctcccaggg atctgctacc    59700
agatggcatc tggtcacagg ctggcagccc aaacccaagg ctccaaaaag aaaattcaag    59760
atttatttcg actcaaatgg cacttttcac tataaaagta ggaaaaaaag cagctaagta    59820
ttatcataat catatttaaa tgcagtgggc gatctggaac aagacaaagt cacacaaatc    59880
accagctact cgcaaaatgc ccgcagtgag tcgtacatca ccgcccttc accacggcat    59940 ggctgcagct ccctggtgga ctgcacatgt gagaccctgg ccatgtctgg tgaccacact    60000
ctccttctgg ctgcttccca ccgaggtccc catcctgctt gcccacttgc cctccgagtc    60060
agaacaccgc acacttttcc ttctgtatta aggagcccag ggaagacaat ccaagccatg    60120 catataccctt attttgctag tgtgcattcc ctttctgcag gaaagtgggc tttcctttct    60180
attccaggga ggcctcgctc ctttacctga tggcctatag ctgggcactc tgaaacctag    60240
aagttatgac agtgtgcatc aaattgccaa cgccattgcc aagtacctgt tacacaggct    60300
tggagttcaa tactttccct cccagggctc atccatctcc caccatggat cctgaaacca    60360
caaaagacta aggctggcgc ttgggctggg atggggctgg gggcagggtg gcatcagtat    60420
ctttagtgtc cacattatgt ttagccaaga acccttcttt caaatgaaac tttatgcaaa    60480
agcccagaac atagaataaa ctgtgactgc tccagccacc cagagacccc cttgttaggc    60540
acctctgccc catcctgctt ctccccacat tccagtcccc tgcacttcta gggatttcct    60600 gggatttttcc agagcacagt tagaagctta cagacctcag ccagcctcct catttgatag    60660
aggagagact ggaaggggca gggcttcccc aaggtcatac ggctgatggg tagcggcatc    60720
acatctgatc cctcttgtct agttttcagt ctgtggtgtt ctcccactgt gaagaataac    60780
tatgttttat aatggaaata attgccaatg ttatagtatt gtaagataat tccctctcta    60840
cagttctctg cactctattc ttttgagctc tcaaaaataa tgttgggatt tggggtttgt    60900
tagatggtct cagattaggg gacgcagagc tgctgaaacc caaccctaga ctacagccac    60960
ccccagagct ccaagggaga tgcacatgag caacaaagac aaaataaagc aaagtggctc    61020
cttacaggga caagtgtcct ctctcagtca gggcaggaag aatggaatgt aaagagccct    61080
ccccagatgg ggacactttt cttcctgctc tttcccttcc cctctcccctt tgtgtgtgtg    61140 cctggcatgg gaggaggagc agaccggggg cggggtgggg gtggggggcgg gtaaatgagg    61200 ctgagcctgc agtaggggac agaaggaagg ggtgggggaa agaccacgtg ggtgcaaagg    61260
agaaatctgg ccacaataga ctctcccctc ccctaatcta gtgacctggt ggcttttcctc    61320 agttgaagct gctcagaggg ctaccccct agtttggctc accagctctc ctctggctcc    61380
ccagctctcc ccatttttccc tggagcacct ccctccgcct tctatctctc agatctgggc    61440
cagggcatgg ggccctctga cttatgtatt cctttacttg gagactcagt ttctatgctc    61500
ttaatcctga gactcttgtg gctgtggtcc cccacctgct tgcctgtttc tggatcccag    61560
atggctcttg gaagagctgg ggcagcttag gagtgacttt ggttaggcat ggccagcccc    61620
cagttcctct gcaattccaa gtgtcctcag tgctcatcct cctgagtgtt ctccggggca    61680
ggtgtctccc ttcgacattg agccttcgag tggccagctt cactctctgg gggagtgcag    61740
ggtggacatc accttggagg ccctgcactg ccagcatctg gagaccgtcc tggagctgga    61800
```

| | | | | | |
|---|---|---|---|---|---|
| ggtggaaaat | ggtgcctgga | ggtaagggtg | ccgtgggaag | agccactaca | acaaactatg | 61860 |
| catattcgtg | atgtatttat | ctatattata | tatttatcta | gagatgttct | ggatttaaaa | 61920 |
| ctattgaatc | cagaaaatta | gtattctata | aaatttgtaa | attacagaaa | agaaactcaa | 61980 |
| aatgacgcat | aatccattcc | ctagggatga | tccactgata | atattatgta | tatatctttc | 62040 |
| tagggtgtgt | gtattaaaga | gatgtaaatt | agtataacta | ctttcgaaac | tacgttagca | 62100 |
| tcagctagtg | tttgcccttc | tgagtatact | cccagggaaa | tccttataca | tgcacagtgg | 62160 |
| gagatgtgtg | ctcatgttgg | aatgctcaga | ctggactgtt | cctacaggaa | aaactagaaa | 62220 |
| aaaccactgt | ctgtcaacag | gagaatggac | atttaaaaag | tgtgacatat | ttaaataagc | 62280 |
| acataccatt | gtattctggg | aggaacatgc | tagaggtttc | aaaggtattg | gtagtattcc | 62340 |
| ttttttctt | cttcattctc | cctccgctcc | cccacttccc | tccttttctt | tctttctagt | 62400 |
| ggaaaacttc | tcatatatat | aaaaacagaa | agaatagtat | aataaacctc | cacatactct | 62460 |
| ttcctcccctt | caataattgt | caactcactg | caagtactgt | ttcatccata | tcccctatct | 62520 |
| ccttctcccc | actccttccc | aaattatttt | caaataaaat | attcattttc | ctgctgggca | 62580 |
| tggtggctca | cgcctgtaat | cccagcactt | tgggaggccg | aggcaggcaa | atcacgaggt | 62640 |
| caggagttcg | agatcagcct | ggcaacatgg | tgaaaccccg | tctttactaa | aaatacaaaa | 62700 |
| attagccagg | tatggtggtg | ctcgcctgta | gtcccagcta | cttaggaggc | tgaggcagaa | 62760 |
| gaatcacttg | aatcctggag | gcagaggttg | cagtgaatga | atatatatat | atattcattt | 62820 |
| tcttaagctg | gctggtgata | atattttgtt | tctaaagttg | tgtggaggta | gtacatagat | 62880 |
| gttgttttat | tattcgttaa | actatatata | tgtttaaact | gtatatatgt | tttatactca | 62940 |
| tttttgcata | tatttggtgt | ttcattgtaa | aaacatttaa | atgctcattt | aaatctctgt | 63000 |
| ggatgctctt | gaattatcct | ccaaaaagac | tgtgtcattt | tatacttctg | cctacagtgt | 63060 |
| gtgagactag | ccattacccc | acactttcac | catgacaaat | gttgttggac | tttgtatact | 63120 |
| tgaccatctg | acagttgttc | aaatgtcccc | tcctgtgata | acaaatacag | gtctaggtat | 63180 |
| gagtctttgc | attggtcctt | cagggcaatt | tgcgggcatt | agatgtgaag | gctaagtctg | 63240 |
| cctgcagctc | aggggaaggg | ctttctatta | agtctgtgct | tatttccttt | ccttttctgt | 63300 |
| ctctgttctt | tctcctgaaa | ggaccttgta | ttatcagaat | gtttacagta | gcaggtgatg | 63360 |
| gaaacacaga | cattaccaac | ttaggcaaaa | aagaggaagc | attggctcac | gtaactgggc | 63420 |
| attcccacct | tgctgaatcc | aagggcccaa | cacttttccc | tttgtctggt | cttctgcttc | 63480 |
| ctctctttct | ctaccctctt | tccccttct | ctacctccat | cccagcccca | acccatctac | 63540 |
| tgctcttttt | ttgtgggccc | ttctctcccc | tattgacaag | ggcccttcgc | actctgcctt | 63600 |
| ggggagaggc | cacttagagc | tccaggctca | cacactccca | ccttaacaat | ctctgagagc | 63660 |
| caatctggct | ctttgcagag | ataggccctg | attgctcttg | ctcttgtgtg | ggtcatgtac | 63720 |
| ccgccccttc | ccctgctggg | tgacagggag | gatctgtctc | cagaagaggc | aatcatgttt | 63780 |
| cgaaatttca | agctttgttg | ttcttgcgtc | tttccttttc | tatagtaatc | tgttatagtc | 63840 |
| ttatcaatgc | aacagcctct | cagattcccc | caagaaaatg | aatttctgtt | tcccagatg | 63900 |
| ttggagttct | tctttacttt | ttgagttttc | ttctgcttct | agtaatcttt | gcctgtccag | 63960 |
| tcctgttttt | gaatggagga | ggaagttgat | ttgcataagg | agctggtgtt | gtaagtttct | 64020 |
| tctgagtaaa | aggggtaga | tgtggagagc | accctattc | taaggatga | agtcatgtg | 64080 |
| agtcaccacc | ctcagagcac | acagctagcc | tgaatccatc | agagaaaggg | acctttgggg | 64140 |
| aaaacagccc | taaacaaaca | gtggagaaaa | cccatactgg | gcagctacac | aaatcaattc | 64200 |

-continued

```
gtgccttcat tcataaataa gaatgaagga atagcatctt tctggttgtt tcctcctcat    64260
gacagttgag aggtccagtg ttactgcagg ctctgccctg gcctctctcc agcgtgatac    64320
ccacagtctt cagtggggc aaatactgtg gcagcccagt cttttcctta attttcaatt    64380 ttaatttta ttatttgtac aaattatgg ggtacatgtg caattgtgtt atgtgcgtag     64440
attatatagt ggtcaagtca gggctttagg gtatccatca cccaaatagc atacattgta    64500
ctcatgaact aatttctcat cacccatttc cctcctatgc cctcacccct ccgagtctcc    64560
gttgtctatc attccaatct ctatgtccat atgtacacgt ttttagcacc cacttgagtg    64620
agatcatgtg atatttgact tctgtgcctg gggcagccca ctcttccatg tgttgctctg    64680
agctctgggg ctggagccct gacctggcta agccaatgga tcttcagcag tgctttgctc    64740
agctcccccg ccctttgatg ccctcattcc atcattaagg attgcattgc acgtaacctg    64800
tgcagggatt tcaagcagca gttttgttct cctctgtttt atcagttaac ctgatcacat    64860
tatttctttc tcctattttc tttccttgt ttgcataaca ttttatttgc tttattatct     64920
tttacttcaa aattttcaca aatagggcat ttgctagata ttacatttct ttgcattcac    64980
aatttgtctg tttggcacaa agctagcttt ctgcctgtgt cagctttgaa tgtgccttcc    65040
tcactaagct taatcatttt ttagcttaat cattttgatt taaagtgaga tacgtacgac    65100
tcttcttttc acttgaagac ttagaggcta ttgtagggtt atcagttggt ctaatttcaa    65160
tattgttgtg tctcaaggaa tagggaggcc tgaggagagg gagagagacg gaaatgacca    65220
gtaagtagag cagtcaaaat gcacacagca tttaccagtt gagcccatta tcgtatatga    65280
ttgctgttta tggcaccca aaacaattac agtagtaaca tcaaagatca ctaatcacag     65340
gttaccataa cagctatagc aaaaaagttt gcaagacatg acacagagac atgaaatgag    65400
gacatgcaat tggaaaaatg acattgatag gcttgctcaa tgcagcgttg tcacaaacct    65460
tcgatttgta aaaatcacag tatctgtgaa gtacaataaa gcagagcata ataacatgag    65520
gtatgtttgt aactgaattt cttatatagg tcaatttaga cttttttctt ggccaggcac    65580
agtggctcat gactgtaatc ccagcacttt gggaggctga ggtggacgga tcacctaagg    65640
tcaggagtac gagaccaggc tagccaacat ggtgaaaccc catttctact aaaaatacaa    65700
aaattagccg ggtgtggtgg tgcacacctg taatcccagc tactcgggag gctgaggcat    65760
gagaatagct tgaacgtggg aggcagaggc tgcagtgagc cgagattgtg ccactgcact    65820
ccagcctggg caacagagca agactctgta tgccccaccc catcccccca aaaaagatt    65880 tttttttttt tctcagtttt ggtagttttgc atcactctag gaatttagga attttgtccat   65940 tttatctgtg atgtaatttg ttggtacata gttgttagtg gtattctctg ataattattt    66000
ttatttctgt atgatcagta gtgatgtccc cactttcatt cctgatttct ctaatttgaa    66060
tcttcagcaa atttttcttg gtcagtctag tctagctaaa ggtttatcaa tgttggtgat    66120
attttcaaag aaccagcttt tgcttttgtt gattttctgt aatgttttc tattttctat     66180 ttcatttatc tctgctttct agtctttatt atttctgtcc ttccacttgc tttgggttta    66240
gtttgctctt ctctttctag tttcttaagg taaaagctga ggttttttgat ttgcaatctt   66300 tcttttttgt ttgtttaaag aaaattgtat ttacaaatat aaatttcct ctaaccactc     66360 ccttagttgc atcctataac ttttcatata tcatgttttc attttcattg atataaaagt    66420
attttctaat tttcttgtg gtttcttatt tgacttgttt atgaatgtgt tatttaattt     66480
gcacatattt tgtttcacaa atttctttct gttgttgatt tctaatttga ttctattgtt    66540
```

```
gttggagaac ccactttata taattatagt cgtttaaaac ttattgagac ttgttttatg   66600
ggctattctg gagaatattc cttgtgcact cgagaaaaat aatgtattct gctgttattg   66660
tgtagagtgt tgcctgttct gtttggttta tagtgctgtt taaatcttct atttcaatgt   66720
ttatcttctg gttagttgtt tttccattat taaaaatggg ctgttgaagt ctccaaccat   66780
tattgttgaa ttgctgatct ctccttcaat tctgtcagtt tttgcttcat gtattttgtg   66840
gtgctgttgt tagatacata catgtttata attgttatat cttctaatt tatctttta    66900
taattataaa atatccttca ttgtctctaa taaccatttt tgtcttaaag cctattttat   66960
ctaacattca tatatctcct ggagctctct tttgggtact gtttgcatga tatatatttt   67020
tccatccttt ttctttgaaa ctatttgtgt ctttgaatct aaagtgtctc ttgtaaacag   67080
catatacttg gatcattttt ttaaaatcca ttttgctaat ctctgccttt tgattggatt   67140
gtttaatccc tttatattta atgtaaatac tgataaagta gaacttcatc tcccgttttg   67200
ctatttgttt tctgtatgta ttttgtgttt cctgcattcc ttgtgtttcc tgcattcctc   67260
cattattgcc ttcttctttg ttagataggt agtttctagt atgccatttt aatttccatg   67320
tttcttttac tttttaaaaa gttattttct tactggttgt ccagggcttt atagtatatc   67380
ttaatttcaa aacagtctgg tttagattaa caccaactta atttcagtag tctgaaatgt   67440
tactgtaata tagctcagct ctattctctc cccttccttt gtactattat tgtcatacaa   67500
attacatatt tatacattat aggtttatca agacagtttt acagttattg gtttgtatag   67560
ttgccccttta aatcagatag aaaagtaagc aaaaatacat ttattctgtc tttgtattta   67620
catatgaatt tatcttgata tggttatatc agtcaaggct taatatttat ttcttaataa   67680
cctattaaga catttattac aaagaatcag gttacacaac tatagggact agctaggcaa   67740
gcctaaaatc tgtagggcag gttttcagga agggcatgct ggcatttttg gggacaagat   67800
gaagatgtta taaacacatg gaatttcttt gtctgggtaa gcccatttct gcttttaaga   67860
cctttttagtg gccaggcatg gtagctcacc tttgtaatcc cagcactttg ggaggccaag   67920
gtgggaggat cacctgaggt caggagtttg agaccaacct ggccaacaca ctgaaacctc   67980
atctctacta aaaatacaaa aacttgcctg gcatggtggc acatgcctgt agtcccagct   68040
actcgggagg ctgaggcagt agaatttctt gaacccagga ggcagaggtt gcagtgagcc   68100
aagatcgcac cactgcaccc cagcctgggt gacagagtga gactctatct caaaaaaaaa   68160
aaaaaaaaa aaaagacct ttcaactaat tgaattaggc ccatctagat tatctaggat   68220
aatctccttt acttaaactt aactgattat gaacattaat catacctaca aaataccttc   68280
agccgttcag acatgtaaag agcttgccca tcaagctcct gctctcacaa caaggaaaga   68340
ctgaacaaac tgaaacaatg attttttctta gatctatcag agagttgagg ttgcaggaca   68400
agtggccacc ccaaaagctg gagatatagg caaatactga gaatacagat cagtttacct   68460
gaagcagaag aacacttaaa tggtagtttc aacaaattcc tggtggctaa gtgtaggcta   68520
gcttaagagt ttaaaaatcc tgggggctca gtaggttctc atggtgaaaa ctggaaaaaa   68580
aattctctct tgtttagcca gggtgggatg gggagggaa gtaaccattc tgaaatacgc    68640
ccagaggaaa agtgaaataa gccacttga ataagccca gagtgttctt gcaacaattt     68700
ctcttacacc cgagatttct acttttgag caattataaa tggtactata ttttaaattt    68760
cgatttccac atgtttgttg ttagtatata aaaatgtgat tcattttgt atattgatct    68820
tatatcctga aactttgccg aacccactca ttaattctag agtttctaaa aatatagata   68880
ccttgggatt ttctacatag actgcatgtc atctagaaat agggacagct ttacttcttc   68940
```

```
ttttctaatc agtatgcctt ttgtttcctc gtgttccagc taccttcctg tgtatgctga   69000
ggtacagaag ccccatgtgt acctacagag cagccaggtg gaggttagaa atctctacct   69060
gggtgtgccc acgaagacaa ccatcacact tatcaatggc acgctcctgc ctacccagtt   69120
ccactggggc aaggtgagtg agcccacagc atcaggcagc agtctgcagc cctcagccac   69180
agaggcccac atagagggg gcattgtccc ccaaatatcc tcacagaaca gagatactca   69240
gcctccctcc cacagcctgt cccttgctcg tagtgtgcat aaaagctcct caaggagca   69300 gcatatctgg tccagctttt tcttgccctg cctctaggga attccagttc cctgaccaag   69360
aaggagtttc tggtgaacat agctagagcc tcccagccaa catagcccat gactgggcca   69420
ggtagctgtt ggagcccagt tgtggtgctg ctcctgcccg tggctgactg gggagctctg   69480
agtgtcatgg acataaggc cacatccatg tgcaccagaa gcatctgccc tctgctcccc   69540
atccctcggg gccttcaagg gcagtttctt ttgtccagat aacctcccaa caagtggtaa   69600
agtccatcca gggttgggga ggagaggaga agggacccgt ggtttatccc cagaagtgag   69660
cacccagccc tgtcggtttt gctgtgggcc ccagtctgcc agtctccagc attgcatgca   69720
gcagtgctga gcactctctg gatactggtc cattctggga gcccagtaag tgacaacagg   69780
ctcactcatg tgtctgccag ctcctcggac accaagcaga attctgcatg gtgacagtct   69840
cccccaaaca tggcctgctg ggcccaagtg aggagtgcca gctcaagttg gagttgactg   69900
ctcataccca ggtgagtaag gcaatgtagg gcctgagtga ccgggaaggc accctgccaa   69960
ccatacgcac ctgtgccacc agggaggccc tagcttaggc cacattgctg gttcttgtgg   70020
gtggggaaga gatttcttgc atttgggtct ggggtcccca ttcctgctgg gtctgctccc   70080
tagggacaca tggtcagaga gcctggagta ggcctgggga tgtgccctga gcccactgg   70140 ccatgcctgg ccttt ggcat gagtttttgc cctccccagg ccattctctg tggccgcagg   70200
tgggcccagc tttctgattt gcccagagat ccagagcaga gctgttgctc acagcaggca   70260
ctgtgccagg tactacccag ggaggctaac tggtacctag gtttcccgct ggaggccacc   70320
agggtggaat atgctcagtc atagggccgt tcctagctgt ccctttgtgg ttcttgtggg   70380
aaaagaaact tcctccttac agagacttgc aaactcaggt ctcagctccc cctggcaaat   70440
atggggatgg ccggcctgag ctctgggacg acagacaggc aggcccaggt gtggaacaga   70500
tcttgctcag ggagggtttg atttctaggg tagcagcttc atcagaggaa gtgcgcagct   70560
tctccagagg ccctctctga ggggtctccc ttcacgtggg catgcccaga tatttggggc   70620
agactcagac agccataagg cctgaggaaa gggccaggct tcctggggct gagggcgggt   70680
cgactggctg ggctcactgg agggactgga gatgagcctg ccagaggtc aaggctccac   70740 agcaatcccc tgtgctgcgg aagaccatct gggctcatct tcagaggccc caggcctggt   70800
ctgacccctg gatgggcttt cttataggaa gagctgaccc atctggccct cccttgtcac   70860
gtgtcaggca tgaagaagcc actggttcta ggcatttctg ggaagcccca gggactgcaa   70920
gtggccatta ccatctctaa ggagagctct gattgcaggt gagcccaggg ttggtggtct   70980
gggggtggca gtggactgag gaatgaggca gccgcgccca ggaccagcac ggcactgtgg   71040
tatcagtctg cgcccatctg attcctgcag gcaggaaaac gccacagtgt tattgcggcc   71100
actcaccact cctgtgggga cagctccctt taccccatcc ctgccctctg tgtggtctcc   71160
ccacacacac ttggaggcgt ggtgccctgg caggcaggag atggcagggg acagggcgt   71220 aggtaccctg ggcttgccca catgaggccc agcaactggg agccatgcca gcatgccgct   71280
```

```
ggccagggac ggtttgtgca gagtttgagg cctctctcag catcatgggt gggcaggaaa    71340
ggtgggtctg tggttggcag ctcaatgaaa caggagtctg aggatgaagc ctggtgtctg    71400
ggcagcttct gcatgcccac ccaagatggc tccctgggca gggccaaggg tggtgtgtta    71460
catagtacca atgggcacag gacagtgttt tcagcacaga gcagtggcca ggccacccaa    71520
aggagctccg cctggacttt ggctcagcgg tgccactgag gacccgtgtg actcgccagc    71580
tcattctcac caatcgctcc ccaatacgga cccgtttctc cctcaagttt gagtatttcg    71640
ggagccccca aaacagcctg agcaaaaaga ccagcctgta agtcttgctt ctttcacttc    71700
ccagggcaga tgaagctgga tggggtgtac cctgttgagc ctctgtgtgg cttaggtggc    71760
cagtggctgg tcggtgtgag agatgggagt gtgtgttttt acaggtagac atggggacag    71820
gcagagagga aatggctcct gctgtccacc tcccgggccc tgagtgggcg tgtgggagag    71880
gctgggattg cggccccttt tcctcagcct ggcctgctgg agtggaggct tctgatggac    71940
caggcagatg ggcctgtagt gagggagagg ttactgtaga cagaaggaac tgtgcaggcc    72000
aaagggtggg aggaatagtt caggagtagg gagtcttcag ggaccactga tagcgtgcct    72060
gggctgacat gtggagagtg agatggggtg ccccatagat cagacagtga tcagcaaagc    72120
tactatgtgt aaggacagag gcaagatcta gagtgctgct tacacagaca cacacacaca    72180
cacacacgta catatacaca cacatgcata cacacataca tatacacatg catacacaca    72240
tacacacatg catatacaca tatacataca catgcataga cacaaatata cacacataca    72300
catatgtata cacatataca catgcacaca cacatataca taaacataca tacatatgca    72360
catacataca tgctcatata cacacacacc cacatacaca catacacata ggtgtgccag    72420
aaccagctag cactggttca ggagaactga ttgttaaata ttcaggaatt ttgcaaatct    72480
ctaacttgaa atcaaacatt ataatttagg actttttttt tctggaatct ccactgtgtg    72540
gacacctcac cacctaatct agtgaagcaa gagggcccaa cttagaaacc acggctatgg    72600
gtggaaggcg acccatgaac agtttataag gcattaactt tctattgtgg aaagctagtg    72660
tgtacccaat gctggacaga tgtcagcagg aaaaactgga aatgggcctg ttgcagaatt    72720
ctgggctaga gatggggagt ctgggctggg tttgtgtcca ggagtaacca tggcacagag    72780
cctgtgggca gggagtcctg cttcagagcc cgcctgggtt tctggggagg taatccctgc    72840
agctggcggg tggcccgcag ctggggatgt ttgaatggta ggggtacagt gggagcaaag    72900
accagagaag gaggtaaagg aaagaactga ccagctctcc cctgggaaga gcaggcaggg    72960
ccaccttcct ctgctgggca cctggtagaa tgctggttgc tctagaacct ggctcaggtc    73020
ttgggacagg cttgtctgac ttgatactat ttctgtgtct ccacttgtaa agtcccaaca    73080
tgcctcctgc cctgctaaag acagtgcgga tgcaagagca cctggccaag cgagagcagc    73140
tgggtaagcg ccaccagggt ggggcttcgg ggcccaggcc acggcagag ccacagcctt     73200
ctgtggatgt gggctggcag ctgccaggga gcgggaccag gaccagagac tgctctcaga    73260
tggccaaggc gctccacctg acaatgcctc ttcctgttga ggccacttcc cttctagggc    73320
acaggctcat gcacagggcc tggactccat ttgggatggg agtggctcat gagggagggc    73380
tcccatgggg acccagcctc tcaggagtta gagaggctga ccacgcagga ccctgagtag    73440
cttgcctctg gattccaggc tcccaggagg agggcacatg tagcctgacc aaggagaggc    73500
tggagggtgg cttatcgggg acagtgcttt gctcacacac gagggtttgg acctcactcc    73560
caaccccagg cccgtgaatc ccccacagtc gcggttcttt cccagatttt atggagagca    73620
tgctatccca cgggaaagga gctgctttct tccctcactt ttcccagggc atgctgggc    73680
```

```
cctaccagca gctgtgcatt gacatcacag gctgtgccaa catgtggggc gagtactggg    73740
acaacctcat ctgcacggta agggtacaca agagggcagt ggcctggggg gtggagagtc    73800
tgcccagccc tcgccttcag cctctctccc ctccaacacc tggccctcag actctcaaac    73860
ctcaccaggt tgaaacgcga tgcccaccga gcttgggatg ggcattcgtg tctgaggcag    73920
cctctggggt tctggctgag gcatttcagg caggaggggt cctcataagc agtagaactt    73980
tccacacctt ttcccaggag atgcagggct ggggccatat cgaggaggga agaggagaca    74040
gtaggctgct gcctgggcca ggacccaaga cttggagtag ggagtgtgga gtggagggac    74100
agtagcagcc tcccagagcc aggtccttgc cccgcccttg gtggggctca cccaggggtc    74160
catttaattg ctccagcact cagcataaat ggagtatcta ctgtgtgtgg gttcctgtgt    74220
gggccgctgt agtgtggagg atacagggat gaataaggta accagcaagg caccccctagt  74280 ttagtctgga gggatgaaac ctgcatacgt tatcctaccg ttaagttgtt aaatagaaga    74340
ttttcatgaa ctatttagta aattgaacag attaattata gtagatattt gctttaaatt    74400
gtgtgtgttc tgtatgacaa agaattgatc atgttaatat aaaaagggat cttaagtaac    74460
aggaagctgg ggaagagtat cccaagtggg caaggtttga ataaacaact ccaagaaaga    74520
caaatacaga cagacggcca ataaacatat taaaatctgt caccaccact gataattaaa    74580
gaaatgcaaa ataaaagagc cacaaaatac tggttttgac acattagcga ggtttaaaag    74640
ttgttggtga agatacaggg gaaagggtgc tttgagcccc cttctccacg tctgtcagta    74700
gaggagtgga tacagacatt gggccacatc cctaagggaa ttctgcacag cctgttatat    74760
gatgctgtaa actctttatt agtaaaaatt aatcctatat tgttcgctgg gtgcagtggt    74820
tcatgcctgt aatcccagca cttagggagg ctgaggtggg tggatgtctt gagctcagga    74880
gtttgagagc agcctgggca acatggcaaa acccttctc tacaaaaaat acaaaaatta    74940
gctgggcgtg atggcatatg tctctggtcc cagctattca ggaggctgag gtgggaggat    75000
cacttgtgcc caggagttag aggttgcagt cagccgagat catgccactg cactccagcc    75060
tgagcgatgg agcaagactc tgtctcaata ataataataa taataataat cctatattgt    75120
taaaagaaaa gattattaaa ggcatgtgca gcatgctccc catttatatc tgggtcttca    75180
caaaagaagt gtagacactt gtacactgaa atgctaacag taagtcatgc tgcagaggta    75240
ggattggagg tgattatcac actcttatat tttctaaaaa taagatttat tacttttgat    75300
tagcagagaa aagtaataaa gttctttttca tttaaaagac agaaatttga tcaaagggac    75360
taccagaggc cgaagagcct caggcttgcc aggtgcagtg gctcacactt gtagatccaa    75420
cactttagga ggctgaggca ggaagattgc ttgaggccag tagtttgaga ccagcctgag    75480
caacatagta agaccctgtg tctactaaaa aaaaaaaaa aaaaaaagt cctcaggctg      75540 ggagctttgt gcaggctgcc tggctgggag ggagagtgga gatggcggga agtgggagag    75600
aagacagagt ggtacacagt gaggctggga ccaaactgtg gggcccctgg gctggctgga    75660
caagtggagg ccttgcccag aggggatgtg gtcgcaaccg gtgacaggag tgacaaaggg    75720
ctggggtgtg tttgcaggtg ggagacctgc tgccggaagt catcccagtg cacatggcag    75780
cggtgggctg ccccatcagc tccctgagga ccacctccta cactattgac caggcccaga    75840
aggaaccagc catgaggtgc tccatgctca gcctgagcct ctgctccctg gtagcccctg    75900
aaaccctccg gcctccgggc tgggctgccc acgttggctt gttattctcc agctggccta    75960
gggccattgg tgccacctac aagaaggttc caggccaggg tttccctggg ggaaggtggc    76020
```

```
ctcaggggac gtggccacca cctggacatc tctgagggat tttgtggggc agaagtggcg    76080
agtagtcagt gtggtccgag gtcagcacca gccctgggc  ccctggcaca gttgaactgg    76140
aatcagcata gtctgctcag ggcaggtggg tgggttgcca gggcacaggg cagcccaga     76200 gcccagctca cctggtgccg cctggggaag gcaccagccc caggtctcat taattctcga    76260
gtgaggccag accactgtgg tatttccccc tgcctgagcc cccagtccca gccctcctcc    76320
ctacctgcaa ggtgtacgct ggctgtggct gtactgagtc cagtctgtcc cctccaggt    76380 tcggcaccca ggtctccgga ggagacacag ttacccgaac ccttcgcctg ataactcca     76440 gcccctgtgg taagacatgc atgagagaag tcagtgttct tgccacaggc tgtgccttgt    76500
ggtgagccag gctgggaggg aaggtgggag ggaagccgat ggcccatgaa caggacccag    76560
gtgtccaggg ggcctgtggt tacggaagtg tggatgggcc cacagatgcc ctgctctcat    76620
cagggttgct gtttggagga acagacaata agaggggatc cctttctcat tcctccagcc    76680
ggcaggacct gacctgcctg agagctgctg gggatacagc ggggacagga cagcagggtt    76740
tctgccgagg ggcttccctc ctgatgggtg ggacagatgt gactgtggac tgcagtgtgt    76800
ggagtgtgtg gcatacaact gaagggaagg ccggagtgct gggggaacgt gttgaagggc    76860
caggctcccc tgtggagggg aggcagagtg taggctgagt ctaagaggaa gggtaagccg    76920
atgtgggcca ggggagcatg tgggggcaaa gagtgctctg ggcctgagaa agggttagga    76980
gaggaagctg gtgacactga agaggggcc  ctggccatgc ctgccctga  ggagagctgc    77040 gagcaggact gaaggcagga ggggagggga agatgggttc gatgcaggca gatgtctagg    77100
tttgggacag gactttgggg acttctcagc ttgggggctt ctgggagatg aggtggggct    77160
accggctggg tgtgggaagg cagatggagg tgtcagagga gggcagggac agcttgacat    77220
tgtcatggtg caggctggag agagagcaat ggggagcccc agcttaggtt ggggacagat    77280 tgatggggt  ggcaatctgt tcagctgggg gacttcccc  agtggtactc agagggacgg    77340
cacagttcag ttctttcagg gttaggtgtt gccaggtggg tgcaaaggga gatacgagga    77400
tgctggcaag acagaggtgg acatggcggc ccccaaagac tagtctgcct ggggaaggac    77460
gtgaaagctg acataggctg atggatagat ggggagaagg aagggcatgt gggggttaga    77520
gagcccagcc tgcccacaaa caggccggaa ggagaagcag ctgtgggaga gagcagagca    77580
cctgcattca ggcatctgga catggagacc tggtcttgtg accatgagga cttcaggtga    77640
tagagccaaa cggcataagc ctgtaaagcc ttttaaaat  tttaaatgag aattgcctgg    77700
aagtggcatt agagaggcag agaggcaccc cctccacctg ggtatgggag aataggtcat    77760
ctctgtctgg gggtatgagg aggaggggc  ccgggggt   tgtctgctcc tcccttattc    77820
ctcaccctgc tccacacatc tgccccagac atccgcctgg attgggagac ctatgttcca    77880
gaagacaagg aagaccggct ggtggagctg ctggtgtttt atgggccacc tttcccgctg    77940
cgggaccaag ccgggaatga gcttgtgtgc cctgatacccc ctgagggtgg ctgcctcctc    78000
tggtccccag gcccctccag ttcatcggaa ttcagccatg aaactgactc atcagtgagc    78060 agggtggag  gggcggggca ggctggccac tgagggccac tgaggtgtgg ccagtaggct    78120
agttgaacct cagtgactgc gtgaacctca gtgattcctt ggtgacaggt tgagggcagc    78180
tccagtgcca gcaatagggt ggcacagaag ctcatctcag tcatcctgca ggcacatgag    78240
ggggtgccct ccggccacct gtactgtatc agccccaagc aggtggtgag ttggggtatg    78300
ggctgggagc tgtctgcatt ggccggccag tgggcatggg acagtgctaa ggctgctgtg    78360
tctatgccag gtggtccctg ctgggggcag cagtaccatc tacatctcct tcacccctat    78420
```

```
ggtgctcagc cctgagatcc tgcacaaggt ggagtgtact ggctacgccc tgggtttcat   78480
gagcttggac agcaaggtga gctcttccgg cctggggtgg gggccgcagc cactgctccc   78540
tcctgggtag catgctgcct actcagccca gggatcagct gtgatcagac ttgggctcag   78600
taggtggaaa gggagattcc agggaagagg catcgcctgc aggactttgc ggtgggaccc   78660
ctgaaactgg acctgcatag ctacgtgagg cctgcacagt gagtcagctg gggtgcccca   78720
tctcctttca tccccatggg gtgcaccctc accaggcact ggtggagcca ggcagggttc   78780
tcagagcaaa aggacgggca tgggtggaga agtcagcaga ggagcccagg gaaaggctgg   78840
cccgaggctg gatgagcaga gtgggggcag ccagaaggcc ccaggcgccc ggcttgcccc   78900
aacaatgcct attgctgggc aggctaagtg tggagctgga ctacggcggc agtatggaat   78960
tccagtgcca ggccagtgac ctcattcccg agcagccctg ctctggggtg agtgtgctgc   79020
caccctctgg ccctgccagc ttacctggac ctcagatgtc tctgtgtgcc cttgtgggac   79080
tcaggcctta tagtctgagc ccaaatcccc tcccccagcc ctcccagccc taccctagag   79140
ccatggggtt gaagagagag acaagatgca ttccctgcct cctacctctg tggctgccca   79200
ggtgctgagt gagctggtga ccacccacca cctgaagctg accaacacta cagagatccc   79260
acactacttc cggcttatgg tctccaggcc cttctccgtt tctcaagatg gggcgagcca   79320
ggaccacaga gctcctggcc ctggccagaa gcaggagtgt gaggaggaga cagcctcagc   79380
ggacaagcag ctggtgctcc aagcacagga gaacatgctg gtcagtgggg gagtctgcag   79440
cccttgcctc gatggcacac cctcacatgt gtacagacag cacccctgca cgccaccctc   79500
aggtgcttgt acccagacgc aaactgcatg cctgaccctg ccatacctg catgaacact   79560 cgggggtgca ctcccaccag agacaccaca ttcagcacct ctgcacaagt ggctcacatg   79620
ggcatggcca caccagacgt tgtgttcaca tacatgcatg cacgtgctcc ataaatgtcc   79680
ccagacttcc cttccctct tagtccccac tgctgagatg ctggtggagg ctgatgcatt   79740
cctgtgagca cctcccttc ccacacacac agactccgtc ctcctgtgca agctcagggt   79800
ttgtgtccca gctcaggtga gcccatgggg ttgccataat tgtaagacac tccaggttct   79860
aacgtaaaat ttcctcttct gacttattct cagtgacaat tggatcctgg atttcagag   79920 ttggttaggt aggggaaggt cttgggaatg tcaggacctc actggaaacc atcaacttcc   79980
tctggtctct gaggcaactg gaatgaggct gagtgtgcgc acacccatat ctgcacagtg   80040
ggcttccagg gtgtgcagag gcaggctgag ggtagacagc gccgccctgt ctcctacttc   80100
ccctcctgct tcagaggccc tctttcttct tctcggaggg cttcccttta tgctgtgctc   80160
ccttgagctc tgccaggtcc tagcctcact ctgcacattt ctgggttgtc tcatccattt   80220
ccagagcctc agtgaacagc catattattt ctatccaatg tatactccac tgtgtagcga   80280
gggcctgctg tgtactagat gctgtgctag gtgatggtac tccccgagga cctcatcatg   80340
gaggtcagga acacacacgg atctgcagaa gacagaatgg cacccttgac ccactttgcg   80400
tttgctccct tcaacgagct aaatggatgg gaaggcccag agcacagcca gaggttccat   80460
tccaccagag cttccaagga gacacggcgg ttagccacca ggcatttaaa agtccttggc   80520
agctctgggg aagcccaaaa gttccagaaa aaggacatca cataattaat ggtgctgcat   80580
ctcaccctcc atgcgctaac aatgctcagg cttctggctc ctggccagaa ttatctccca   80640
ggctctagag ccaaactcaa tctgtccaaa gtgaactccc catccctcc ccaccttgtc   80700 ctgccccaca tctgtgcctc cttttgtgg tggcattttg tctcagcaaa taccaacccc   80760
```

-continued

| | | | | | |
|---|---|---|---|---|---|
| agccccttg | ctcatgccca | gagctctggc | accccttgtc | ctagacccat | ctctgaccaa | 80820 |
| gccaccaagc | cctgcggatg | ccccctccta | aagttctccc | aacactattc | tcttttcttc | 80880 |
| atccctacac | ccatatcttg | gtttaggaca | gcagtttcta | agcctggcaa | tagatcagtg | 80940 |
| gccttttttt | ttttagattg | ggtcttgctg | tgtcacctag | gccggagtgc | agtggcgtga | 81000 |
| tcatggttca | ctgaagcctc | gactgcctgg | ggggttcaag | caattctccc | acctcggcct | 81060 |
| cccaagtagc | tgggaccaca | ggtgcatgcc | accatgccca | gctattattt | gcagagataa | 81120 |
| ggtctcatta | tattgcccag | gctggtcttg | aactcctggg | ctcaagcgat | cctcccaact | 81180 |
| cagcctccca | aagtgctggg | attacagatg | taagccactg | ctcccagcaa | attagtaccc | 81240 |
| ttgacaaagc | ttgttaaggc | agcagctccc | agacccacc | tccagacatg | tgaaggtctg | 81300 |
| ggtgaggcgc | aagaatttat | attttaaca | agtgcctcac | cgttgattct | gagaagcttg | 81360 |
| taccaaggac | ctgtgctggg | agccaggagt | ccaagcttca | tcctgtccag | cctcagttac | 81420 |
| agcctcagcc | cctggtctgg | catcatcaca | ctcatgtgtg | gtctgcagcc | cacctcccca | 81480 |
| ccaggtcagt | gacctgtcag | aggctcctca | ctatcctcag | cacacagacc | aagtccttcc | 81540 |
| tctgcctctg | agcccaacca | cagccctggg | catttgaagc | tgtaaagggc | aacttgctca | 81600 |
| tgtcccttcc | cttctagcct | ctgacctctg | agggcagaca | tgacttgtcc | ctgacactag | 81660 |
| cagggtgctg | ggcagagtag | gtgctgggca | gcgcttgtgg | aatgaaagca | ccaggttggg | 81720 |
| gagctgctgg | gctgttggct | gggcaaggct | gggcctggga | ggaaaggagg | atggagctcc | 81780 |
| aggtggggaa | gtggccacct | gccctctgca | gccggagttg | acaccatgtc | cacatctgct | 81840 |
| caggtgaacg | tgtccttctc | actctccctg | gagctgctct | cctatcagaa | gctcccagct | 81900 |
| gaccagacac | tgcctggggt | ggacattcag | cagagtgcga | gtggagagag | agagatggtg | 81960 |
| tttactcaga | acctgctcct | ggagtacacc | aaccagacca | tcaggcacg | ccccaggccc | 82020 |
| acctacatgt | ggaggagggt | ggaagtgggc | tgggctgtgt | tctgctgggg | ccagaggagg | 82080 |
| aaagacctag | cagggccctc | agaaataagg | agccctgcc | cctgtcctgg | ggctcagtct | 82140 |
| cccctagaag | aggccctgtg | tgcagagaga | tgagggccat | ccaacctcac | ctgcctcatg | 82200 |
| agctcaaaac | caggtgaggg | gccagagtgt | gggaaatcag | ggaaggctcc | ctgcgggagg | 82260 |
| aaggacatga | agcctgaaca | ccatttaatc | aaggaaggga | aacacgttga | cagccaggcc | 82320 |
| aaaagaaagg | cctgatgggt | gggacagagc | acctgaagca | gctgcgaagg | acagccctgg | 82380 |
| ggcttgccag | gcttcaagca | ccagggcgag | caccatggac | caggtcacca | ggccgtagtg | 82440 |
| tggaggctaa | gcaggggctg | ctagtaagga | gtgtgaagga | gtggcctggg | gaagactcta | 82500 |
| gagaggccgg | gggcaggagg | ctgagcagtg | gagccgaggc | gctctagcct | ggcacctggg | 82560 |
| cagctgctgg | ggctgaggct | gtgggatggt | gcatggcagt | gcctgagtgt | gatgcagggg | 82620 |
| ctgccaggag | atagaggagg | gcacaggtgg | ggcctgcggc | caaggaacac | agacaaatgg | 82680 |
| tccacggctg | agaggagctg | agggctgggc | cttgggggcc | accacaggag | gagcagtgaa | 82740 |
| ggagggcaga | gcccaaccag | ccagggtgca | gggactgaag | ctttatgagt | tagggaggca | 82800 |
| gggacagcgg | gggaatggat | ggcatcaccc | tggcccttc | cctgtgcaga | ctcccagtag | 82860 |
| cagcctgtgg | ccttttaagg | tggcgctggt | ccctgccaa | cttctgggag | cttcccgttt | 82920 |
| tcttcaggag | catcagcact | tggggtcagc | agggttctgt | gtgtcccaga | ggccctggct | 82980 |
| cagagcccac | ccagaatgga | caaggttgcc | tggtctccca | caggtggtgc | cctgcgggc | 83040 |
| tgtggtggcc | gtgcctgagc | tgcagctctc | caccagctgg | gtggactttg | ggacctgctt | 83100 |
| tgtgagccag | cagcgagtcc | gggaggtcta | cctgatgaac | ctgagcgggt | gccgaagcta | 83160 |

```
ctggactatg ctgatgggta tgtcctaccc tgccacctac ccaccgttcc cctacagggc    83220
tgtgccaaga gaagaccccc caggaagggg ccctgtgcg ccgtccctgc atgctggctc      83280
ccagggcagg caccacttgg aatttctgca gagcagccag tcccccaatc ccacatgatc    83340
tcagggttgc cctgccctgc agtgctgagc aagaccagag gtacaggccc gggggtgggt    83400
aaagtcttcc tgtgggagta catggggctg cctgcactca tgtgtcttcc cttccctttg    83460
gtgcaggcca gcaggagcca gccaaggccg ctgtggcctt cagggtctcc ccaaacagtg    83520
ggctgctaga agcacgatcc gccaatgcac ccccaacctc catcgccttg caggttttct    83580
tcactgccag gtgcagcccc ttccaacctt cccaaactg cccacagagc ctggacccc      83640 tgcccaggtg cctcctaacc tcagccccca catgctcccc acaggagtag tgagctgtac    83700
gagtccacga tggtggtgga aggtgtgctc ggtgagaagt cctgcaccct gcggctccgg    83760
ggccaaggct cctatgatga gagatacatg ttgcctcacc agccctgagg ctccgcccca    83820
gccctcagcc ccaggcccca gctggagaaa aaacattgcc cagggattag gagcagctct    83880
tcagcacaaa gacacagact tggggacctg gggacctctg ggcagctcct ggaatggaag    83940 aaccccttc cacaatggtc tcagcctagg ccctcatgat atgtcctcag agctaacata     84000
aaggacaggc cacaccacag cagagaccac cacattgaga tcactactca gtgcatagcg   84060
aagaccagta tggcaaaatt agtcttggaa aaaaaccaca gccactaaga taaattcatg   84120
cacttttact atgcccattg cacttctcat ccatggattt gccttgcctt aagaattaac   84180 catgccttg tggcctgggt gacccaggct gctttatct tgcacagcta aagagggtct     84240
gatgggtggc tcaacacccc acccactcct ataccatgtc atcagtgttc acattttcca   84300
aatgagttga agtgccttga tctgtccact gccaccacca ccagtgctga gttttcccat   84360
gtggttttgc ttttgtggtg ttactgcctt gctgctagag cagcaggact gtctgcgtag   84420
cgcctccagc ctgggacctc actcagttcc cagggtattc aaagacggca gcggctccca   84480
ttccagtccc gatgcacatg gacaccactc cgtatgccct gtgaaaacaa aacttaattg   84540
gctgggcaaa ggcacccacc aaattacctc cagaccaggc tgacccagaa ggacgtcatg   84600
gacaagtagg atgcaaaacc atcagaccag atctgtgggc aagcggtacc ctggcctccc   84660
acttgggcac acacacggtg acagatgccc actgcaggct agtatcccctt tcaaggctgg   84720 cccttaagga aaacagggat catgcccta catcctaagt tcagggtgtt tctgtgtgca    84780
tgttcccctc cccagggatc gatcataatc ccaaaagaca caatcccaaa cacaatcatc   84840
ccaaatgttg aaatcctgga agaacaaaat ccctaaagtc taaaatcctg aaaatcacaa   84900
tcctaaaaga tcaaaatcct gaaaatataa ttctggaaaa aataatttgg aagcctggcc   84960
tggtggcatc tacttgtagt cccagctatt cagcaggctg aggcaagagg atcacttgtg   85020
cctaggagtt caagaccagc ctaggcaata tagcaagacc ccatcttaga aaaaaacttt   85080
tttaaaagat tgatttaaaa gatatttaca ttttaggcc aggtgtggtg gctcaaacct    85140
gtaatcccaa cactttggga ggccgaggcg ggaggatcac gaggtcagga gttcaagacc   85200
agcctcgcca acatggtgaa accctgtctc taccaaaaat acaaaaatta gctgggtgtg   85260
gtggcagaca cctataatcc cagatactcg ggaggctgag gctgaggcag gaaaattgct   85320
tgaacccaaa aggcagaggt tgcagtgagc cgagatcaca ccactgcact ccagccagcc   85380
tggacaacgg agtgagattc catgtcaaaa aaaaaaaaa atgtacattt ttaaagggg     85440 atttatttga gaaacaaaaa caacagaaca cttcacaggc tactttacac aataaaatag   85500
```

| | |
|---|---:|
| aaaataatta caaatttctg caagcataaa cactcaggta tgctaacaat agtcacagga | 85560 |
| ttataacaat tataaacaga caaactgtat tcataaatag gttaaaagca aactgtataa | 85620 |
| attgctggta atcatgtgca cccagcttta taactgcagt catatgaata ccatgatgga | 85680 |
| caacctacgt cttttgatga gattgatcaa aaactgatag agccaggcac tgtggctcac | 85740 |
| acctgtaatc ccagcacttt ggaagctaag gtgggaagat cacttgaacc caggagttcc | 85800 |
| agaccagcct gggcaacata gcaaaaccct gtctctacaa aaaatacgaa aaattagctg | 85860 |
| ggtgtggtgg cacccacgtg tagtctcagc tactcaggag gctgaggtgg gaggattgct | 85920 |
| tgagtcaggg aagcagaggt tgcagtgagc caagatggag ccactccact ccagcctggg | 85980 |
| cgcctgagta agaccctgtc tcaacaaacc aacctgtgat g | 86021 |

<210> SEQ ID NO 2
<211> LENGTH: 6426
<212> TYPE: DNA
<213> ORGANISM: Homo sapiens

<400> SEQUENCE: 2

| | |
|---|---:|
| gttagcggcg tctcggttgc catggagacc aggagctcca aaacgcggag gtctttagcg | 60 |
| tcccggacca acgagtgcca ggggacaatg tgggcgccaa cttcgccacc agccgggtcc | 120 |
| agcagcccca gccagcccac ctggaagtcc tccttgtatt cctccctcgc ctactctgag | 180 |
| gccttccact acagcttcgc agcccggccc cgccgcctca cgcagcttgc gctggcgcag | 240 |
| cgtcccgagc ctcagctgct tcgtctgcgc ccctcctcgc tgcgcaccca agatatctcg | 300 |
| cacttgctca ccgcgtcttt ccgcaacttg tactcagccg aggtcatcgg cgacgaagtg | 360 |
| agcgcaagct tgatcaaggc ccgcggcagc gagaatgagc gccacgagga gttcgtggac | 420 |
| cagctgcagc agattcggga gctctataag cagcggctgg atgagtttga aatgttggag | 480 |
| agacatatca ctcaggccca agcacgggct attgcggaaa atgagcgggt catgagccag | 540 |
| gctggagtac aggacctcga gagccttgtc aggttgcctc cagtgaagag tgtctccaga | 600 |
| tggtgtatag acagcgagtt gctacggaaa catcatttga tctccccaga agattactac | 660 |
| accgatacag tgccgtttca ctctgcacct aaaggcatct ccctacctgg atgttcaaaa | 720 |
| ctgacattta gctgtgagaa gcgttccgtc cagaagaaag agctgaacaa gaagcttgaa | 780 |
| gattcatgca ggaagaagct tgctgagttc gaagatgagt tagaccacac tgtggacagc | 840 |
| ctgacatgga atttaactcc taaggccaaa gaaaggacca gagaacctct caagaaagca | 900 |
| agtcaaccaa ggaataaaaa ctggatgaac cacttacgtg tgccacagag agagctagac | 960 |
| agacttctgc ttgccagaat ggagagtcgg aaccacttcc taaaaaatcc ccgttttttt | 1020 |
| cctcctaaca ctcgatatgg aggcaagtct cttgtttttc ctccaaagaa gccagcaccg | 1080 |
| ataggagaat tccagagtac agagccagaa cagagttgtg ctgatactcc agtgtttcta | 1140 |
| gctaagccac caattgggtt tttcacagat tatgaaattg gtccagttta tgagatggta | 1200 |
| attgcgctgc agaacaccac cacgaccagc cgctacctgc gagtcctccc gccttccacg | 1260 |
| ccatacttcg ctctgggact ggggatgttc ccaggaaaag gtggaatggt ggctcctgga | 1320 |
| atgacctgcc agtacattgt ccagtttttt cccgactgcc ttggggattt tgatgatttt | 1380 |
| attttagtgg agacccagtc agcccacaca cttctgatcc ccctgcaggc ccggaggccg | 1440 |
| ccccccgtgc tgacattgtc accggtgttg gactgtggtt actgcctcat tgggggagtc | 1500 |
| aagatgacca gattcatctg caaaaatgtg ggtttcagtg ttggcaggtt ctgcattatg | 1560 |
| cccaaaacaa gctggccacc actaagtttc aaggccattg caaccgtcgg ctttgttgaa | 1620 |

| | |
|---|---|
| caacctcctt ttggaatcct gccttcggtg tttgagctgg ccccgggaca tgctatatta | 1680 |
| gtggaggtct tgtttttccc aaagagccta ggaaaggcag agcagacctt catcatcatg | 1740 |
| tgcgacaact gccagataaa ggagctggtg accataggaa ttgggcagct gattgctttg | 1800 |
| gatctgatct atatttctgg tgaaaaaagc cagccagacc ctggagagct cacagactta | 1860 |
| acagcccagc acttcatacg atttgagcct gaaaaccttc ggtccacggc taggaagcag | 1920 |
| ctgattatta gaaatgctac gcacgtggag ctggccttct actggcagat catgaagccc | 1980 |
| aacctgcagc ccctcatgcc tggagaaacc ttcagcatgg acagcatcaa gtgctacccc | 2040 |
| gacaaggaga ctgccttctc catcatgccc agaaagggg ttctaagccc ccacacagac | 2100 |
| cacgagttca tcctgagctt ttctcctcat gagctgaggg attttcacag tgtgctccag | 2160 |
| atggtgctag aggaagtccc agagcctgta agttcagaag cggagagcct ggggcactcc | 2220 |
| tcctactctg tggatgatgt gattgtcctg gaaatcgagg tgaaaggctc agtagaacct | 2280 |
| ttccaggttc tcttagagcc atatgccctc atcatcccag gggagaacta cattgggata | 2340 |
| aatgtgaaga aggcttttaa gatgtggaac aacagcaagt cacccatcag atacctgtgg | 2400 |
| gggaagatca gcgactgcca catcattgaa gtggagcccg gcacagggt catagagccc | 2460 |
| agtgaggtcg gggattttga gttgaacttt actgggggtg tccctggccc cacaagccag | 2520 |
| gacctgctgt gtgaaatcga agactcgccc tcgccagtgg tgttacacat tgaggctgtc | 2580 |
| tttaagggc ctgccctcat catcaacgtc tcagcccttc agtttggtct gctccgcctg | 2640 |
| gggcagaaag ccacaaactc catccagatc cggaacgtca gccagctccc agccacatgg | 2700 |
| cgcatgaagg agagcccagt ctccctccag gaaaggcctg aggatgtgtc tccttcgac | 2760 |
| attgagcctt cgagtggcca gcttcactct ctgggggagt gcagggtgga catcaccttg | 2820 |
| gaggccctgc actgccagca tctggagacc gtcctggagc tggaggtgga aaatggtgcc | 2880 |
| tggagctacc ttcctgtgta tgctgaggta cagaagcccc atgtgtacct acagagcagc | 2940 |
| caggtggagg ttagaaatct ctacctgggt gtgcccacga agacaaccat cacacttatc | 3000 |
| aatggcacgc tcctgcctac ccagttccac tggggcaagc tcctcggaca ccaagcagaa | 3060 |
| ttctgcatgg tgacagtctc ccccaaacat ggcctgctgg gccaagtga ggagtgccag | 3120 |
| ctcaagttgg agttgactgc tcatacccag gaagagctga cccatctggc cctcccttgt | 3180 |
| cacgtgtcag gcatgaagaa gccactggtt ctaggcattt ctgggaagcc ccagggactg | 3240 |
| caagtggcca ttaccatctc taaggagagc tctgattgca gcacagagca gtggccaggc | 3300 |
| cacccaaagg agctccgcct ggactttggc tcagcggtgc cactgaggac ccgtgtgact | 3360 |
| cgccagctca ttctcaccaa tcgctcccca atacggaccc gtttctccct caagtttgag | 3420 |
| tatttcggga gccccaaaa cagcctgagc aaaaagacca gccttcccaa catgcctcct | 3480 |
| gccctgctaa agacagtgcg gatgcaagag cacctggcca agcgagagca gctggatttt | 3540 |
| atggagagca tgctatccca cgggaaagga gctgctttct ccctcacttt tcccagggc | 3600 |
| atgctggggc cctaccagca gctgtgcatt gacatcacag gctgtgccaa catgtggggc | 3660 |
| gagtactggg acaacctcat ctgcacggtg ggagacctgc tgccggaagt catcccagtg | 3720 |
| cacatggcag cggtgggctg ccccatcagc tccctgagga ccacctccta cactattgac | 3780 |
| caggcccaga aggaaccagc catgaggttc ggcacccagg tctccggagg agacacagtt | 3840 |
| acccgaaccc ttcgcctgaa taactccagc ccctgtgaca tccgcctgga ttgggagacc | 3900 |
| tatgttccag aagacaagga agaccggctg gtggagctgc tggtgtttta tgggccacct | 3960 |

```
ttcccgctgc gggaccaagc cgggaatgag cttgtgtgcc ctgataccc  tgagggtggc    4020 tgcctcctct ggtccccagg cccctccagt tcatcggaat tcagccatga aactgactca    4080
tcagttgagg gcagctccag tgccagcaat agggtggcac agaagctcat ctcagtcatc    4140
ctgcaggcac atgaggggt gccctccggc cacctgtact gtatcagccc caagcaggtg    4200
gtggtccctg ctgggggcag cagtaccatc tacatctcct tcacccctat ggtgctcagc    4260
cctgagatcc tgcacaaggt ggagtgtact ggctacgccc tgggtttcat gagcttggac    4320
agcaaggtgg aaagggagat tccagggaag aggcatcgcc tgcaggactt tgcggtggga    4380
cccctgaaac tggacctgca tagctacgtg aggcctgcac agctaagtgt ggagctggac    4440
tacggcggca gtatggaatt ccagtgccag gccagtgacc tcattcccga gcagccctgc    4500
tctggggtgc tgagtgagct ggtgaccacc caccacctga agctgaccaa cactacagag    4560
atcccacact acttccggct tatggtctcc aggcccttct ccgtttctca agatggggcg    4620
agccaggacc acagagctcc tggccctggc cagaagcagg agtgtgagga ggagacagcc    4680
tcagcggaca agcagctggt gctccaagca caggagaaca tgctggtgaa cgtgtccttc    4740
tcactctccc tggagctgct ctcctatcag aagctcccag ctgaccagac actgcctggg    4800
gtggacattc agcagagtgc gagtggagag agagagatgt gtttactca gaacctgctc    4860 ctggagtaca ccaaccagac cactcaggtg gtgcccctgc gggctgtggt ggccgtgcct    4920
gagctgcagc tctccaccag ctgggtggac tttgggacct gctttgtgag ccagcagcga    4980
gtccgggagg tctacctgat gaacctgagc gggtgccgaa gctactggac tatgctgatg    5040
ggccagcagg agccagccaa ggccgctgtg gccttcaggg tctccccaaa cagtgggctg    5100
ctagaagcac gatccgccaa tgcacccca acctccatcg ccttgcaggt tttcttcact    5160
gccaggagta gtgagctgta cgagtccacg atggtggtgg aaggtgtgct cggtgagaag    5220
tcctgcaccc tgcggctccg gggccaaggc tcctatgatg agagatacat gttgcctcac    5280
cagccctgag gctccgcccc agccctcagc cccaggcccc agctggagaa aaaacattgc    5340
ccagggatta ggagcagctc ttcagcacaa agacacagac ttggggacct ggggacctct    5400
gggcagctcc tggaatggaa gaaccccctt ccacaatggt ctcagccctag ccctcatga    5460 tatgtcctca gagctaacat aaaggacagg ccacaccaca gcagagacca ccacattgag    5520
atcactactc agtgcatagc gaagaccagt atggcaaaat tagtcttgga aaaaaaccac    5580
agccactaag ataaattcat gcacttttac tatgcccatt gcacttctca tccatggatt    5640
tgccttgcct taagaattaa ccatggcctt gtggcctggg tgaccaggc tgcttttatc    5700 ttgcacagct aaagagggtc tgatgggtgg ctcaacaccc cacccactcc tataccatgt    5760
catcagtgtt cacattttcc aaatgagttg aagtgccttg atctgtccac tgccaccacc    5820
accagtgctg agttttccca tgtggttttg cttttgtggt gttactgcct tgctgctaga    5880
gcagcaggac tgtctgcgta cgcctccag cctgggacct cactcagttc ccagggtatt    5940
caaagacggc agcggctccc attccagtcc cgatgcacat ggacaccact ccgtatgccc    6000
tgtgaaaaca aaacttaatt ggctgggcaa aggcacccac caaattacct ccagaccagg    6060
ctgacccaga aggacgtcat ggacaagtag gatgcaaaac catcagacca gatctgtggg    6120
caagcggtac cctggcctcc cacttgggca cacacggt gacagatgcc cactgcaggc    6180
tagtatccct ttcaaggctg gcccttaagg aaaacaggga tcatgcccct acatcctaag    6240
ttcagggtgt ttctgtgtgc atgttcccct ccccagggat cgatcataat cccaaaagac    6300
acaatcccaa acacaatcat cccaaatgtt gaaatcctgg aagaacaaaa tccctaaagt    6360
```

```
ctaaaatcct gaaaatcaca atcctaaaag atcaaaatcc tgaaaatata attctggaaa    6420
aaataa                                                                6426

<210> SEQ ID NO 3
<211> LENGTH: 5268
<212> TYPE: DNA
<213> ORGANISM: Homo sapiens

<400> SEQUENCE: 3
atggagacca ggagctccaa aacgcggagg tctttagcgt cccggaccaa cgagtgccag      60
gggacaatgt gggcgccaac ttcgccacca gccgggtcca gcagcccag ccagcccacc     120 tggaagtcct ccttgtattc ctccctcgcc tactctgagg ccttccacta cagcttcgca     180
gcccggcccc gccgcctcac gcagcttgcg ctggcgcagc gtcccgagcc tcagctgctt     240
cgtctgcgcc cctcctcgct gcgcacccaa gatatctcgc acttgctcac cggcgtcttc     300
cgcaacttgt actcagccga ggtcatcggc gacgaagtga cgcaagctt gatcaaggcc     360 cgcggcagcg agaatgagcg ccacgaggag ttcgtggacc agctgcagca gattcgggag     420
ctctataagc agcggctgga tgagtttgaa atgttggaga acatatcac tcaggcccaa     480 gcacgggcta ttgcggaaaa tgagcgggtc atgagccagg ctggagtaca ggacctcgag     540
agccttgtca ggttgcctcc agtgaagagt gtctccagat ggtgtataga cagcgagttg     600
ctacggaaac atcatttgat ctccccagaa gattactaca ccgatacagt gccgtttcac     660
tctgcaccta aaggcatctc cctacctgga tgttcaaaac tgacatttag ctgtgagaag     720
cgttccgtcc agaagaaaga gctgaacaag aagcttgaag attcatgcag gaagaagctt     780
gctgagttcg aagatgagtt agaccacact gtggacagcc tgacatggaa tttaactcct     840
aaggccaaag aaaggaccag agaacctctc aagaaagcaa gtcaaccaag gaataaaaac     900
tggatgaacc acttacgtgt gccacagaga gagctagaca gacttctgct tgccagaatg     960
gagagtcgga accacttcct aaaaaaatccc cgttttttc ctcctaacac tcgatatgga    1020
ggcaagtctc ttgttttttcc tccaaagaag ccagcaccga taggagaatt ccagagtaca    1080
gagccagaac agagttgtgc tgatactcca gtgtttctag ctaagccacc aattgggttt    1140
ttcacagatt atgaaattgg tccagttat gagatggtaa ttgcgctgca gaacaccacc    1200
acgaccagcc gctacctgcg agtcctcccg ccttccacgc catacttcgc tctgggactg    1260
gggatgttcc caggaaaagg tggaatggtg gctcctggaa tgacctgcca gtacattgtc    1320 cagtttttc ccgactgcct tggggatttt gatgatttta ttttagtgga gacccagtca    1380
gcccacacac ttctgatccc cctgcaggcc cggaggccgc cccccgtgct gacattgtca    1440
ccggtgttgg actgtggtta ctgcctcatt gggggagtca agatgaccag attcatctgc    1500
aaaaatgtgg gtttcagtgt tggcaggttc tgcattatgc ccaaaacaag ctggccacca    1560
ctaagtttca aggccattgc aaccgtcggc tttgttgaac aacctccttt tggaatcctg    1620
ccttcggtgt ttgagctggc cccgggacat gctatattag tggaggtctt gtttcccca    1680 aagagcctag gaaaggcaga gcagaccttc atcatcatgt gcgacaactg ccagataaag    1740
gagctggtga ccataggaat tgggcagctg attgctttgg atctgatcta tatttctggt    1800
gaaaaaagcc agccagaccc tggagagctc acagacttaa cagcccagca cttcatacga    1860
tttgagcctg aaaaccttcg gtccacggct aggaagcagc tgattattag aaatgctacg    1920
cacgtggagc tggccttcta ctggcagatc atgaagccca acctgcagcc cctcatgcct    1980
```

```
ggagaaacct tcagcatgga cagcatcaag tgctacccccg acaaggagac tgccttctcc    2040
atcatgccca gaaaggggt tctaagcccc cacacagacc acgagttcat cctgagcttt      2100
tctcctcatg agctgaggga ttttcacagt gtgctccaga tggtgctaga ggaagtccca    2160
gagcctgtaa gttcagaagc ggagagcctg gggcactcct cctactctgt ggatgatgtg    2220
attgtcctgg aaatcgaggt gaaaggctca gtagaacctt tccaggttct cttagagcca    2280
tatgccctca tcatcccagg ggagaactac attgggataa atgtgaagaa ggcttttaag    2340
atgtggaaca acagcaagtc acccatcaga tacctgtggg ggaagatcag cgactgccac    2400
atcattgaag tggagcccgg cacagggggtc atagagccca gtgaggtcgg ggattttgag    2460 ttgaactttta ctgggggtgt ccctggcccc acaagccagg acctgctgtg tgaaatcgaa    2520
gactcgccct cgccagtggt gttacacatt gaggctgtct ttaaggggcc tgccctcatc    2580
atcaacgtct cagcccttca gtttggtctg ctccgcctgg ggcagaaagc cacaaactcc    2640
atccagatcc ggaacgtcag ccagctccca gccacatggc gcatgaagga gagcccagtc    2700
tccctccagg aaaggcctga ggatgtgtct cccttcgaca ttgagccttc gagtggccag    2760
cttcactctc tgggggagtg cagggtggac atcaccttgg aggccctgca ctgccagcat    2820
ctggagaccg tcctggagct ggaggtggaa aatggtgcct ggagctacct tcctgtgtat    2880
gctgaggtac agaagcccca tgtgtaccta cagagcagcc aggtggaggt tagaaatctc    2940
tacctgggtg tgcccacgaa gacaaccatc acacttatca atggcacgct cctgcctacc    3000
cagttccact ggggcaagct cctcggacac caagcagaat ctgcatggt gacagtctcc    3060 cccaaacatg gcctgctggg cccaagtgag gagtgccagc tcaagttgga gttgactgct    3120
catacccagg aagagctgac ccatctggcc ctcccttgtc acgtgtcagg catgaagaag    3180
ccactggttc taggcatttc tgggaagccc cagggactgc aagtggccat taccatctct    3240
aaggagagct ctgattgcag cacagagcag tggccaggcc acccaaagga gctccgcctg    3300
gactttggct cagcggtgcc actgaggacc cgtgtgactc gccagctcat tctcaccaat    3360
cgctccccaa tacggacccg tttctcccctc aagtttgagt atttcgggag ccccccaaaac   3420 agcctgagca aaaagaccag ccttcccaac atgcctcctg ccctgctaaa gacagtgcgg    3480
atgcaagagc acctggccaa gcgagagcag ctggattta tggagagcat gctatcccac    3540
gggaaaggag ctgctttctt ccctcacttt tcccagggca tgctggggcc ctaccagcag    3600
ctgtgcattg acatcacagg ctgtgccaac atgtggggcg agtactggga caacctcatc    3660
tgcacggtgg gagacctgct gccggaagtc atcccagtgc acatggcagc ggtgggctgc    3720
cccatcagct ccctgaggac cacctcctac actattgacc aggcccagaa ggaaccagcc    3780
atgaggttcg gcacccaggt ctccggagga gacacagtta cccgaacccct tcgcctgaat    3840 aactccagcc cctgtgacat ccgcctggat tgggagacct atgttccaga agacaaggaa    3900
gaccggctgg tggagctgct ggtgttttat gggccacctt tcccgctgcg ggaccaagcc    3960
gggaatgagc ttgtgtgccc tgatacccct gagggtggcc gcctcctctg gtccccaggc    4020
ccctccagtt catcggaatt cagccatgaa actgactcat cagttgaggg cagctccagt    4080
gccagcaata gggtggcaca gaagctcatc tcagtcatcc tgcaggcaca tgaggggggtg   4140 ccctccggcc acctgtactg tatcagcccc aagcaggtgg tggtccctgc tgggggcagc    4200
agtaccatct acatctcctt cacccctatg gtgctcagcc ctgagatcct gcacaaggtg    4260
gagtgtactg gctacgccct gggttttcatg agcttggaca gcaaggtgga aagggagatt    4320
ccagggaaga ggcatcgcct gcaggacttt gcggtgggac ccctgaaact ggacctgcat    4380
```

-continued

```
agctacgtga ggcctgcaca gctaagtgtg gagctggact acggcggcag tatggaattc   4440
cagtgccagg ccagtgacct cattcccgag cagccctgct ctggggtgct gagtgagctg   4500
gtgaccaccc accacctgaa gctgaccaac actacagaga tcccacacta cttccggctt   4560
atggtctcca ggcccttctc cgtttctcaa gatggggcga gccaggacca cagagctcct   4620
ggccctggcc agaagcagga gtgtgaggag gagacagcct cagcggacaa gcagctggtg   4680
ctccaagcac aggagaacat gctggtgaac gtgtccttct cactctccct ggagctgctc   4740
tcctatcaga gctcccagc tgaccagaca ctgcctgggg tggacattca gcagagtgcg    4800
agtggagaga gagagatggt gtttactcag aacctgctcc tggagtacac caaccagacc   4860
actcaggtgg tgcccctgcg ggctgtggtg gccgtgcctg agctgcagct ctccaccagc   4920
tgggtggact ttgggacctg ctttgtgagc cagcagcgag tccgggaggt ctacctgatg   4980
aacctgagcg ggtgccgaag ctactggact atgctgatgg gccagcagga gccagccaag   5040
gccgctgtgg ccttcagggt ctccccaaac agtgggctgc tagaagcacg atccgccaat   5100
gcacccccaa cctccatcgc cttgcaggtt ttcttcactg ccaggagtag tgagctgtac   5160
gagtccacga tggtggtgga aggtgtgctc ggtgagaagt cctgcaccct gcggctccgg   5220
ggccaaggct cctatgatga gagatacatg ttgcctcacc agccctga               5268
```

<210> SEQ ID NO 4
<211> LENGTH: 1755
<212> TYPE: PRT
<213> ORGANISM: Homo sapiens

<400> SEQUENCE: 4

Met Glu Thr Arg Ser Ser Lys Thr Arg Arg Ser Leu Ala Ser Arg Thr
1               5                   10                  15

Asn Glu Cys Gln Gly Thr Met Trp Ala Pro Thr Ser Pro Pro Ala Gly
                20                  25                  30

Ser Ser Ser Pro Ser Gln Pro Thr Trp Lys Ser Ser Leu Tyr Ser Ser
            35                  40                  45

Leu Ala Tyr Ser Glu Ala Phe His Tyr Ser Phe Ala Ala Arg Pro Arg
        50                  55                  60

Arg Leu Thr Gln Leu Ala Leu Ala Gln Arg Pro Glu Pro Gln Leu Leu
65                  70                  75                  80

Arg Leu Arg Pro Ser Ser Leu Arg Thr Gln Asp Ile Ser His Leu Leu
                85                  90                  95

Thr Gly Val Phe Arg Asn Leu Tyr Ser Ala Glu Val Ile Gly Asp Glu
            100                 105                 110

Val Ser Ala Ser Leu Ile Lys Ala Arg Gly Ser Glu Asn Glu Arg His
        115                 120                 125

Glu Glu Phe Val Asp Gln Leu Gln Gln Ile Arg Glu Leu Tyr Lys Gln
    130                 135                 140

Arg Leu Asp Glu Phe Glu Met Leu Glu Arg His Ile Thr Gln Ala Gln
145                 150                 155                 160

Ala Arg Ala Ile Ala Glu Asn Glu Arg Val Met Ser Gln Ala Gly Val
                165                 170                 175

Gln Asp Leu Glu Ser Leu Val Arg Leu Pro Val Lys Ser Val Ser
            180                 185                 190

Arg Trp Cys Ile Asp Ser Glu Leu Leu Arg Lys His His Leu Ile Ser
        195                 200                 205

Pro Glu Asp Tyr Tyr Thr Asp Thr Val Pro Phe His Ser Ala Pro Lys

```
            210                 215                 220
Gly Ile Ser Leu Pro Gly Cys Ser Lys Leu Thr Phe Ser Cys Glu Lys
225                 230                 235                 240

Arg Ser Val Gln Lys Lys Glu Leu Asn Lys Leu Glu Asp Ser Cys
                245                 250                 255

Arg Lys Lys Leu Ala Glu Phe Glu Asp Glu Leu Asp His Thr Val Asp
            260                 265                 270

Ser Leu Thr Trp Asn Leu Thr Pro Lys Ala Lys Glu Arg Thr Arg Glu
            275                 280                 285

Pro Leu Lys Lys Ala Ser Gln Pro Arg Asn Lys Asn Trp Met Asn His
            290                 295                 300

Leu Arg Val Pro Gln Arg Glu Leu Asp Arg Leu Leu Ala Arg Met
305                 310                 315                 320

Glu Ser Arg Asn His Phe Leu Lys Asn Pro Arg Phe Phe Pro Pro Asn
                325                 330                 335

Thr Arg Tyr Gly Gly Lys Ser Leu Val Phe Pro Pro Lys Lys Pro Ala
            340                 345                 350

Pro Ile Gly Glu Phe Gln Ser Thr Glu Pro Glu Gln Ser Cys Ala Asp
            355                 360                 365

Thr Pro Val Phe Leu Ala Lys Pro Pro Ile Gly Phe Phe Thr Asp Tyr
            370                 375                 380

Glu Ile Gly Pro Val Tyr Glu Met Val Ile Ala Leu Gln Asn Thr Thr
385                 390                 395                 400

Thr Thr Ser Arg Tyr Leu Arg Val Leu Pro Pro Ser Thr Pro Tyr Phe
                405                 410                 415

Ala Leu Gly Leu Gly Met Phe Pro Gly Lys Gly Gly Met Val Ala Pro
            420                 425                 430

Gly Met Thr Cys Gln Tyr Ile Val Gln Phe Phe Pro Asp Cys Leu Gly
            435                 440                 445

Asp Phe Asp Asp Phe Ile Leu Val Glu Thr Gln Ser Ala His Thr Leu
            450                 455                 460

Leu Ile Pro Leu Gln Ala Arg Arg Pro Pro Val Leu Thr Leu Ser
465                 470                 475                 480

Pro Val Leu Asp Cys Gly Tyr Cys Leu Ile Gly Gly Val Lys Met Thr
                485                 490                 495

Arg Phe Ile Cys Lys Asn Val Gly Phe Ser Val Gly Arg Phe Cys Ile
                500                 505                 510

Met Pro Lys Thr Ser Trp Pro Pro Leu Ser Phe Lys Ala Ile Ala Thr
            515                 520                 525

Val Gly Phe Val Glu Gln Pro Pro Phe Gly Ile Leu Pro Ser Val Phe
            530                 535                 540

Glu Leu Ala Pro Gly His Ala Ile Leu Val Glu Val Leu Phe Ser Pro
545                 550                 555                 560

Lys Ser Leu Gly Lys Ala Glu Gln Thr Phe Ile Ile Met Cys Asp Asn
                565                 570                 575

Cys Gln Ile Lys Glu Leu Val Thr Ile Gly Ile Gly Gln Leu Ile Ala
                580                 585                 590

Leu Asp Leu Ile Tyr Ile Ser Gly Glu Lys Ser Gln Pro Asp Pro Gly
                595                 600                 605

Glu Leu Thr Asp Leu Thr Ala Gln His Phe Ile Arg Phe Glu Pro Glu
            610                 615                 620

Asn Leu Arg Ser Thr Ala Arg Lys Gln Leu Ile Ile Arg Asn Ala Thr
625                 630                 635                 640
```

-continued

His Val Glu Leu Ala Phe Tyr Trp Gln Ile Met Lys Pro Asn Leu Gln
                645                 650                 655

Pro Leu Met Pro Gly Glu Thr Phe Ser Met Asp Ser Ile Lys Cys Tyr
            660                 665                 670

Pro Asp Lys Glu Thr Ala Phe Ser Ile Met Pro Arg Lys Gly Val Leu
        675                 680                 685

Ser Pro His Thr Asp His Glu Phe Ile Leu Ser Phe Ser Pro His Glu
    690                 695                 700

Leu Arg Asp Phe His Ser Val Leu Gln Met Val Leu Glu Glu Val Pro
705                 710                 715                 720

Glu Pro Val Ser Ser Glu Ala Glu Ser Leu Gly His Ser Ser Tyr Ser
                725                 730                 735

Val Asp Asp Val Ile Val Leu Glu Ile Glu Val Lys Gly Ser Val Glu
            740                 745                 750

Pro Phe Gln Val Leu Leu Glu Pro Tyr Ala Leu Ile Ile Pro Gly Glu
        755                 760                 765

Asn Tyr Ile Gly Ile Asn Val Lys Lys Ala Phe Lys Met Trp Asn Asn
    770                 775                 780

Ser Lys Ser Pro Ile Arg Tyr Leu Trp Gly Lys Ile Ser Asp Cys His
785                 790                 795                 800

Ile Ile Glu Val Glu Pro Gly Thr Gly Val Ile Glu Pro Ser Glu Val
                805                 810                 815

Gly Asp Phe Glu Leu Asn Phe Thr Gly Gly Val Pro Gly Pro Thr Ser
            820                 825                 830

Gln Asp Leu Leu Cys Glu Ile Glu Asp Ser Pro Ser Pro Val Val Leu
        835                 840                 845

His Ile Glu Ala Val Phe Lys Gly Pro Ala Leu Ile Ile Asn Val Ser
    850                 855                 860

Ala Leu Gln Phe Gly Leu Leu Arg Leu Gly Gln Lys Ala Thr Asn Ser
865                 870                 875                 880

Ile Gln Ile Arg Asn Val Ser Gln Leu Pro Ala Thr Trp Arg Met Lys
                885                 890                 895

Glu Ser Pro Val Ser Leu Gln Glu Arg Pro Glu Asp Val Ser Pro Phe
            900                 905                 910

Asp Ile Glu Pro Ser Ser Gly Gln Leu His Ser Leu Gly Glu Cys Arg
        915                 920                 925

Val Asp Ile Thr Leu Glu Ala Leu His Cys Gln His Leu Glu Thr Val
    930                 935                 940

Leu Glu Leu Glu Val Glu Asn Gly Ala Trp Ser Tyr Leu Pro Val Tyr
945                 950                 955                 960

Ala Glu Val Gln Lys Pro His Val Tyr Leu Gln Ser Ser Gln Val Glu
                965                 970                 975

Val Arg Asn Leu Tyr Leu Gly Val Pro Thr Lys Thr Thr Ile Thr Leu
            980                 985                 990

Ile Asn Gly Thr Leu Leu Pro Thr Gln Phe His Trp Gly Lys Leu Leu
        995                 1000                1005

Gly His Gln Ala Glu Phe Cys Met Val Thr Val Ser Pro Lys His
    1010                1015                1020

Gly Leu Leu Gly Pro Ser Glu Glu Cys Gln Leu Lys Leu Glu Leu
    1025                1030                1035

Thr Ala His Thr Gln Glu Glu Leu Thr His Leu Ala Leu Pro Cys
    1040                1045                1050

-continued

His Val Ser Gly Met Lys Lys Pro Leu Val Leu Gly Ile Ser Gly
1055                1060                1065

Lys Pro Gln Gly Leu Gln Val Ala Ile Thr Ile Ser Lys Glu Ser
1070                1075                1080

Ser Asp Cys Ser Thr Glu Gln Trp Pro Gly His Pro Lys Glu Leu
1085                1090                1095

Arg Leu Asp Phe Gly Ser Ala Val Pro Leu Arg Thr Arg Val Thr
1100                1105                1110

Arg Gln Leu Ile Leu Thr Asn Arg Ser Pro Ile Arg Thr Arg Phe
1115                1120                1125

Ser Leu Lys Phe Glu Tyr Phe Gly Ser Pro Gln Asn Ser Leu Ser
1130                1135                1140

Lys Lys Thr Ser Leu Pro Asn Met Pro Pro Ala Leu Leu Lys Thr
1145                1150                1155

Val Arg Met Gln Glu His Leu Ala Lys Arg Glu Gln Leu Asp Phe
1160                1165                1170

Met Glu Ser Met Leu Ser His Gly Lys Gly Ala Ala Phe Phe Pro
1175                1180                1185

His Phe Ser Gln Gly Met Leu Gly Pro Tyr Gln Gln Leu Cys Ile
1190                1195                1200

Asp Ile Thr Gly Cys Ala Asn Met Trp Gly Glu Tyr Trp Asp Asn
1205                1210                1215

Leu Ile Cys Thr Val Gly Asp Leu Leu Pro Glu Val Ile Pro Val
1220                1225                1230

His Met Ala Ala Val Gly Cys Pro Ile Ser Ser Leu Arg Thr Thr
1235                1240                1245

Ser Tyr Thr Ile Asp Gln Ala Gln Lys Glu Pro Ala Met Arg Phe
1250                1255                1260

Gly Thr Gln Val Ser Gly Gly Asp Thr Val Thr Arg Thr Leu Arg
1265                1270                1275

Leu Asn Asn Ser Ser Pro Cys Asp Ile Arg Leu Asp Trp Glu Thr
1280                1285                1290

Tyr Val Pro Glu Asp Lys Glu Asp Arg Leu Val Glu Leu Leu Val
1295                1300                1305

Phe Tyr Gly Pro Pro Phe Pro Leu Arg Asp Gln Ala Gly Asn Glu
1310                1315                1320

Leu Val Cys Pro Asp Thr Pro Glu Gly Gly Cys Leu Leu Trp Ser
1325                1330                1335

Pro Gly Pro Ser Ser Ser Ser Glu Phe Ser His Glu Thr Asp Ser
1340                1345                1350

Ser Val Glu Gly Ser Ser Ser Ala Ser Asn Arg Val Ala Gln Lys
1355                1360                1365

Leu Ile Ser Val Ile Leu Gln Ala His Glu Gly Val Pro Ser Gly
1370                1375                1380

His Leu Tyr Cys Ile Ser Pro Lys Gln Val Val Pro Ala Gly
1385                1390                1395

Gly Ser Ser Thr Ile Tyr Ile Ser Phe Thr Pro Met Val Leu Ser
1400                1405                1410

Pro Glu Ile Leu His Lys Val Glu Cys Thr Gly Tyr Ala Leu Gly
1415                1420                1425

Phe Met Ser Leu Asp Ser Lys Val Glu Arg Glu Ile Pro Gly Lys
1430                1435                1440

Arg His Arg Leu Gln Asp Phe Ala Val Gly Pro Leu Lys Leu Asp

```
               1445                1450                1455

Leu His Ser Tyr Val Arg Pro Ala Gln Leu Ser Val Glu Leu Asp
        1460                1465                1470

Tyr Gly Gly Ser Met Glu Phe Gln Cys Gln Ala Ser Asp Leu Ile
    1475                1480                1485

Pro Glu Gln Pro Cys Ser Gly Val Leu Ser Glu Leu Val Thr Thr
1490                1495                1500

His His Leu Lys Leu Thr Asn Thr Thr Glu Ile Pro His Tyr Phe
    1505                1510                1515

Arg Leu Met Val Ser Arg Pro Phe Ser Val Ser Gln Asp Gly Ala
    1520                1525                1530

Ser Gln Asp His Arg Ala Pro Gly Pro Gly Gln Lys Gln Glu Cys
    1535                1540                1545

Glu Glu Glu Thr Ala Ser Ala Asp Lys Gln Leu Val Leu Gln Ala
    1550                1555                1560

Gln Glu Asn Met Leu Val Asn Val Ser Phe Ser Leu Ser Leu Glu
    1565                1570                1575

Leu Leu Ser Tyr Gln Lys Leu Pro Ala Asp Gln Thr Leu Pro Gly
    1580                1585                1590

Val Asp Ile Gln Gln Ser Ala Ser Gly Glu Arg Glu Met Val Phe
    1595                1600                1605

Thr Gln Asn Leu Leu Leu Glu Tyr Thr Asn Gln Thr Thr Gln Val
    1610                1615                1620

Val Pro Leu Arg Ala Val Val Ala Val Pro Glu Leu Gln Leu Ser
    1625                1630                1635

Thr Ser Trp Val Asp Phe Gly Thr Cys Phe Val Ser Gln Gln Arg
    1640                1645                1650

Val Arg Glu Val Tyr Leu Met Asn Leu Ser Gly Cys Arg Ser Tyr
    1655                1660                1665

Trp Thr Met Leu Met Gly Gln Gln Glu Pro Ala Lys Ala Ala Val
    1670                1675                1680

Ala Phe Arg Val Ser Pro Asn Ser Gly Leu Leu Glu Ala Arg Ser
    1685                1690                1695

Ala Asn Ala Pro Pro Thr Ser Ile Ala Leu Gln Val Phe Phe Thr
    1700                1705                1710

Ala Arg Ser Ser Glu Leu Tyr Glu Ser Thr Met Val Val Glu Gly
    1715                1720                1725

Val Leu Gly Glu Lys Ser Cys Thr Leu Arg Leu Arg Gly Gln Gly
    1730                1735                1740

Ser Tyr Asp Glu Arg Tyr Met Leu Pro His Gln Pro
    1745                1750                1755

<210> SEQ ID NO 5
<211> LENGTH: 107
<212> TYPE: DNA
<213> ORGANISM: Homo sapiens

<400> SEQUENCE: 5
gcttcgcagc ccggccccgc cgcctcacgc agcttgcgct ggcgcagcgt cccgagcctc    60
agctgcttcg tctgcgcccc tcctcgctgc gcacccaaga tatctcg                107

<210> SEQ ID NO 6
<211> LENGTH: 638
<212> TYPE: DNA
<213> ORGANISM: Homo sapiens
```

<400> SEQUENCE: 6

```
gaagacacaa atgtttacaa tgaccacagc gatgacggga tccgagagaa aggcaaggcg    60
gaagggtga ggccggaagc cgaagtgccg cagggagtta gcggcgtctc ggttgccatg    120
gagaccagga gctccaaaac gcggaggtct ttagcgtccc ggaccaacga gtgccagggg   180
acaatgtggg cgccaacttc gccaccagcc gggtccagca gccccagcca gcccacctgg   240
aagtcctcct tgtattcctc cctcgcctac tctgaggcct tccactacag cttcgcagcc   300
cggccccgcc gcctcacgca gcttgcgctg gcgcagcgtc ccgagcctca gctgcttcgt   360
ctgcgcccct cctcgctgcg cacccaagat atctcgcact tgctcaccgg cgtcttccgc   420
aacttgtact cagccgaggt catcggcgac gaagtgagcg caagcttgat caaggcccgc   480
ggcagcgaga atgagcgcca cgaggagttc gtggaccagc tgcagcaggt aacgtggcgg   540
tggcgtcgcg tctgcggacg gtgccggggt ctcagcgctc ggcacgcgtc agcacctgcc   600
aggtgccagg cgctgttcca ggatctgggg ctgcagtt                           638
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gly Gly Gly Gly
1

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 8

```
ttcctccctc gcctactc                                                   18
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 9

```
aaactcatcc agccgctg                                                   18
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10

```
caaagaagcc agcaccgata                                                 20
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcagtaacca cagtccaaca                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgggacatg ctatattagt                                                    20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggctctggg acttcctc                                                      18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttcctccctc gcctactc                                                      18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caactgcagc cccagatc                                                      18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgcctcttgc ctctcctg                                                      18

<210> SEQ ID NO 17
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcagcaatca gcacagacc                                                  19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaccgagacg ccgctaac                                                   18

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccgccacca tggagaccag ggc                                             23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgaaaaacc caattggtgg                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agtgtttcta gctaagccac                                                 20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gagggcatat ggctctaag                                                  19

<210> SEQ ID NO 23
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttagagcca tatgccctc                                                    19

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccatgtgca ctgggatg                                                     18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catcccagtg cacatggc                                                     18

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctcgagcgg agcctcaggg                                                   20

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cttgctcacc ggcgtctt                                                     18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caactgcagc cccagatc                                                     18

<210> SEQ ID NO 29
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 29
aaactcatcc agccgctg                                                 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttcctccctc gcctactc                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagacgccgg tgagcaag                                                 18

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgtgttggc gtacaggtc                                                19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtggagactg tctcccgg                                                 18

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtttcgtagt tcggtttcgt c                                             21

<210> SEQ ID NO 35
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 35
cgaaatatct aaatacgca acg                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tagttttgta gtttggtttt gtt                                             23

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acaaaatatc ttaaatacac aaca                                            24

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagatataa atgtttataa tgatt                                           25

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aactacaacc ccaaatccta a                                               21

<210> SEQ ID NO 40
<211> LENGTH: 10
<212> TYPE: PRT
<213> ORGANISM: Homo sapiens

<400> SEQUENCE: 40

Phe Arg Asn Leu Tyr Ser Ala Glu Val Ile
1               5                   10

<210> SEQ ID NO 41
<211> LENGTH: 10
<212> TYPE: PRT
<213> ORGANISM: Homo sapiens

<400> SEQUENCE: 41
```

```
Met Thr Cys Gln Tyr Ile Val Gln Phe Phe
1               5                   10
```

<210> SEQ ID NO 42
<211> LENGTH: 10
<212> TYPE: PRT
<213> ORGANISM: Homo sapiens

<400> SEQUENCE: 42

```
Leu Leu Leu Glu Tyr Thr Asn Gln Thr Thr
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Phe Arg Asn Leu Gly Gly Gly Gly Val Ile
1               5                   10
```

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Met Thr Cys Gln Gly Gly Gly Gly Phe Phe
1               5                   10
```

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Leu Leu Leu Glu Gly Gly Gly Gly Thr Thr
1               5                   10
```

<210> SEQ ID NO 46
<211> LENGTH: 24
<212> TYPE: DNA
<213> ORGANISM: Homo sapiens

<400> SEQUENCE: 46

```
gctctgggac tggtgtcacc ggtg                                          24
```

<210> SEQ ID NO 47
<211> LENGTH: 8
<212> TYPE: PRT
<213> ORGANISM: Homo sapiens

<400> SEQUENCE: 47

```
Ala Leu Gly Leu Gly Ser Pro Val
1               5
```

<210> SEQ ID NO 48

```
<211> LENGTH: 27
<212> TYPE: DNA
<213> ORGANISM: Homo sapiens

<400> SEQUENCE: 48
atattagtgg aggaattggg cagctga                                              27

<210> SEQ ID NO 49
<211> LENGTH: 23
<212> TYPE: DNA
<213> ORGANISM: Homo sapiens

<400> SEQUENCE: 49
ttagaaatgc tacctgaggg att                                                  23

<210> SEQ ID NO 50
<211> LENGTH: 8
<212> TYPE: PRT
<213> ORGANISM: Homo sapiens

<400> SEQUENCE: 50

Ile Leu Val Glu Glu Leu Gly Ser
1               5

<210> SEQ ID NO 51
<211> LENGTH: 36
<212> TYPE: DNA
<213> ORGANISM: Homo sapiens

<400> SEQUENCE: 51
ctgggactgg gccattgcaa ccgtcggctt tgttga                                    36

<210> SEQ ID NO 52
<211> LENGTH: 15
<212> TYPE: DNA
<213> ORGANISM: Homo sapiens

<400> SEQUENCE: 52
agtggaggaa ttggg                                                           15

<210> SEQ ID NO 53
<211> LENGTH: 23
<212> TYPE: DNA
<213> ORGANISM: Homo sapiens

<400> SEQUENCE: 53
ttagaaatgc tacctgaggg att                                                  23

<210> SEQ ID NO 54
<211> LENGTH: 11
<212> TYPE: PRT
<213> ORGANISM: Homo sapiens

<400> SEQUENCE: 54

Leu Gly Leu Gly His Cys Asn Arg Arg Leu Cys
1               5                   10
```

BIOMARKER DLEC1 FOR CANCER

This application claims priority to U.S. Provisional Patent Application No. 62/714,506, filed Aug. 3, 2018, the contents of which are hereby incorporated by reference in the entirety for all purposes.

SEQUENCE LISTING

The instant application contains a Sequence Listing which has been submitted electronically in ASCII format and is hereby incorporated by reference in its entirety. Said ASCII copy, created on Nov. 20, 2019, is named 080015-1148963-024410US_SL.txt and is 153,945 bytes in size.

BACKGROUND OF THE INVENTION

Cancer-related causes are among the top reasons of death in developed countries. In the US alone, the number of new cases of cancer of any site averages about 450 per 100,000 men and women per year, and the number of deaths averages about 170 per 100,000 men and women per year. Cancer is a disease with a high mortality rate: while about 1,700,000 newly diagnosed cancer cases are expected each year, over 600,000 deaths annually are attributable to various types of cancer. Based on data from recent years, it is estimated that over 38% of men and women will be diagnosed with cancer at some point during their lifetime.

Esophageal cancer, for example, is the 8$^{th}$ most common cancer world-wide with nearly 500,000 new cases diagnosed each year. Globally, it is responsible for approximately 400,000 deaths annually. While its incidence varies significantly from country to country, nearly half of esophageal cancer consistently occurs in China. Due to its lack of early symptoms and therefore often late diagnosis, this disease has a grim prognosis with only 13-18% patient is surviving beyond 5 years after the initial diagnosis.

Because of the prevalence of cancer and its enormous social and economical impact globally, there exists an urgent need for new and more effective methods to diagnose, monitor, and treat cancer. This invention fulfills this and other related needs.

BRIEF SUMMARY OF THE INVENTION

The present inventors have identified DLEC1 as a novel tumor suppressor and diagnostic/prognostic marker for various types of human cancer, especially esophageal cancer such as esophageal squamous cell carcinoma (ESCC). More specifically, the inventors show that, compared with normal individuals, CpG islands of DLEC1 gene are hypermethylated in biological samples of cancer tissues taken from cancer patients. Such hypermethylation leads to DLEC1 silencing at both mRNA and protein levels. Re-expression of DLEC1 inhibits cancer cell growth and induces programmed cell death. Protein/mRNA expression level of DLEC1 and promoter methylation level of DLEC1 genetic sequence closely correlate with the survival of cancer patients and are therefore also useful as prognostic markers for cancer.

Thus, in the first aspect, the present invention provides a method for (1) assessing risk for later developing esophageal squamous cell carcinoma (ESCC) in a subject who may not have exhibited any symptoms of ESCC or (2) diagnosing ESCC in a patient who has manifested one or more clinical symptoms suspected of ESCC. The method includes these steps: (a) measuring expression level of DLEC1 in a sample taken from the subject; (b) comparing the expression level obtained in step (a) with a standard control; and (c) determining the subject, who has a reduced DLEC1 expression level compared with the standard control, as having an increased risk for ESCC.

In some embodiments, the sample used for practicing the method is a esophageal epithelial tissue sample. In some embodiments, the expression level of DLEC1 is DLEC1 protein level. In some embodiments, the expression level of DLEC1 is DLEC1 mRNA level. In some embodiments, step (a) comprises an immunoassay using an antibody that specifically binds the DLEC1 protein; or step (a) may comprise an amplification reaction, such as a polymerase chain reaction (PCR), especially a reverse transcriptase-PCR (RT-PCR). In some embodiments, step (a) comprises a polynucleotide hybridization assay, such as a Southern Blot analysis or Northern Blot analysis, or an in situ hybridization assay. In some embodiments, when the subject is indicated as having an increased risk for ESCC, the method is further includes repeating step (a) at a later time using the sample type of sample from the subject, wherein an increase in the expression level of DLEC1 at the later time as compared to the amount from the original step (a) indicates a lessened risk of ESCC, and a decrease indicates a heightened risk for ESCC.

In the second aspect, the present invention provides a method for assessing risk for later developing ESCC in a subject who may not have exhibited any symptoms of ESCC or (2) diagnosing ESCC in a patient who has manifested one or more clinical symptoms suspected of ESCC. The method includes these steps: (a) treating DNA from an esophageal epithelial tissue sample taken from the subject with an agent that differentially modifies methylated and unmethylated DNA; (b) determining number of methylated CpGs in a genomic sequence, which is SEQ ID NO:5 or 6 or a fragment thereof comprising at least 10 CpGs, and (c) comparing the number of methylated CpGs from step (b) with the number of methylated CpGs in the genomic sequence from a non-ESCC sample and processed through steps (a) and (b); and (d) determining the subject, whose sample contains more methylated CpGs in the genomic sequence determined in step (b) compared to the number of methylated CpGs with the number of methylated CpGs in the genomic sequence from a non-ESCC sample and processed through steps (1) to (3), as having an increased risk for ESCC compared with a healthy subject not diagnosed with ESCC.

In some embodiments, the genomic sequence is SEQ ID NO:5 or SEQ ID NO:6. In embodiments, the agent that differentially modifies methylated DNA and unmethylated DNA is an enzyme that preferentially cleaves methylated DNA, an enzyme that preferentially cleaves unmethylated DNA, or a bisulfite. In some embodiments, step (b) comprises an amplification reaction, such as a PCR.

In the third aspect, the present invention provides a method for assessing likelihood of mortality from ESCC in an ESCC patient. The method comprises the steps of: (a) treating DNA from an ESCC sample taken from a first ESCC patient with an agent that differentially modifies methylated and unmethylated DNA; (b) determining number of methylated CpGs in a genomic sequence, which is SEQ ID NO:5 or 6 or a fragment thereof comprising at least 10 CpGs, and (c) comparing the number of methylated CpGs from step (b) with the number of methylated CpGs in the genomic sequence from another ESCC sample of the same type obtained from a second ESCC patient and processed through steps (a) and (b); and (d) determining the first patient, whose ESCC sample contains more methylated CpGs in the genomic sequence determined in step (b) compared to the number of methylated CpGs with the number of methylated CpGs in the genomic sequence from the ESCC sample obtained from the second patient and processed through steps (1) to (3), as having an increased likelihood of mortality from ESCC compared with the second ESCC patient.

In some embodiments, the genomic sequence is SEQ ID NO:5 or SEQ ID NO:6. In some embodiments, the agent that differentially modifies methylated DNA and unmethylated DNA is an enzyme that preferentially cleaves methylated DNA, an enzyme that preferentially cleaves unmethylated DNA, or a bisulfite. In some embodiments, step (b) comprises an amplification reaction such as a PCR.

In the fourth aspect, the present invention provides a kit for detecting ESCC in a subject. The kit includes (1) a standard control that provides an average amount of DLEC1 protein or DLEC1 mRNA; and (2) an agent that specifically and quantitatively identifies DLEC1 protein or DLEC1 mRNA. In some embodiments, the agent in (2) is an antibody that specifically binds the DLEC1 protein. In some embodiments, the agent in (2) is a polynucleotide probe that hybridizes with the DLEC1 mRNA. In some embodiments, the agent comprises a detectable moiety. In some embodiments, the kit may further include two oligonucleotide primers for specifically amplifying at least a segment of SEQ ID NO:3 or its complement in an amplification reaction. Optionally, the kit in some cases may further include an instruction manual to provide instructions for the users.

In the fifth aspect, the present invention provides a method for inhibiting growth of an ESCC cell, comprising contacting the ESCC cell with an effective amount of a polypeptide comprising the amino acid sequence set forth in SEQ ID NO:4 or a nucleic acid comprising a polynucleotide sequence encoding SEQ ID NO:4. In some embodiments, the nucleic acid is an expression cassette comprising a promoter (e.g., an epithelium-specific promoter) operably linked to the polynucleotide sequence encoding SEQ ID NO:4. In some embodiments, the nucleic acid comprises the polynucleotide sequence set forth in SEQ ID NO:1 or 3. In some embodiments, the method is practiced to inhibit the growth of ESCC cells within a patient's body, when the patient may or may not have exhibited clinical symptoms of ESCC.

BRIEF DESCRIPTION OF THE DRAWINGS

The patent or application file contains at least one drawing executed in color. Copies of this patent of patent application publication with color drawing(s) will be provided by the Office upon request and payment of the necessary fee.

(FIG. 1A) Methylome analysis showed signal enrichment in the DLEC1 promoter CGI in ESCC, NPC and lung cancer by MeDIP and Illumina 27k methylation array (bottom panels). Positive MeDIP signal peaks (blue) are marked. (FIG. 1B) Broad expression of DLEC1 in human normal adult tissues by semi-quantitative RT-PCR, with GAPDH as a control. (FIG. 1C) Reduction and silencing of DLEC1 in ESCC and lung carcinoma cell lines. M: methylated; U: unmethylated. (FIG. 1D) Pharmacological demethylation with 5-Aza and TSA restored DLEC1 expression in methylated and silenced carcinoma cell lines. (FIG. 1E) Representative BGS results of carcinoma cell lines. Each single allele of the DLEC1 CGI is shown as an individual row, with filled circle representing methylated while open circles representing unmethylated CpG sites. ESCC: esophageal squamous carcinoma; NPC: nasopharyngeal carcinoma; Ca: carcinoma.

(FIG. 2A) DLEC1 expression levels in esophageal, lung and head/neck tissues through GENT online analysis (upper panel). C: cancer; N: normal. (FIG. 2B) DLEC1 protein expression was detected by Western blot in human normal tissues of esophageal, lung and testis, immortalized esophageal epithelial cell lines and ectopically expressed tumor cell lines. (FIG. 2C) Analyses of TCGA datasets revealed an inverse correlation between DLEC1 mRNA expression and promoter methylation in esophageal and lung cancers. (FIG. 2D) Promoter methylation and expression of DLEC1 were detected in esophageal, nasopharyngeal and lung primary carcinomas, but rarely in matched adjacent esophageal and nasopharynx tissues. DLEC1 expression in representative primary ESCC, NPC tumors samples and normal tissues, as measured by semi-quantitative RT-PCR. (FIG. 2E) Detailed BGS analysis of representative tumor samples. (FIG. 2F) Association of DLEC1 methylation and expression with overall survival was analyzed in ESCC and (FIG. 2G) lung cancer samples from TCGA datasets. ESCC: esophageal squamous carcinoma; NPC: nasopharyngeal carcinoma; Ca: carcinoma.

(FIG. 3A) Representative colony formation assay by monolayer culture in DLEC1-expressing ESCC, NPC and lung carcinoma cells. Quantitative analyses of colony numbers are shown as values of mean±SD. ***p<0.001. (FIG. 3B) DLEC1 expression was measured by Western blot. (FIG. 3C) Cell proliferation assay comparing the proliferation rates of multiple carcinoma cells stably-expressing DLEC1. At each indicated time point, cell viability was determined and represented as the degree of absorbance at 570 nm using MTT assay. The mean SD absorbance (triplicate wells) for each time point is plotted against days after seeding. C1: clone 1, C2: clone 2. (FIG. 3D) Representative cell cycle and flow cytometry data are shown (left panel). Cell apoptosis was examined by flow cytometry analysis with Annexin V-FITC and propidium iodide (PI) doubles staining (right panel). Values are the mean±SD of three independent experiments. *p<0.05, **p<0.05. (FIG. 3E) Upregulation of apoptotic markers (cleaved-PARP and caspase 3) detected by Western blot.

(FIG. 4C) Morphology changes of H1299 cells after ectopic DLEC1 expression. Original magnification, ×252. Scale bar 100 µm. (FIG. 4D) Impaired actin stress fiber organization in DLEC1-expressing H1299 cells. (FIG. 4E) Indirect immunofluorescence detecting the expression of E-cadherin and vimentin. Original magnification, ×400. Scale bar 20 µm. (FIG. 4F) Western blot showing the expression of EMT markers (E-cadherin, vimentin) and metastasis markers (MMP7, Twist) in DLEC1- or vector-transfected cells. For the internal controls refer to FIG. 3B. (FIG. 4G) Downregulation of representative stem cell markers in DLEC1-expressing carcinoma cells by qPCR. *p<0.05, **p<0.01.

(FIG. 5A) Subcellular localization of DLEC1 (green) in cell cytoplasm of carcinoma cells. DAPI counterstaining (blue) was used to visualize nuclear DNA. Images of osteosarcoma cell line U-2 OS were retrieved from Human Protein Atlas database. Original magnification, ×400. Scale bar 10 µm. (FIG. 5B) Promoter luciferase activities of NF-κB, AP-1, STATs-bs, TopFlash, SRE and PAI-1 reporters were normalized to the values of Renilla luciferase activity in tumor and immortalized normal cell lines. Results are expressed as fold reduction of activity and shown as means±SD of three independent experiments performed in triplicate. *p<0.05, **p<0.01. (FIG. 5C) DLEC1 inhibited the phosphorylation levels of ERK, AKT and STAT3. Western blot was used to examine protein levels of total ERK, p-ERK (Thr202/Tyr204), total AKT, p-AKT (ser473), total STAT3, p-STAT3 (Tyr705, Ser727), total β-catenin and active β-catenin in DLEC1-expressing multiple carcinoma cells. (FIG. 5D) Results are expressed as ratio between phosphorylated/activated (p-ERK, p-AKT, p-STAT3 (Tyr705), Active-β-catenin) and non-phosphorylated/total (ERK, AKT, STAT3, 0-catenin) forms. Three different experiments were performed and data are expressed as mean±SD. *p<0.05, p<0.01, *p<0.001.

(FIG. 6B) different dose of DLEC1 expression plasmid. (FIG. 6C) Overexpression of DLEC1 decreases IL-6-induced p-STAT3 level. KYSE150 and H1299 cells were treated with or without IL-6 (10 ng/mL) for 30 min. Phosphorylated and total STAT3 levels were examined. (FIG. 6D) Heat-map showing the expression pattern of DLEC1 and IL-6/STAT3 signaling molecules in ESCC and lung carcinoma patients (Oncomine database).

(FIG. 7A) Predicted models of DLEC1-STAT3 protein docking. 3D structure of DLEC1 and STAT3 PDB are shown. The N-terminal of DLEC1 (residues 108-165) resembles the solution structure of the C-terminal PapD-like domain of human HYDIN protein (protein phosphatase 1) (PDB id: 2E6J), while its C-terminal (residues 806-857) yields 7 matches to respiratory complex I or bovine mitochondrial super-complex. Fourteen structural similarities were observed for STAT3 PDBs, with only three covering the tyrosine residue Y705 (PDB id: 1BG1, 1BF5, 4E68). (FIG. 7B, FIG. 7C) Three dimensional protein models of interaction between DLEC1 and STAT3 proteins. DLEC1 (PDB id: 2E6J) and STAT3 (PDB id: 1BG1, 1BF5 and 4E68) were predicted by ZDOCK server. Grey represents DLEC1 PDB; Color represents STAT3 PDB. (FIG. 7D) Association of endogenous DLEC1 and STAT3 proteins in HEK293T cells. Lysates of HEK293T cells were subjected to IP with DLEC1, STAT3 or JAK2 antibodies. DLEC1 interacts and interferes with STAT3-JAK2 complex. Flag-DLEC1 was transfected in (FIGS. 7E-G) multiple carcinoma cells and (FIG. 7H) HEK293T cells for IP with anti-STAT3, anti-Flag or anti-JAK2 antibody. 5% of DLEC1-transfected cell lysis for each IP was used as input.

(FIG. 8A) Localization of the consensus STAT3-binding motifs (YXXQ) in the DLEC1 protein (upper panel). Schematic of the DLEC1-YXXQ mutant was shown (lower panel). FIG. 8A discloses SEQ ID NOS 40-45, respectively, in order of appearance. (FIG. 8B) DLEC1-YXXQ mutant retained the phosphorylation level of STAT3, which was decreased in DLEC1-expressing cells. KYSE150 and H1299 cells were treated with or without IL-6 (10 ng/mL) for 30 min. Phosphorylated and total STAT3 levels were examined by Western blot. (FIGS. 8C-E) The interaction of DLEC1 and its YXXQ mutant with JAK2-STAT3 under IL-6 stimulation by co-IP assay. DLEC1 or DLEC1-YXXQ mutant (DLEC1-3Y) was transfected in HEK293T, KYSE150 and H1299 cells for the IP experiment. 5% of DLEC1-transfected cell lysis for each IP was used as input. (FIG. 8F) A schematic model showing the regulation of oncogenic STAT3 signaling activation by DLEC1. DLEC1 suppresses STAT3 phosphorylation through binding to STAT3 via YXXQ motif and further interring with JAK2-STAT3 interaction.

(FIG. 9B) The abundance of DLEC1 gene copies relative to GAPDH was determined by multiplex differential genomic DNA-PCR in ESCC cell lines, with homozygous deletion of DLEC1 detected in one. NE1, NE3 and normal PBMCs were used as normal controls. The position of DLEC1 primers used for deletion examination is shown. ESCC, esophageal squamous cell carcinoma.

(FIG. 12A) Diagram of DLEC1 promoter and its CpG island. CpG sites are numbered according to the order marked in BGS, with MSP primer sites and BGS region indicated. Potential binding sites for p53, c-Myb, HSF, E2F and Sp1 are labeled. (FIG. 12B) Luciferase activity assay of different promoter constructs in carcinoma cell lines. Luc, luciferase gene; enh, enhancer. The shortest fragment (+18 to −295, located in the CGI) could function as a core promoter to drive gene expression. (FIG. 12C) Promoter activities after co-transfection of different promoter constructs with p53 plasmids. Wild-type p53 upregulated DLEC1 promoter activity. (FIGS. 12D-E) Box plot graphs for the distribution of DLEC1 methylation and expression levels in esophageal and lung cancer patients from TCGA database.

(FIG. 13A) DLEC1 is methylated and repressed in NPC cell lines. M: methylated; U: unmethylated. (FIG. 13B) Expression of DLEC1 was restored or increased by 5-aza-dC (Aza) treatment in NPC cells, along with increased unmethylated promoter alleles. (FIG. 13C) Detailed BGS analysis of DLEC1 methylation in representative NPC cell lines and primary tumors. NPx: normal nasopharynx.

(FIG. 14A) Locations of primers used in ChIP assay in the DLEC1 CGI. (FIG. 14B) TSA-treated Lung carcinoma cell line H1299 showed moderately induced DLEC1 expression and concomitantly increased acetylation of histone H4 at the endogenous DLEC1 CGI;

while the transfected carcinoma cells showed high level of DLEC1 expression but no increment of H4 acetylation at the endogenous DLEC1 CGI at all.

Figure 15A:
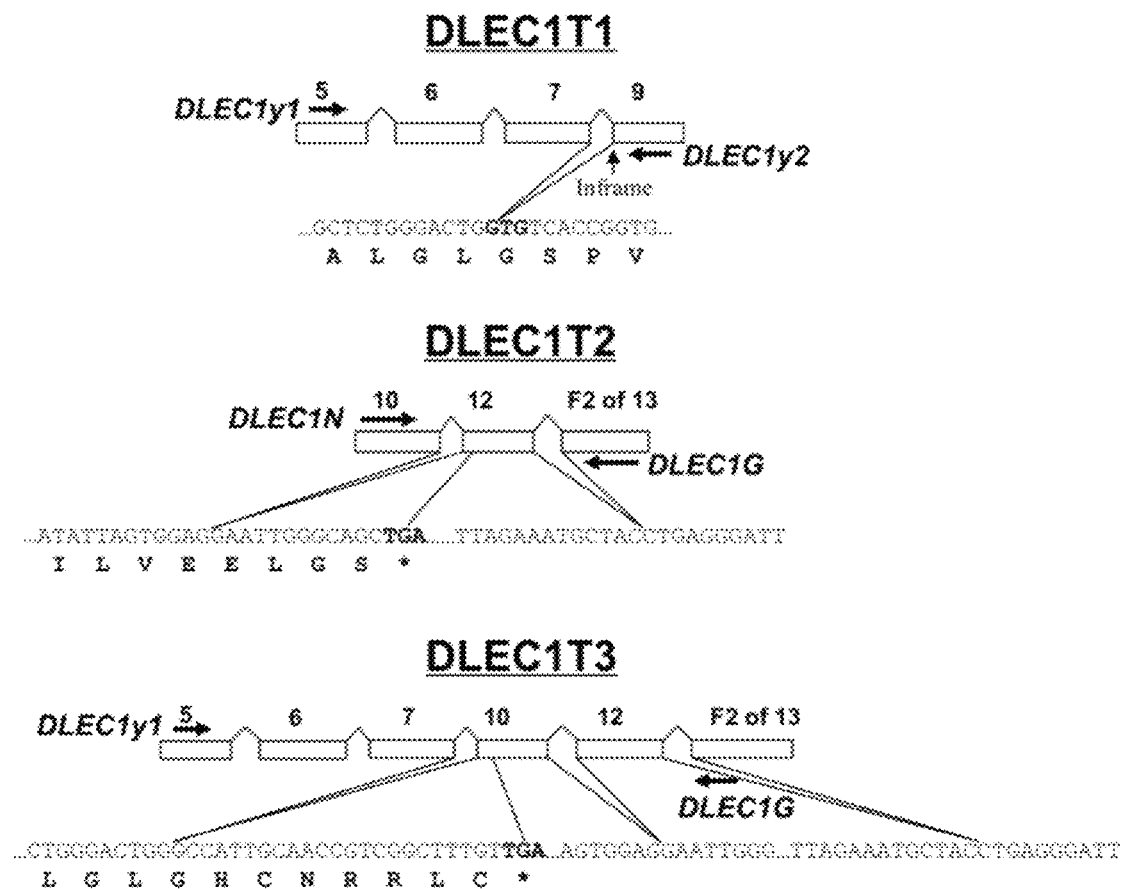
Figure 15B:
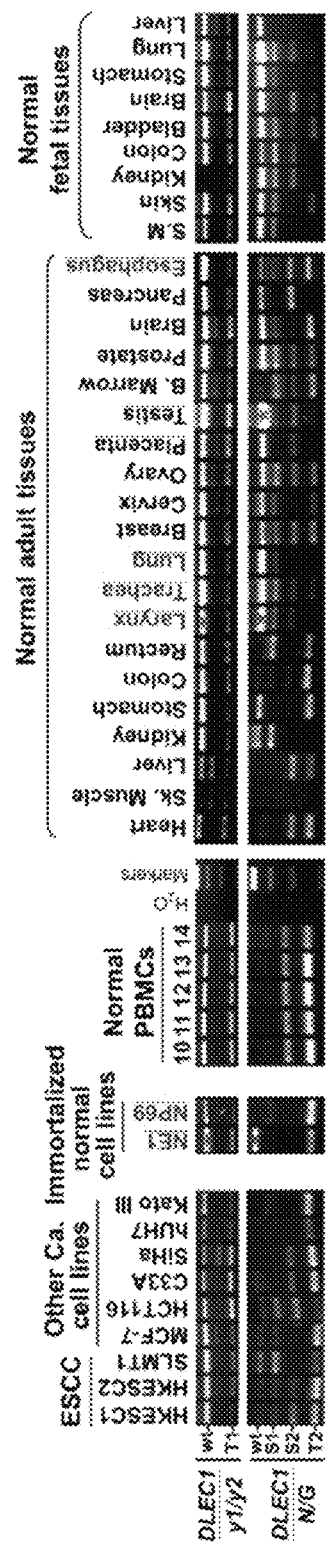

FIGS. 15A-15B Analysis of DLEC1 alternative splicings. (FIG. 15A) Detailed diagrams of splicing forms. Figure discloses SEQ ID NOS 46-54, respectively, in order of appearance. (FIG. 15B) Different splicings of DLEC1 were detected in multiple cell lines, normal adult and fetal tissues, as well as PBMCs.

Figure 16A:
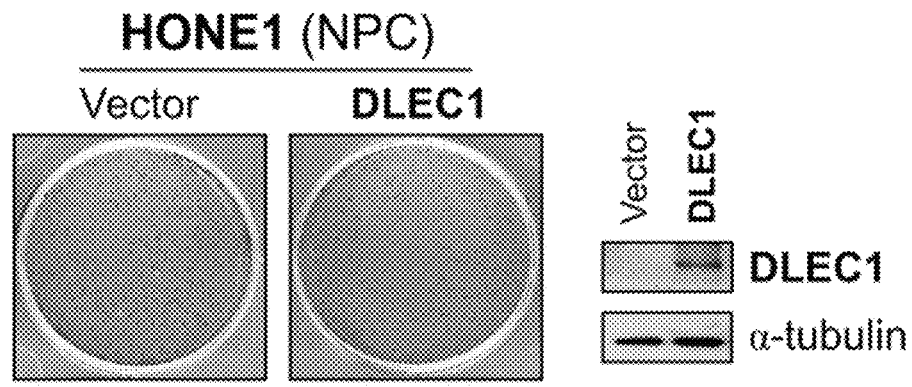
Figure 16B:
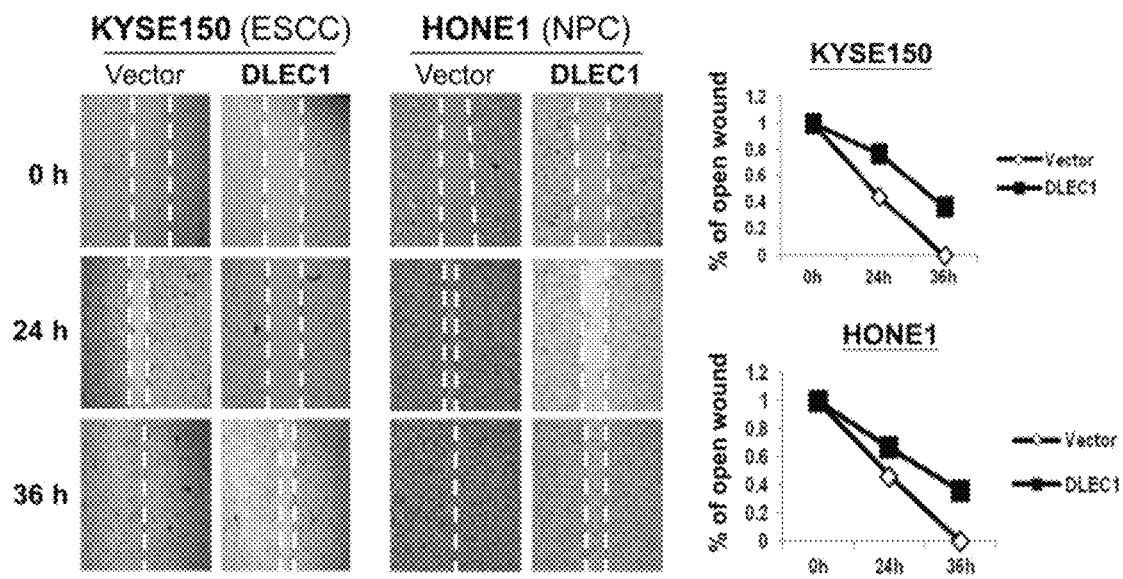

FIGS. 16A-16B (FIG. 16A) Representative colony formation assay of DLEC1-transfected carcinoma cells. DLEC1 expression was measured by Western blot. (FIG. 16B) Wound-healing assay of carcinoma cells transfected with either vector or DLEC1. Pictures were taken at 0, 24 or 36 h. Right panel: width of remaining open wound measured in relation to time 0 h separation.

DEFINITIONS

The term "DLEC1 gene" or "DLEC1 protein," as used herein, refers to any naturally occurring variants or mutants, interspecies homologs or orthologs, or man-made variants of human DLEC1 gene or DLEC1 protein. The human DLEC1 is localized on chromosome 3p21-22. The genomic DNA sequence for the gene is set forth in SEQ ID NO:1, and the cDNA sequence corresponding to a human wild-type DLEC1 mRNA is set forth in GenBank Accession No. NM_007335.3 (provided herein as SEQ ID NO:2), which translate to a coding sequence (provided herein as SEQ ID NO:3) for a 1755-amino acid DLEC1 protein (GenBank Accession No. NP_031361, provided herein as SEQ ID NO:4). A DLEC1 protein within the meaning of this application typically has at least 80%, or 90%, or 95% or higher sequence identity to the human wild-type DLEC1 protein.

In this disclosure the term "esophageal squamous cell carcinoma" or "ESCC" refer to a type of cancer of the esophagus. Such cancer arises from the epithelial cells that line the esophagus and is usually (but not always) found in the higher portion of the esophagus. In contrast, a second type of esophagus cancer, esophageal adenocarcinoma (EAC), arises from the glandular cells that are typically present in the lower third of the esophagus. An "ESCC" cell is a esophageal epithelial cell possessing characteristics of ESCC and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human DLEC1 protein) or the translation of a protein encoded by a polynucleotide sequence. In other words, both mRNA level and protein level encoded by a gene of interest (e.g., human DLEC1 gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, esophagus biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, esophagus, etc.) among other factors. Representative biopsy techniques include, but are not limited to, excisional biopsy, incisional biopsy, needle biopsy, surgical biopsy, and bone marrow biopsy and may comprise colonoscopy or endoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant DLEC1 protein used in the method of this invention (e.g., for treating esophageal cancer, especially ESCC) has at least 80% sequence identity, preferably 85%, 90%, 91%, 92%, 93, 94%, 95%, 96%, 97%, 98%, 99%, or 100% identity, to a reference sequence, e.g., a wild-type human DLEC1 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, Proc. Natl. Acad. Sci. USA 89:10915 (1989)).

The BLAST algorithm also performs a statistical analysis of the similarity between two sequences (see, e.g., Karlin and Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. For any one "CpG-containing genomic sequence" at a given location, e.g., within a region of the human DLEC1 genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of DLEC1 mRNA or DLEC1 protein found in non-cancerous esophagus tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within +10% of the standard control, or within +5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human DLEC1 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., DLEC1 mRNA or DLEC1 protein, that is present in an established normal disease-free tissue sample, e.g., a normal esophagus epithelial tissue sample. The standard control value is suitable for the use of a method of the present invention, to serve as a basis for comparing the amount of DLEC1 mRNA or DLEC1 protein that is present in a test sample. An established sample serving as a standard control provides an average amount of DLEC mRNA or DLEC1 protein that is typical for a esophagus epithelial tissue sample (e.g., esophagus lining) of an average, healthy human without any esophagus disease especially esophageal cancer as conventionally defined. A standard control value may vary depending on the nature of the sample as well as other factors such as the gender, age, ethnicity of the subjects based on whom such a control value is established.

The term "average," as used in the context of describing a human who is healthy, free of any esophagus disease (especially esophageal cancer) as conventionally defined, refers to certain characteristics, especially the amount of human DLEC1 mRNA or DLEC1 protein, found in the person's esophagus tissue, e.g., epithelial tissue or esophagus lining, that are representative of a randomly selected group of healthy humans who are free of any esophageal diseases (especially esophageal cancer). This selected group should comprise a sufficient number of humans such that the average amount of DLEC1 mRNA or protein in the esophagus epithelium among these individuals reflects, with reasonable accuracy, the corresponding amount of DLEC1 mRNA/protein in the general population of healthy humans. In addition, the selected group of humans generally have a similar age to that of a subject whose esophagus tissue sample is tested for indication of esophageal cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human DLEC1 mRNA or DLEC1 protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding DLEC1 mRNA is the amount of said polynucleotide to achieve an increased level of DLEC1 protein expression or biological activity, such that the symptoms of esophageal cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, esophageal cancer especially ESCC. Subjects also include individuals currently undergoing therapy that seek manipulation of the therapeutic regimen. Subjects or individuals in need of treatment include those that demonstrate symptoms of esophageal cancer (especially ESCC) or are at risk of suffering from esophageal cancer (especially ESCC) or its symptoms. For example, a subject in need of treatment includes individuals with a genetic predisposition or family history for esophageal cancer (especially ESCC), those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of DLEC1 protein are used to refer to inhibitory, activating, or modulating molecules, respectively, identified using in vitro and in vivo assays for DLEC1 protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of DLEC1 protein. In some cases, the inhibitor directly or indirectly binds to DLEC1 protein, such as a neutralizing antibody. Inhibitors, as used herein, are synonymous with inactivators and antagonists. Activators are agents that, e.g., stimulate, increase, facilitate, enhance activation, sensitize or up regulate the activity of DLEC1 protein. Modulators include DLEC1 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Despite the rapid advancement in medical sciences and steady improvement in cancer therapy, cancer remains a significant health concern with grave implications in both developed countries as well as in developing countries. ESCC patients often face a grim prognosis since their disease is most often discovered in more advanced stages due to the lacking of specific symptoms during early development stages. Early detection of cancer such as ESCC is therefore critical for improving patient survival rate. Moreover, it is also of practical importance to predict the likelihood of mortality from cancer among patients who have already received a cancer diagnosis for any time period after the diagnosis.

3p22-21.3 is one of the most frequently deleted chromosome regions in solid tumors including esophageal squamous cell carcinoma (ESCC), even altered at the early premalignant stage. Various genetic studies have been carried out to identify candidate tumor suppressor genes (TSG) at this locus. Deleted in lung and esophageal cancer 1 (DLEC1), located at 3p22-21.3, has been identified frequently methylated in multiple human cancers, which is correlated with tumor poor survival and malignant progression. Thus, DLEC1 methylation could be an important event in tumorigenesis, and serve as a valuable, non-invasive biomarker for human cancers. However, there is no study of investigating DLEC1 methylation in ESCC. This invention provides a method to specifically detect promoter CpG methylation of DLEC1 in ESCC, and its methylation serving as a biomarker for early detection. Methylation-specific PCR (MSP) primers for DLEC1 are tested for not amplifying any not-bisulfited DNA, confirming the detection specificity of DLEC1 methylation in this invention. DLEC1 downregulation/silencing by promoter methylation is detected in ESCC cell lines and primary tumors, but not in immortalized esophageal epithelial cells or normal esophageal tissues. In addition, the present invention provides a method for treating tumor cells by restore DLEC1 gene expression and unmethylation in DLEC1-silenced ESCC cells. The invention also provides a detection method for ESCC and a detection kit useful for such a method.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human DLEC1 gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of DLEC1 mRNA or DNA

The present invention relates to measuring the amount of DLEC1 mRNA or analyzing the methylation pattern of DLEC1 genomic DNA found in a person's esophagus issue, especially esophageal epithelial sample, as a means to detect the presence, to assess the risk of developing, and/or to monitor the progression or treatment efficacy of esophageal squamous cell carcinoma (ESCC). Thus, the first steps of practicing this invention are to obtain a esophageal epithelial tissue sample from a test subject and extract mRNA or DNA from the sample.

A. Acquisition and Preparation of Esophageal Tissue Samples

An esophageal tissue sample is obtained from a person to be tested or monitored for esophagus cancer (e.g., ESCC) using a method of the present invention. Collection of esophageal epithelial tissue sample from an individual is performed in accordance with the standard protocol hospitals or clinics generally follow, such as during an endoscopy. An appropriate amount of esophagus epithelium is collected and may be stored according to standard procedures prior to further preparation.

The analysis of DLEC1 mRNA or DNA found in a patient's esophageal epithelial sample according to the present invention may be performed using, e.g., esophagus lining tissue. The methods for preparing tissue samples for nucleic acid extraction are well known among those of skill in the art. For example, a subject's esophageal epithelial sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human DLEC1 mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human DLEC1 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of a mRNA species in a sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA species in a sample. For a review of branched-DNA signal amplification for direct quantitation of nucleic acid sequences in clinical samples, see Nolte, *Adv. Clin. Chem.* 33:201-235, 1998.

2. Other Quantitative Methods

The DLEC1 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to DLEC1 mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

C. Detection of Methylation in DLEC1 Genomic Sequence

Methylation status of a segment of DLEC1 genomic sequence containing one or more CpG (cytosine-guanine dinucleotide) pairs is investigated to provide indication as to whether a test subject is suffering from esophageal cancer (especially ESCC), whether the subject is at risk of developing esophageal cancer (especially ESCC), or whether the subject's esophageal cancer (especially ESCC) is worsening or improving.

Typically a segment of the DLEC1 genomic sequence that includes the 5' untranslated region (such as the promoter region) and includes one or more CpG nucleotide pairs is analyzed for methylation pattern. For example, SEQ ID NO:5 or 6 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of ESCC cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have esophageal cancer (especially ESCC) or have an elevated risk of developing esophageal cancer (especially ESCC). For example, SEQ ID NO:5, a segment of DLEC1 genomic sequence, and the 107 bp segment of SEQ ID NO:6 are such CpG-containing genomic sequences useful for the analysis. Some or majority of the CpG pairs in this region are found to be methylated in established ESCC cell lines and samples taken from ESCC, whereas non-cancerous esophagus epithelial cells showed very few, if any at all, methylated CpG sites. For the purpose of determining the methylation pattern of a DLEC1 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the DLEC1 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of esophageal epithelium from a subject being tested, assessed, or monitored for ESCC, the risk of developing ESCC, or the severity/progression of the condition. Samples of the same type should be taken from both a control group (normal individuals not suffering from any esophagus disorder especially neoplasia) and a test group (subjects being tested for possible esophagus cancer, for example). Standard procedures routinely employed in hospitals or clinics are typically followed for this purpose, as stated in the previous section.

For the purpose of detecting the presence of esophageal cancer (e.g., ESCC) or assessing the risk of developing esophageal cancer (e.g., ESCC) in test subjects, individual patients' esophagus epithelium samples may be taken and the level of human DLEC1 protein may be measured and then compared to a standard control. If a decrease in the level of human DLEC1 protein is observed when compared to the control level, the test subject is deemed to have ESCC or have an elevated risk of developing the condition. For the purpose of monitoring disease progression or assessing therapeutic effectiveness in ESCC patients, individual patient's esophageal epithelial samples may be taken at different time points, such that the level of human DLEC1 protein can be measured to provide information indicating the state of disease. For instance, when a patient's DLEC1 protein level shows a general trend of increase over time, the patient is deemed to be improving in the severity of esophageal cancer or the therapy the patient has been receiving is deemed effective. A lack of change in a patient's DLEC1 protein level or a continuing trend of decrease on other hand would indicate a worsening of the condition and ineffectiveness of the therapy given to the patient. Generally, a lower DLEC1 protein level seen in a patient indicates a more severe form of the ESCC the patient is suffering from and a worse prognosis of the disease, as manifested in shorter life expectancy, higher rate of metastasis, resistance to therapy etc. Among ESCC patients, one who has a lower level of DLEC1 protein expression in the esophageal cancer sample than that found in a second ESCC patient has a higher likelihood of mortality compared to the second patient for any defined time period, such as 1-5 years post-diagnosis.

B. Preparing Samples for DLEC1 Protein Detection

The esophagus tissue sample from a subject is suitable for the present invention and can be obtained by well-known methods and as described in the previous section. In certain applications of this invention, esophagus lining or epithelial tissue may be the preferred sample type.

C. Determining the Level of Human DLEC1 Protein

A protein of any particular identity, such as DLEC1 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human DLEC1 protein) can also be detected by gel electrophoresis (such as 2-dimensional gel electrophoresis) and western blot analysis using specific antibodies. Alternatively, standard immunohistochemical techniques can be used to detect a given protein (e.g., human DLEC1 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human DLEC1 protein) can be generated by known techniques.

Other methods may also be employed for measuring the level of DLEC1 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any esophagus disease (especially any form of tumor such as esophageal cancer) as conventionally defined is first selected. These individuals are within the appropriate parameters, if applicable, for the purpose of screening for and/or monitoring esophageal cancer (especially ESCC) using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human DLEC1 mRNA or DLEC1 protein in the esophagus epithelial tissue sample obtained from the group can be reasonably regarded as representative of the normal or average level among the general population of healthy people. Preferably, the selected group comprises at least 10 human subjects.

Once an average value for the DLEC1 mRNA or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of ESCC

By illustrating the correlation of suppressed expression of DLEC1 protein and cancers such as ESCC, the present invention further provides a means for treating patients suffering from the cancer or at heightened risk of developing the cancer at a later time: by way of increasing DLEC1 protein expression or biological activity. As used herein, treatment of ESCC encompasses reducing, reversing, lessening, or eliminating one or more of the symptoms of esophageal cancer (especially ESCC), as well as preventing or delaying the onset of one or more of the relevant symptoms. Additionally, since certain risk factors for ESCC (smoking, drinking, drinking very hot drinks, chewing betel nuts, etc.) are well-known, preventive measures can be prescribed to patients at risk of developing ESCC such as reducing or eliminating alcohol and tobacco consumption and adopting a healthy diet. For individuals who have been deemed to have an increased risk of developing ESCC by the method of this invention and who are then diagnosed as actually having already developed ESCC (e.g., by conventional diagnostic methods such as X-ray and/or CT scan of the chest area in addition to pathological assessment), various treatment strategies are available for treating ESCC in these patients including but not limited to, surgery, chemotherapy, radiotherapy, immunotherapy, photodynamic therapy, or any combination thereof.

A. Increasing DLEC1 Expression or Activity

1. Nucleic Acids Encoding DLEC1 Proteins

Enhancement of DLEC1 gene expression can be achieved through the use of nucleic acids encoding a functional DLEC1 protein. Such nucleic acids can be single-stranded nucleic acids (such as mRNA) or double-stranded nucleic acids (such as DNA) that can translate into an active form of DLEC1 protein under favorable conditions.

In one embodiment, the DLEC1-encoding nucleic acid is provided in the form of an expression cassette, typically recombinantly produced, having a promoter operably linked to the polynucleotide sequence encoding the DLEC1 protein. In some cases, the promoter is a universal promoter that directs gene expression in all or most tissue types; in other cases, the promoter is one that directs gene expression specifically in epithelial cells, especially in esophagus epithelium. Administration of such nucleic acids can increase the DLEC1 protein expression in the target tissue, e.g., esophagus epithelium. Since the human DLEC1 gene sequence is known as Genbank Accession No. NM_007335.3 and provided herein as SEQ ID NO:2, and its cDNA sequence is provided herein as SEQ ID NO:3, one can derive a suitable DLEC1-encoding nucleic acid from the sequence, species homologs, and variants of these sequences one can derive a suitable DLEC1-encoding nucleic acid from the sequence, species homologs, and variants of these sequences.

2. DLEC1 Proteins

By directly administering an effective amount of an active DLEC1 protein to a patient suffering from ESCC and exhibiting suppressed DLEC1 protein expression or activity, the disease may also be effectively treated. For example, this can be achieved by administering a recombinantly produced DLEC1 protein possessing its biological activity to the patient suffering from esophageal cancer (e.g., ESCC). Formulations and methods for delivering a protein- or polypeptide-based therapeutic agent are well known in the art.

3. Activators of DLEC1 Protein

Increased DLEC1 protein activity can be achieved with an agent that is capable of activating the expression of DLEC1 protein or enhancing the activity of DLEC1 protein. For example, a demethylating agent (e.g., 5-Aza) may be able to activate DLEC1 gene expression by removing the suppression of DLEC1 gene expression caused by methylation of the promoter region of this gene. Other activating agents may include transcriptional activators specific for the DLEC1 promoter and/or enhancer. Such activating agents can be screened for and identified using the DLEC1 expression assays described in the examples herein.

Agonists of the DLEC1 protein, such as an activating antibody, are another kind of activators of the DLEC1 protein. Such activators act by enhancing the biological activity of the DLEC1 protein, typically (but not necessarily) by direct binding with the DLEC1 protein and/or its interacting proteins. Preliminary screening for such agonists may start with a binding assay for identifying molecules that physically interact with DLEC1 protein.

B. Pharmaceutical Compositions

1. Formulations

Compounds of the present invention are useful in the manufacture of a pharmaceutical composition or a medicament. A pharmaceutical composition or medicament can be administered to a subject for the treatment of esophageal cancer, especially ESCC.

Compounds used in the present invention, e.g., a DLEC1 protein, a nucleic acid encoding DLEC1 protein, or an activator of DLEC1 gene expression, are useful in the manufacture of a pharmaceutical composition or a medicament comprising an effective amount thereof in conjunction or mixture with excipients or carriers suitable for application.

An exemplary pharmaceutical composition for enhancing DLEC1 expression comprises (i) an express cassette comprising a polynucleotide sequence encoding a human DLEC1 protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A DLEC1 protein or a nucleic acid encoding a DLEC1 protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., esophageal epithelial cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a DLEC1 protein or a nucleic acid encoding a DLEC1 protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a DLEC1 protein or a nucleic acid encoding a DLEC1 protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of DLEC1 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control esophageal cancer (especially ESCC) as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of DLEC1 protein or nucleic acid encoding a DLEC1 protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for DLEC1 protein or a nucleic acid encoding a DLEC1 protein described herein are provided. Dosage for a DLEC1-encoding nucleic acid, such as an expression cassette, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. DLEC1 Protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a DLEC1 protein or a nucleic acid encoding the protein). The additional therapeutic compound can also be administered separately, in a separate composition, or a different dosage form from the main active ingredient. Some doses of the main ingredient, such as a DLEC1 protein or a nucleic acid encoding a DLEC1 protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of DLEC1 mRNA or DLEC1 protein in a subject, which can be used for various purposes such as detecting or diagnosing the presence of esophageal cancer (especially ESCC), determining the risk of developing esophageal cancer (especially ESCC), and monitoring the progression of esophageal cancer (especially ESCC) in a patient, including assessing the likelihood of mortality from esophageal cancer (especially ESCC).

Kits for carrying out assays for determining DLEC1 mRNA level typically include at least one oligonucleotide useful for specific hybridization with at least one segment of the DLEC1 coding sequence or its complementary sequence. Optionally, this oligonucleotide is labeled with a detectable moiety. In some cases, the kits may include at least two oligonucleotide primers that can be used in the amplification of at least one segment of DLEC1 DNA or mRNA by PCR, particularly by RT-PCR.

Kits for carrying out assays for determining DLEC1 protein level typically include at least one antibody useful for specific binding to the DLEC1 protein amino acid sequence. Optionally, this antibody is labeled with a detectable moiety. The antibody can be either a monoclonal antibody or a polyclonal antibody. In some cases, the kits may include at least two different antibodies, one for specific binding to the DLEC1 protein (i.e., the primary antibody) and the other for detection of the primary antibody (i.e., the secondary antibody), which is often attached to a detectable moiety.

Typically, the kits also include an appropriate standard control. The standard controls indicate the average value of DLEC1 protein or mRNA in the esophagus epithelium of healthy subjects not suffering from esophageal cancer. In some cases such standard control may be provided in the form of a set value. In addition, the kits of this invention may provide instruction manuals to guide users in analyzing test samples and assessing the presence, risk, or state of esophageal cancer (especially ESCC) in a test subject.

In a further aspect, the present invention can also be embodied in a device or a system comprising one or more such devices, which is capable of carrying out all or some of the method steps described herein. For instance, in some cases, the device or system performs the following steps upon receiving an esophagus tissue sample, e.g., an esophagus epithelial tissue sample taken from a subject being tested for detecting esophageal cancer (especially ESCC), assessing the risk of developing esophageal cancer (especially ESCC), or monitored for progression of the condition: (a) determining in sample the amount or concentration of DLEC1 mRNA, DLEC1 protein; (b) comparing the amount or concentration with a standard control value; and (c) providing an output indicating whether esophageal cancer (especially ESCC) is present in the subject or whether the subject is at risk of developing esophageal cancer (especially ESCC), or whether there is a change, i.e., worsening or improvement, in the subject's esophageal cancer (especially ESCC) condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Abstract

Rationale: Oncogenic STAT3 signaling activation and 3p22-21.3 locus alteration are common in multiple tumors, especially carcinomas of the nasopharynx, esophagus and lung. Whether these two events are linked remains unclear. CpG methylome analysis has identified a 3p22.2 gene, DLEC1, as a methylated target in esophageal squamous cell (ESCC), nasopharyngeal (NPC) and lung carcinomas. Its epigenetic abnormalities and functions were then further characterized.

Methods: CpG methylomes were established by methylated DNA immunoprecipitation. Promoter methylation was analyzed by methylation-specific PCR and bisulfite genomic sequencing. DLEC1 expression and clinical significance were analyzed using TCGA database. DLEC1 functions were analyzed by transfections followed by various cell biology assays. Protein-protein interaction was assessed by docking, Western blot and immunoprecipitation analyses.

Results: The present inventors defined the DLEC1 promoter within a CpG island and p53-regulated. DLEC1 was frequently downregulated in ESCC, lung and NPC cell lines and primary tumors, but was readily expressed in normal tissues and immortalized normal epithelial cells, with mutations rarely detected. DLEC1 methylation was frequently detected in ESCC tumors and correlated with lymph node metastasis, tumor recurrence and progression, with DLEC1 as most frequently methylated among the established 3p22.2 tumor suppressors (RASSF1A, PLCD1 and ZMYND10/BLU).

DLEC1 inhibits carcinoma cell growth through inducing cell cycle arrest and apoptosis, and also suppresses cell metastasis by reversing epithelial-mesenchymal transition (EMT) and cell stemness. Moreover, DLEC1 represses oncogenic signaling including JAK/STAT3, MAPK/ERK, Wnt/β-catenin and AKT pathways in multiple carcinoma types. Particularly, DLEC1 inhibits IL-6-induced STAT3 phosphorylation in a dose-dependent manner. DLEC1 contains three YXXQ motifs and forms a protein complex with STAT3 via protein docking, which blocks STAT3-JAK2 interaction and STAT3 phosphorylation. IL-6 stimulation enhances the binding of DLEC1 with STAT3, which diminishes their interaction with JAK2 and further leads to decreased STAT3 phosphorylation. The YXXQ motifs of DLEC1 are crucial for its inhibition of STAT3 phosphorylation, and disruption of these motifs restores STAT3 phosphorylation through abolishing DLEC1 binding to STAT3.

Conclusions: This study demonstrates, for the first time, predominant epigenetic silencing of DLEC1 in ESCC, and a novel mechanistic link of epigenetic DLEC1 disruption with oncogenic STAT3 signaling in multiple carcinomas.

Introduction

Chromosomal locus 3p22-21.3 frequently has abnormalities like loss of heterozygosity (LOH) in multiple cancers [1-6], including esophageal squamous cell (ESCC), lung and nasopharyngeal (NPC) carcinomas. Thus, as a typical tumor suppressor gene (TSG) locus, allele loss at 3p21.3 has been shown to be the early premalignant change detected in lung and breast cancers [1, 4]. Multiple genetic and epigenetic studies have been performed to determine the related TSGs at this locus, such as RASSF1A [7], ZMYND10 [8-10] and PLCD1 [11]. Another candidate 3p22 TSG, deleted in lung and esophageal cancer 1 (DLEC1), was firstly identified in esophageal and lung cancers through sequencing 3p21.3 genomic DNA cosmid clones and expression analysis [12]. However, although DLEC1 downregulation and rare mutations were initially detected in some carcinoma cell lines and primary tissues, its promoter methylation was not detected in any ESCC or lung cancer cell lines or tumor samples [12], raising questions about its role as a bonafide 3p22-21.3 TSG. After its first identification, DLEC1 promoter methylation and downregulation have been reported in multiple cancers by several groups [13-22], but still not in ESCC yet. DLEC1 methylation/downregulation has been shown to be significantly related to disease progression and poor prognosis of some cancers including lung, ovarian and breast [18-21]; thus, it is a potential biomarker for tumor diagnosis.

The DLEC1 protein has 1,755 amino acids encoded by a polynucleotide sequence of 5,268 nucleotides, with no homology to any known proteins or domains reported so far. Previous studies showed that DLEC1 is a growth suppressor with anti-tumorigenic abilities in vivo [17]. However, the molecular mechanism underlying its tumor suppression still remains unknown.

STAT3 is commonly activated in human malignancies as an oncogenic signaling hallmark, involved in the regulation of cell proliferation, apoptosis, cancer stemness and immune checkpoint [23, 24]. Persistent STAT3 activation is associated with tumor progression of ESCC, NPC and lung cancers [25-27]; thus it is a feasible therapeutic target. STAT3 activation is stimulated by cytokines and growth factors (e.g., IL-6, IFNs, EGF), featured by tyrosine phosphorylation at residue Y705 together with Ser727 phosphorylation, and further functions as a transcription factor to activate target gene transcription [28]. The YXXQ motif is well known as a consensus motif for STAT3 recruitment, which acts as a docking site selectively binding STATs [29]. In addition, STAT3 could also be inactivated by negative regulators, including suppressors of cytokine signaling (SOCS), protein tyrosine phosphatases (PTPs) and protein inhibitors. Although the critical role of oncogenic STAT3 activation in tumorigenesis has been well defined, the mechanisms regulating STAT3 activation are diverse and worthy of further exploration.

An integrative epigenomic and genomic study of ESCC was conducted through genome-wide CpG methylation (methylome) and high-resolution array comparative genomic hybridization (aCGH) analyses, and identified DLEC1 as a methylated target in ESCC, as well as lung cancer and NPC. Its expression and methylation in cell lines and primary tumors of ESCC, lung cancer and NPC, was further examined and its tumor suppressive functions in carcinoma cells was systematically assessed. The underlying mechanism of JAK/STAT3 signaling regulation by DLEC1 in carcinoma cells was also investigated.

Results

Figure 1A:
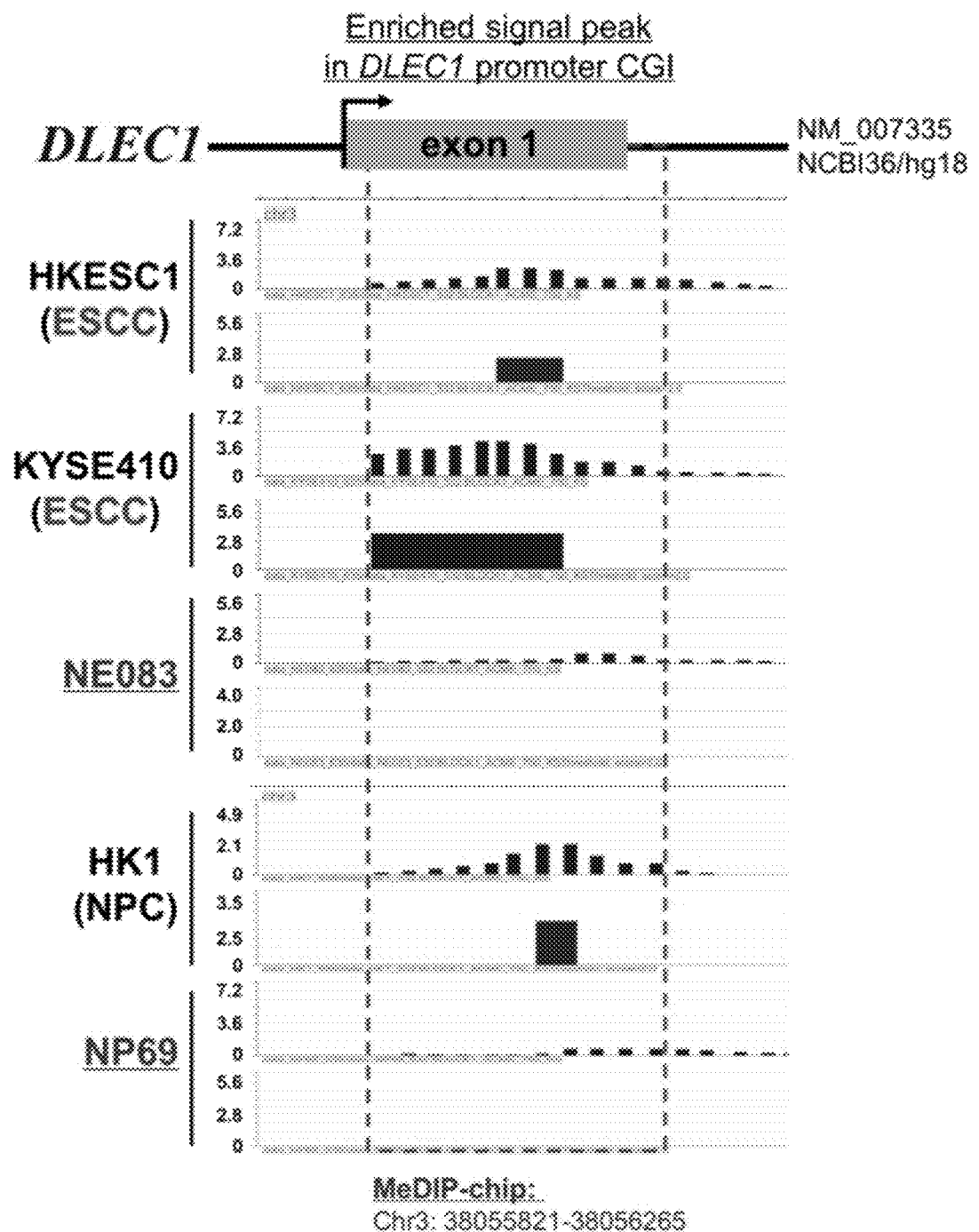
FIGS. 1A-1E CpG methylome study identified DLEC1 as a methylated target downregulated in multiple carcinomas.

Epigenomic Identification of DLEC1 as a Methylated Target for Esophageal and Other Carcinomas Enriched methylated signal in the DLEC1 promoter was detected in ESCC, but not in immortalized esophageal epithelial cells (FIG. 1A), indicating that DLEC1 is a methylated target for ESCC. Similar positive signal peaks at the DLEC1 promoter were detected in previous NPC methylome data (FIG. 1A). Moreover, DLEC1 was identified as a methylated target in a previous lung cancer methylome study (5/6 paired carcinomas) [30].

Figure 9A:
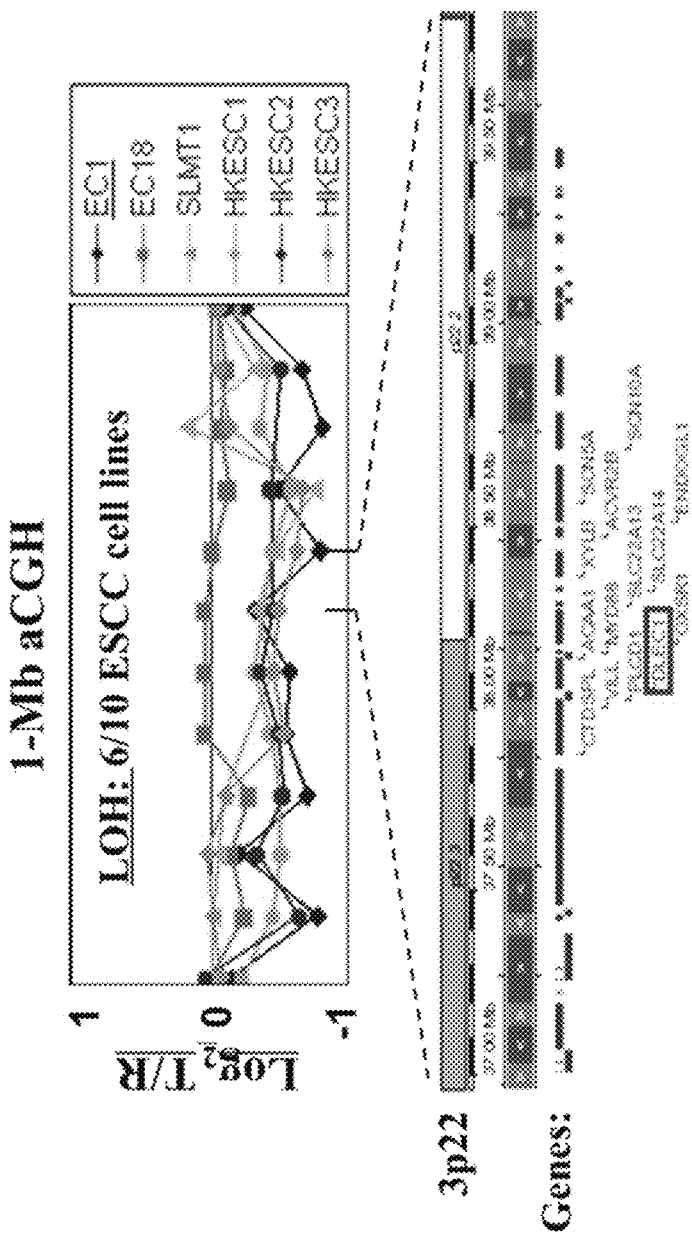
FIGS. 9A-9B (FIG. 9A) DLEC1 resides at 3p21-22, a locus with hemizygous deletion detected by 1-Mb array-CGH in ESCC cell lines.
Figure 9B:
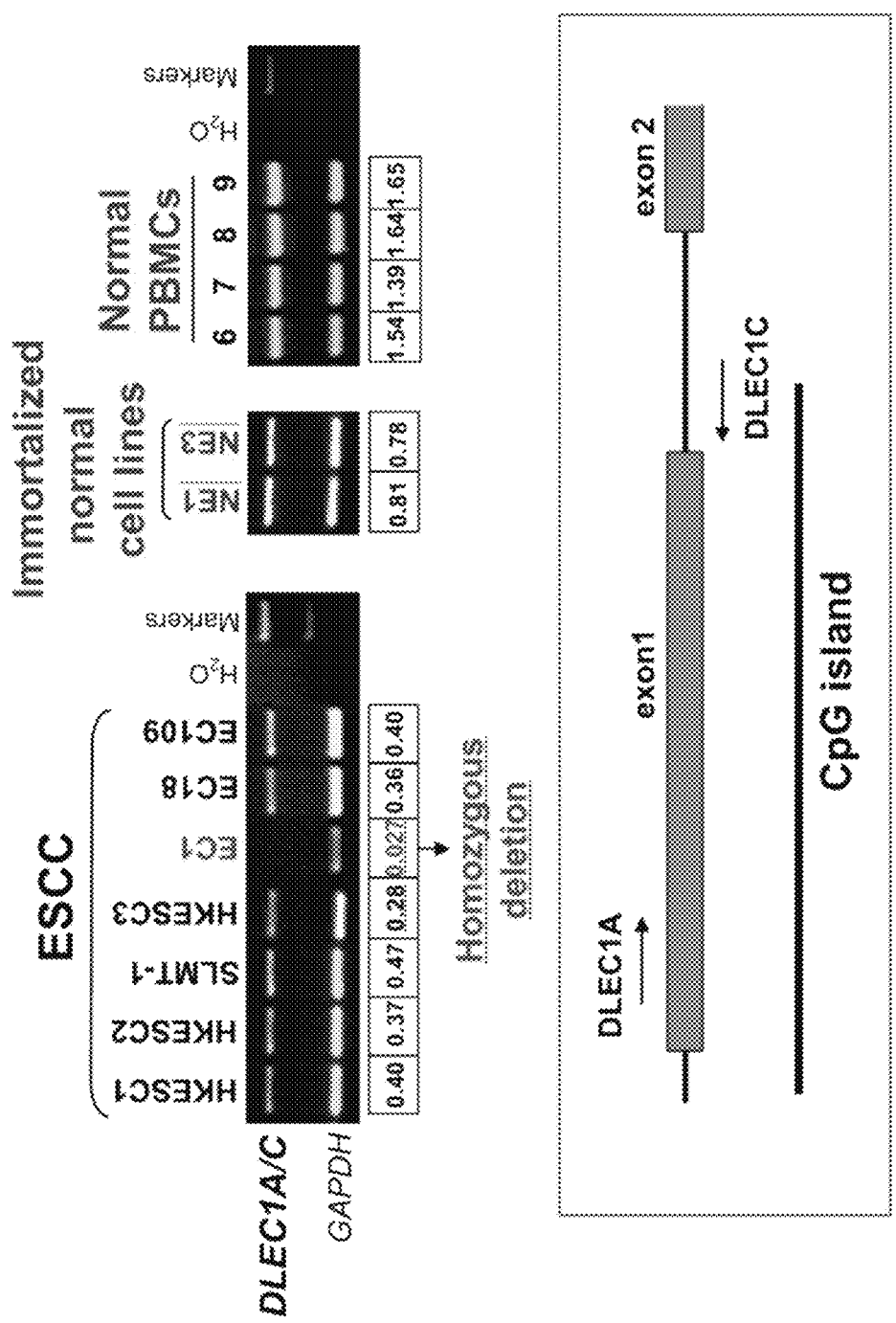
Figure 10:
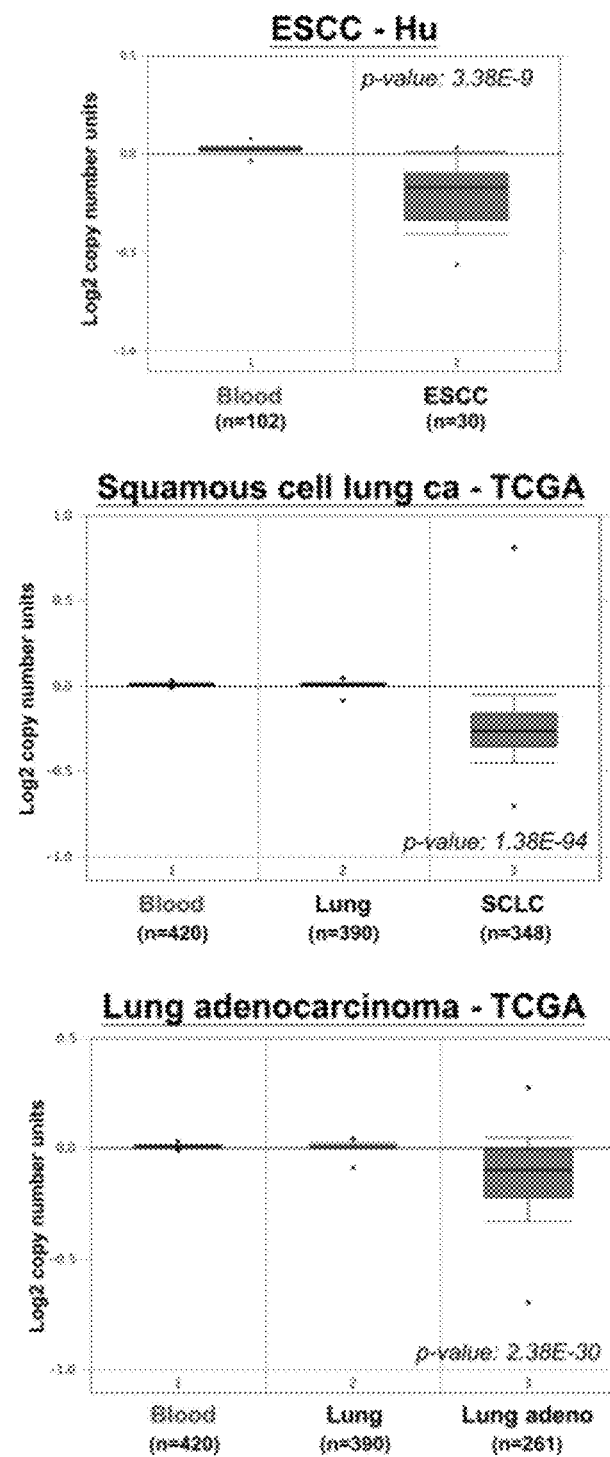
FIG. 10 Alterations of DLEC1 DNA copy numbers in ESCC and lung carcinomas, analyzed through Oncomine database. ESCC, esophageal squamous cell; Ca, carcinoma; SCLC, squamous cell lung carcinoma; Lung adeno, lung adenocarcinoma.
Figure 11:
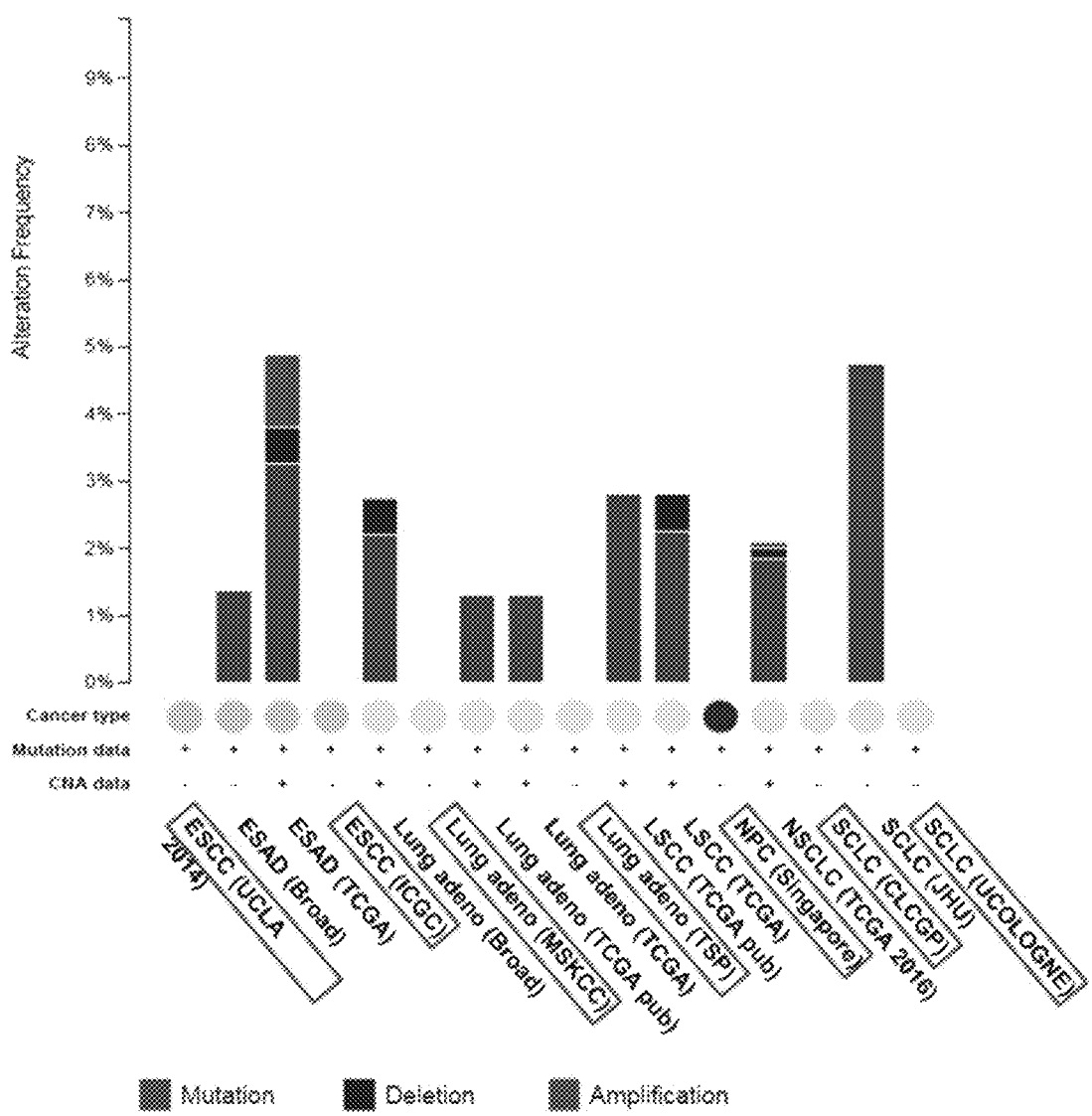
FIG. 11 Profiling of DLEC1 mutations in esophageal and other carcinomas. Mutation profile was analyzed using TCGA dataset. No mutation was detected in ESCC. ESCC, esophageal squamous cell; ESAD, esophageal adenocarcinoma; Lung adeno, lung adenocarcinoma; LSCC, lung squamous cell carcinoma; NSCLC, non-small cell lung cancer; SCLC, squamous cell lung carcinoma; NPC, nasopharyngeal carcinoma.

Meanwhile, an array CGH study of ESCC [31] also detected hemizygous 3p22 deletion in 5/10 cell lines where DLEC1 is located (FIG. 9A), with homozygous deletion of DLEC1 in one cell line (EC1) (FIG. 9B). Further analysis of TCGA and Oncomine databases revealed DNA copy number loss of DLEC1 in ESCC, lung and NPC primary tumors (FIG. 10), However, no mutation of DLEC1 was found in the ESCC and NPC cohorts, while mutations were only detected in <5% esophageal adenocarcinomas and some lung cancer cohorts (FIG. 11). These results suggest that DLEC1 is disrupted through both epigenetic and, less frequently, genetic (LOH/deletion) mechanisms in ESCC and other carcinomas.

The DLEC1 Promoter is a CpG Island and p53-Regulated

Figures 12A, 12B:
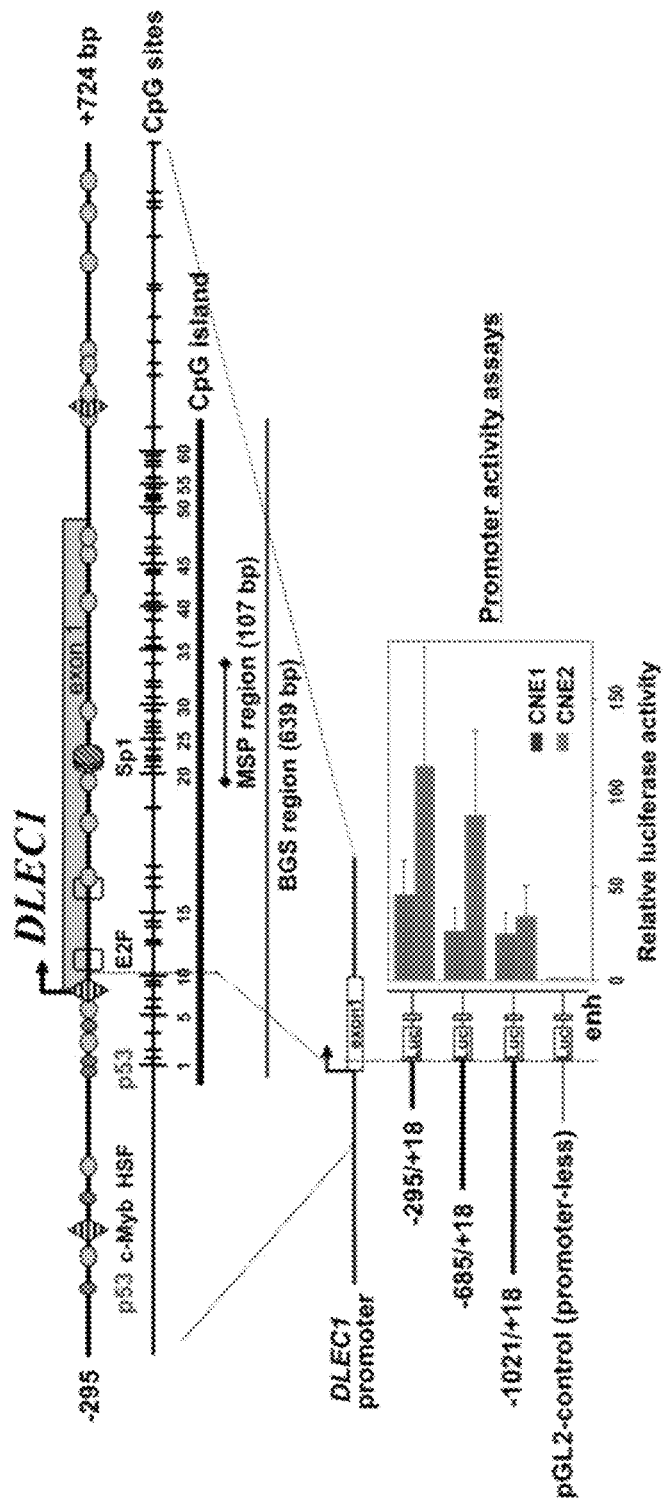
FIGS. 12A-12E Defining the functional DLEC1 promoter.

As promoter CpG methylation directly mediates transcription repression, the DLEC1 promoter was further analyzed. A 756 bp region spanning its promoter and exon 1 as a typical CpG island (CGI) was found (FIG. 12A). Potential binding sites for multiple transcription factors, including p53, c-Myb, heat-shock factor (HSF), STATs, E2F and Sp1, were predicted using TFSEARCH (Website: cbrc.jp/research/db/TFSEARCH) and MotifSearch (motif.genome.jp) (FIG. 12A), indicating that this promoter is subject to the regulation of these transcription factors. Thus, several segments covering this region were cloned and tested for promoter reporter activities. Results showed that the shortest construct (+18 to −295), located within the CGI, had the maximal luciferase activity (FIG. 12B), indicating that it could act as a functional promoter driving DLEC1.

Figure 12C:
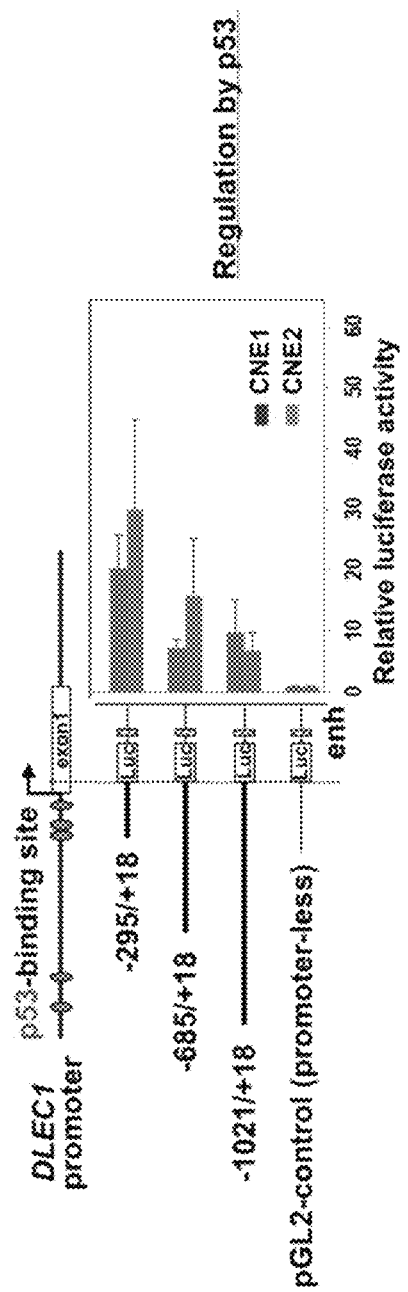
Figure 12D:
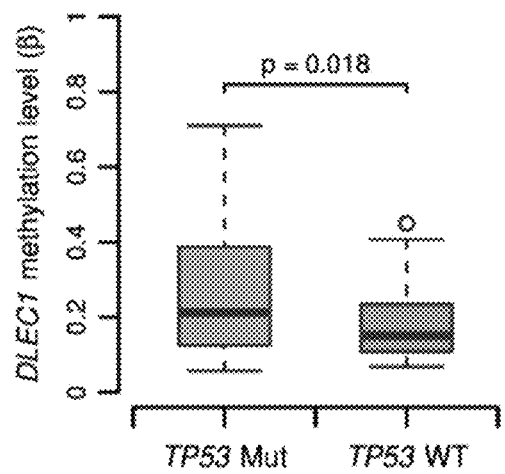
Figure 12E:
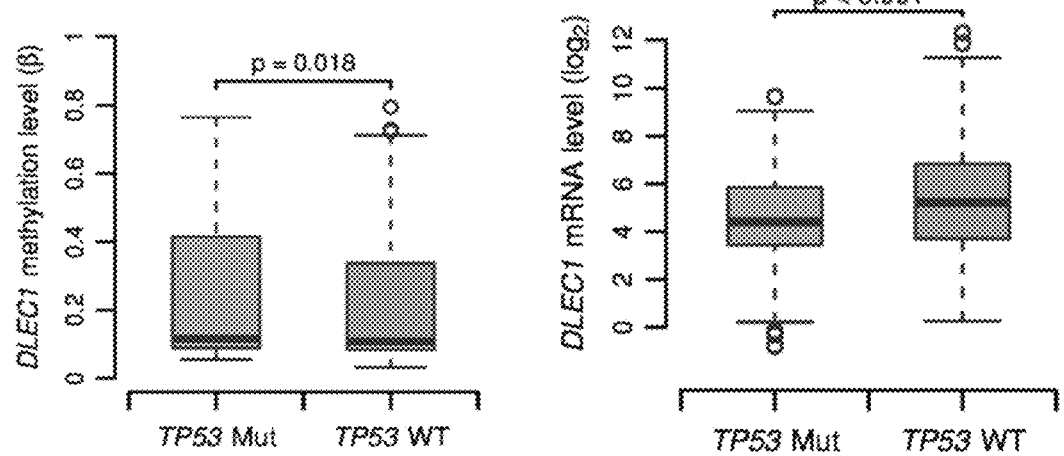

As five putative p53-binding sites were found in DLEC1 promoter (+18 to −1021) (website: tfbind.hgc.jp/), the effect of p53 on DLEC1 promoter activity was then examined. Results showed that p53 upregulated DLEC1 promoter activity, and the region (+18 to −295) might be the core p53 regulatory region (FIG. 12C), indicating that DLEC1 is indeed a p53-regulated gene. The relationship between p53 status and DLEC1 methylation or expression was further analyzed using TCGA database cohorts, and found that wild-type p53 is significantly correlated with DLEC1 high expression/low methylation, supporting the findings of p53 regulation of DLEC1 promoter (FIG. 12D, E).

Figure 1B:
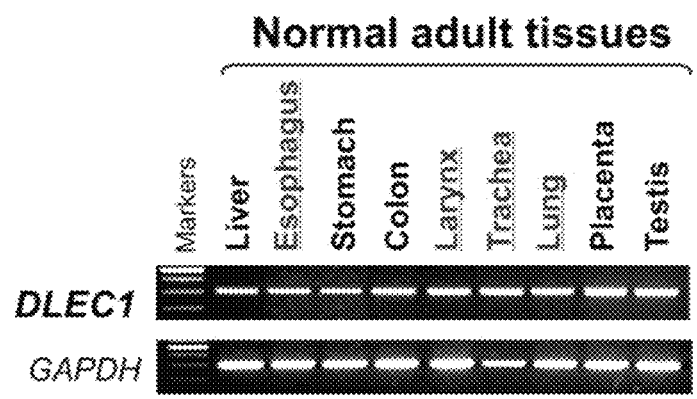
Figure 1C:
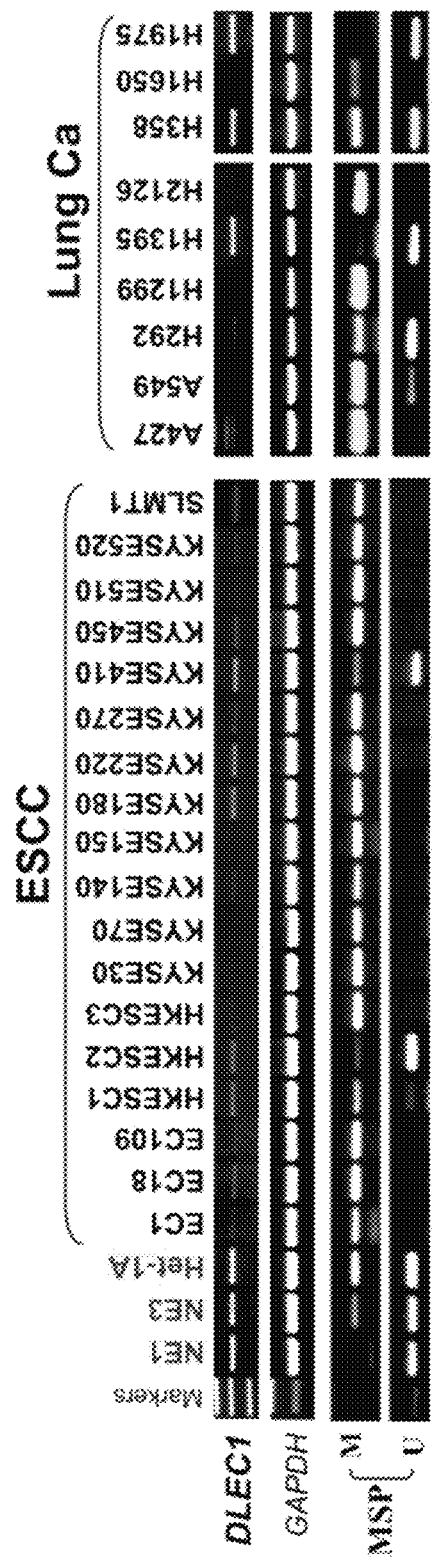
Figure 1D:
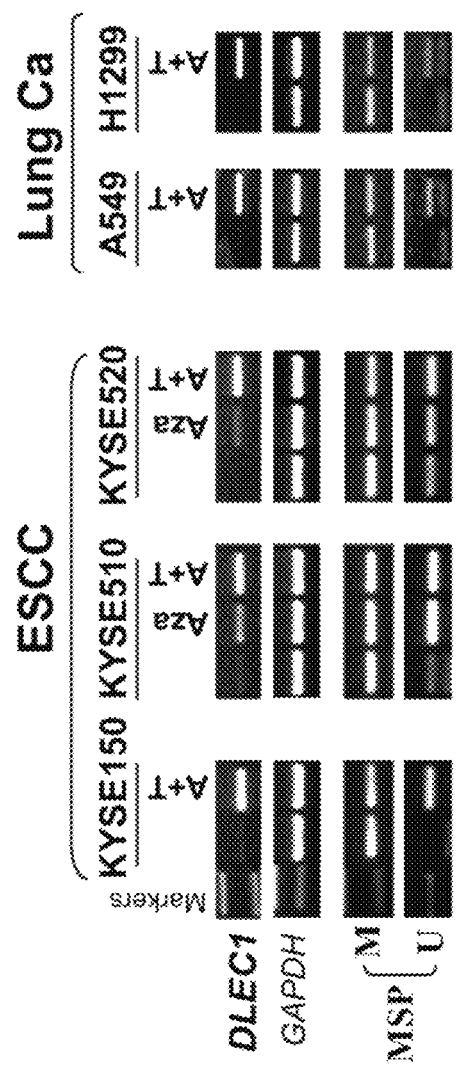
Figure 1E:
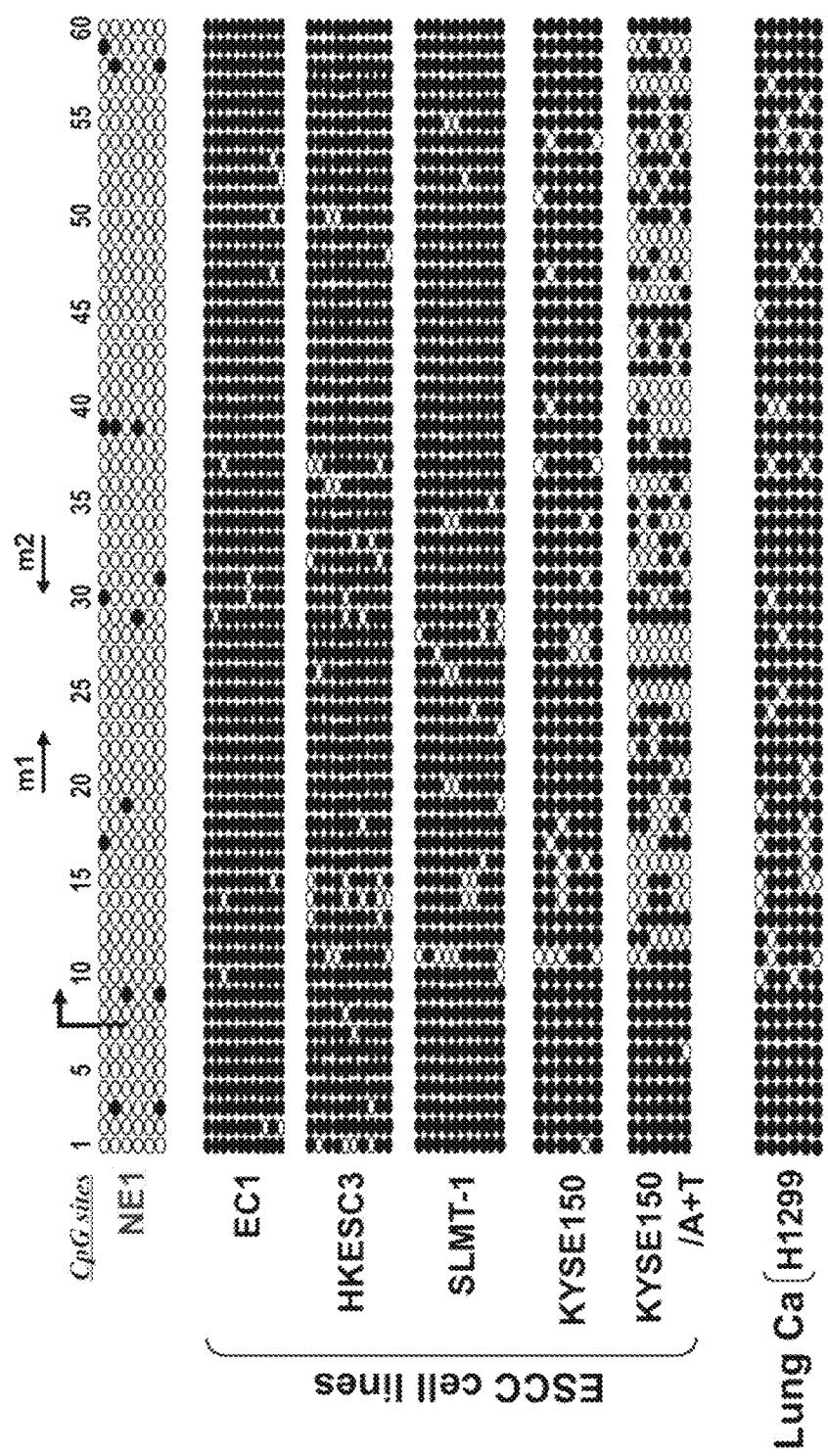
Figure 13A:
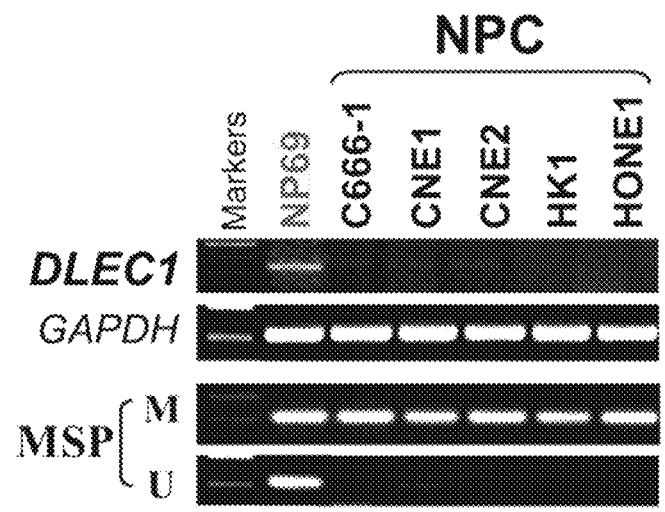
FIGS. 13A-13C Promoter methylation and loss of expression of DLEC1 in NPC.
Figure 13B:
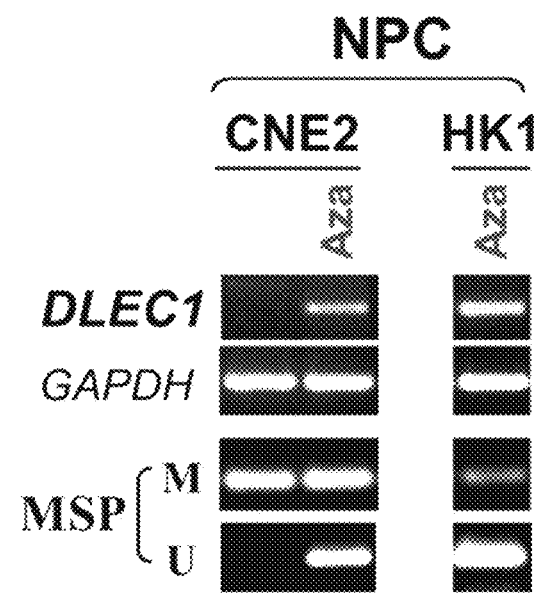
Figure 13C:
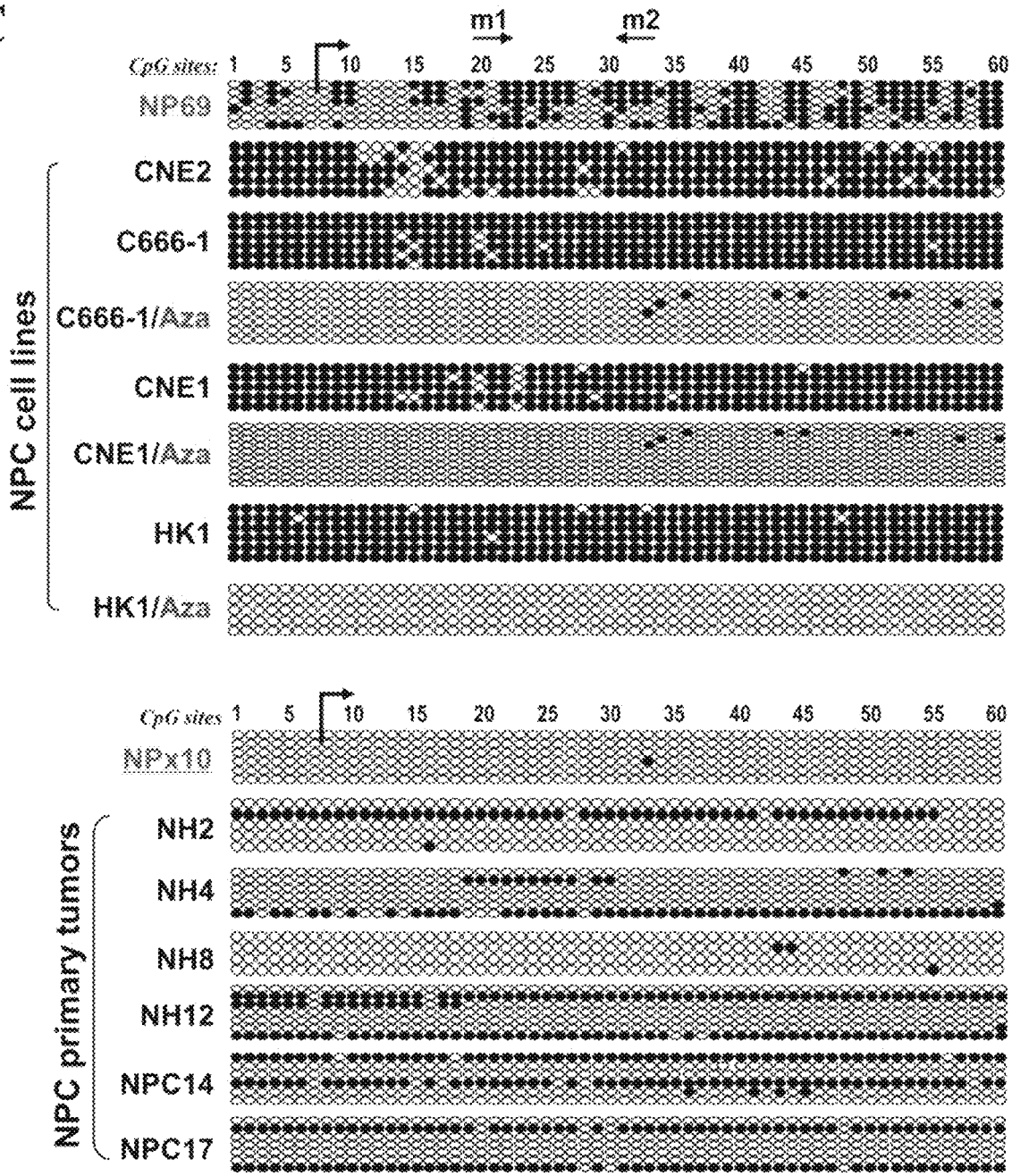

DLEC1 is Downregulated by Methylation in Esophageal and Other Carcinoma Cell Lines DLEC1 expression and methylation were further examined in a panel of ESCC and other carcinoma cell lines. DLEC1 was readily detected in normal esophageal, respiratory and digestive tissues including esophagus, larynx, trachea, lung, stomach and colon (FIG. 1B), as well as normal immortalized esophageal and nasopharyngeal cell lines (NE1, NE3, Het-1A and NP69) (FIG. 1C; FIG. 13A). In contrast, DLEC1 was silenced or significantly downregulated in 17/18 ESCC, 6/9 lung and 5/5 NPC cell lines (FIG. 1C, FIG. 13A). Methylation-specific PCR (MSP) showed that the DLEC1 promoter was methylated in virtually all the downregulated cell lines, but hemi-methylated in two immortalized normal epithelial cell lines (Het-1A, NP69). Further detailed bisulfite genomic sequencing (BGS) methylation analysis of individual CpG sites on the DLEC1 promoter showed heavily methylated alleles in silenced cell lines, a few methylated alleles in hemi-methylated NP69 cells, but only few scattered methylated CpG site in NE1 cells, confirming the MSP data (FIG. 1E, FIG. 13C). Thus, DLEC1 expression is well correlated with its methylation status in esophageal and other carcinoma cells.

Figure 14A:
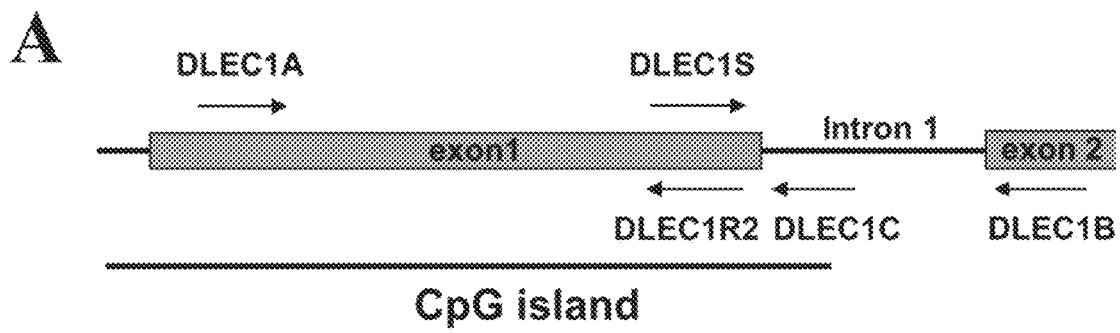
FIGS. 14A-14B Regulation of DLEC1 expression by histone H4 acetylation.
Figure 14B:
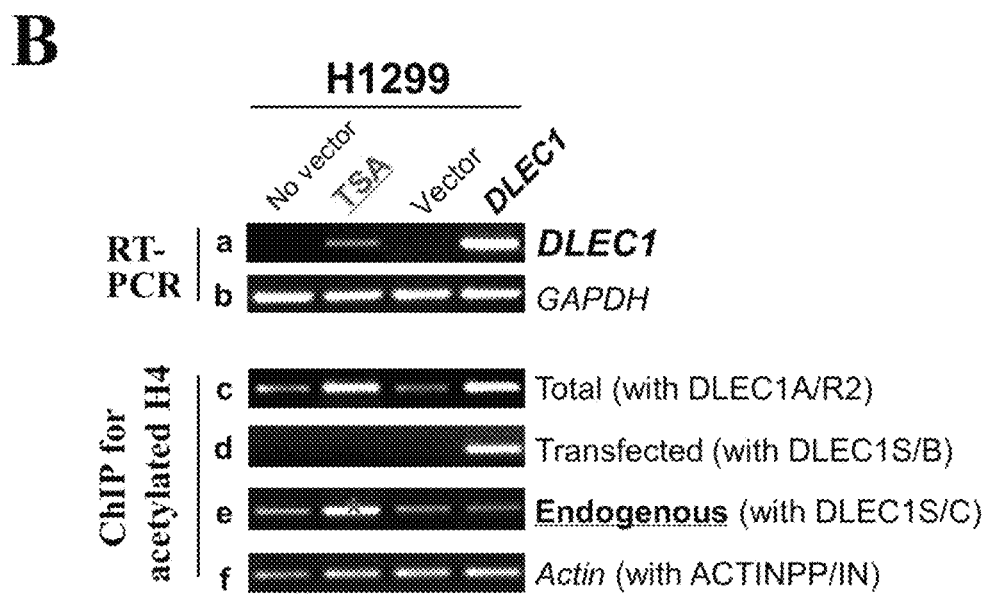

To determine whether an epigenetic mechanism directly mediates DLEC1 silencing, DNA methyltransferase inhibitor 5-aza-2'-deoxycytidine (Aza) and histone deacetylase inhibitor Trichostatin A (TSA) were used. After the treatment, DLEC1 expression was increased in cell lines of ESCC, lung and NPC with silenced DLEC1, and even more dramatically increased with Aza+TSA treatment, accompanied by increased unmethylated alleles and decreased methylated alleles as detected by both MSP and BGS (FIG. 1D, E, FIG. 13B, C). Moreover, ChIP assay showed increased binding of acetylated histone 4 to the DLEC1 CGI, following TSA treatment in carcinoma cells (FIG. 14). These results suggest that both CpG methylation and histone deacetylation contribute to DLEC1 silencing in carcinoma cells.

Frequent DLEC1 Methylation in Primary Carcinomas with Clinical Correlation

Figure 2A:
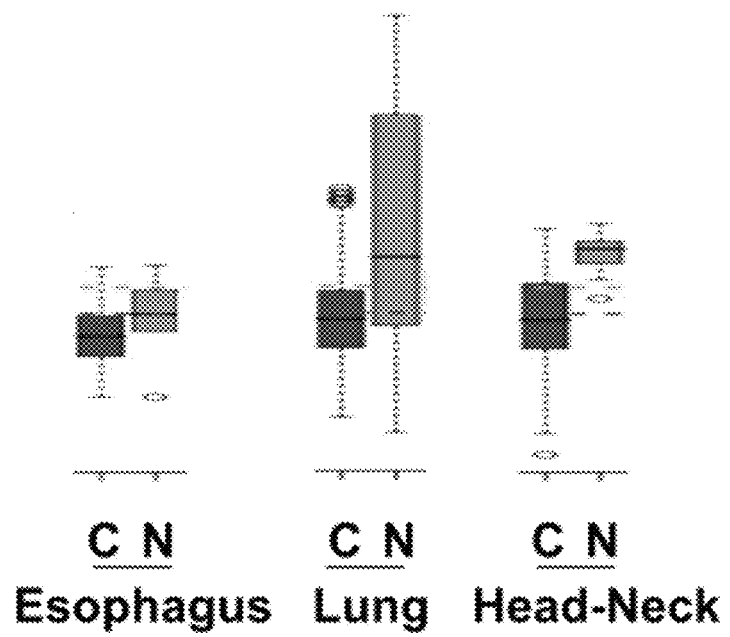
FIGS. 2A-2G DLEC1 downregulation and methylation in esophageal and other carcinomas.
Figure 2B:
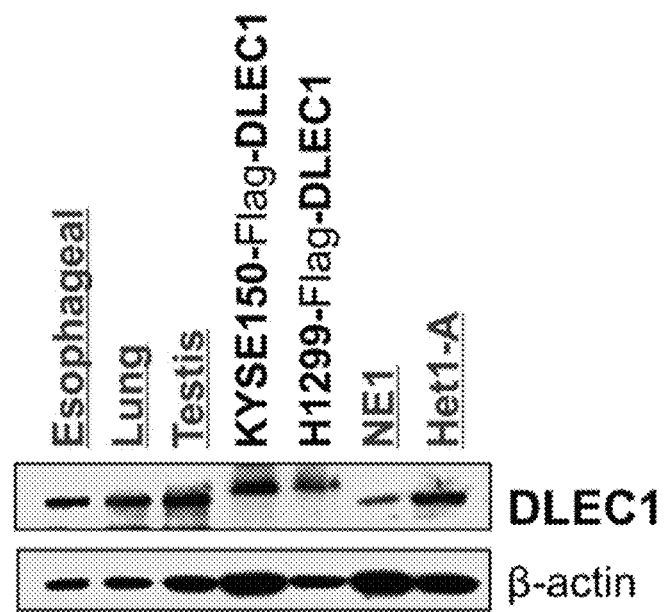
Figure 2C:
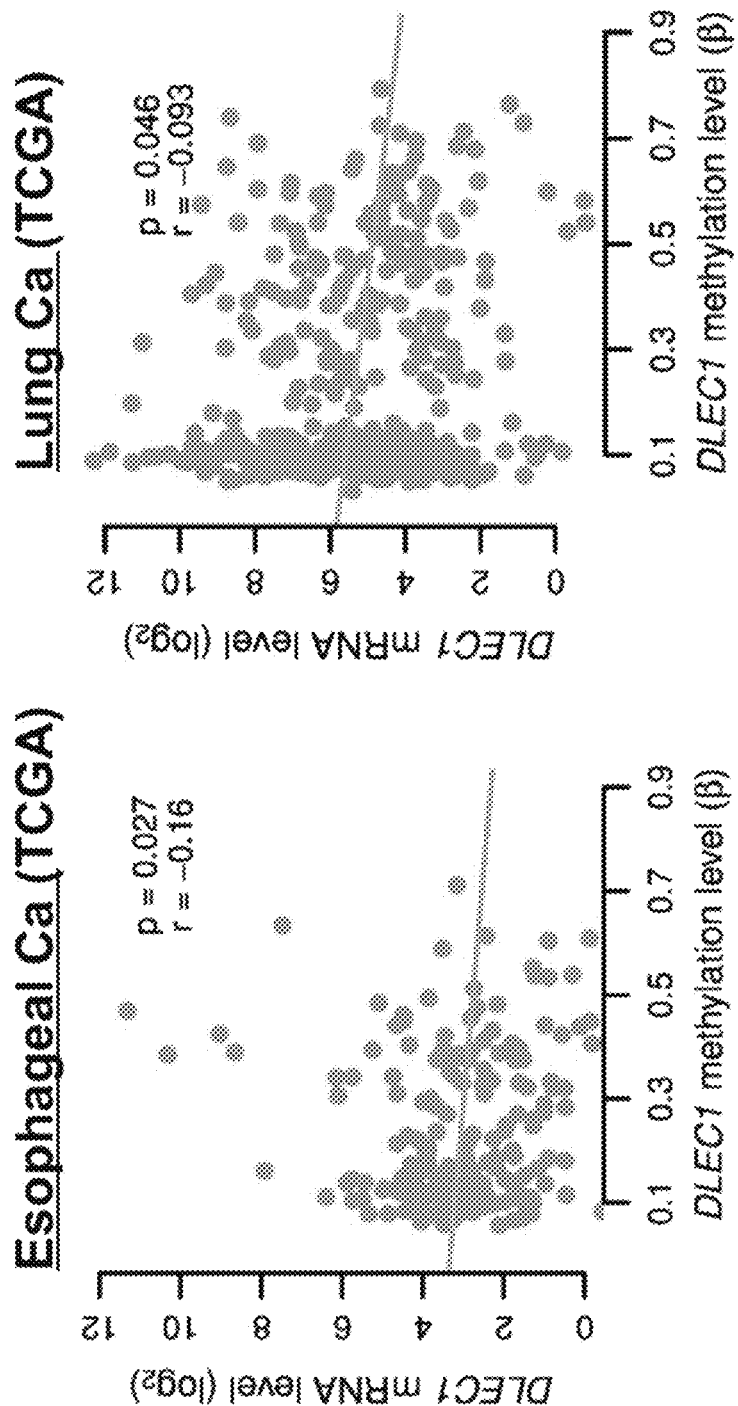
Figure 2D:
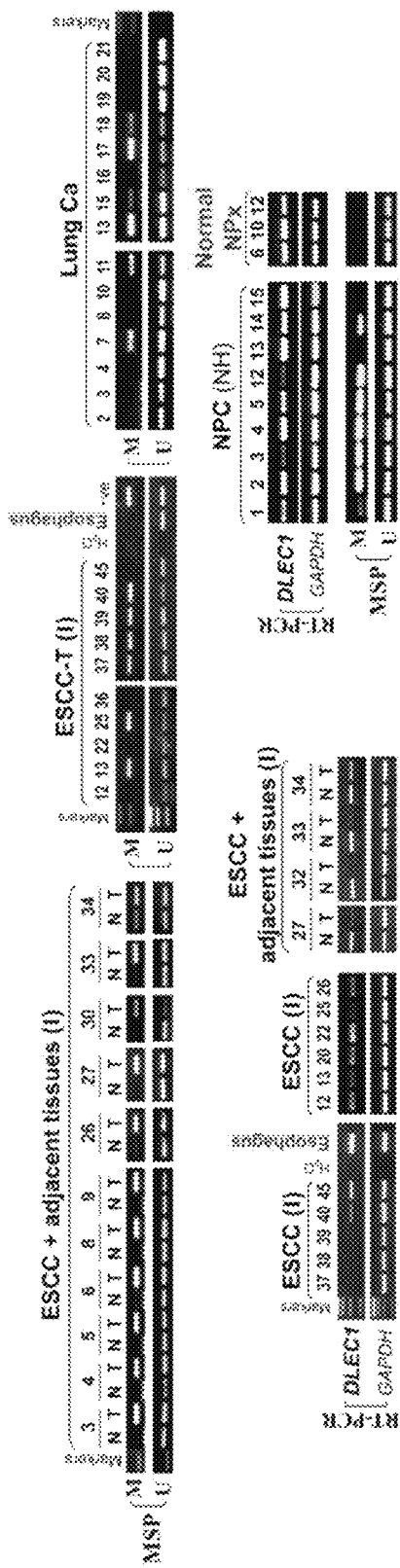
Figure 2E:
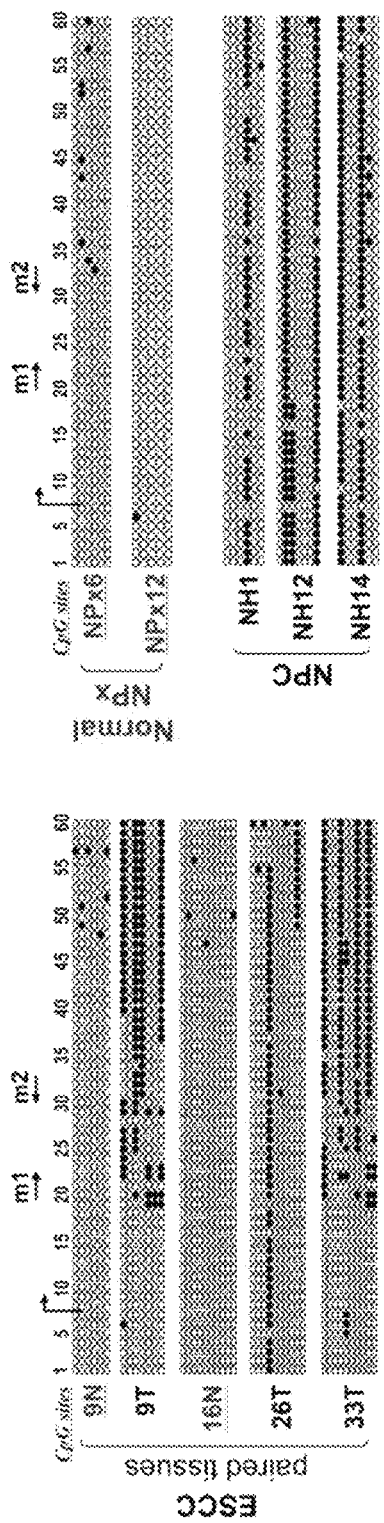

DLEC1 expression and methylation were then analyzed in primary ESCC and other carcinomas. First, online GENT database analysis showed significant reduction of DLEC1 RNA in esophageal, lung, and head and neck cancer tissues compared with corresponding normal tissues (FIG. 2A). Moreover, DLEC1 protein was abundantly expressed in normal tissues including esophageal, lung and testis (FIG. 2B). Further semi-quantitative RT-PCR analysis detected DLEC1 downregulation/silencing in primary ESCC tissues, but medium/high expression in normal esophageal, nasopharyngeal (NPx) and paired tumor adjacent normal tissues (FIG. 2D). Furthermore, DLEC1 promoter methylation was detected in 66% (27/41) of ESCC tumors but rarely in tumor adjacent normal and normal esophageal tissues. In another cohort, DLEC1 methylation was detected in 48% (40/83) of ESCC primary tissues (FIG. 2D, Table 1). Overall, DLEC1 is methylated in 54% (67/124) of primary ESCC tumors, which correlates with its downregulation. An inverse correlation between DLEC1 mRNA expression and promoter methylation was observed in esophageal and lung cancer patients from TCGA datasets (FIG. 2C).

Figure 2F:
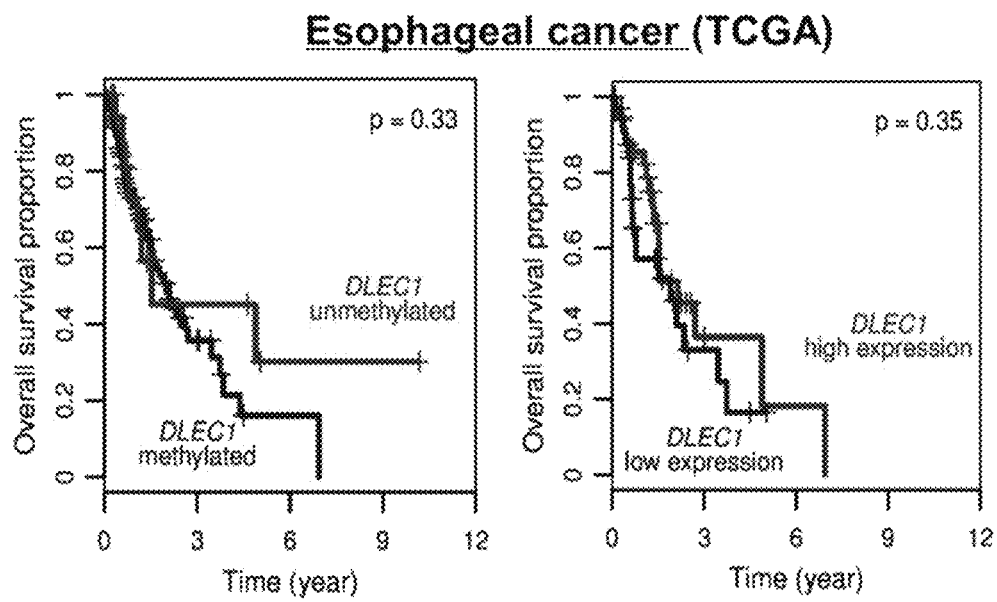
Figure 2G:
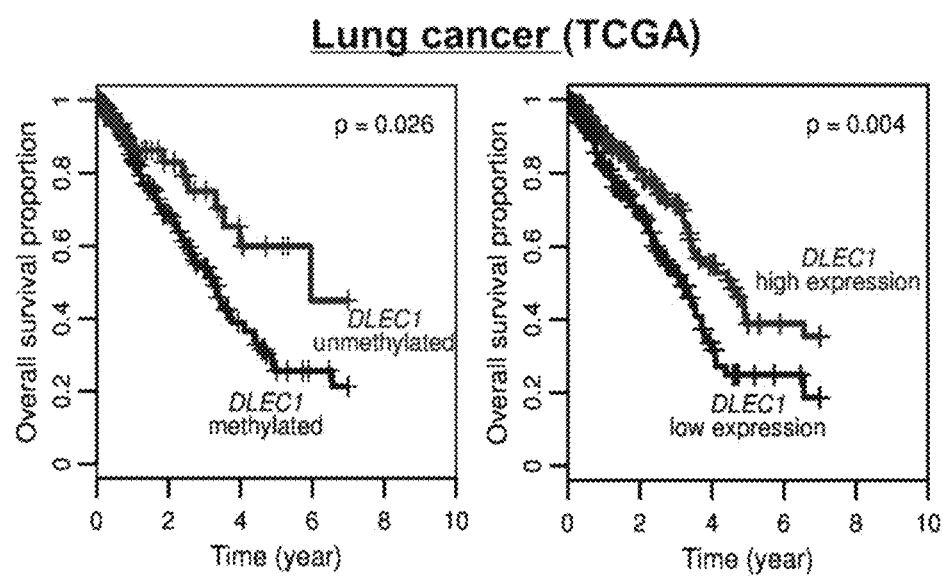

There was a significant correlation between DLEC1 methylation with ESCC tumor size and lymph node metastasis, but not with age, gender, stage, grade, or differentiation in the cohort (Table 2). Further analysis of TCGA datasets showed that esophageal and lung cancer patients with low methylation or high expression of DLEC1 had longer survival (FIG. 2F, G). DLEC1 methylation/expression was also significantly associated with disease progression and age of esophageal and lung cancer patients (Table 3, 4).

DLEC1 methylation status was also compared with other well-known TSGs at the 3p21-22 locus (PLCD1, RASSF1A, ZMYND10) in ESCC cell lines and primary tumors. DLEC1 (23/35, 66%) appears to have the highest rate of promoter methylation in these tumors compared to PLDC1 (14%), RASSF1A (20%) and ZMYND10 (35%) (Table 5). DLEC1 methylation was also detected in 74% (37/50) of NPC tumors but no (0/3) normal nasopharyngeal tissues, as well as in 57% (35/61) of lung carcinomas (FIG. 2D, Table 1). Promoter methylation was further confirmed by BGS, with densely methylated promoter alleles detected in representative tumors but only rare scattered methylated CpG sites detected in normal tissues (FIG. 2D, FIG. 13C). These results indicate the importance of tumor-specific DLEC1 methylation in the pathogenesis of ESCC and other carcinomas.

Alternative Splicing of DLEC1 in Cell Lines and Tissues

As alternative splicings of DLEC1 have been reported previously in tumor and normal tissues [12], the aberrant splicing of DLEC1 was also examined in carcinoma and normal cell lines in addition to normal tissues. Amplicons generated by primers (listed in Table 6) on exon 5 and 9 had 2 major bands, one wild-type (WT) and one novel aberrant splicing (T1), in most tumor cell lines and normal tissues (FIG. 15). In splice variant T1 (NCBI accession number: AY789462), exon 8 was spliced out resulting in in-frame deletion with the exception of L479→V421 (ttg→gtg). Amplicons generated by primers on exon 10 and 13 included one WT and 3 spliced forms: DLEC1S1, DLEC1S2 [12] and a novel splicing DLEC1T2 (NCBI accession number: AY789463). For DLEC1T2, exon 11 and frame 1 of exon 13 were spliced out (FIG. 15), producing a protein identical to DLEC1S1 [12]. Amplifying larger fragments using primers on exon 5 and 13 detected another transcript variant DLEC1T3 (NCBI accession number: AY789464), lacking exons 8, 9, 11 and frame 1 of exon 13, with its translation stopped at exon 10 with premature truncation (FIG. 15).

It was found that all four DLEC1 splice variants are expressed in examined tissues and cell lines with varied expression levels. The expression levels of these splice variants were also higher in most normal tissues than that observed in tumor cell lines (FIG. 15), indicating that the downregulation of DLEC1 splice variants may also be involved in tumor pathogenesis.

DLEC1 Inhibits Carcinoma Cell Proliferation and Induces Apoptosis

Figure 3A:
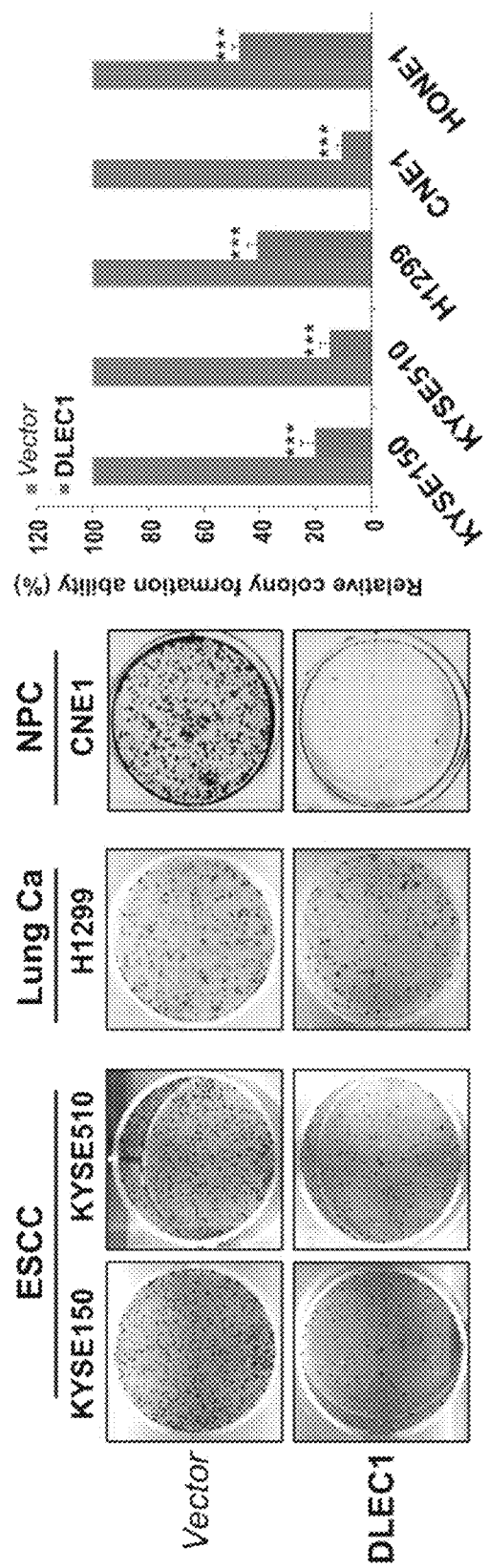
FIGS. 3A-3E DLEC1 inhibits the growth of esophageal and other carcinoma cells.
Figure 3B:
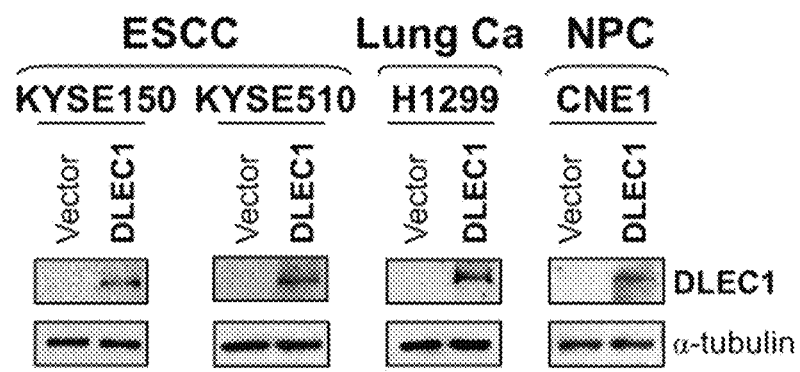
Figure 3C:
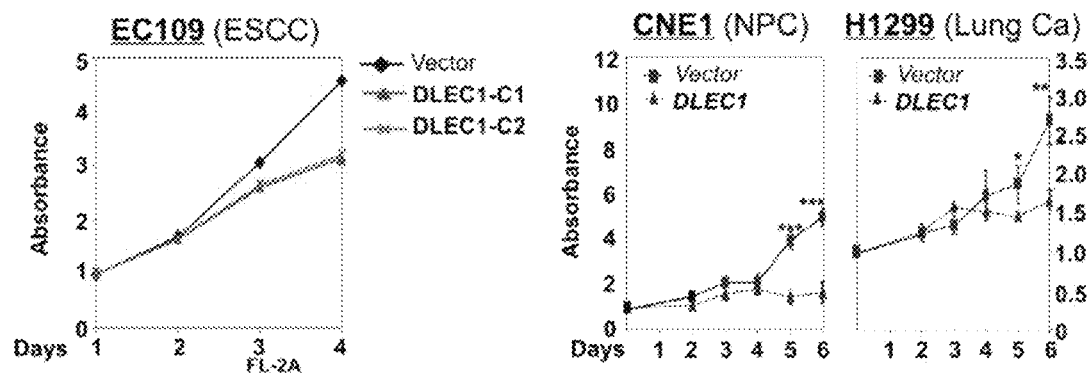

The tumor-specific promoter methylation of DLEC1 indicates its critical role in multiple carcinoma pathogenesis. Its tumor suppressor functions were thus further evaluated in ESCC and other carcinomas. As confirmed by Western blot, the ectopic expression level of DLEC1 was similar to its physiological expression level in normal tissues and immortalized esophageal epithelial cells (FIG. 2B). Monolayer colony formation assay showed significant reduction (down to ~10-40%) in colony numbers and sizes in ESCC, lung and NPC carcinoma cells with ectopically expressed DLEC1 (FIG. 3A, B. FIG. 16A), compared to controls. Cell proliferation assay exhibited slower growth rates in multiple carcinoma cells stably-expressing DLEC1 (FIG. 3C). The clonogenicity results indicate that DLEC1 does have strong growth inhibitory activity in ESCC and other carcinoma cells.

Figure 3D:
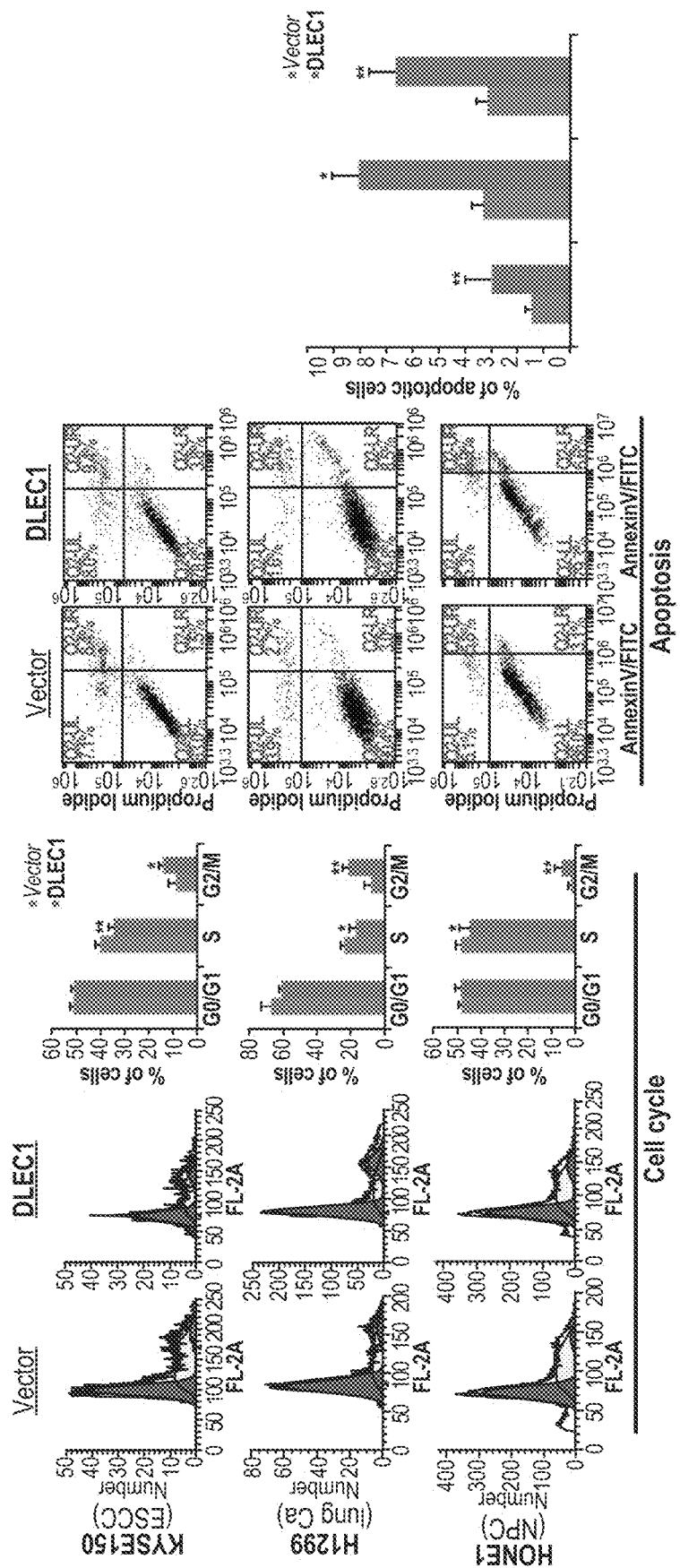
Figure 3E:
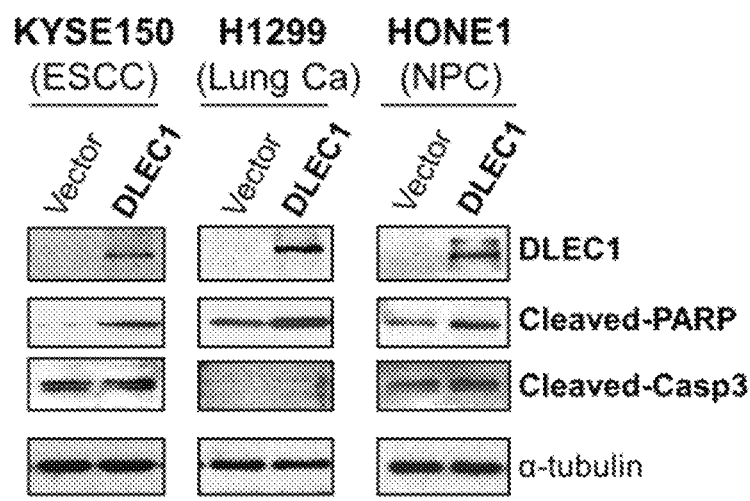

To explore the mechanism of its growth inhibition, the effects of DLEC1 expression on carcinoma cell apoptosis and cell cycle distribution were next examined. Cell cycle analysis by propidium iodide incorporation showed that DLEC1-expressing KYSE150, H1299 and HONE1 cells obviously had increased G2-M phase cells and decreased S phase cells, indicating that DLEC1 expression induces G2-M arrest in multiple carcinoma cells (FIG. 3D). Cell apoptosis assay showed that apoptotic cells significantly increased after being transfected with DLEC1-expression vector (FIG. 3D), as further confirmed by the increase in apoptosis markers (cleaved caspase-3 and PARP) by Western blot (FIG. 3E). Thus, DLEC1 suppresses carcinoma cell growth through inducing cell cycle arrest and apoptosis.

Figure 4A:
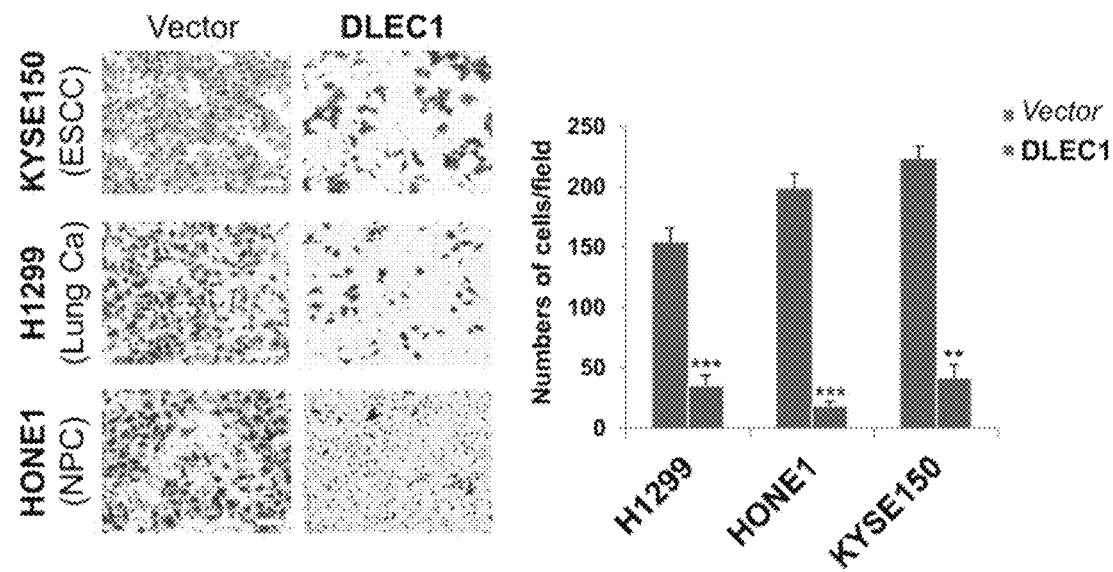
FIGS. 4A-4G DLEC1 suppresses cell migration and invasion of esophageal and other carcinoma cells, with transwell (FIG. 4A) migration and (FIG. 4B) invasion assay of DLEC1-expressing tumor cells. Migrated and invaded cells at the lower surface of the transwell filter were stained and counted. p<0.001, *p<0.0001. Original magnification, ×252. Scale bar 100 µm.
Figure 4B:
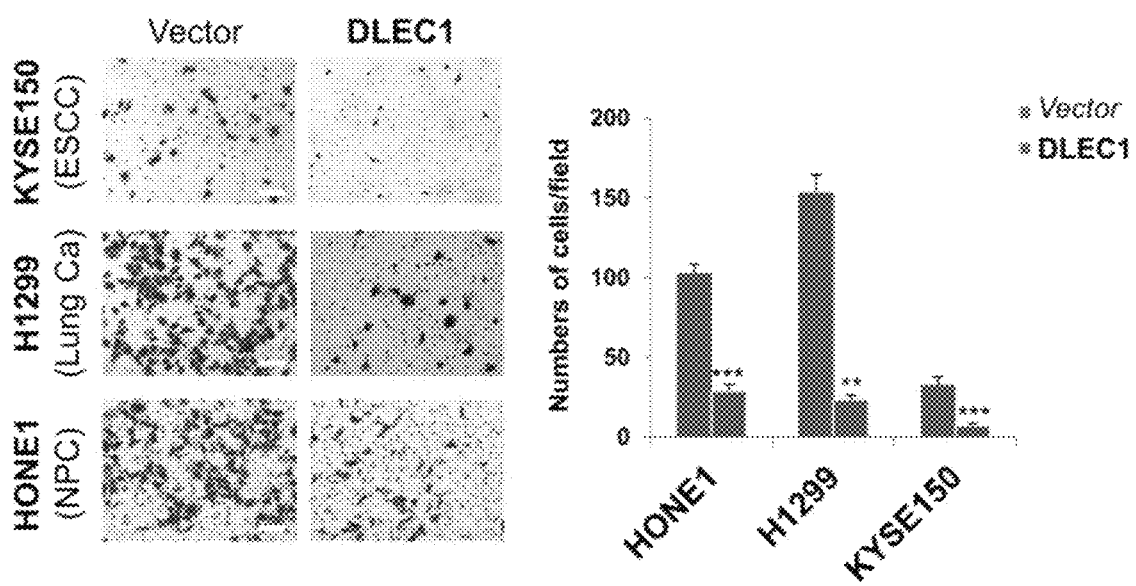
Figure 4C:
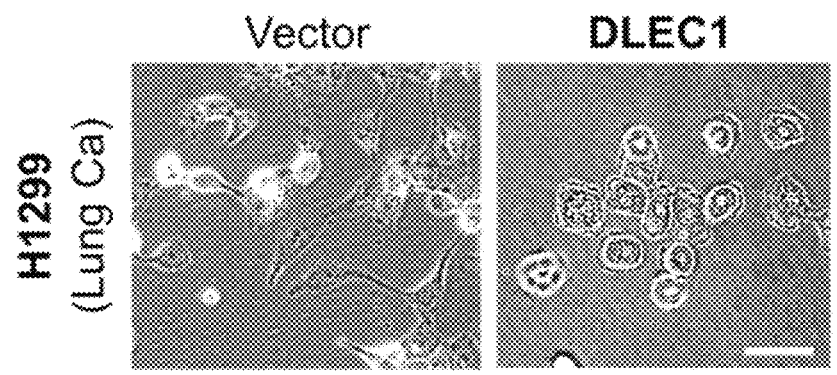
Figure 4D:
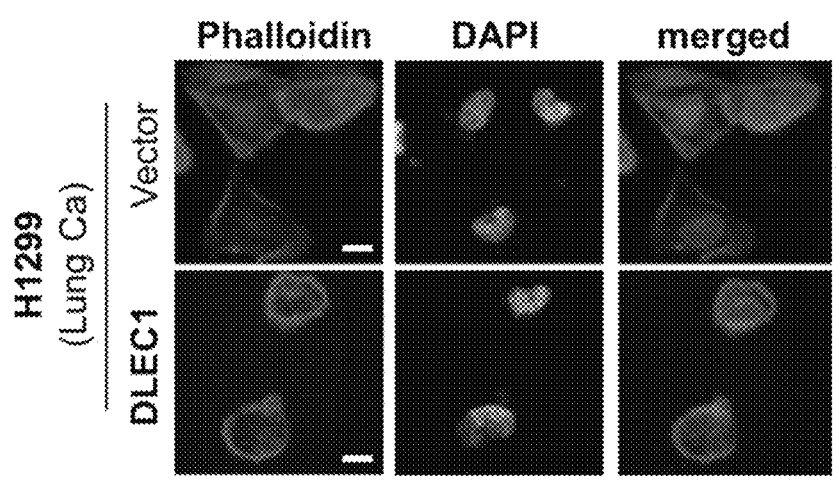

DLEC1 Suppresses Cell Migration Invasion Through Reversing EMT and Cell Stemness The effects of DLEC1 on carcinoma cell migration and invasion were further assessed. Ectopic expression of DLEC1 dramatically suppressed the migration and invasion of ESCC, lung and NPC carcinoma cells in transwell assays (FIG. 4A, B). DLEC1-expressing cells also showed less proficiency in closing artificial wounds than mock cells on a confluent monolayer in scratch wound-healing invasion assays (FIG. 16B). Meanwhile, dramatic morphological changes were observed in DLEC1-expressing carcinoma cells, with similar cobblestone-like appearance as normal epithelial cells (FIG. 4C). Moreover, expression of DLEC1 disassembled the formation of actin stress fibers in carcinoma cells (FIG. 4D).

Figure 4E:
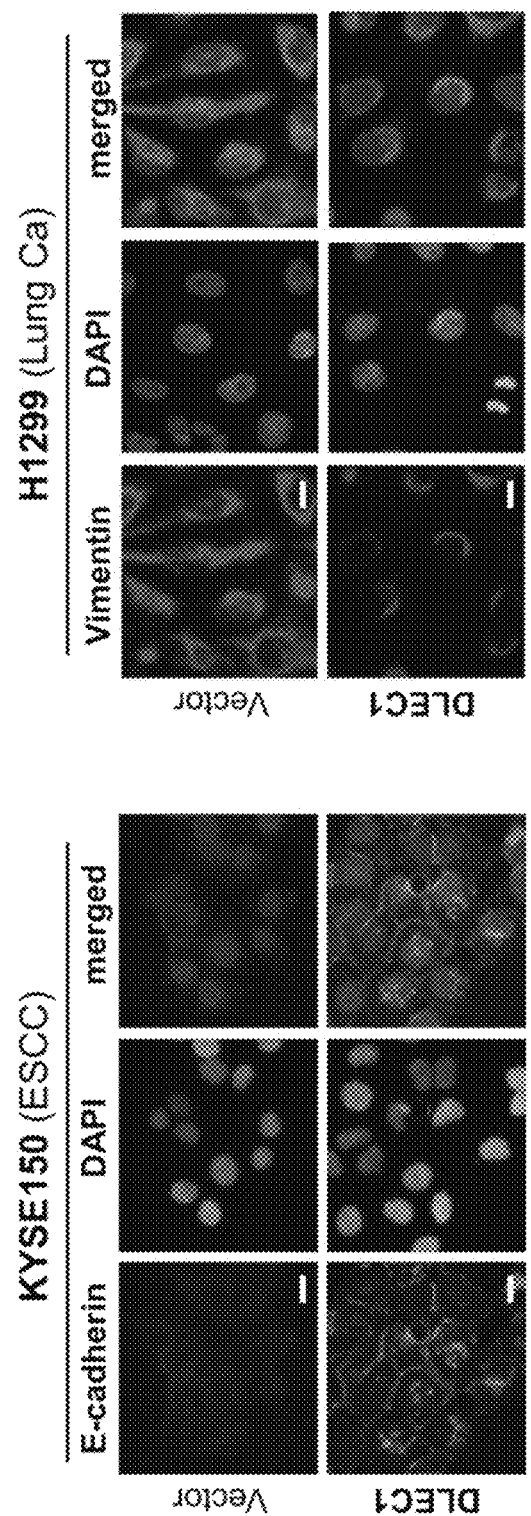
Figure 4F:
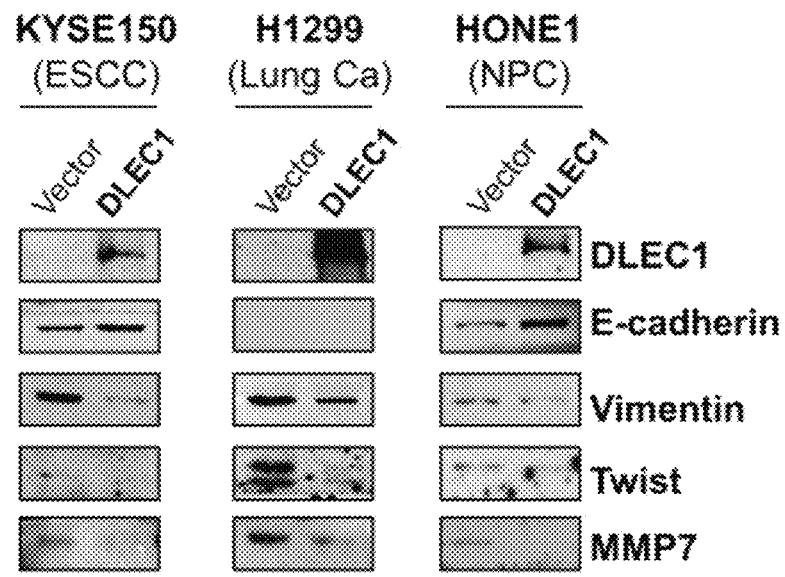
Figure 4G:
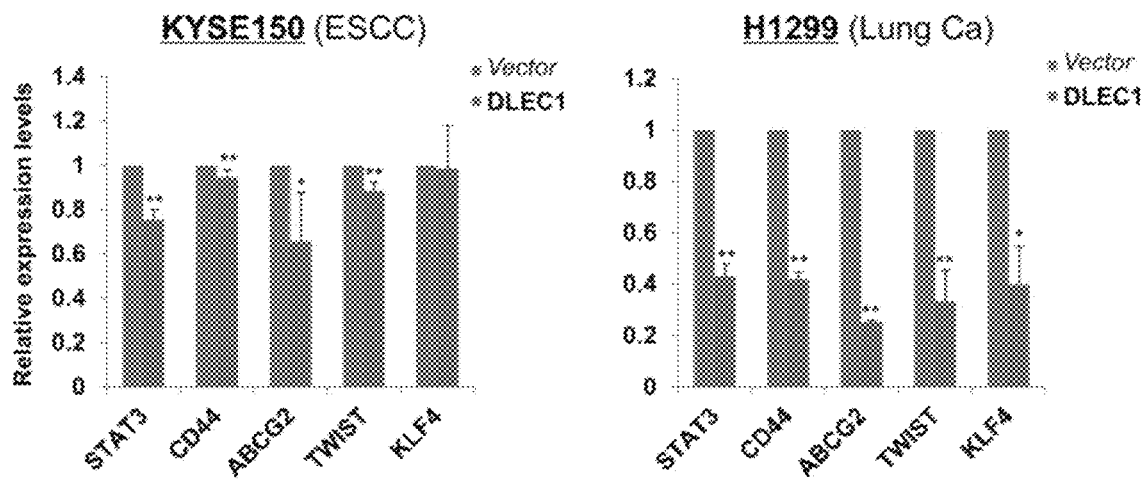

It was then investigated whether DLEC1 regulates epithelial mesenchymal transition (EMT) in carcinoma cells. DLEC1-expressing cells adopted an epithelial morphology, concomitant with gain of epithelial marker E-cadherin and loss of mesenchymal marker vimentin (FIG. 4E). Upregulated E-cadherin and downregulated vimentin and metastasis markers (MMP7, Twist) were also confirmed by Western blot (FIG. 4F). As cells generate stem-like properties during EMT, the regulatory effect of DLEC1 on carcinoma cell stemness was further examined. Stem cell markers (STAT3, CD44, ABCG2, TWIST and KLF4) were downregulated in ESCC and lung carcinoma cells after DLEC1 expression, with the effect more potent in lung carcinoma cells (FIG. 4G). These results clearly indicate that DLEC1 possesses anti-metastatic ability through reversing EMT and stemness of carcinoma cells.

DLEC1 Represses Oncogenic Signaling Pathways in Carcinoma Cells

Figure 5A:
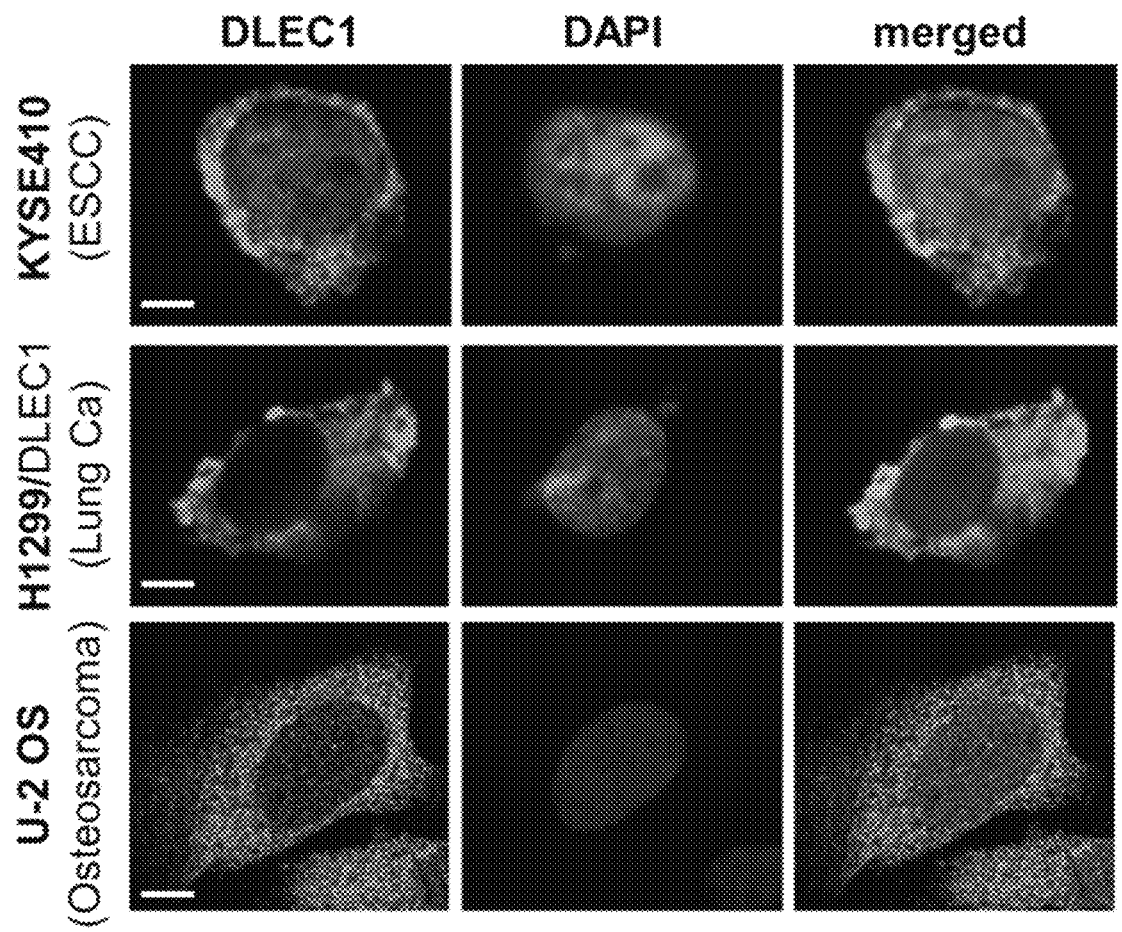
FIGS. 5A-5D DLEC1 as a cytoplasmic protein regulates multiple cell signaling pathways.

The subcellular localization of DLEC1 in KYSE410 (endogenous) and H1299 (ectopically expressed) cells was examined using the DLEC1 antibody. Immunostaining showed that DLEC1 is mainly located in the cytoplasm of examined cells (FIG. 5A). Its cytoplasmic localization was also clearly demonstrated by confocal microscopy in U-2 OS cells from Human Protein Atlas database, with the same DLEC1 antibody used (FIG. 5A).

Figure 5B:
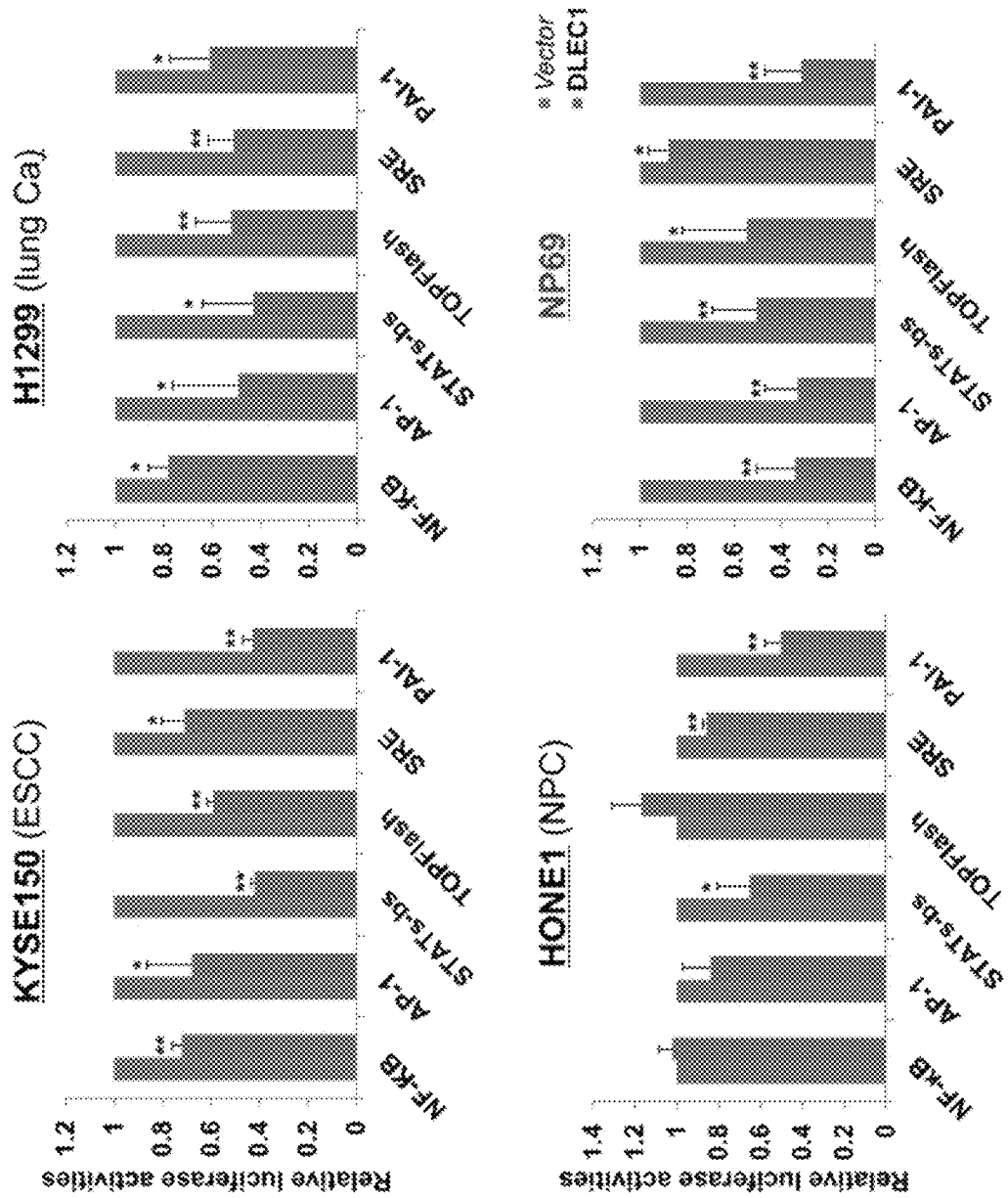
Figure 5C:
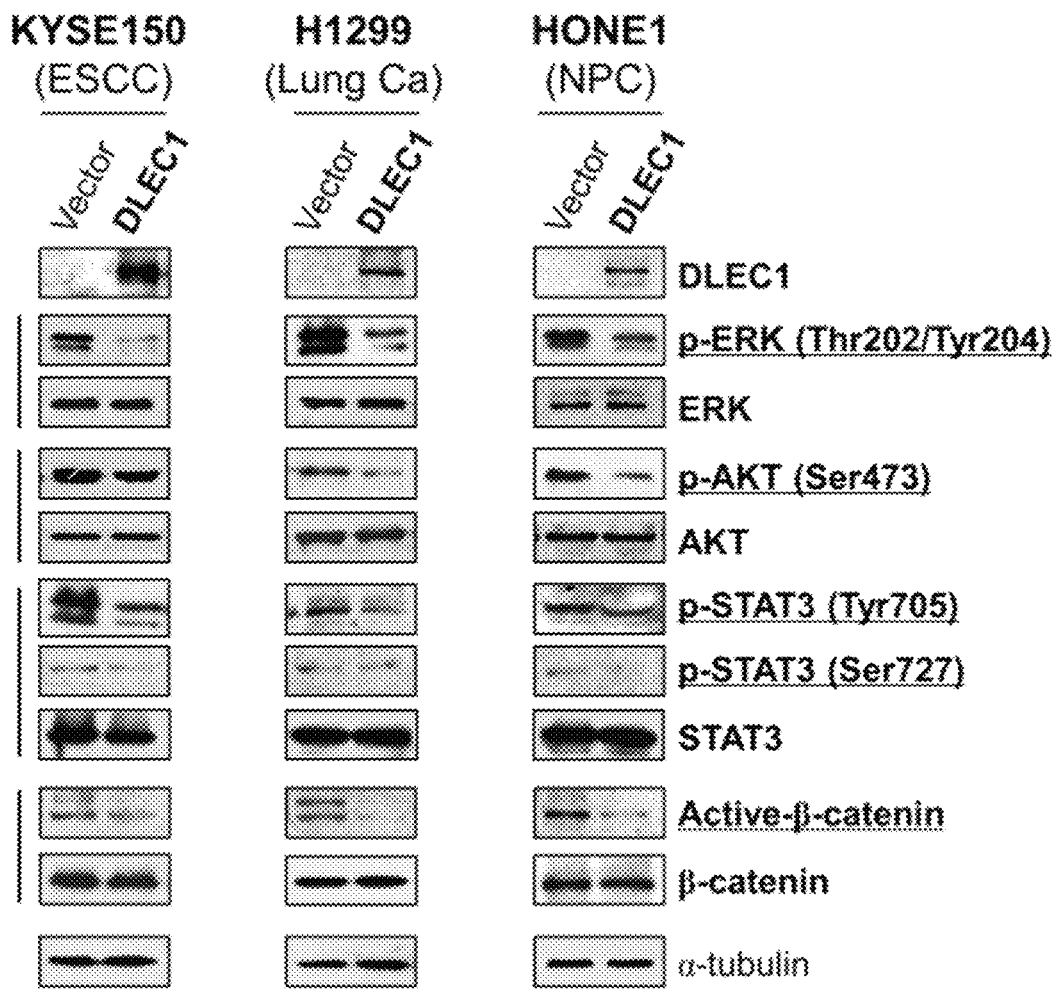
Figure 5D:
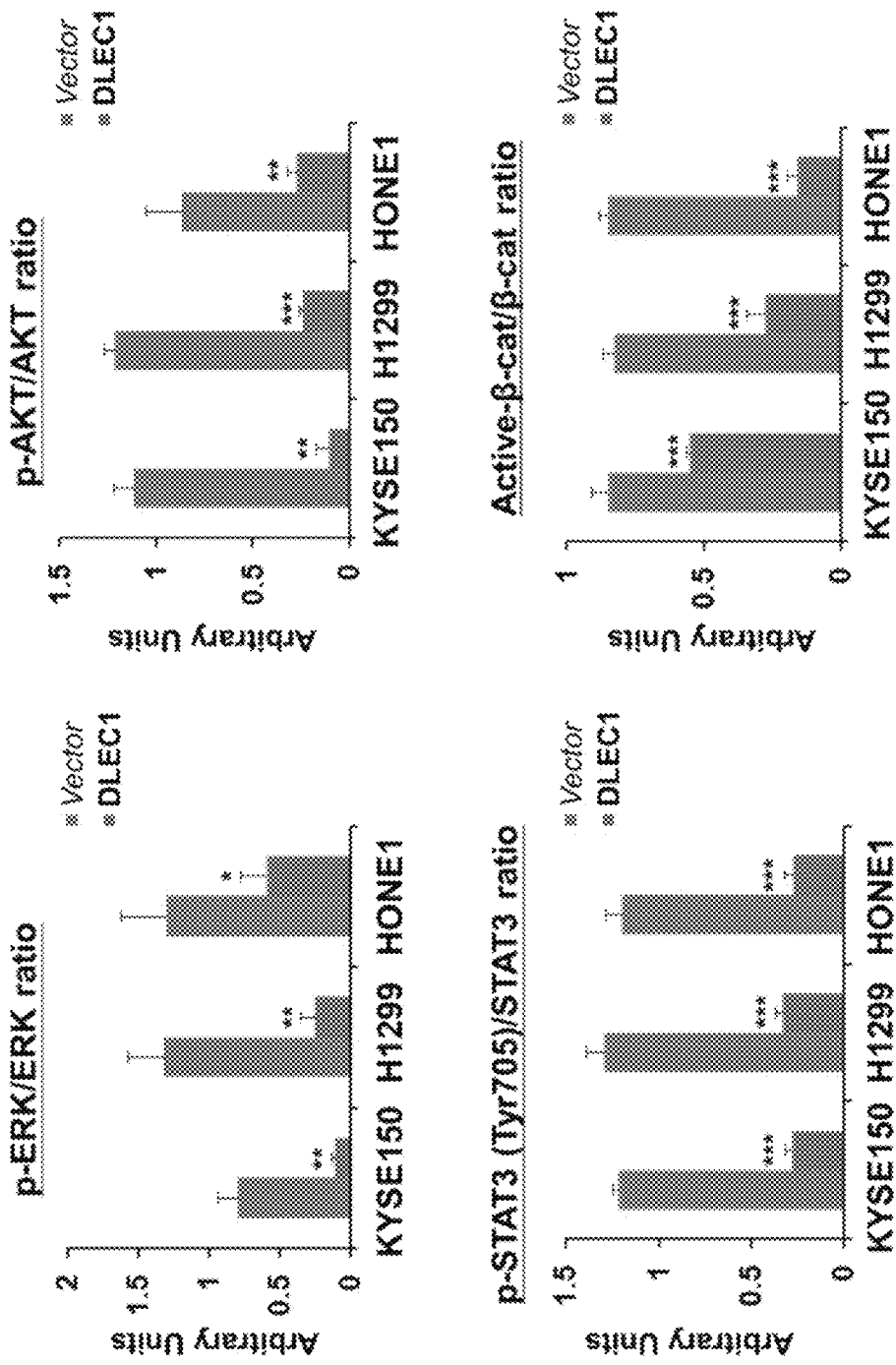

To gain more insight into the mechanisms underlying tumor suppression by DLEC1, luciferase reporter assay was used to examine its effects on oncogenic signaling pathways in carcinoma cells. Results showed that ectopic expression of DLEC1 markedly repressed the reporter activities of NF-κB, AP-1, STATs-bs, TopFlash, SRE and PAI-1 elements-regulated promoters in either carcinoma cells (ESCC, lung, NPC) or immortalized normal epithelial cells (NP69) (FIG. 5B). Western blot confirmed significantly decreased levels of p-ERK (Thr202/Tyr204), p-AKT (Ser473), p-STAT3 (Tyr705 and Ser727) and active-$-catenin in DLEC1-expressing carcinoma cells (FIG. 5C, D). These results indicate that DLEC1 is able to repress multiple oncogenic signaling pathways, including JAK/STAT3, MAPK/ERK, AKT, Wnt/β-catenin and TGF-β signaling during the tumorigenesis of multiple carcinomas.

DLEC1 Suppresses STAT3 Phosphorylation in Multiple Carcinoma Cells

Figure 6A:
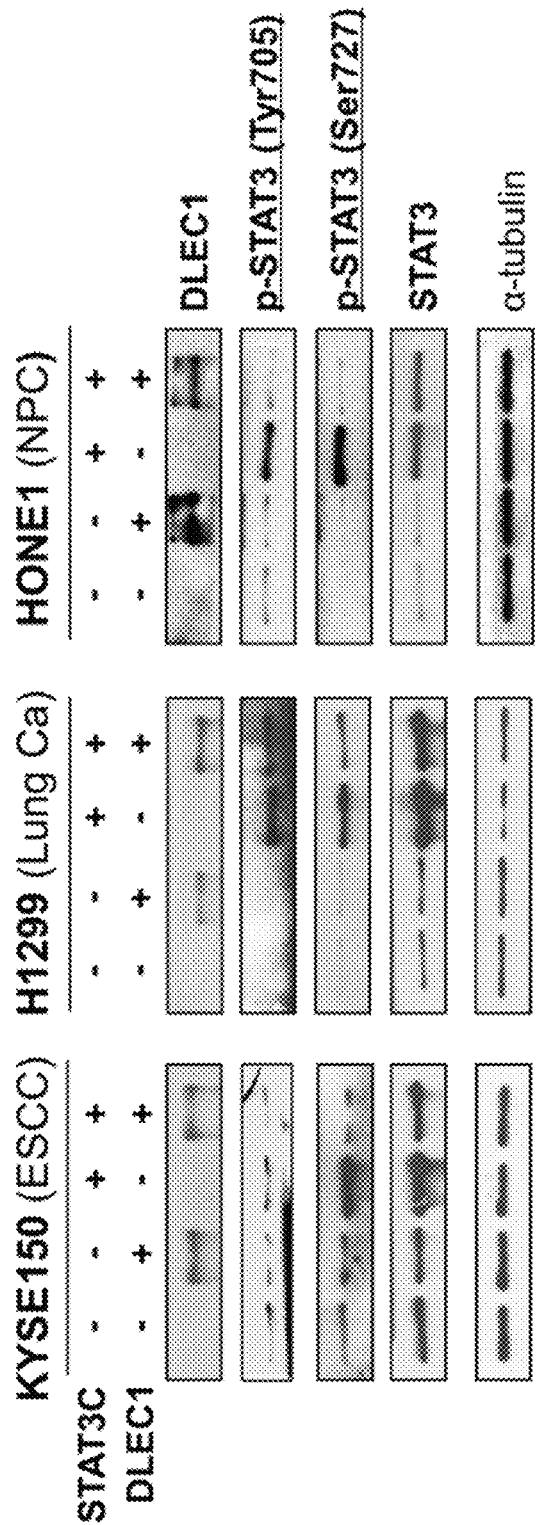
FIGS. 6A-6D DLEC1 inhibits STAT3 signaling activation through suppressing its phosphorylation in tumor cells. Expression levels of p-STAT3 (Tyr705, Tyr727) and STAT3 were assessed by Western blot in cells transfected with (FIG. 6A) both DLEC1 and STAT-3C.
Figure 6B:
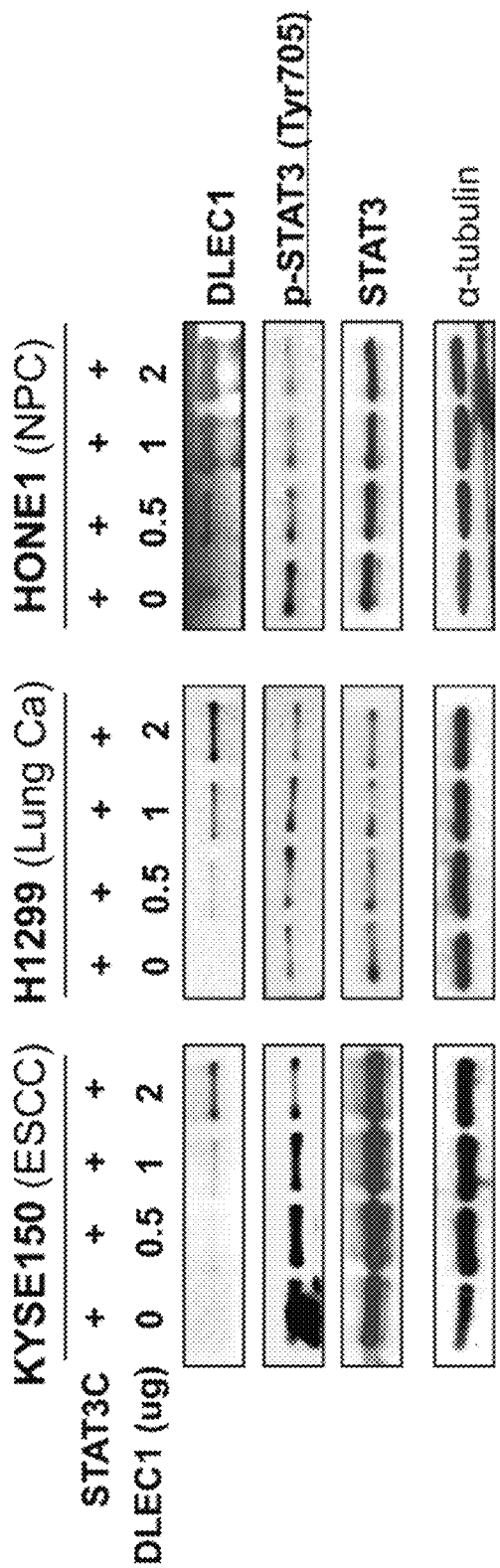

The regulation of STAT3 signaling by DLEC1 was further investigated in more detail. Carcinoma cells were co-transfected with DLEC1- and STAT3C (a constitutive active form of STAT3)-expression plasmids. Exogenously expressed DLEC1 greatly suppressed the p-STAT3 levels at both Tyr705 and Ser727 sites in STAT3C-transfected carcinoma cells, with no changes in STAT3 total protein levels (FIG. 6A). Marked decrease of p-STAT3 (Tyr705), in a dose-dependent manner, was observed in carcinoma cells transfected with increasing doses of DLEC1-expressing plasmids (FIG. 6B).

Figure 6C:
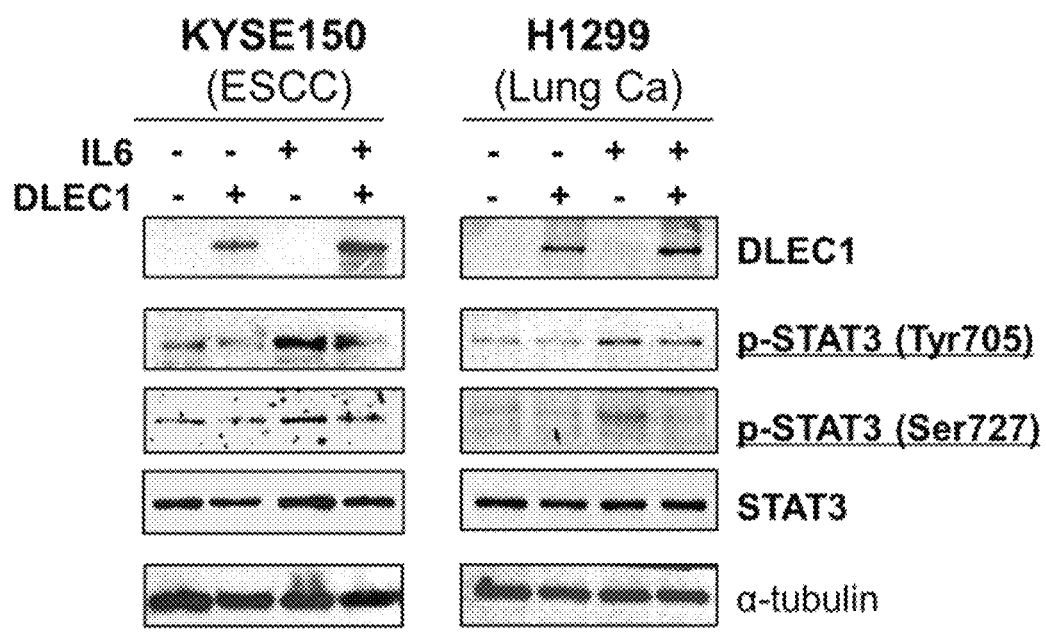
Figure 6D:
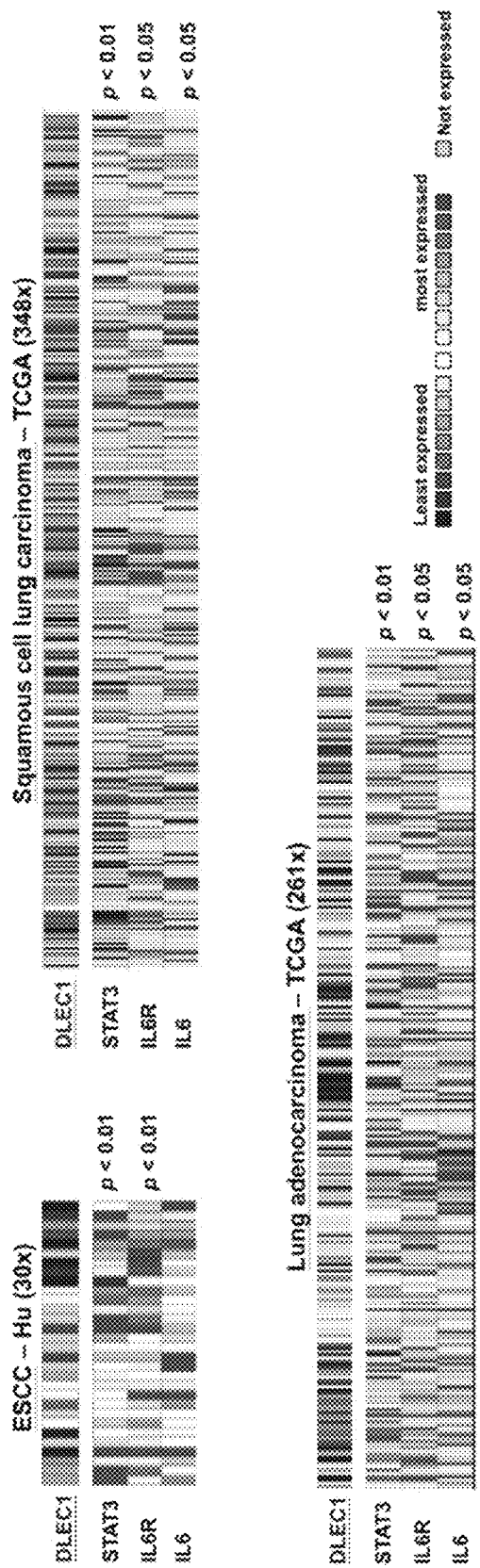

Moreover, DLEC1 was even able to suppress IL-6 treatment-enhanced STAT3 phosphorylation levels in carcinoma cells, without affecting STAT3 total protein level (FIG. 6C). The co-expression of DLEC1 and STAT3 signaling molecules in multiple carcinomas was thus further analyzed online, and it was found that DLEC1 underexpression is indeed associated with elevated expression of STAT3, IL-6 and IL-6R in ESCC and lung carcinoma patients (p<0.05, p<0.01) (FIG. 6D), indicating inhibitory regulation of STAT3 signaling activation by DLEC1. These results suggest that DLEC1 indeed suppresses STAT3 signaling activation through reducing its phosphorylation levels in multiple carcinoma cells.

DLEC1 Binds to STAT3, which Interferes with its Interaction with JAK2

Figure 7A:
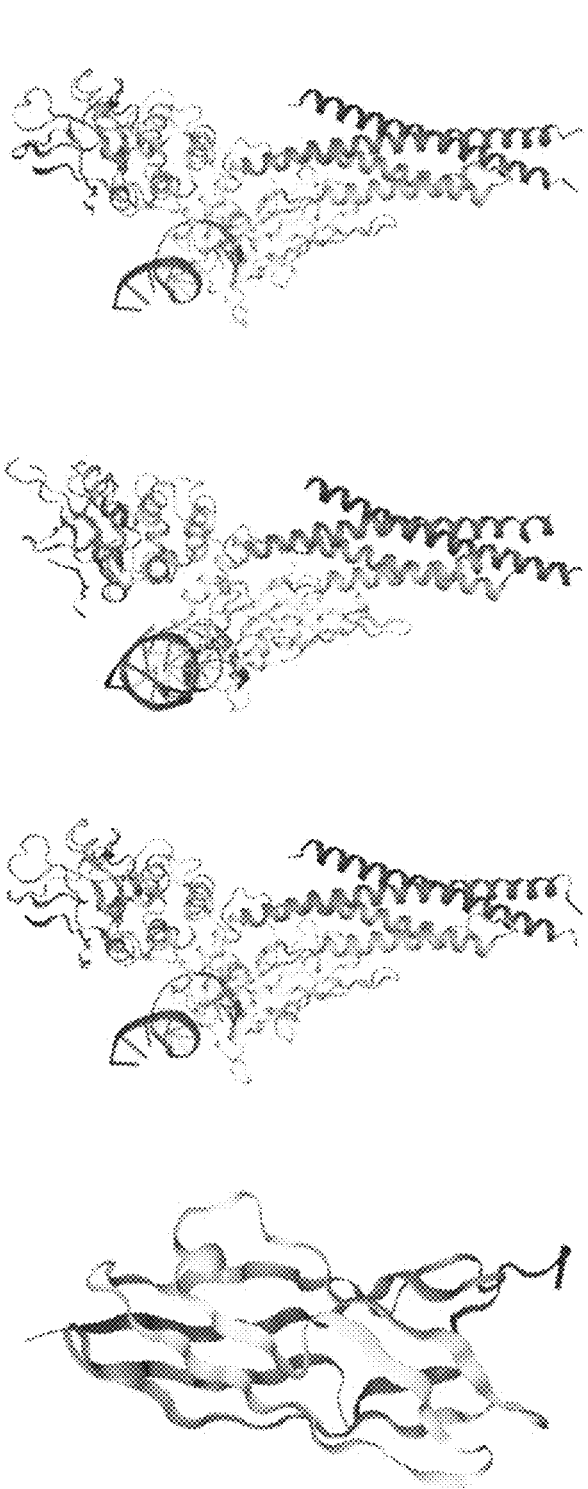
FIGS. 7A-7H DLEC1 binds to STAT3 and blocks its interaction with JAK2.
Figure 7B:
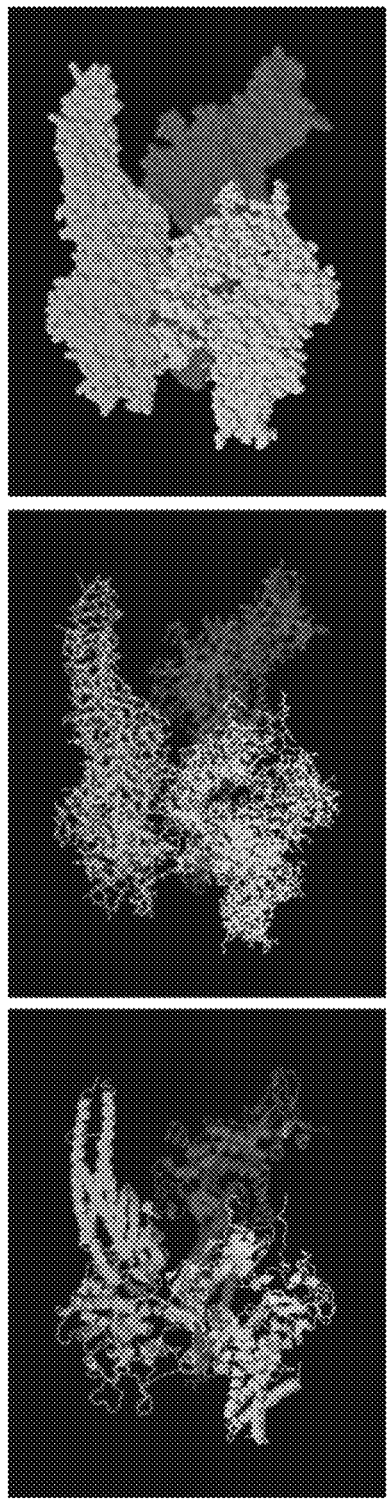
Figure 7C:
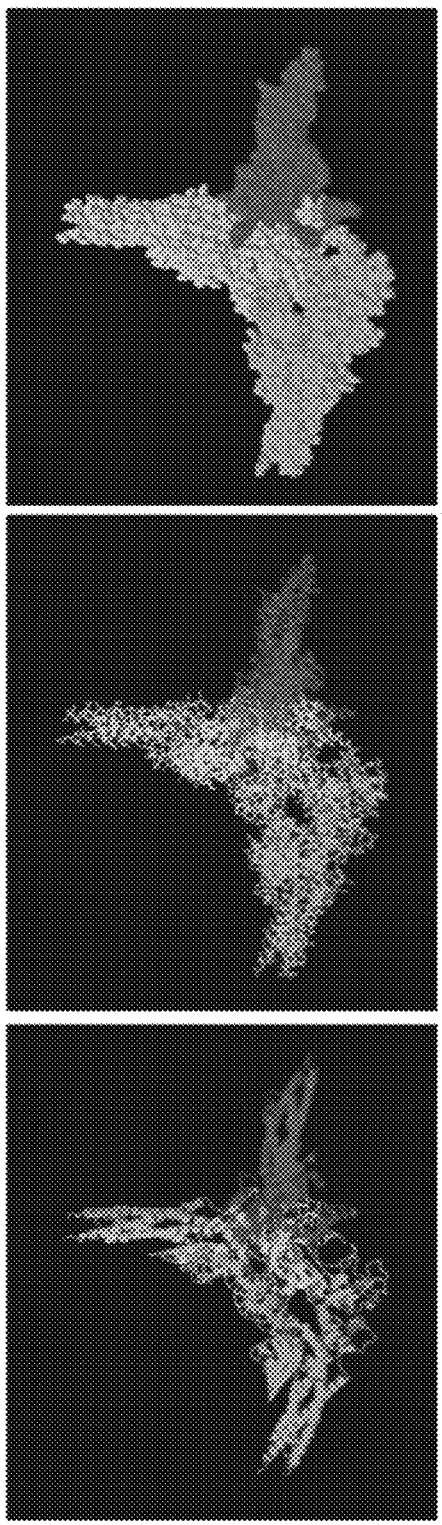

To investigate the mechanism of STAT3 phosphorylation suppression by DLEC1, the structure basis for possible interaction between DLEC1 and STAT3 was analyzed. RCSB Protein Data Bank (PDB) was used to search for structures and folds related to DLEC1 and STAT3 (FIG. 7A). As the DLEC1 N-terminal PDB is similar to phosphatase, computational docking analysis for DLEC1 and STAT3 was thus performed via the ZDOCK server [32]. Following docking of these two proteins without residue selection, two highest-scored predicted models of interaction between DLEC1 (PDB id: 2E6J) and STAT3 (PDB id: 1BG1 and 4E68) were discovered (FIG. 7B, C), while STAT3 (PDB id: 1BF5) failed to dock with DLEC1 due to its large molecule size. This docking analysis reveals the 3D structural basis for possible interaction between the DLEC1 and STAT3 proteins.

Figure 7D:
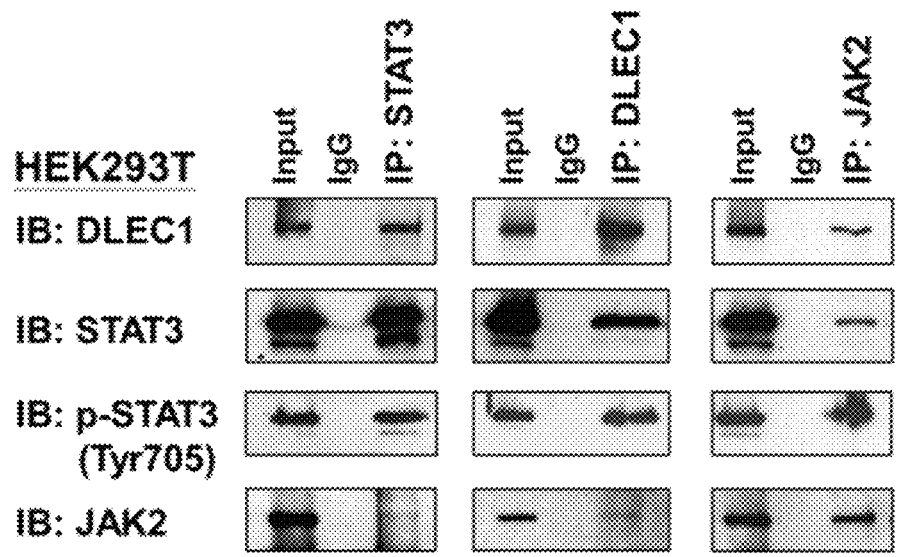
Figure 7E:
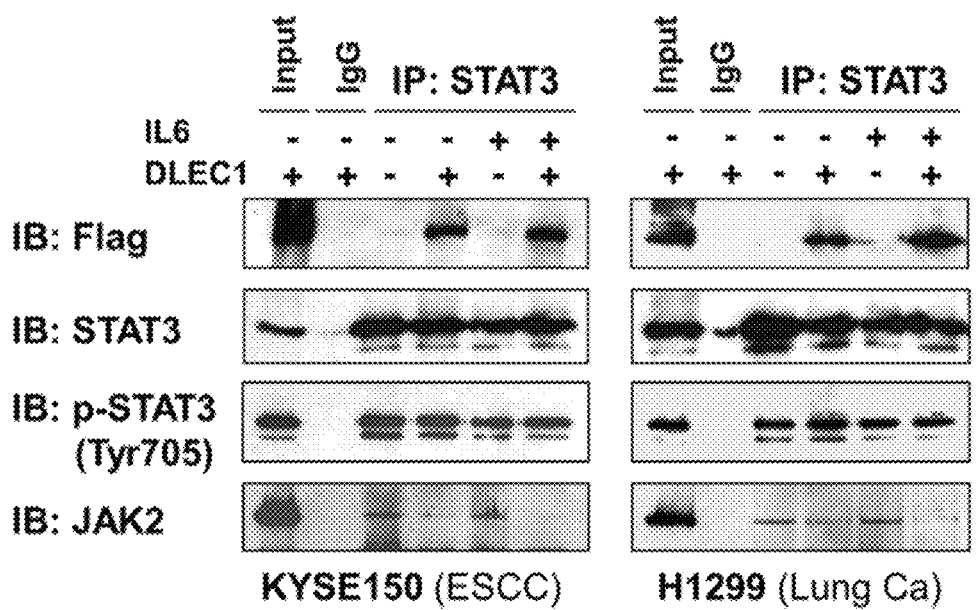
Figure 7F:
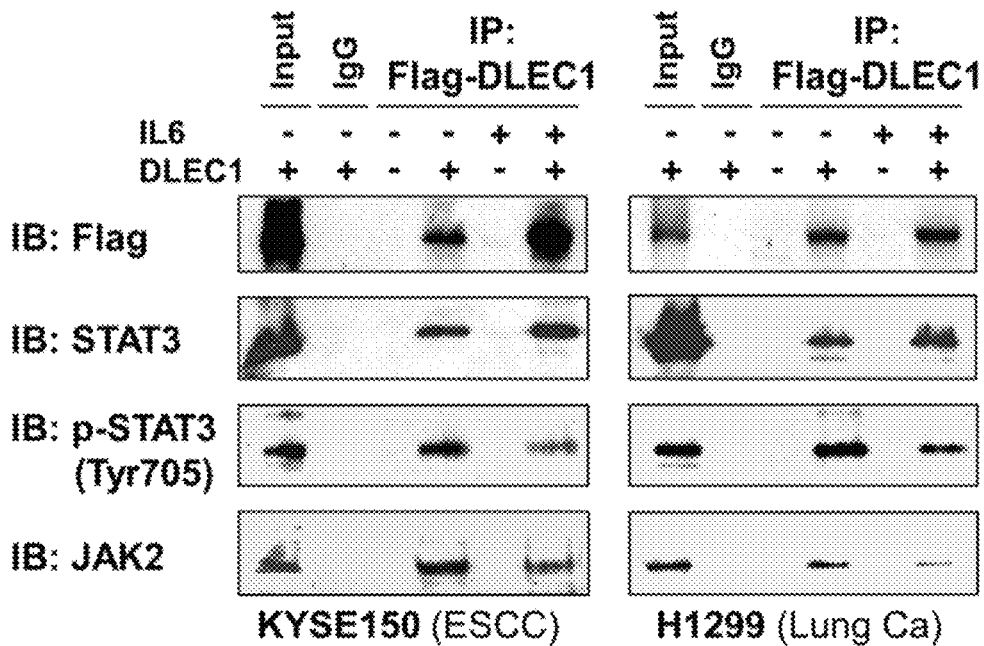
Figure 7G:
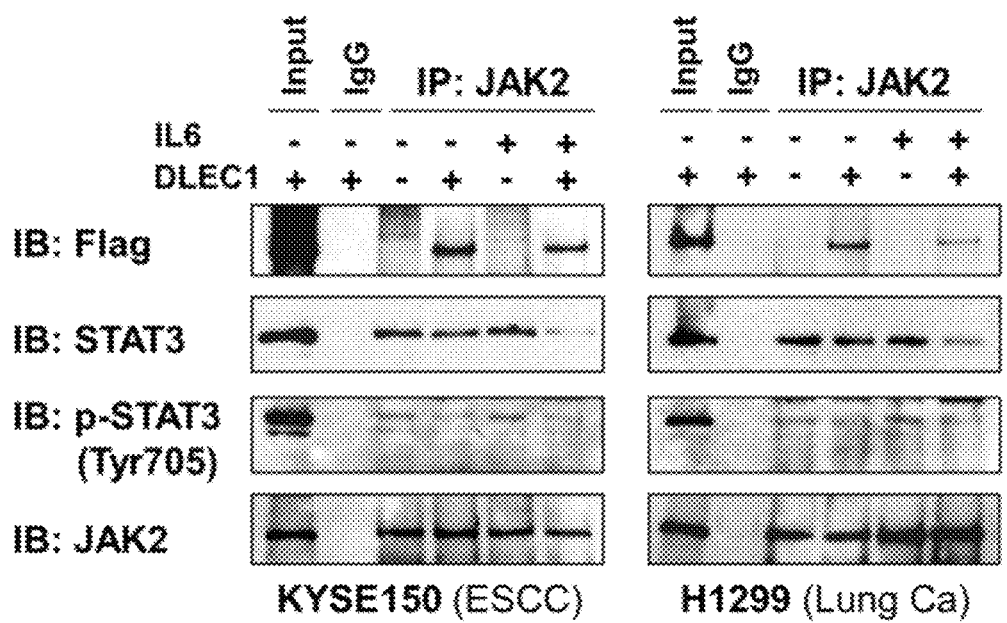
Figure 7H:
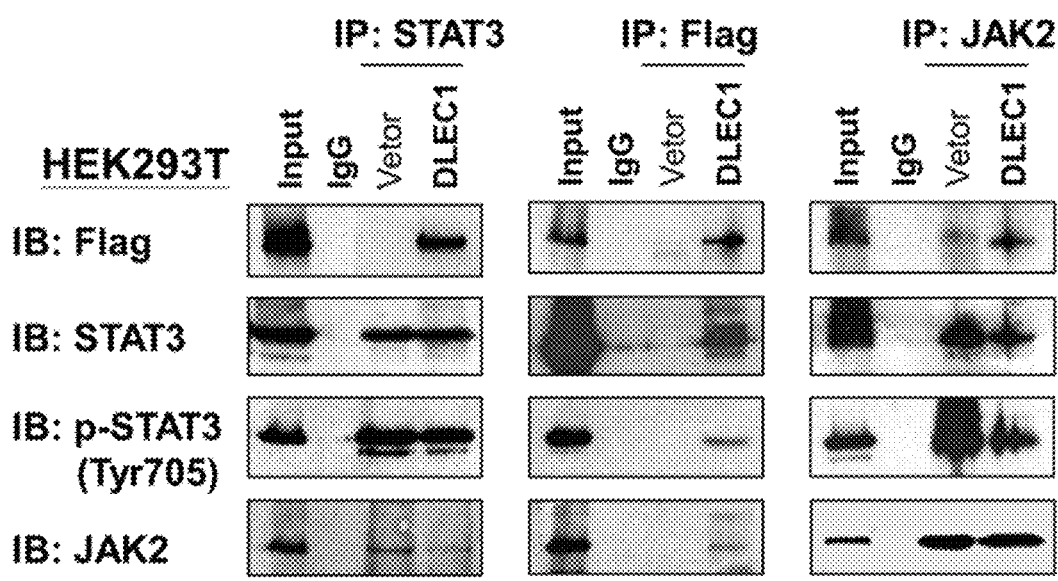

As JAK2 directly phosphorylates STAT3 at Tyr705, the possible interactions of DLEC1 with STAT3 and JAK2 were next examined by reciprocal co-immunoprecipitation (co-IP) experiments with Flag or DLEC1, STAT3 and JAK2 antibodies in carcinoma (KYSE150, H1299) and immortalized cells (HEK293T). Results showed a strong interaction between endogenous DLEC1 and STAT3/p-STAT3 (Tyr705) in HEK293T cells by immunoprecipitation, accompanied by relatively weaker co-precipitation of JAK2. Endogenous JAK2 could also precipitate with both DLEC1 and STAT3/p-STAT3 (Tyr705) (FIG. 7D). Similarly, exogenous DLEC1 could be co-IP with both STAT3/p-STAT3 (Tyr705) and JAK2 (FIG. 7E-H). Moreover, IL-6 stimulation increased the interaction of DLEC1 with STAT3, while decreasing its interaction with JAK2 and p-STAT3 (Tyr705). Thus, DLEC1 inhibited the interaction of STAT3 with JAK2 in an IL-6 dependent manner (FIG. 7E-G). These results suggest that DLEC1 is associated with STAT3 and their binding interferes with JAK2-STAT3 interaction and further STAT3 phosphorylation.

DLEC1 Inhibits STAT3 Phosphorylation Via its YXXQ Motif

Figure 8A:
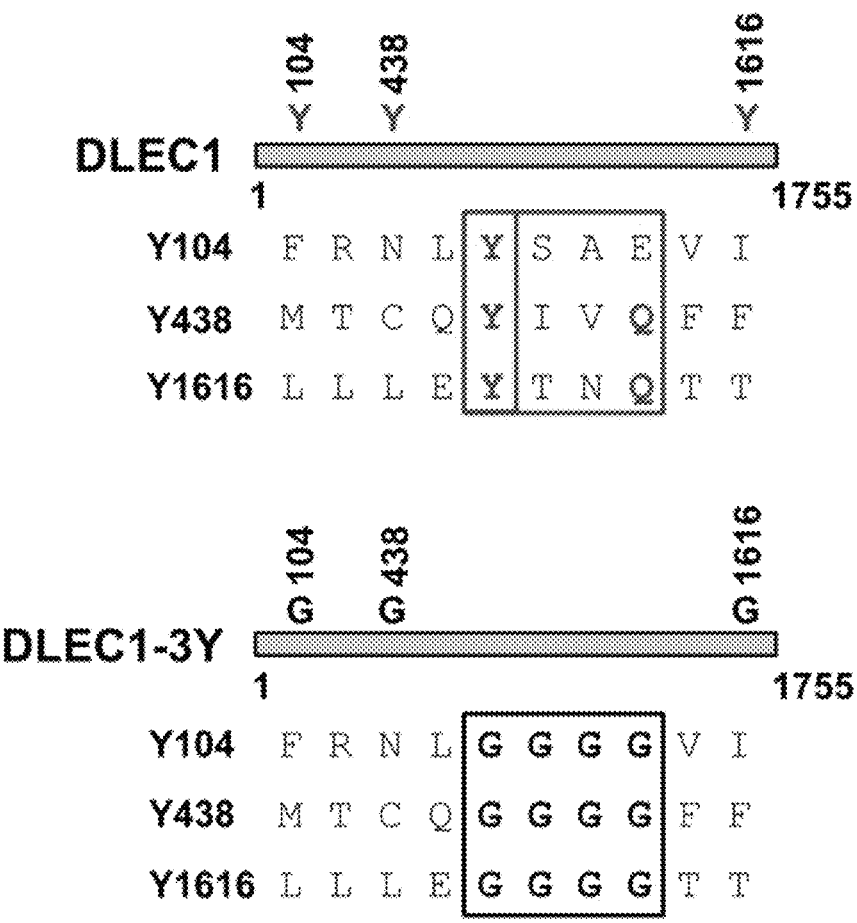
FIGS. 8A-8F Roles of the YXXQ motif in DLEC1-mediated inhibition of STAT3 phosphorylation/activation.
Figure 8B:
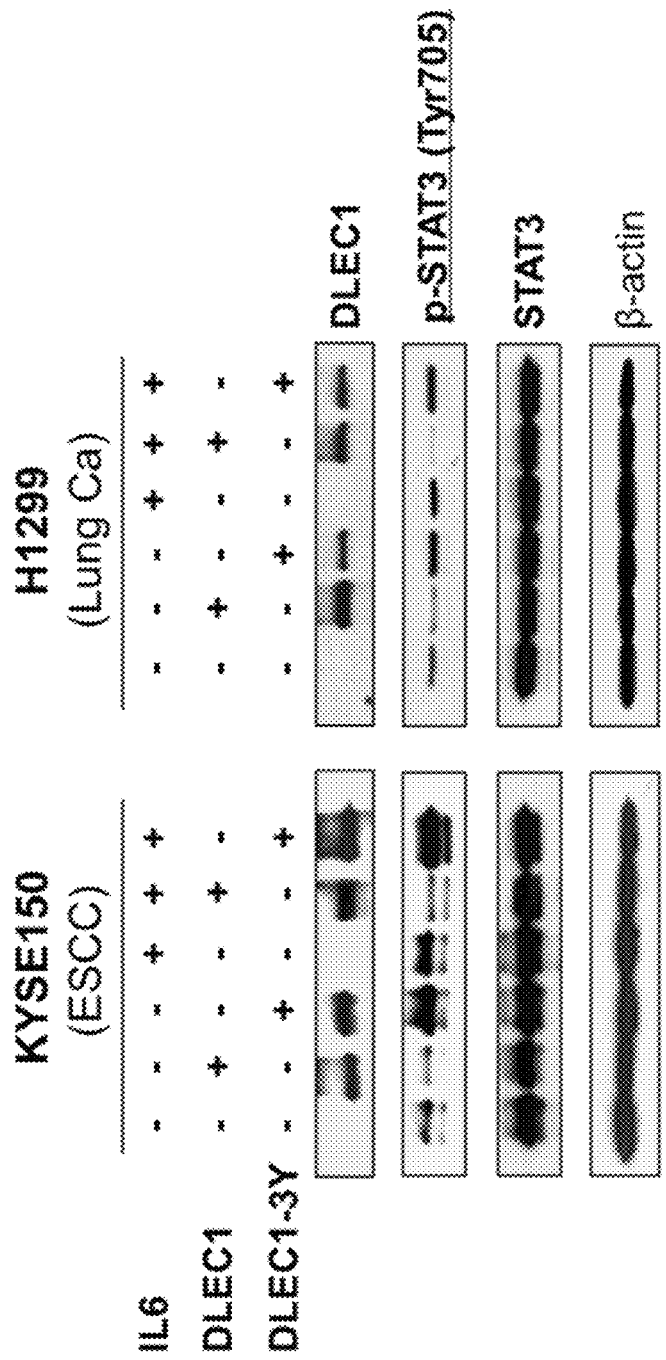
Figure 8C:
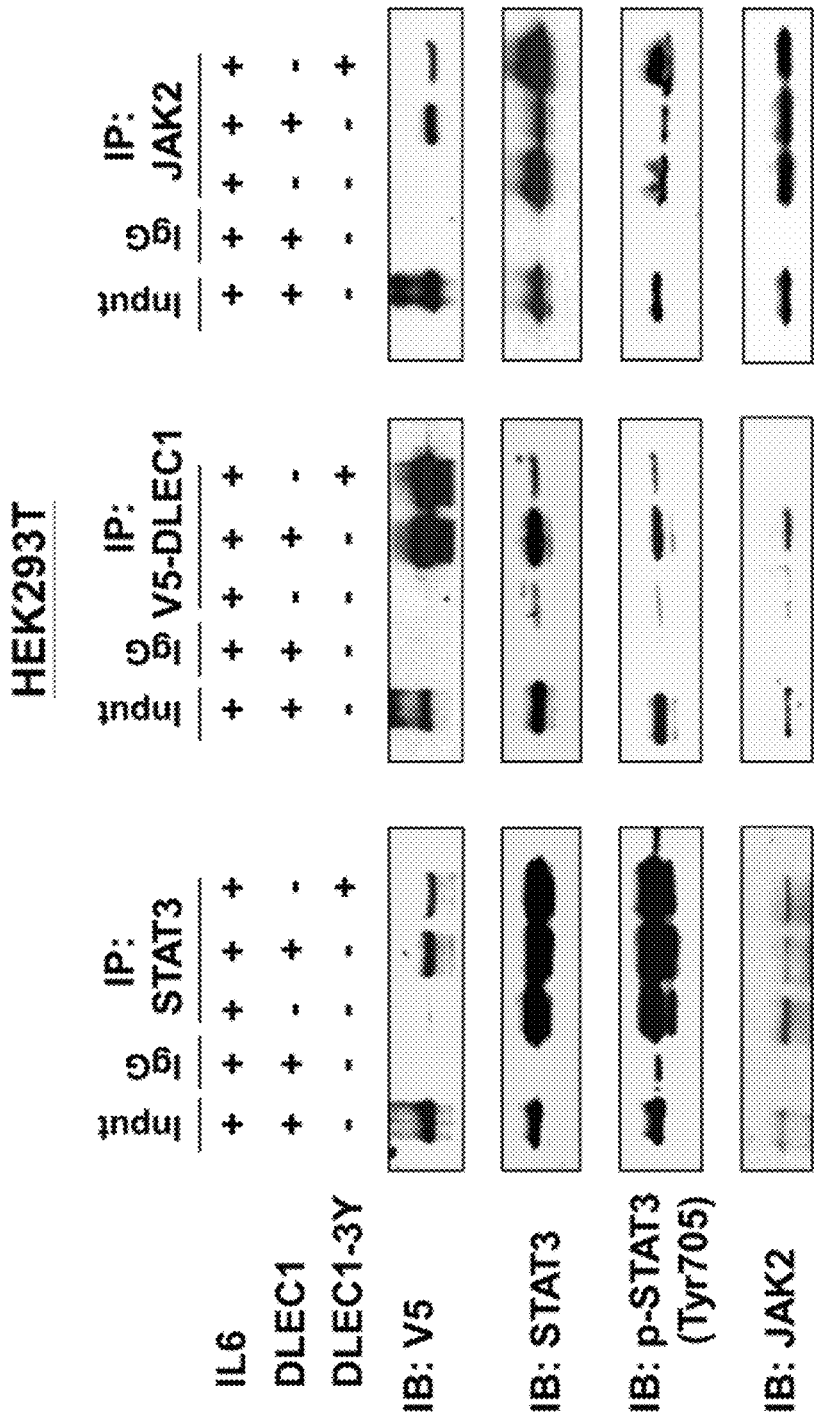
Figure 8D:
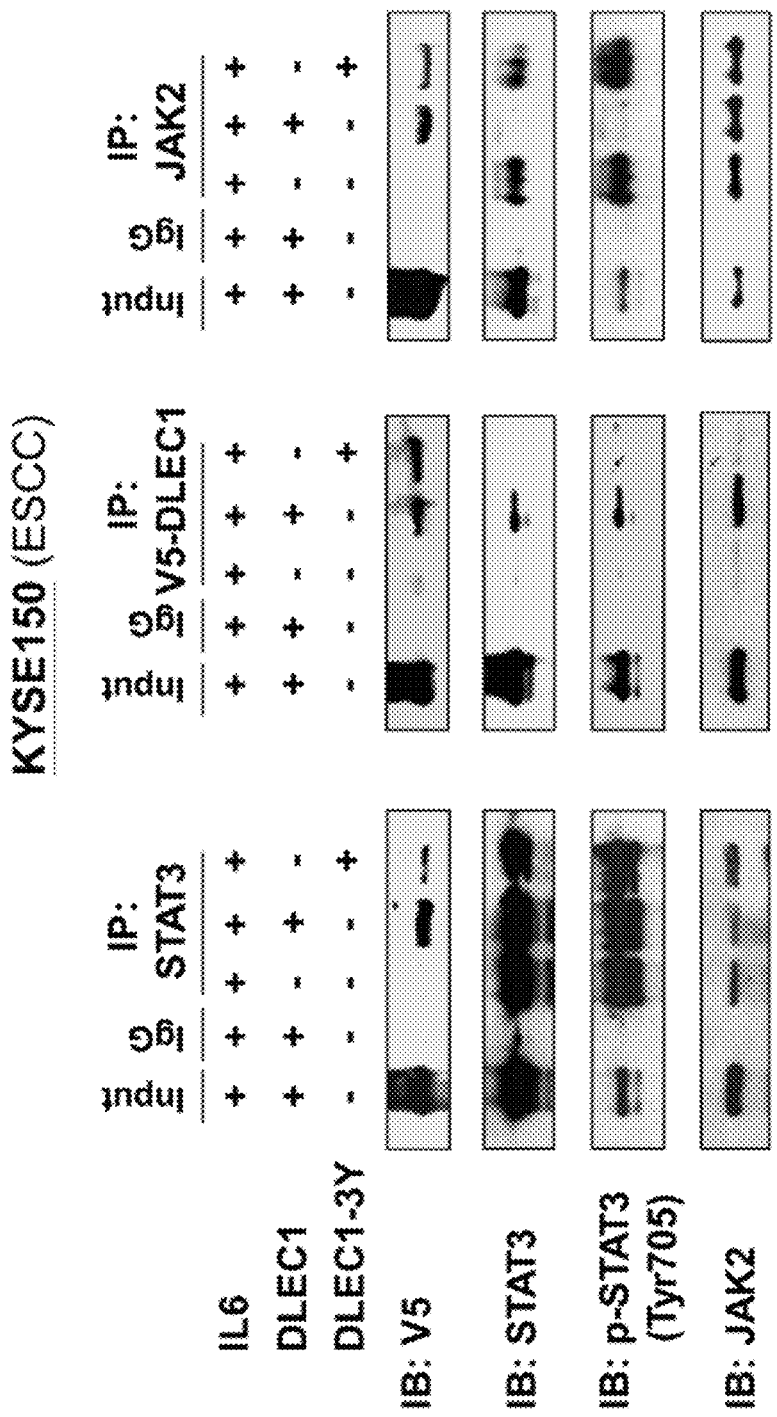
Figure 8E:
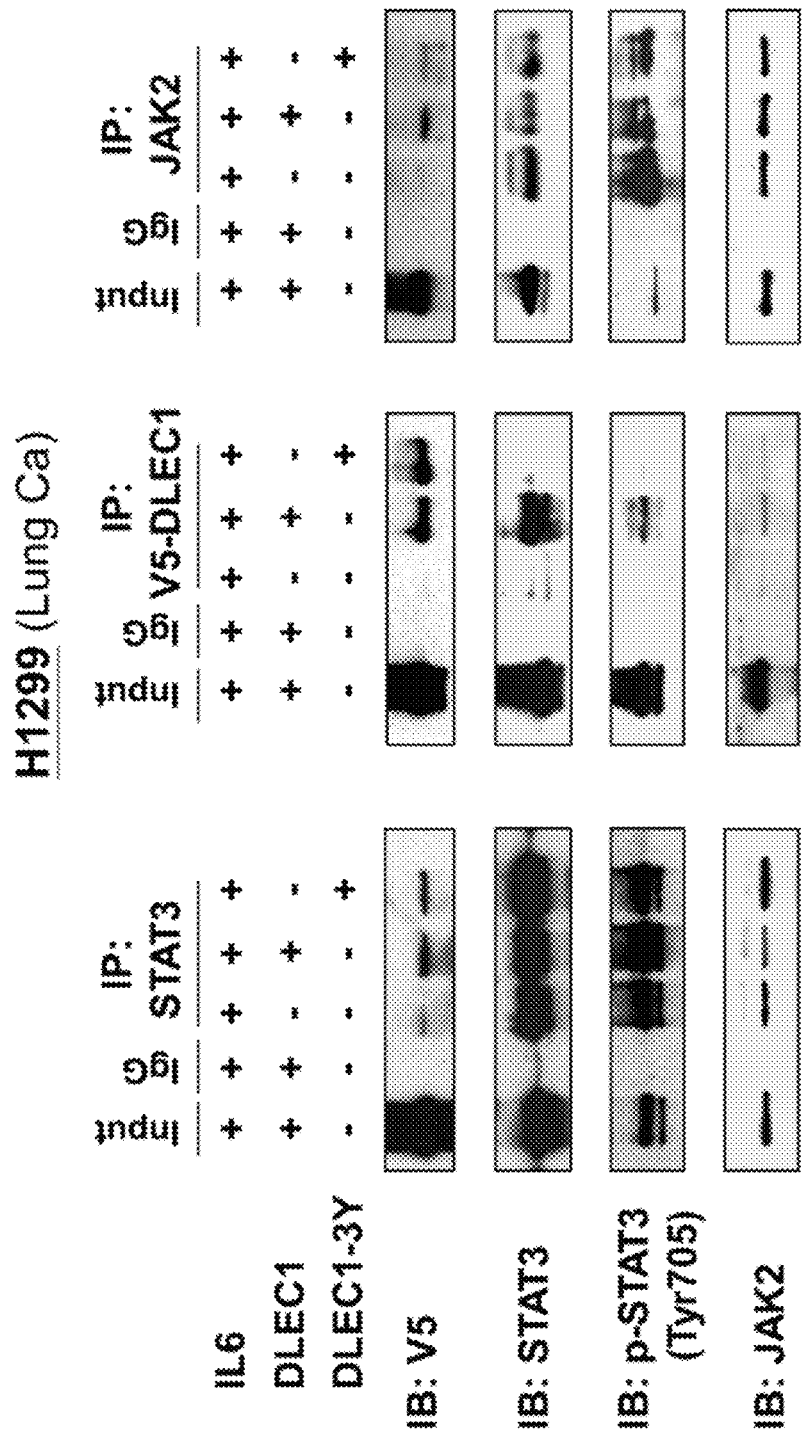

In agreement with the above computational docking analysis, further protein structure analysis showed that DLEC1 contains three STAT3-specific docking sites—YXXQ motifs (FIG. 8A), indicating that YXXQ motif may mediate the inhibition of STAT3 phosphorylation by DLEC1. DLEC1 was also found to have high homology to multiple chaperone proteins (data not shown). A DLEC1-YXXQ mutant (DLEC1-3Y) was thus generated with mutations of all three YXXQ motifs to investigate the role of these residues in STAT3 phosphorylation. Ectopic expression of the DLEC1-YXXQ mutant DLEC1-3Y led to significant upregulation of p-STAT3 (Tyr705) levels in both KYSE150 and H1299 cells, compared to wild-type controls, with no change observed in total STAT3 protein levels (FIG. 8B), confirming the regulation of STAT3 phosphorylation/signaling by YXXQ motifs of DLEC1.

the effect of YXXQ motifs on DLEC1-STAT3 interaction was further examined by co-IP assay. Results showed that the interaction of DLEC1-YXXQ mutant with STAT3/p-STAT3 (Y705) was greatly decreased (FIG. 8C-E), which then enhanced the interaction of STAT3 with JAK2 and led to increased STAT3 phosphorylation. These results suggest that the YXXQ motifs of DLEC1 are critical for STAT3 phosphorylation and signaling activation.

Discussion

This study, for the first time, identifies DLEC1 as a methylated 3p22 tumor suppressor gene (TSG) for esophageal squamous cell carcinoma (ESCC). With its early genetic alterations, the 3p22-21.3 locus is well known for being critical in multiple carcinomas and lymphomas. Several candidate TSGs reside in this locus, including RASSF1A, ZMYND10 [8, 10], FUS1 [33], RBSP3 [34], NPRL2 [35] and PLCD1 [11, 36]. These TSGs were identified through either genetic approaches (LOH, array-CGH, large-scale chromosomal region cloning and gene mapping, genome sequencing), or functional analysis using mono-chromosome transfer. Nowadays, epigenetic identification of tumor-specific promoter CpG methylation becomes a new efficient way for TSG discovery [22]. The inventors' group has previously identified DLEC1 methylation and silencing in gastric [13], colon [13], hepatocellular [14], renal [37] and prostate [15] cancers, as well as non-Hodgkin and Hodgkin lymphomas [16]. DLEC1 methylation has also been frequently detected in other carcinomas including nasopharyngeal [17], lung [18, 19, 22], breast [20] and ovarian [21].

However, so far there has been no in-depth mechanism study on the molecular basis of its tumor suppression in human cancers yet, although DLEC1 has been shown to possess growth suppressive abilities in multiple carcinoma types (ovarian [21], nasopharyngeal [17], esophageal [12], gastric [13], colon [13], hepatocellular [14] and renal [37]). DLEC1 also inhibits NPC cell tumorigenic potential in vivo [17]. Some preliminary mechanisms on its tumor suppression have been proposed. For example, DLEC1 contains 27 potential casein kinase II (CK2) phosphorylation sites, which deregulates cell proliferation, migration and signaling [13]. A bipartite nuclear localization signal (NLS) spanning aa 245-262 is present in DLEC1, but no transcription factor function has been detected [14]. DLEC1 also induces cell cycle arrest in tumor cells [14]. It was previously also shown that in prostate cancer, DLEC1 inhibited NF-κB transcription activity, upregulated p53-binding activity and induced cell apoptosis [15].

Figure 8F:
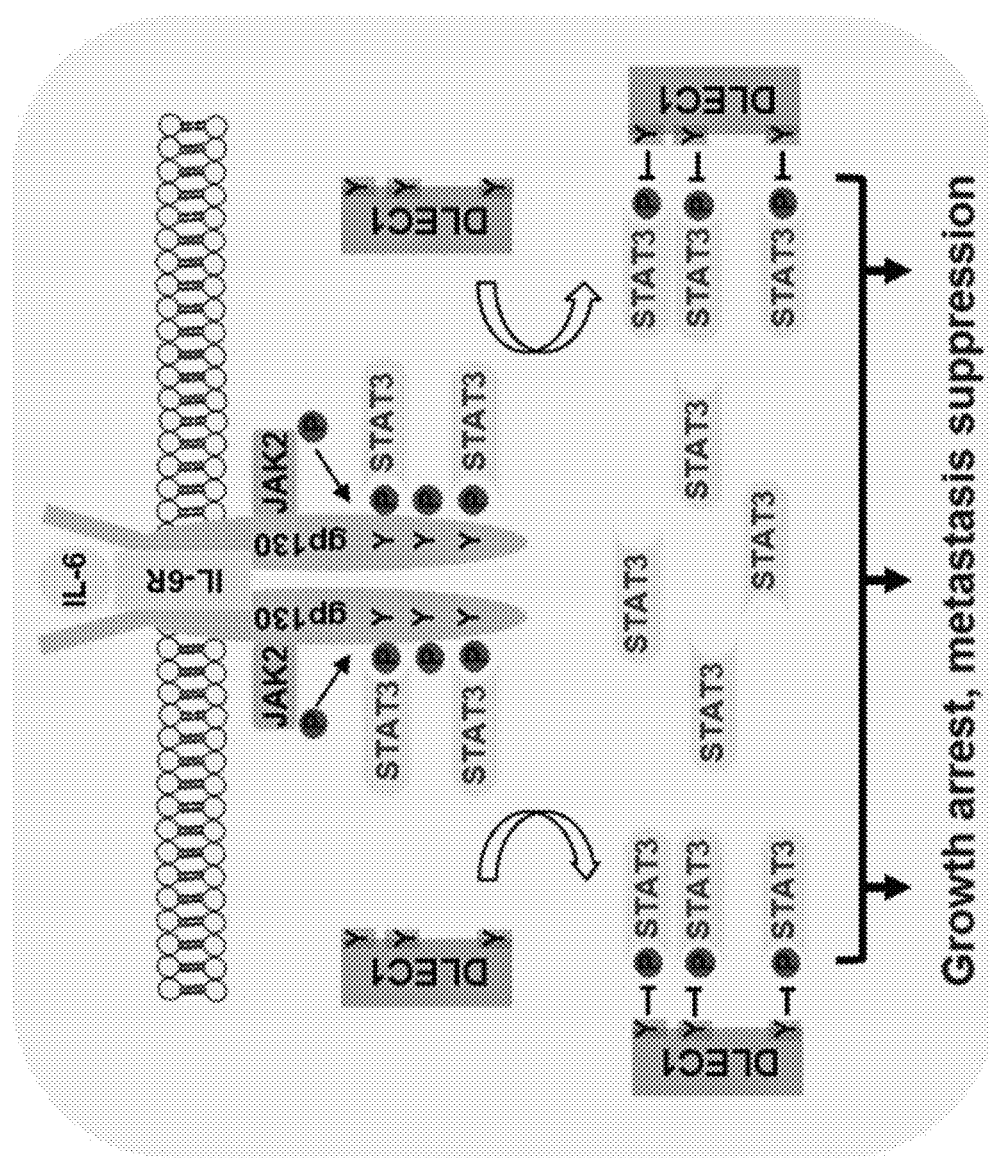

Here, this study has comprehensively analyzed the cancer-related signaling possibly regulated by DLEC1. DLEC1 was found to suppress multiple oncogenic signaling pathways, including JAK/STAT3, MAPK/ERK, AKT, Wnt/β-catenin and TGF-β signaling. Constitutive activation of JAK/STAT3 signaling contributes to multiple tumor initiation and progression, which is maintained by a few positive or negative regulators. The YXXQ motif is crucial for STAT3 activation in response to multiple signaling receptors through phosphorylation at its Tyr 705 and Ser727 sites. Studies have shown that chaperone proteins are involved in the regulation of STAT signaling [38, 39]. For example, acylglycerol kinase potentiates JAK2/STAT3 signaling in ESCC [40]; Epstein-Barr virus (EBV)-encoded proteins constitutively activated STAT3 in NPC [41, 42]; and, EGFR mutation mediates STAT3 activation via IL-6 production in lung cancer [43]. However, far fewer negative regulators of STAT3 signaling have been reported in ESCC, NPC and lung cancer so far, unlike other carcinomas. The inventors discovered the structural basis for direct regulation of STAT3 by DLEC1, including three YXXQ motifs, resembling phosphatase and chaperone proteins, suggesting its possible binding to STAT3 and regulation of its dephosphorylation. Their experimental data further demonstrated that DLEC1 negatively regulates STAT3 activation through docking and binding to STAT3 and further inhibiting its phosphorylation (FIG. 8F). Whether the suppression of STAT3 phosphorylation by DLEC1 is due to its phosphorylation inhibition or enhanced de-phosphorylation should be further investigated.

The present inventors discovered that promoter CpG methylation of DLEC1 directly mediates its silencing/downregulation in multiple carcinomas, with histone acetylation also playing some role in DLEC1 regulation. Epigenetic silencing has been found to be the predominant cause of DLEC1 inactivation, as only rare mutations of DLEC1 have been detected in multiple carcinoma tissues from TCGA cohorts even with large sample sizes, suggesting a dominant role of epigenetic disruption of DLEC1 in carcinoma pathogenesis. In this study, four alternative splicings of DLEC1 were also found; however, further investigations of these variants are needed, including their functional significance, relative proportion to other longer functional transcripts, as well as possible connection between the splicing and CpG methylation of the DLEC1 gene body.

Compared with other known methylated 3p22-21.3 TSGs, DLEC1 has relatively higher methylation frequency in ESCC, further supporting its critical role in ESCC pathogenesis. The previous failure of detecting DLEC1 methylation first in Japanese ESCC tumors may be due to a technical issue [12], or less likely ethnic difference since the ESCC samples in this study are of Chinese origin. As DLEC1 methylation is tumor-specific in ESCC and detectable even in immortalized normal esophageal epithelial cells, it might serve as a non-invasive epigenetic biomarker for the early detection of ESCC. It was also found that DLEC1 methylation is correlated with ESCC recurrence and progression, suggesting its potential even as a marker for prognosis prediction in carcinoma patients. In parallel, DLEC1 methylation has been shown to be of good biomarker value in other malignancies, including non-small cell lung [18, 19], gastric [44], hepatocellular [14], renal [37] and oral carcinomas [45], as well as pre-invasive lesions of breast cancer [20]. Moreover, DLEC1 methylation has been detected in plasma samples from lung cancer patients, and sera of Hodgkin lymphoma patients [16].

In summary, this study demonstrates the first evidence of predominant, tumor-specific, DLEC1 methylation in ESCC with its biomarker value. As a critical 3p22 TSG regulated by p53, DLEC1 inhibits the growth and metastasis of multiple carcinoma cells through binding to STAT3 and inhibiting its phosphorylation, and also suppressing other oncogenic signaling pathways. The YXXQ motifs of DLEC1 are crucial for STAT3 phosphorylation. The identification of DLEC1 as a negative regulator of STAT3 signaling reveals a mechanistic link between 3p22 alteration and oncogenic STAT3 signaling activation in multiple carcinoma pathogeneses.

Materials and Methods
Cell Lines, Tissue Samples and Demethylation Treatment

A panel of ESCC, NPC and lung carcinoma cell lines was used. Immortalized normal esophageal epithelial (NE1, NE3, Het-1A), normal nasopharyngeal epithelial (NP69) and HEK293T cell lines were used. Cell lines were maintained in RPMI or DMEM medium (Gibco BRL, Rockville, Md.) with 10% fetal bovine serum. Human normal adult tissue RNA samples were obtained commercially (Stratagene, La Jolla, Calif., or Millipore Chemicon, Billerica, Mass.). Primary carcinoma tissues of Chinese ESCC, NPC and lung, some with matched normal samples, have been descried before [46-49]. Cell lines were treated with 5 μM of 5-Aza-2'-deoxycytidine (Aza) (Sigma, St. Louis, Mo.) for 3 days, or even followed with ~16 h additional TSA (final concentration 10 mM) treatment as described [46, 47].
Establishment of CpG Methylomes of Cell Lines and Carcinoma Samples Methylated DNA immunoprecipitation (MeDIP) coupled with promoter microarray hybridization (MeDIP-chip) was performed as previously [50, 51]. Briefly, methylated DNA of ESCC (HKESC1, KYSE410) and NPC cell lines (HK 1), as well as immortalized esophageal and nasopharyngeal epithelial cells (NE083, NP69) were immunoprecipitated by monoclonal antibody against 5-methylcytidine (33D3, Diagenode, Seraing, Belgium), and then hybridized to Nimble-Gen™ HG18 Meth (385K CGI plus) promoter arrays (Array Star, Inc., MD). Bioinformatics analysis of methylome data was performed as previously described [50, 51].

Illumina 27K DNA methylation microarray was conducted previously [30]. DLEC1 methylation status was analyzed accordingly.

Bisulfite Treatment and Promoter Methylation Analysis

MSP and BGS were conducted according to previous reports [46, 47]. MSP and BGS primers are listed in Table 6. MSP was conducted for 40 cycles at the annealing temperatures of 60° C. for M and 58° C. for U. Amplified products from BGS primer set were cloned into pCR4-Topo vector (Invitrogen, Carlsbad, Calif.), with 6-8 colonies randomly chosen and sequenced.
Construction of DLEC1 Expression Plasmids and Transfection Four pairs of primers (Table 6) were used to generate 4 DLEC1 fragments based on published DLEC1 sequence (GenBank accession number AB020522). Reverse transcription was carried out using normal testis RNA as template (BD Biosciences, Palo Alto, Calif.). The 4 product fragments were ligated to generate pcDNA3.1(+)-Flag-DLEC1 and pCMV-Flag-DLEC1-V5 expression plasmids. The mutation for three YXXQ motifs of DLEC1 (DLEC1-3Y, YXXQ-GGGG ("GGGG" disclosed as SEQ ID NO: 7)) was introduced by PCR into pCMV-Flag-DLEC1-V5 vector, with sequence confirmed. STAT3C expression plasmid was a gift from Prof. Honglin Chen (University of Hong Kong) [41]. Cells were transfected with lipofectamine 3000 (Invitrogen, Carlsbad, Calif.), and the cells were cultured in RPMI 1640 supplemented with 10% FBS and selected in 400 μg/mL of G418 for 20-30 days to establish some stable cell pools, with confirmed DLEC1 expression.
Colony Formation and Cell Proliferation Assays Colony formation assay was conducted as previously described [49]. All experiments were performed in triplicate wells 3 times. To monitor cell proliferation, 1000 cells were plated in a 96-well plate and incubated at 37° C. in selective media for 3-(4,5-dimethylthiazolyl-2)-2,5-diphenyltetrazolium bromide (MTT) assay.
Cell Cycle and Apoptosis Analysis Flow cytometry analysis of cell cycle and apoptosis was described previously [11]. Cells were stained with propidium iodide (PI) and Annexin V-FITC (BD Biosciences, Bedford, Mass.), and sorted by Accuri C6 (BD Biosciences, Bedford, Mass.) according to the manufacturer's protocol.
Migration and Matrigel Invasion Assays Transwell migration and invasion assays were performed as previously described [32, 40]. The numbers of migrated or invaded cells were observed and counted using a light microscope. Five fields were randomly chosen and the numbers of penetrated cells were counted.
Antibodies, Proteins, Western Blot and Immunoprecipitation (IP)

Antibodies used were: cleaved caspase-3 (#9661), cleaved poly (ADP-ribose) polymerase (#9541), AKT-total (#4691), phospho-AKT(Ser473) (#4060), JAK2 (#9945S), phospho-SAPK/JNK (Thr183/Tyr185) (#6251S), STAT3 (#9139S), phospho-STAT3 (Tyr705) (91455) and phospho-STAT3 (Ser 727), E-cadherin (#4065) (9134) (Cell Signaling, Beverly, Mass.); Flag M2 (F3165), Vimentin (V6630), DLEC1 (HPA019077) and β-actin (AC-74) (Sigma-Aldrich, St. Louis, Mo.); anti-mouse Ig G-HRP (P0161), anti-rabbit Ig G-HRP (P0448) (Dako, Glostrup, Denmark); Twist (sc-15393; Santa Cruz, Calif., USA); a-tubulin (Lab Vision Corporation, Fremont, Calif.); V5-Tag (MCA1360; AbD Serotec, Raleigh, N.C.).

Human IL-6 (PF01229) (Peprotech, Rocky Hill, N.J.) was used. Western blot and IP experiments were performed according to previous protocols [48, 49].
Protein-Protein Docking Analysis To find possible interaction in 3D structure between DLEC1 and STAT3, RCSB Protein Data Bank online tool (website: resb.org/pdb/home/home.do) was firstly used to predict 3D structures of DLEC1 and STAT3. Protein-protein docking was conducted using the ZDOCK server (website: zdock.umassmed.edu/), which provides 5 top models regarding possible interaction between two proteins.

Statistical Analysis

All statistical analyses were conducted with R-3.3.0 (website: r-project.org). Statistical significance was defined asp value<0.05. Basic statistical tests and generation of boxplots and scatterplots were performed by using built-in functions including the base distribution of R. Survival analyses and the generation of related plots were performed by using the survival package v2.41-3 (website: cran.r-project.org/web/packages/survival/index.html). Kaplan-Meier method was used to estimate the overall survival of patients; log-rank test was used to compare survival distributions of groups of patients with different levels of DNA methylation or gene expression.

For expression data, log 2 transformed and normalized values were used. For methylation data, the β-value, a measure of DNA methylation level ranging from 0 to 1 for completely unmethylated to completely methylated, was used. The correlation of DNA methylation with gene expression or continuous numerical clinical features was investigated by calculating Spearman's rank correlation coefficients and two-tailedp values using the 'cor.test' function in R. For two groups (mutant or wild-type) of DNA methylation, gene expression or clinical data, Wilcoxon rank sum test was applied to calculate two-tailedp values using the 'wilcox.test' function in R. For data with more than two groups, Kruskal-Wallis rank sum test was applied to calculate the P values using the 'kruskal.test' function in R.

Array-CGH (aCGH)

Whole-genome arrays (1-Mb resolution) and aCGH was performed and analyzed as previously [47]. Hybridized slides were scanned and analyzed with the GenePixPro 4.0 image analysis software.

Semi-Quantitative RT-PCR and Quantitative RT-PCR Analysis

RNA was reverse-transcribed using MuLV reverse transcriptase (GeneAmp RNA PCR kit, Applied Biosystems). RT-PCR was performed as described previously using GAPDH as a control [49]. Primers used were listed in Table 6.

Multiplex Differential DNA-PCR

Multiplex differential genomic DNA-PCR was performed using primer pair DLEC1A/C for 35 cycles (annealing temperature 58° C.) with AmpliTaq Gold, using 0.1 ug of DNA per 12.5 ul PCR reaction [10]. GAPDH and DLEC1 were employed to detect DLEC1 deletion in a region spanning exon 1 and intron 1.

Promoter Activity Assay

Different regions of the DLEC1 promoter were cloned by PCR from normal human placenta DNA (sigma-Aldrich, USA). PCR was carried out with a high-fidelity Platinum PfX DNA polymerase (Life Technologies, USA) with 10% DMSO. The sequences and orientations of the cloned fragments were confirmed by sequencing. The longest and shorter fragments were amplified from primer pairs DLEC1F1-R and DLEC1F2-R respectively (Table 6). Restriction enzyme Bst XI was employed to digest the longest fragment to produce an intermediate one. These fragments were then linked to pGL2-Enhancer Vector (Promega) to generate p(−295)DLEC1EN, p(−685)DLEC1EN and p(−1021)DLEC1EN. Promoter activities of these fragments were assessed by transient transfection in CNE1 and CNE2 cell lines using Transfast (Promega).

Analysis of Alternative Splicing

DLEC1y1, DLEC1y2, DLEC1N and DLEC1G (Table 6) were used to generate different splicing fragments. Desired PCR products were purified using QIAex II (Qiagen). Purified PCR amplicons were sequenced and aligned with DLEC1 mRNA sequence using the "bl2seq" program (website: ncbi.nlm.nih.gov/blast).

Chromatin Immunoprecipitation (ChIP) Assay

ChIP assay was performed as described previously. Primers used were listed in Table 6. Antibody to acetylated histone H4 (Upstate Biotechnology) was used to precipitate cross-linked chromatin. ACTIN was employed as a control for normalization of each PCR product.

Online Analysis of TCGA Data Sets

Clinical, mRNA expression and genome-wide DNA methylation data of 185 esophageal cancer, 585 lung adenocarcinoma and 504 lung squamous cell carcinoma patients was obtained from public databases of The Cancer Genome Atlas (TCGA). Raw datasets were downloaded from TCGA Data Portal (website: gdac.broadinstitute.org/) and analyzed. "Level 3" methylation data (Illumina Infinium Human DNA Methylation 450 platform) was retrieved from Johns Hopkins University and University of Southern California. mRNAseq expression data (level 3, normalized gene expression data, Illumina HiSeq 2000 platform) was retrieved from University of North Carolina or Canada's Michael Smith Genome Sciences Centre. Genomic mutation data (Illumina Genome Analyzer platform) was retrieved from Washington University School of Medicine Proteomics (for esophageal cancer) and Broad Institute of MIT and Harvard (for lung cancer) and analyzed.

Wound-Healing Assay

Cell motility was assessed using a scratch wound-healing assay. Cells transient transfected with DLEC1 were cultured in 6-well plates until confluent. A single scratch was produced in the cell layer using a sterile tip. After incubation for 24 and 48 hours, cells were photographed under a phase contrast microscope. The experiments were performed in triplicates.

Immunofluorescence

Cells grown on coverslips were stained by indirect immunofluorescence as described previously [11, 49]. Briefly, cells were incubated with primary antibodies against DLEC1, E-cadherin, or Vimentin and then incubated with Alexa Fluor 594-conjugated secondary antibody against mouse IgG (A11062) (Invitrogen Molecular Probes, Carlsbad, Calif.), or FITC-conjugated secondary antibody against rabbit IgG (F0205) (DAKO, Denmark). To analyze the effects of DLEC1 on actin stress fiber formation, cells were serum starved for 24 h before incubation in medium-containing 5% fetal bovine serum. After 1 h, cells were fixed and stained by Rhodamine-labeled phalloidin (Invitrogen Molecular Probes). Cells were then counterstained with DAPI and imaged with an Olympus BX51 microscope (Olympus Corporation, Tokyo, Japan).

Dual-Luciferase Reporter Assay

The promoter activities were determined by luciferase reporter assays. Luciferase reporters of several key signaling pathways, including NF-κB-luc, AP-1-luc, SRE-luc, STATs-bs-luc, TopFlash-luc, and PAI-luc were used to examine signaling pathway regulated by DLEC1 Cells were transiently co-transfected with DLEC1 expression vector and phRL-TK (the luciferase reporters). DLEC1-promoter luciferase reporters were co-transfected with expression vector encoding wild-type p53. After 48 h, cells were lysed and luciferase activities were measured using Dual-Luciferase® Reporter Assay System (Promega, Madison, Wis.). To normalize transfection efficiency, phRL-TK luciferase activities were measured as an internal control. At least three independent experiments were performed, with each repeated in triplicates.

All patents, patent applications, and other publications, including GenBank Accession Numbers, cited in this application are incorporated by reference in the entirety for all purposes.

TABLE 1

Summary of DLEC1 methylation status in multiple carcinomas

| Samples | Promoter methylation (%) |
|---|---|
| Carcinoma cell lines | |
| Esophageal | 17/18 |
| Nasopharyngeal | 5/5 |
| Lung | 6/9 |
| Primary carcinomas | |
| ESCC (cohort I, paired tumor, Chinese) | 27/41 (66%) |
| ESCC (cohort II, Chinese) | 40/83 (48%) |
| NPC (endemic, Chinese) | 37/50 (74%) |
| Lung Ca | 35/61 (57%) |
| Normal epithelial cell lines (immortalized) | |
| Esophageal (Het-1 A, NE1, NE3) | 2/3 |
| Nasopharyngeal (NP69) | 1/1 |
| Normal tissues | |
| Normal nasopharyngeal tissues | 0/3 |
| Paired surgical-margin tissue of ESCC | 0/35 |

TABLE 2

Relationship of DLEC1 methylation and clinicopathological parameters of ESCC patients in Chinese cohort II

| Clinicopathological features | Number (n = 83) | methylated | unmethylated | p-value |
|---|---|---|---|---|
| Gender | | | | |
| Male | 65 | 33 (50.8%) | 32 (49.2%) | 0.372 |
| Female | 18 | 7 (38.9%) | 11 (61.1%) | |
| Age | | | | |
| ≤50 | 6 | 4 (66.7%) | 2 (33.3%) | 0.642 |
| >50 < 65 | 43 | 20 (46.5%) | 23 (53.5%) | |
| ≥65 | 34 | 16 (47.1%) | 18 (52.9%) | |
| Staging | | | | |
| 1 | 26 | 10 (40.0%) | 16 (60.0%) | 0.422 |
| 2 | 42 | 23 (54.8%) | 19 (45.2%) | |
| 3 | 15 | 7 (46.7%) | 8 (53.3%) | |
| Grade | | | | |
| I | 12 | 4 (33.3%) | 8 (66.7%) | 0.707 |
| II | 15 | 8 (53.3%) | 7 (46.7%) | |
| III | 43 | 22 (51.2%) | 21 (48.8%) | |
| IV | 13 | 6 (46.2%) | 7 (53.8%) | |
| Tumor size | | | | |
| <2.0 cm | 4 | 0 | 4 (100%) | 0.041 |
| ≥2.0 cm ≤ 5.0 cm | 68 | 32 (47.1%) | 36 (52.9%) | |
| >5.0 cm | 11 | 8 (72.7%) | 3 (27.3%) | |
| Lymph node metastasis | | | | |
| Present | 24 | 16 (66.7%) | 8 (33.3%) | 0.032 |
| Absent | 59 | 24 (40.7%) | 35 (59.3%) | |

TABLE 2-continued

Relationship of DLEC1 methylation and clinicopathological parameters of ESCC patients in Chinese cohort II

| Clinicopathological features | Number (n = 83) | methylated | unmethylated | p-value |
|---|---|---|---|---|
| Distant metastasis | | | | |
| Present | 1 | 1 (100%) | 0 | 0.482 |
| Absent | 82 | 39 (47.6%) | 43 (52.4%) | |
| Differentiation | | | | |
| Poorly differentiated | 6 | 4 (66.7%) | 2 (33.3%) | 0.439 |
| Moderately Differentiated | 54 | 27 (50.0%) | 27 (50.0%) | |
| Well differentiated | 23 | 9 (39.1%) | 14 (60.9%) | |

TABLE 3

Relationship of DLEC1 methylation and clinicopathological parameters of esophageal cancer patients from TCGA cohort

| Clinicopathological features | Esophageal cancer cohort (TCGA) | | | |
|---|---|---|---|---|
| | Number (n = 185) | methylated | unmethylated | p-values |
| Age | | | | |
| ≤50 | 28 | 27 (96.4%) | 1 (3.60%) | <0.001 |
| >50 < 65 | 80 | 72 (90.0%) | 8 (10.0%) | |
| ≥65 | 77 | 66 (85.7%) | 11 (14.3%) | |
| Gender | | | | |
| Female | 27 | 26 (96.3%) | 1 (3.70%) | 0.68 |
| Male | 158 | 139 (88.0%) | 19 (12.0%) | |
| Histologic grade | | | | |
| g1 | 19 | 18 (94.7%) | 1 (5.30%) | 0.03 |
| g2 | 77 | 71 (92.2%) | 6 (7.80%) | |
| g3 | 49 | 41 (83.7%) | 8 (16.3%) | |
| gx | 40 | 35 (87.5%) | 5 (12.5%) | |
| Pathologic stage | | | | |
| Stage i | 19 | 15 (78.9%) | 4 (21.1%) | 0.001 |
| Stage ii | 79 | 76 (96.2%) | 3 (3.80%) | |
| Stage iii | 56 | 49 (87.5%) | 7 (12.5%) | |
| Stage iv | 9 | 9 (100%) | 0 | |
| Pathologic m | | | | |
| 0 | 136 | 125 (91.9%) | 11 (8.10%) | 0.42 |
| 1 | 9 | 9 (100%) | 0 | |
| Pathologic n | | | | |
| 0 | 77 | 73 (94.8%) | 4 (5.20%) | 0.39 |
| 1 | 69 | 59 (85.5%) | 10 (14.5%) | |
| 2 | 12 | 12 (100%) | 0 | |
| 3 | 8 | 7 (87.5%) | 1 (12.5%) | |
| Pathologic t | | | | |
| 0 | 1 | 1 (100%) | 0 | 0.3 |
| 1 | 31 | 25 (80.6%) | 6 (19.4%) | |
| 2 | 43 | 42 (97.7%) | 1 (2.30%) | |
| 3 | 88 | 80 (90.9%) | 8 (9.10%) | |
| 4 | 5 | 5 (100%) | 0 | |

TABLE 4

Relationship of DLEC1 expression and clinicopathological parameters of lung adenocarcinoma patients from TCGA cohort

| Clinicopathological features | Number (n = 576) | High expression | Low expression | p-values |
|---|---|---|---|---|
| Age | | | | |
| ≤50 | 41 | 12 (29.3%) | 23 (56.1%) | 0.02 |
| >50 < 65 | 201 | 74 (36.8%) | 83 (41.3%) | |
| >65 | 296 | 130 (43.9%) | 109 (36.8%) | |
| Gender | | | | |
| Female | 311 | 135 (43.4%) | 108 (34.7%) | 0.008 |
| Male | 265 | 95 (35.8%) | 122 (46.0%) | |
| Residual tumor | | | | |
| r0 | 371 | 150 (40.4%) | 150 (40.4%) | 0.046 |
| r1 | 15 | 4 (26.7%) | 7 (46.7%) | |
| r2 | 4 | 2 (50.0%) | 2 (50.0%) | |
| rx | 27 | 16 (59.3%) | 4 (14.8%) | |
| Pathologic stage | | | | |
| Stage i | 307 | 136 (44.3%) | 105 (34.2%) | <0.001 |
| Stage ii | 135 | 48 (35.6%) | 60 (44.4%) | |
| Stage iii | 97 | 33 (34.0%) | 45 (46.4%) | |
| Stage iv | 28 | 10 (35.7%) | 17 (60.7%) | |
| Pathologic m | | | | |
| 0 | 387 | 149 (38.5%) | 161 (41.6%) | 0.09 |
| 1 | 27 | 9 (33.3%) | 17 (63.0%) | |
| Pathologic n | | | | |
| 0 | 363 | 154 (42.4%) | 136 (37.5%) | 0.03 |
| 1 | 108 | 38 (35.2%) | 49 (45.4%) | |
| 2 | 87 | 29 (33.3%) | 43 (49.4%) | |
| 3 | 2 | 0 | 0 | |
| Pathologic t | | | | |
| 0 | 0 | 0 | 0 | <0.001 |
| 1 | 189 | 92 (48.7%) | 57 (30.2%) | |
| 2 | 315 | 109 (34.6%) | 144 (45.7%) | |
| 3 | 49 | 18 (36.7%) | 19 (38.8%) | |
| 4 | 20 | 9 (45.0%) | 9 (45.0%) | |

TABLE 5

Methylation status of 3p21-22 TSGs (with genome positions) in ESCC

| | Sample | PLCD1 (~38.00 Mb) | DLEC1 (~38.03 Mb) | RASSF1A (~50.32 Mb) | ZMYND10 (~50.34 Mb) |
|---|---|---|---|---|---|
| ESCC cell lines | NE1 | u | u | u | u |
| | NE3 | u | u | u | u |
| | EC1 | u | m | m + u | u |
| | EC18 | u | m | m + u | u |
| | EC109 | u | m | m + u | m |
| | HKESC1 | u | u | m + u | m + u |
| | HKESC2 | u | u | m + u | m + u |
| | HKESC3 | m | m | u | m + u |
| | SLMT1 | u | m | u | u |
| | KYSE30 | m | m | m | m + (u) |
| | KYSE70 | m + u | (m) | m + (u) | m + u |
| | KYSE140 | u | m | u | m + (u) |
| | KYSE150 | m | m | u | m + (u) |
| | KYSE180 | (m) + u | m | u | u |
| | KYSE270 | u | m | m | u |
| | KYSE410 | m + u | u | m + u | m + u |
| | KYSE450 | u | m | m + u | m + u |
| | KYSE510 | m + (u) | m | m + u | m + u |
| | KYSE520 | u | m | u | m + u |
| | Total | m: 7/17 (41%) | m: 14/17 (82%) | m: 11/17 (65%) | m: 11/17 (65%) |
| ESCC primary tumors (Chinese) (Cohort I) | ESCa1T | u | m | u | u |
| | ESCa2T | u | u | u | u |
| | ESCa3T | u | m | u | m |
| | ESCa4T | u | m | u | (m)+u |
| | ESCa5T | u | m | u | u |
| | ESCa6T | m | m | u | m |
| | ESCa7T | u | u | u | u |
| | ESCa8T | m | m | u | m |
| | ESCa9T | u | m | u | u |
| | ESCa10T | u | m | m | u |
| | ESCa11T | u | m | u | u |
| | ESCa12T | u | u | u | u |
| | ESCa13T | u | m | u | u |
| | ESCa14T | u | u | u | u |
| | ESCa15T | u | m | u | (m) + u |
| | ESCa16T | u | u | u | (m) + u |
| | ESCa17T | u | u | u | m |
| | ESCa18T | u | u | u | u |
| | ESCa19T | u | u | u | u |
| | ESCa20T | u | u | u | m |
| | ESCa21T | u | m | u | u |
| | ESCa22T | u | u | u | m |
| | ESCa23T | u | u | u | u |
| | ESCa24T | m | m | m | m |
| | ESCa25T | u | m | u | u |
| | ESCa26T | u | m | m | u |
| | ESCa27T | m | u | u | u |
| | ESCa28T | u | m | u | u |
| | ESCa29T | u | m | (u) | u |
| | ESCa30T | m | m | m | m |
| | ESCa31T | u | m | u | u |
| | ESCa32T | u | u | m | m |
| | ESCa33T | u | m | m | u |
| | ESCa34T | u | m | (m) + u | u |
| | ESCa35T | u | m | u | u |
| | Total | m: 5/35 (14%) | m: 22/35 (66%) | m: 7/35 (20%) | m: 12/34 (35%) |

TABLE 6

Primers used in this study

| PCR | Gene or fragment | Primer | Sequence (5'→3') | SEQ ID NO: | Location | Product size (bp) |
|---|---|---|---|---|---|---|
| RT-PCR | DLEC1 | DLEC1A | ttcctccctcgcctactc | 8 | Exon 1 | 309 |
| | | DLEC1B | aaactcatccagccgctg | 9 | Exon 2 | |
| Alternative splicing | DLEC1 | DLEC1γ1 | caaagaagccagcaccgata | 10 | Exon 5 | 422 |
| | | DLEC1γ2 | gcagtaaccacagtccaaca | 11 | Exon 9 | |
| | | DLEC1N | ccgggacatgctatattagt | 12 | Exon 10 | 541 |
| | | DLEC1G | aggctctgggacttcctc | 13 | Exon 13 | |

TABLE 6-continued

Primers used in this study

| PCR | Gene or fragment | Primer | Sequence (5'→3') | SEQ ID NO: | Location | Product size (bp) |
|---|---|---|---|---|---|---|
| Deletion | DLEC1 | DLEC1A | ttcctccctcgcctactc | 14 | Exon 1 | 385 |
| | | DLEC1C | caactgcagccccagatc | 15 | Intron 1 | |
| Cloning | Promoter | DLEC1F1 | tgcctcttgcctctcctg | 16 | Promoter | 1046 (F1/R) |
| | | DLEC1F2 | tcagcaatcagcacagacc | 17 | Promoter | 313 (F2/R) |
| | | DLEC1R | aaccgagacgccgctaac | 18 | Exon 1 | |
| | ORF | Fragment I | gccgccaccatggagaccagggc | 19 | Exon 1 | ~1.1 (kb) |
| | | | gtgaaaaacccaattggtgg | 20 | Exon 6 | |
| | | Fragment II | agtgtttctagctaagccac | 21 | Exon 6 | ~1.2 (kb) |
| | | | gagggcatatggctctaag | 22 | Exon 14 | |
| | | Fragment III | cttagagccatatgccctc | 23 | Exon 14 | ~1.4 (kb) |
| | | | gccatgtgcactgggatg | 24 | Exon 25 | |
| | | Fragment IV | catcccagtgcacatggc | 25 | Exon 25 | ~1.6 (kb) |
| | | | gctcgagcggagcctcaggg | 26 | Exon 36 | |
| ChIP assay | DLEC1 | DLEC1S | cttgctcaccggcgtctt | 27 | Exon 1 | 241 (s/c) |
| | | DLEC1C | caactgcagccccagatc | 28 | Intron 1 | 166 (s/b) |
| | | DLEC1B | aaactcatccagccgctg | 29 | Exon 2 | |
| | | DLEC1A | ttcctccctcgcctactc | 30 | Exon 1 | 162 |
| | | DLEC1R2 | aagacgccggtgagcaag | 31 | Exon 1 | |
| | ACTIN | ACTINPP | ctgtgttggcgtacaggtc | 32 | Exon | 181 |
| | | ACTININ | gtggagactgtctcccgg | 33 | Intron | |
| MSP | DLEC1 | m1 | gtttcgtagttcggtttcgtc | 34 | Exon 1 | 107 |
| | | m2 | cgaaatatcttaaatacgcaacg | 35 | Exon 1 | |
| | | u1 | tagttttgtagtttggttttgtt | 36 | Exon 1 | 110 |
| | | u2 | acaaaatatcttaaatacacaaca | 37 | Exon 1 | |
| BGS | DLEC1 | BGS1 | gaagatataaatgtttataatgatt | 38 | Promoter | 597 |
| | | BGS4 | aactacaaccccaaatcctaa | 39 | Intron 1 | |

Sequence listing

SEQ ID NO: 1 (genomic DNA sequence for the DLEC1 gene)
>chromosome:GRCh38:3:38038605:38124625:1
TAGTACTGCATTGTGGTTTTAATTTCCACTTCTTTGATGACTAATGATGTTCAGTCTACT
CCTTCTTTGAAATCTCTGCTTGGTTTTCATTTGTTCCAAGAAGTAATCGCTCCTTCTACA
GACTAAGTTCCTGTCCTCCTTTGTAGTTCCATGACAACCAATATTTATCTCCACCTTGGC
CTTAACCCACTAAAGTACAGTTGTTTTACTTTTACCTCCACACCCACCGCCATCATCACA
AACACACACATACACGACTGTGCACTTCCTGAAGGCAGAAGCAGCATCATACTTCTTTGG
TATCTTCAGCAATCAGCACAGACCTGAAACACAATCTTTACACAATAAATATGATGAGTG
AATGAACAGTTGCTTAACAAATTAAAGAATGGATGAAGGTAGGTAGTTAGGTACAAGGTT
TTGCAGATAGGCCTGGCTGTGTCAATTAAACCTTTCTTCATGGGTCCTCACACTTAGTAA
GCTCACTTTTAAAAGGACAATGCTGAAGACACAAATGTTTACAATGACCACAGCGATGAC
GGGATCCGAGAGAAAGGCAAGGCGGAAGGGGTGAGGCCGGAAGCCGAAGTGCCGCAGGGA
GTTAGCGGCGTCTCGGTTGCCATGGAGACCAGGAGCTCCAAAACGCGGAGGTCTTTAGCG
TCCCGGACCAACGAGTGCCAGGGGACAATGTGGGCGCCAACTTCGCCACCAGCGGGTCC
AGCAGCCCCAGCCAGCCCACCTGGAAGTCCTCCTTTGTATTCCTCCCTCGCCTACTCTGAG
GCCTTCCACTACAGCTTCGCAGCCCGGCCCCGCCGCCTCACGCAGCTTGCGCTGGCGCAG
CGTCCCGAGCCTCAGCTGCTTCGTCTGCGCCCCTCCTCGCTGCACCCAAGATATCTCG
CACTTGCTCACCGGCGTCTTCCGCAACTTGTACTCAGCCGAGGTCATCGGCGACGAAGTG
AGCGCAAGCTTGATCAAGGCCGCGGCAGCGAGAATGAGCGCCACGAGGAGTTCGTGGAC
CAGCTGCAGCAGGTAACGTGGCGGTGGCGTCGCGTCTGCGGACGGTGCCGGGGTCTCAGC
GCTCGGCACGCGTCAGCACCTGCCAGGTGCCAGGCGCTGTTCCAGGATCTGGGGCTGCAG
TTGAGAAACAGCCCATCATGCCGAAGTGGGCCCGACATTCTAGTGGAAGGACGCTCTATC
CATACACACACATGCGCAAATACCACACATACCACACAACGTGCGGCATATATCTGTAGC
ACCTGTCTATATTTCTCTAGACACATACGTTATATATTGCATATATCAATGAACGACTGC
GGCAGACCGCTGAATAGTTGTTCCATGGAGAGGATAAAGCCAAAAGTCACCCGGCTTTGG
GGTGCCTTTGTATCACAAACCACAATCTTGACTGGGCCATTCATGCGCAGATTTTAGGAA
GCGTGTCTAGCCTCTAGAACAGCAACTCTGCTTCCTCATCTGTACAAGGAGAAACCAGC
TGACTCGCGGCCTCTGTGCTGAGTCGGCCTCTGCTGGCCACACTACTGAAGACTCCCTTA
AACTTGTGGGCACTCCTCCCATACCCGATCCTTTACCCCGGTGTGCTTCCTGCCTCTCAG
ATCTTCTTCTTCTCCTTTCTGTTCTGTCCTCTACCTGCCCCTTAAGTGACATGCATCCCA
CGTCGTTAGCTTCAGTCATTCCTTCACTTAACACATTTGTTGAATGTCTGCTGGGTGTCA
TACTCTGTTCTAGGCAGTGGGGATTCAGCAGTGAATAAAAACGCCAGTGTTCGGCACAC
CCACACTCACACACGCAACCTGTCCTCTGTAGCTTTCAACCTAACTGAGGTAGATAGACA
TTAACAAAATGAATACCTATACAGTATGTGAGATACTTACAGGACCAGTCTCGCCGCCTC
CACGGGTTATAGGCTTCTTAAAGTGCAGCCAGAGCCCCTGGCTGGGATCCTGTACTCTGT
GATTCGTGGGTCACCACATTCACTCTGCTAAGACTTCAGCCTACCCAGCCAGACCTTGCC
CTTGAACTTCAGACTCACATCCCTGTCATTCACATGAGCCAGAATATATGGAGCATTATA
AACCTATAAACCCCATGACCAGTCACCCAGTTCACTGGATTCTATCTTCTCAGTATCTGT

```
Sequence listing

CCCATAAGTAGCCACTATACCAGAGTCTGAATTGGCAAATAGTGATCCCTTTTTTTGAAG
AAAAAAAGTAATACATATTACAAATTTTTTTTTTGACAGAGTCTGGCTCTGTTGCCCAG
GCTGGAGTGCAGTGATGTGATCACAGCTCACTGCAGCCTTAACATCAGGGGCTCAACTGA
TCCTCCCTCCTCAGCATCTGGAGTAGCTAGGACCACAGGTGTGCACCAGTATGCCCAGCT
TATTTATTTATTTATTTATTTATTTGAGATGGAGTCTCACTCTGTCACCCAGGCTGGAGT
GCATGGCGCAATCTCAGCTCACTGCAAGCTCCACCTCCCACATTCATGCCATTCTCCTGC
CTCAGCCTTCTGAGTAGCTGGCGCCTGCCACCACACCTGGCTAATTTTTTTGTATTTTTA
GTAGAGACAGGGTTTCACTGTGTTAGCCAGGATGGTCTCGATCTCCTGACCTCGTGATCT
GCCCACCTTGGCCTCCCAAAGTGTTGGGATTACAGGCATGAGCCACCACATCTGGCCTAA
ATTTTTATTTTTAAAAATTGTGAGATGGGGTCCCACTATGTTGCCCAGGCTGGTCTCAA
ATTTCTGGCCTCAATTGATCCTTCCACCTCAGCCTCTCCAGATGCCGGTATTACAGGTGT
GAGCCACTGTGCCTGGCCCACATTATAAAAATCTTAATTTAGAAGCTGAAATTTAATTTA
AACATTTGAAGTTTTAAAATTGCAGAAATTTCAGAATGCAGAAAAGTTTAAAGAGTGATC
CCCTATAGAAATACAACTATGCGGCCGGGCGTGGTGGCTCACGCCTATAATCCCAGCACT
TTGGGAGGCCGAGGCGGGCAGATCACGAGGTCAGAAGTTTGAGTCCAGTCTGACCAACAT
AGTGAAACCCTGTCTGTACTAAAAATACCAAAAATTAGCCGGGCGTGGTGGTGTGTGACT
GTAATCCCAGGTACTCGGGAGGCTGAGACAGGAGAATTGCATGAACCCAGGAGGCGGAGG
TTGCAATGAGCCAAGACTGCACCACTGCACTCCAGCCTGGGCGACAGAACGAGACTCCGT
TTCAAAAAAAAAAAAAAAAAAGAAATACAACTATGCAAAGATAAGTTGACTTTATAAAT
TATGGTATATTCACACTATGGAATACTACAAAGTTGTTAAAAAGAATGAATTATACCTGC
ATTGTAGACAAACACAGCTGCCATTTATTTATTTATTTATTTTTTGAGGCAGAGTCTCG
CTCTGTTGCCCAGTCTGGAGTGCAGTGCCACGATCTTGGCTCACTACAACTTCCGTCTCC
TGGGTTCAAGCGATTCTCCTGCCTCAGCCTCCTGAGTAGCTGGGATTACAGACATGCACC
ACCATGCCTGGCTAATTTTTGTATTTTTAGTAGAGATGGGGTTTCACCATGTTGGCCAGG
CTGGTCTCCAACTCCTGACCTCAAGTGATCTGCCCGCCTCAGCATCCCAAAGTGCTAGGA
TTACAAGAGTGTGCCACTGCGCCTGGCCCGCCATTTATTAATTTAGCAAAAAAGCCATAG
AACAATGTTAGGATAATTTAATTTTTTATAATATATATGCATGGGAAAAAAGCTGAAAAC
TTTCACAACAAAATGTTAACAATATTCTTATGGGACATTTAACTTTTTCTTTGCACATTT
CTATATTGTCTGAATTTTGCAATGTACACGAATTAATTTTGTAATTACAAAAAAAGAAAC
TTTGAAAAGAGCAGGCATCTGTTATTCCACTTCTGTAATGTTGCTGGCTTTTTTTTTTT
TTTTTTTTGAGACAGAGTCTTGCACTGTTGCCTGGGCTAGAGTGCAGTGGCACGATCTC
AGCTCACTGCAACCCCTGCCTCCCGGGTTCATGTGATTCTCCTGCCTCAGCCTCCCAAGT
AGCTGGGATTACAGGCACACACCACCACACCAGGCTAATTTTTTGTATTTTTAGTAAAGA
CAGGGTTTCACTATGTTGGCCAGACTGGTCTTGAACTCCTGACCTCGTGATCCACCCGCC
TCGGCCTCCCAAAGTGCTGGGATTACAGACGTGAGACACTGCGCCCAGCAATGTTGCTGT
TCTTATACCTATATTCCTCTCCCTCTTTCCTTTTTCGTCATCTGTTCTTTGCTTTTCCTC
ACTCGTCTCTAGATGTCACTGCCATGTGACCATCTGTACAGGACTCAGATTCATTCTCCC
TGGGAGGAGCAATAATCACTATTCCGTATGAGTGTCTGCATTGCCTGAGTTTTTCCCTCA
GATAACCCCGTTGGCAGCTGATCTTCCCCAAGCCCACCTATAGAAATATCTCATGGTCTA
ATGATTGAGAGCAAATGCTCTGGAACCATACACCCTGGGTTCAAGTCCTGGCTCCTACAC
ATACCATCTATAGGACCTTGGGTGATATTTACTTCTATAAGCCTCAGTTTCCTTATCTGT
AAAATGCAGATAATAATAATATTCACCCCATAGGTTGGTTGTTTTGAGGATTAAATGAGT
CAATACAGTAAAGCATTTACAATATTGAGCATTTACAACATGGTAAGCCCTCAGTAAGTG
ATAGTTGGTCTTGTTATTTGGACTAGATGCTAATTCCTACATCCAGAAATTAGGGTCAGA
GATTGTCAGCAGACCCAAATAGTAAGACACATAACACAGAACATAGTACTTTATATTTGA
GGAACTGTCCCAGGCCACTGTCTCCTGAAAAACATTTCCTGACTCCAAGAAGATTTAGTT
ACTTCTTCTTAGCCTTCCATATATCCTCATTCATATGCTATTATAGCGCTTTTAAGAGTT
GATTTCACCTATTTGTATCCTTGCCAGGCCCCTCCTGCTAAACTGTAAACTCTTTAAGAG
CAGAAACCATATCTGATTCATTTCCCCAAATGTAAATGGTAATTACACAATAAATCTTTT
TTTTTTAAGATGGGGTTTTGCTCCTGTTGCCCAGGCTGCAGTGCAATGGCACAATCTCAA
CTCACTGTAATCTCTGCCTCCTGGGTTCAAGTGATTCTCCCGCCTCAGCCTACCGAATAG
CTGGGATTACAAGTGCCTGCCACCACGCCTGGGTACACAATAAATCTTTATTAAAAGAAT
GACTAAATAAATCTTTGCGATCCCACCAACTTTAGGAATACAATAAGGAACACTGTCTTC
CTACATAAACTGTTTTTTTTTTTCTTTAAAAGAAATGGGGTTAGCTGGGCATGGTGGCTT
GTGCCTGTAATCCCAGCACTTTAGGAGGCTGAGATGAGAGGATTACTTGAGTCCAGGAGT
TTGAGACCCCATCTCTACAAAAAAATTTAAAAATTAGCTGGATATGGTGGTGTATGCCTG
TAATCCCAGCTACTTGGAGGCTGAGGCAGGAGGATCCCTTGACCCCCAGGAATAGCAGGCA
GGAGTGAGCTGTGATTGCGCCACTGTACTCCAGGCTAAGCCACAAAGCAAGACTCCAGTT
CTAAAAAATAAATAAATAAGAAAGGAAATAAGACTGGGCGCAGTGGCTCATAACTGCAA
TCCCAGCGCTTTGGGAGGCTGAGGTGAGTAGATCATCTGAGGTCAGGAGTTCAAGACCAG
CCTGGCCAACATGGTGAAACCCCATCTCTACTAAAAAATATACAAAAATTAGCTGGGCA
TCATGGCGGGCACCTGTAATCCCAGCTGCTTCAGAGGCTGAGGCAGGAGAATCACTTGAA
CCCGGGAGGCAGAGGTTTCAGTGAGCCAAGGCCATGCCATTGCACTCCAGCCTGGGCAAC
AAGAGCAAAACTCTGTCTCAAAAAAGAAAAAAAAGAAAGAAAGGAAAAGAAAGAAACAG
GGTCTCACTGTGTTGCCCAGGCTGATCTTGCACTCCTAGGCTCAAGCGATTCTCTTGCCT
GCCAAGTAGCTGGGACTACAGGTGCACCACCATGCCTGGCTAATGCAAACTATCTTTC
ATATTACCTGTACCAGTGAGCTCTCTGCTTCTTGCCTCGAGAAGTCTGAACCAGAAAATA
TGGATCAGAAGTTTGGCTGTTGAATAGTCAATCAGTAATTAGTCTTGAGGAGTATGTTG
GGCATCCAAGTGGACTCTCTGGGCGCAAGTACTGTGACAGAGTTTGGGCTACAGGTGTTT
GTTAGCTATCAACACCTGTGAGGGGAGGGGAATGAAAGAAGGAGTGAGCCACGGAAGAAG
CTGAACTGTGATGGGGGCCAACAAGCCTTGACAAATGCAGCATGTTGCTCTGAAGAGAG
TATTGCCTGTCAAAGTTTCTCTCTTTGGGTCAAAATGGCCAGGTCTTTATACCCCTGCCT
CTCTCAGTCACAGGATGTGGGTGCTGCAGAAAGGACATGGTCTCAGGTGACTCCTTTTCA
GCAGCTTAGGTAGACTGTGAAGGGGCTGTCTGCTGACGACGTTCCCTGTAGCTAGGGAGC
AAGTCCTTCCTTGAACGTGGATCTGGGTGGCACCACAGGAAGTGTGCTAACTTGTATTTG
GTATTTCACTGTTTGGATGGCAGCTCTCTTTATTGTGAAGCCAGGAGACAGGTAACCAAG
CTCAAGTCTGTTACTGGCCTTACTATGGAAACCTTTAAACCATTCCCCTCTATGGGTCTC
```

Sequence listing

```
AGTTTTCAGATCTAGTAGTTCAGACCAGATGGTTGGAATAGTTCTCTGACTATTCTATGC
TTCACTGGAAGCCCTGATCCTGGGGTAGGGCTGAGTAAAGCTAAGTAATGGTAAGTAATC
TCACCATATTTCTGTGCATTTGATCATCCCCCTGCCAGATTCGGGAGCTCTATAAGCAGC
GGCTGGATGAGTTTGAAATGTTGGAGAGACATATCACTCAGGCCCAAGCACGGGCTATTG
CGGAAAATGAGCGGGTCATGAGCCAGGCTGGAGTACAGGACCTCGAGAGCCTTGTCAGGT
TGCCTCCAGGTGTGTATAAAGAACTCCCACATGCCTGCCCAATTCCCGGGCTGTTGATAT
TTCACTGTGTTTGCTCCATTGCCCACTCTCTAGGCTTTTTCTGGATATTTGGAGAGCAAG
TCGCAGACATGATAATATGAATATTACCACAAAAGAATATTTCATTACCACAAAACACTT
CTGTATGTGTATCTTCAAAACAAGGACGCTCTCCTACATAACCAGCATATAACCCCCACA
ACCTGGAAATCAGTTTCTGTGCAACACTAACCTCTGACCCACAGATACTTGTCAACCTAA
ATAGCAGAGAGAGACTCTCTAAAAGAAAATGATGGACACTGCAATGGGAATACATGTGCC
ATTGTAAACTGTGTGCATATTCAGGGAGGTAAAGGAAGACAAAGGTTTTTAAAGGAAAAG
TGAGGAGGATTACACAATGGTTTTGAAGTAATTATCCTTGGCTGAAAAATCATTAACAAG
AGTAGTACCAGTCTGAGATTAAACAGGCGGTTGCTGGGCAGATTTGTGTGTGTGTAGG
GTTGCAATGACCTTTGTGTGAGGTTGTGATTTTTGTGGCGTGATATGGTTTGTCTGCATC
CCCACCCAAATCTCACCTTGAATTGTAGCTCCCGTAATCCCCACGTGTCATGGGAGGGAC
CTGGTGGAAGGTATTGAATCATGGGGGCAGGTTTTTCCCTTGCTATTCTCATGATAGTGA
GTAAGTCTGATGAGATCTGATGGTTTTATAAAGGGCAATTCTCCTGCACACACTCTCTTG
CCTTCGCTCATGTAAGACATGCCTTTGCTCCTCCTTCACCTTCTACCATGATTGTGAGGC
CTCCCCAGCCATGTGGAACTGTGAGTCCATTAAACCTCTTTTTCTTTATAAATTACACAG
TCTCGGGTATTTATTCATAGCAGTATGAAAATGGACTAATACAAGGCATCTTTTGTGATA
ATTCTTGTTATCAGGCACTTATGCATGGCCTTCCCCAGCACCATTTGTCAGGGTTTTTTA
ACACAAGTGACTCCATTTTGATTCAGACAACTTTTACATCCCATTCAAATTTTACTGACT
GTCCTACTGTGGCTTTTTCCCCCCCTCAGGCCCAGGATCCTGTCCAGGAAGTCATGTCAC
ATGCAATTGTCATGTCTCTTTTTGAGATGCCTTCATTTGGAACAATTCCTTGATCTTTTC
TTGTCTTTCATCTTCCTGACAGTTCTTGACCAGACTTATATTCTGTAGGATGGGGATGGT
TCTGTCTGATGCTTCCCCATGACCAGACTTAGGCAAACATTCTGGGCAACAGGACCACAT
AAAGTTATTCCTTGTTCATCTCACTGCAGCACAGCAGGAGGGTCACGTGATGTTAACCTC
CATCCCCTGAGTAGGTTGGTGTCTGCCAGGATTTTCTGCATTAAATTCTCCAAATCAAAT
TATAATTGATTAGCATTTTATAGAGAGGTATTCTCAGATTACACCAATATCTTGTTCCTC
ATCAAAGCTCCATCGCCATACCACCAGCATTCACTGAAAATTCTTTTCTTAATGCAGAAG
TTTAAAGAGTGATCCTTTAGAAATACAACTATGCAAAGATAAGTTGACTTTATTAATTAT
GGTATATCCACACTATGGAATACTGCAAAGTTGTTTAAAAGAATGAATTATACCTGTGTT
GTAGATATAGATGGCTGTCTGCTATTTATTAATTTAGCAAAAAGTCACAGAACAATGTT
AGGATAATCCCATTTTTATAGTATAGATGCATGAAAAAAAGCTGAAAATTTGTATATCAG
AATGTTAATAATGTTCTTAGGGGGCAATTAACTACCTATAATCAAAATTGGGTTGTTTTT
CCTATGGACTTGTCCATAGTCTGGATTTTACTGATATCAGCATCATGGTGTCATTTAACC
TGTTCTTCCTTGTATTTCCTATAAATCTGTAATTAGTTCTAGAGACTTTATGAGGTTTAG
GTTCAATGATGGTCAGGTGGTGGGGAAAGAGCACTTCATAGGTGATGCTGTGTGTTTCCC
TCAGGAGGTACATGATATGTGGTTGCTATCTCTCCTTTCATGATGCTGGCAGCCTTTTA
TTTTATTTTTATTAGGGGTTACAAATTATAATGAAATGCTAATGGTAATAATAATTCT
ATCTTTATTTATTTGTCAGCTGAACTACTTCTATAAAGACAAACTTTTCAGAAACTACTT
TGATTACCCCAAAGTATGGGCAGCATTAATTCTTTCCCTTTATTTGCCAGTGTTTAAAAT
AGTGAGTTGGTTCCCCTAACATCTGCCAAAGGTGACTAATGAGGTTTGTTTGGTTGTTTT
AGTATCATTGTGCACGCTTGGATTTCATGACTGCAAATTATTTATTATCCTTTTGGTGCT
CAAATTGTTCCATCTTTGGCAGAGAGCCTTTTCCAGTTGACTGCTGATTCATTTGACAAT
CAGCTGTCTTTGATAACTTCCTTGCTTTCTGAGCTGGTGAGATGTTCCAGGCCATCTTGG
GTATTTCTGGCCCCAGATCTGGAATCAGCCATTTCTTCAAGAAACGCTGATTCCTTTTAT
TCCCTCCACCACTCCCCACAAAGACCTTGACCTGTTCTCCTGAATTCTTGAAAATCTTGA
AAATTCTTGAAAATTATCATTTTCCAGTGCAGTAGACAGAAAAGACAGTATATTTAGGAG
ACCTGTTATATCTATGCCTAGAGGGAAAGATCTAAGGGAGGAAGAAGTGGAAGATACAG
TGCCTTAAAAGGCATTTAAACTTATGAGGACCTACTAGGGCCCAGATGCTAATATGCTTT
GCATAGGTTATCCCACTAAATCCTCCCGACAACCCTGTAAGGTAGGTTTTCTTTCTATCT
TACAGGTGTAGGAACTAAACTTAGATGATCAAACGACTTCCCTGAAGCCCCACAGCTTGG
AAGGGGGTGGGACTTAGATTTGAACTTGGGTGTGTCTGCTGTCAAAACCCATGGCTTTCT
TCTATCGGGAGGAGGAAGGATTGTTGATGAGCCATGGTGTCTCAGGAGTGTTGATGACTT
CTCTTAGAGTGTGGCTCTGAGCAGCAGAAGCCCTATCCTTCATGAGCCTGCCAGACCTC
TGAGACTCAAGTCCCATTAAACAGTAACACTCAGGCACAGGTTCTGTATCTCTTCCTGTT
TCCCCCTCCACCACAGCACAGTGTAGCTGCAAGGACCCCTCCCTCAATGGTGGCCCAGAT
AATGTGGATTTTGCAGAAATTATTGGTAGCAAATGTCCAGAGTCTTTACTGGTTGCCTGA
TGTTCCCTGAATCCTGGGAGTCAGCTACTGTCCCTTTTTGTTGTTGTTGGCTAGAGATT
AGGGGAGATTAAATAATTAACTATTTGGGTTTTTTTTTTTAATGAAAGTGAAATAAAACA
TTGAGAACCAGGAGACAAATGTCAGTTTGGAGAATTTTTCAATGACTTTCATTTTATTTT
TACCCAAGAATGATATTAAGTTCTAATCAGCCATTATCTGTCCTGGTTTCTCAGGTCTCT
GCTGGTGATGTGTCTTTCTTTTAAGAAGTGAAGAAGTAGACACACTAATCCAGTTCCATG
GATACCCCTCTGGTGTGTCTGCTTCTCAGAGAAGGGTGAGGTAACTTTTTTTTATAACTC
AGATAACTGGCAATGAGGACATTCCCCTAAAAGTTTCTTATTTGAGGCATAGAGGCAACC
TTTCTGTGTTTGCTAATAAAAATGTGACAAAGTGGCAAGCACATGTAAATTCTCCAAAGT
GAGGGAGAAAGATCAGAATGCTGCAGAACATCTTGTGCTTTCATTCTTGTCCCTTGCTGG
AAACTTGTCCACATTATCCAAGACCTCGCAGAGCCATGCCCAGGAGCCACAGTGTTAGTA
TAGGAAGCCCACCCTTCCCAGGGGAGAAGAGATGGTCACAAGGCCAGAGCAGGCTTTTCC
AAGGCTCGGGGTACATGCCCAGGCCTGACAGCTCCTGCAGACACAGCACCTAGCCACCCA
TAACCTGGGGCAGGACTGTGGAAAGAATTGTATCAGAAGAGAGAGGATACATCTCTTGTC
ACATGGCCTTTATCCTTTGTATAGAAGTCTTATCTTTTGATATTTTAAATAGGCCATCAC
CAAAGTCCTTGGGAACTGGGCTAGTTTGTGTCAACTTGGCATTGCTGTTACCGCCTGCTA
AAGTCTCTGTTGCCAAGGAGAGACCAGGGAGTACATTTCCCAGAAGGCACCTCCCACTTG
TGCTTCCAGGATAGGTCAGCTGATGAGAAGCCCTTGGTGAGTTTTGGAAAGGAAGGCCAT
```

```
TTATTTCAAAAAGCAGTAGTAGGCAGATGATTGAGTGGCTGTGAGTTTGAAAACAACTTC
CAGATAACTTTTTTTTTTTTCAAGACAGGGTCTCGCTTCATCACCCAGGCTGGAGTGCA
GTGGTGCAATCTTAGCTCACTGCAACCCCTGACTCCTGGGCTCAAGTAATCCTCCCACCT
CAGCCTCCCTAGTAGCTGGGACCACAGGCACATACCACCACACCCGGCTAGTTTTTTGTA
TTTTTAGTAGAGACAGGGTCTTGCCATGTTGCCCAGGCTGAGTTTCAGATAACGTCTTA
AGAAAGCCCTGCTTCAGTGCTACTGGCTGAAGTTGTTAATGATGATGTCTTAGTTCATTT
GTGTTGCTGTAAAGGAATACCTGAGGCTGGGTAATTTATAAAGAAAAGAGATTGATTTGG
CTCATGATTCTGCAGGCTGGAATACTGGGCATCTGGTGAAAGCCTCAGTCTGCTTCCACT
CATGGGGAAGGCAAAGGGGAGCCACGCAGATATCACATGGCGAGAAAGCAAGTGAGAGT
GGGGGTTTTGGGGGGGCCAGGTGAGCTAATATAGTGAGGACTCACTCCCTGCCTGCCCCC
ACCTAGGGCATTCATCTACACATGAGGGGTCCACTCCCATGACCCAACACTTCCCATTGG
GCCCCACCTCCAACTTTAGGAAAAAATTTCAGTATAAGATTTGAGGGAACAAACTCCTAA
ACTATAGCAGATGGCTTCCCTGACATTATTTCCCTCAGTCTTCAATCCTTTGTATTAAAA
CCTTTAATATTTGATATACATAGATTAGTTTCTGTTTTCCTGATGGAACTCTCAATGAAC
ATATGTGATGGGGAATGCATGTCTTCACTGATAGGTTGGTTATAGGAGACCTCCAAAAG
GAAAGACCATTCAAAGGCACCATGTCTCTCTCTCTCTTTTTTTTTTTTGCTGGAGGGCAT
TGGCCCCATACTGGCTCACTGCAACCTCCACCTCCCAAGGGATCCTCCCACCTCAGCCTC
CAGAGTAGCTGGAACCACAGACGGGCACCACCACACCCACTAATTTTTGTATTTTTTGTA
GAGATGGGGTTTCACTGTGTTGCCCAGGCTGGTCTTGAACTCCTGGGCTCAAGCAATCCG
CCCACCTCAGCCTCCCACAGTGCTGGGATTACAGGCGTGAGCTACCTCACCTGGCTGGCA
ACATGTCTTAAGATAATGTTGGCTAATGGAGCAAACAACAAAGTTTGAAAACTTCCAACA
AGTCTTCTGTTCGGGCGCTGGTGACAGCCGGGACTGATCGCTCAGCGGCAGTGGCGCAGA
GGCCTCCTCCCTGGTCCACCGCGGTCCCCACCCAACCCCACCTGTCCCTGCTGCCTGCTG
CCGTAGCAGGAGCTGGAGGCTGCTGCTGCCAGAGGGCAATGAGTTCCAGTGGTGCTTCTC
CCAAGTCAATGGGGCCATCGAGGAGGACATGGCTGAAGATCTGCCACAGGGGAGAGGCCA
GAAGAGGCTTTGACGACCATCAGTGAGTGACCAGGGGGCTACACAGCCTCACTCTGCAGC
AGATATCATTTCCACTGTTGAGTTTAATTACTCTGGAGATCCTGTGGCAGGAGACAAGGA
CGGTGGAGTCGTTTTTCAGCAGAGCTAGAGAATAAAAGCCGCCCTCATTCTAGGGGAGAA
TATAATGTTTACAGTACCTTTAAAGGTCATGAACCAGGGTTTGGCTATTAGAAAAGTCTA
GAAATTGAGCAAAAATAAAATTAGGTGGTTACAACAGAACACTGCTCATTTTCTACTCT
CTACAAATGATAAAACTATAAAATTATGGAAAAGAAGCGGATGAGATAAAAGAGCAGAAA
GTTATAACTTGAATGATGAAGATGATGACTTCAAGATTCATTTAGAATTACAGCACTAT
CAATGACCTGAGGATTAATTTATGACACTTAGAAATCACACATAGACATTTTGACGTGGT
AGACATCAAACCTGCTAACCTGGAGCAGCTGACAGAAGTCATTGTGGCAGCCAAGTTCCA
CTCATACCAGTGCAATGTGCTTGTCTACAGTAGTAGCAAAGGAACCATTGACTAAGCAGC
ATGGGCTCCTCGACCCTGTGCAACAGACACTCCAAGTTTTTTGAAGAGCCTCAAGATCCC
AGCAGTAGGTCCTTCTTCTCAGAAATAATTTCATCCATACCCAATGTAAAATGTAGCCAT
AGTGGGCAGTACCTGATGACCAGAGACTCCCTGTTGGTGAAGGTGTGGGACCTCAACATA
GAGAGCAGGCTGGGACCACACCGGGACCACGAGTACCTGCACAGCAAGCTCTGCTTTCTC
TATGAGAATGACTGCATCTTTGATAGCTTTGAATGTTGCTGGAATGGTTCGGATAGGTGC
ATAGTTGAACCACAAATAAGCAAGGGAAATCTCCAACAGCCAGAAACGAAGAGGGAGCT
GAAACCAGAACCGTAGCCTCTAAAGACGTTTATTGCGAGAGAAGCCCCACACCCCTGGCT
GGCCTTGGGTGCATCAGCCAATAGCAGGAACCGCTGCCTCCTGTGAACAGCAAGTTGTGG
CGCAGAGCTGAAGCCTTGGACCATGAGGTGTGGAGTTGGAACTGCGCCCTCAAAGATGAT
GAGGTCTCCGTCCACTGGAGTCCAGAGGGAAGTTTATCTGAAGATCTTGCATTGGGGTGGC
CAAAGCTCCCCTGAGATGTGTAAGCATAGCTTCCCATTACAAGGGTTTGAAGTCCCTCTC
TCTCCCTCCCCCTCCGCCTCCTCCTCCCCCTCTCCCTCTCACTGGTCTCCCTCTGATGCC
ACCAAAGTTGTGAAAGCCGAGGCTGGACTGTACTGCCGCCATCTCGGCTCACTGCAACCT
CCCTGCCTGATTCTCCTGCCTCAGCCTGCCGAGTGCCTGAGATTGCAGGGGCGCGCCGCC
ACGCCTGACTGGTTTTCGTATTTTTTTGGTGGAGACGGGGTTTCGCTGTGTTGGCCGGGC
TGGTCTCCAGCTCCTAACCGCGAGTGATCTGCCAGCCTCGGCCTCTCGAGGTGCCGGGAT
TGTAGACGGAGTCTCGTTCACTCAGTGCTCAATGTTGCCCAGGCTGGAGTGCAGTGGCGT
GATCTCGGCTCGCTACAACCTCCACCTCCCAGCCGCCTGCCTTGGCCTCCCAAAGTGCCG
AGATTGCAGCCTCTGCCCAGCGGCCACCCCCATCTGGGAAGTGAGGAGCGTCTCTGCCTGG
CCGCCCATCGTCTGGGATGTGAGGAGCCCCTCTGCCCGGCCGCCCAGTCTGGGAAGTGAG
GAGCGCCTCTTCCCGGCCGCCATCCCATCTAGGAAGTGAGGAGCGTCTCTGCCCGGCCGC
CCATTGTCTGAGATGTGGGGAGTGCCTCTGCCCCGCCGCTCCGTCTGGGATGTGAGGAGC
GCCTCTGCCCGGCCGCGACCCCGTCTGGGAGGTGAGGAGCATCTCTGCCCAGCCGCCCTG
TCTGAGAAGTGAGGAGCCCCTCCGCCCGGCAGCCGCCCCGTCTGGGAAGTGAGGAGCGTC
TCCACCCGGCAGCTGCCCCGTCCGGGAGGTGGGGGGCAGCCCCGCCCGGCCAGCCGCCC
CATCCGGGAGGTGGGGGCGCCTCTGCCCGGCCGCCCCTTCTGGGAAGTGAGGAGCCCCT
CTGCCCAGCGGCCACCCCGTCTGGGAGGTGTACCCAACAGCTCATTGAGAACGGGCCATG
ATGACGATGGCGGTTTTGTTGAATGGAAAAGGGGGAAATGTGGGGAAAAGATAGAGAAAT
CAGATTGTTGCTGTGTCTGTGTAGAAAGAAGTAGACATAGGGAGACTCCATTTTGTTCTGT
ACTAAGAAAAATTCTTCTGCCTTGGGATGGTGTTAATCTATAACCTTACCCCCAACCCCG
TGCTCTCTGAAACATGTGCTGTTTCCACTCAGGGTTAAATGGATTAAGGGCGGTGCAAGA
TGTGCTTTGTTAAACAGATGCTTGAAGGCAGCATGCTCCTTAAGAGTCATCACCACTCCC
TAATCTCAAGTACCCAGGGACACAAACACTGCGGAAGGCCGCAGGGTCCTCTGCCTAGGA
AAACCAGAGACCCTTGTTCACTTGTTTATCTGCTGACCTTCCCTCCACTATTGTCCTATG
ACCCTGCCAAATCCCCCTCTCCGAGAAACACCCAAGAATGATCAATAAATACTAAAAAAA
AAAACAAAACAAAAAAACAAACAAACAAACAAAAAACAAAAACAAGGGTTTGAAGTTTGTG
TTGGTGGCAGCTGCGTGATCTGGAAAAGCTCACACTGAGGAGCTCTCCTGCCTCCATGAG
GGCAGCGTGCAGGCGCCTGGAGGCACTGACGTTTTTCTGGGTCTGACTTCTACTCTGTTT
ACAGACTAATCTGCTAGCCTACAGTGTTTCACAGATGTTGACTGAAGACATGAGGTTCCT
GGGTCCTTGGAGCACAGCAAGCAGCATGAGCCTCTTGCTGGCACAGGTTTCCCAGGGGGT
GACACAAGGGGCCCAGGCAGATGCTATGCAAGCAGTGGGGCTGATGTCATGGCCGATGCA
TGCTGAGGTTGGAGAACTCACTGCTTTTTCAGTGGACAGTCAACAAACCTGCACTTTGAC
```

-continued

Sequence listing

```
TAGAAGAAACATGACCTCATTCCTCTAGACCACTTGCTGTAAGCACAGCCCTGAGAAGTG
GCCCAGGTTAAAAGAATGGTGTTCTTTGCAAACTTAGTGAGAACATGCATGGTGGGTGGC
TGCTCCCAGCACACCCAGGTCTCTCTGGATTTCCCCAGATTAAAACCAGCTAAACATGAG
CTCACAGGTAAAATTACCAAGCACATATGGGAAAAGCCACCACGAGTAAGTCAGCAGAAC
CACAGCGGAACTGAACCTCAGAGAACCCAGCCTTTGACATCCTAAATTAAACTAAGAATG
CTTGAGATATTTACAGACTAAAGGAAGGAAACAGCCTGAACCAGGAGCCACAAGACCACT
AAAATGACCTGGCAGACTGGAGAGGAATCAAAGAGAACGTCTGGAAATGACAAGTACAAT
AGATGAAACTGTGGGTTTAACAACAGGCCCATTTTGGCTAGAGATTTTGAATTAGTAGAT
GGAAAGGAAAATCAGAAGAAATGCAGACTAGAGAGCCAAAGAGATAGAAAACATGAAACA
TAAGAAGTGTGGAGGTCAGGATGAGGCACAGCACACATTTAAACAGAGAAGTGTGGGGAC
ATGAGGCTTAAAGTGACAGTGGCCAGGAATTTTCTGTAAGTTATGAAAGCCTGAATACAC
AGAAGCAGGAAGCACAGAAATCCACATCCATATCATCATGAAACTGCAGGACACCAAGTG
CAAAGAGAAGATCTTAAATGCAGCCAAGGAAAAAGCACAAATTACAGAGAGCAGATGCTG
AGACTGAGAGTAGACTTTATAGCAGCCACAGTGGGAGCCGGAAGCCATGTGATACAGTGA
GTGTGACTTGGGACTCTTCACCATCAGCTTAGAATCAGGCATTGAAATAGATGGTTGTTC
AAGAATCTGCTTATGGTAAAGGCATTTCCAGATGGGAAACAGAATTTATCACAACAGGAA
ACTCAGGAGAGTGAGACTCAAGGAACTCACTGAAGAACGTACTTCCAGCAGAAGGAGAGT
GGTCCTGGAGAAAGGGTGTGATTCTGAGATAGGCAGATGAACAGAGCAGTCAGTGAAGAC
GTGAGCAACGGAAAGCAACGTGGACTCTAAAGCTCTGTTAACTGGGTGACCCTGGTTATC
TGGGTTGCGGGGAGAAAAATTAGAGCCCTCACCAACACCACACAGCAAATAAGCTCTGAA
TGTTTTAAAGCCTAGAAGACGCTATGGGAGAGCATCTTCATGGCTCTGGAGATGAAAGGC
CTTCTTTAACAAGGTCCTAAATGCCCAGTGAAGGAAAACATTAAGAAATTCAGGCTGATC
GTGCTGGCTCAAGCCTGTAATCCCAGCACTTCGGGAGACCGAGTTGGGTGGATCACTTGA
GCCCAGGAGTTTGAGACCAGCCTGGGCAAAATGGTGAAATCTGATCTCTACAAAAAATAC
ACACACACACACACACACACACACACACACACACACACACACACACACACACAAATAGCT
GAGTGTGGTGGCATGCGCCTCCCAGCTACTTGGGAGGCTGAGATGGGAGGATCACCTGAG
CTAGGGAGGTGGAGGTTGCAATAAGCTGAGATCGTGCCATCACACTCCAGCCTGGGTGAT
AGAATGAGACCCTGTCTCAAAAAAAAACAATACTGTAGTTAAATTTAGTGGTTTTTGGTT
TTTTGGTTTTGTTTTTGTTTTTGAGACAGAGTCTTGCTGTGTTGCCCAGGCTGGAGTGT
AGTGGCTCAATCTAGATCCACTGCAACCTCTCTCCTGGGTTCAAGTGATTCTCCTGCC
TCAGCCTCCTGAGTAGCTGGGATTACAGGCATGTGCCACGAGGCCTGGCTGATTTTTGTA
TTTTTAATAGAGATGGGGTTTTACCATGTTGGCCAGGCTGGTCTTGAACTCTTGACCTCA
AGTGATCTGCCCACCTCGGCCTCCCAAAGTGCTGGGATTACAGGCGTGAGCCACCATGCC
CGGCCAACTACATTAAATTTTAAACTTCTTTATTTTGAAATAAAAAGTAAAAACAGGCTG
CTCTGCCTATGGAGTAGCCATTCTTTTATTCCTTTACTTTGTTAATAAACTAGCTTTCAT
CTTAAAAAAAAAGTGAAAACAAAATCCACAAAAGCAAATATAACGAACAGATTCAGTATC
CAAAATATGTAAAGAATTAGGAGTCAACAAGAAGGTGGCAAACAGCTCACTTAGGAAAGA
GCAAAAACCATGACTGGGAATTTGCAGAAATGGAAAAATAAATAAAAATGCTCATTCTTA
GTGATCAGCAAATTAGAGCCAGAGGGATGTCCTTTCACACCCATCAGAATGATGATGATG
ATGTCAGGGAAAGGAATGAAGGCCAGTGGGCGAGACCACTGCCTTTTTGTGGGCCTCCTT
GGTGGCAGCAAGTCCAGTTGGGAGCTTCTTGTATGTACAGACAAGAAAATGTATTCAGAA
GCTTGAAATAGCAAACACCTGGAGACAGCTCAGGGGTGCATCATTAGGGGAATGGATAGG
TAGGTTGTTGTCTATCATATGCTAAAAAGCAGTAAGAATCAATTATTTGAACTACATGGA
TCACAGCTGGGCACAGTGGCTCACGCCTGTAATCCCAGTACTTTGGGAGGCCAAGGCGGG
CAGATCACCTGAGGTCAGGAGTTTGAGACCAGCCTGGCCAACATGGTGAAACCCCGTCTC
TACTAAAAATACAAAACATTAGCTGGGCGTGGTGGCACGAGCCTGTAGTCCCAGCTACTC
AGGCAGCTGAGGTAGGAGAAGCGCTTGAACCCAGGAAGCAGAAGTTGCAGTGAGCTGAGA
TCATGCCACTGCACTCCAGCCTGGATGACAGAGCGAGACTGTGTCTCAAAAAAAAAAAGA
ACTACATGGATCACATAGGTGGATCTCACAAAGATAAAGATAATCCGCAAAGAAAGAAAA
TTCAGGCGGAACACATACAGTGTGATGACATTTGACATGTTATATTTAAGGCATGCAGAA
GTTTTATTTGTTTTAAGAATCTGTAACTATTCAAAAATATAAACGTGCATGGGGATGAT
ACATACGTACTCTAGTGAGTGATTTCCCCAGCTGGGGACAGGATTGGAGATGATCTTTCT
AGAGTGGGACATGGTGGAGGTTAACTGTCTTAGCAATGACTTATGGGTACTTGGATACTC
ACTGTATTATTCCTTTTTTTTTTTTTTTGAGACAGAGTCTCGCTCTGTTGCCCAGGCT
GGAGTGCAGTGGCGCAATCTCGGCTCACTGCAAACTCCACCTCCTGGGTTCACGCCATTC
TCCTGCCTCAGCCTCCTGAGTAGCTGGGACTATAGGCGCCCGCCACCACACCTGGCTAAT
TTTTGTATTTTCAGTAGAGACGGGGTTTCACCGTGGTCTCGATCTCCTGACCTCGTGATC
CGCCTGCCTCAGCCTCCCAAAGTGGTGGGATTACAGCATGAGCCACCGTGCCCGGCCCAC
TGTATTATTCTTTGTTCCTCTTGATATATCTGAAATATTGTGAAGTATACTTAAATTACA
CATCCCTAAGAATATCCAAAAGCTCTCCTGGTAATATTTGCTTACTCCATTCACTCTTAC
AAACACTCCCATATCTTCTTGCCTGGAAACATCTGTTGAGGGATGGGATGAAGGGGAATG
AGATTTTTCAGTGCTCTCTCTGCCCAGTCCTGATCCCCTGTGTGACACCACTTTCTGGTG
CTCTAGGTTGCCCCGCAAAACCAGACATAGCCGCTTGCTCTTGAGTGTGTCTGCACTGTC
CCTACCTCAGGCCAGCACCGATGCAGGCGGCTAGGCGGCTGTCTTGTTTACAGTGTGGAA
ATGCCCACTCCCAGGCCAGCATTGCCTATCAATAATTGACAAGTGATAATAAAACTGTAT
AAAAGCTGAAAAGTCTTATATTCTTCCTGTTTTTTCTTTAATTTTTATCAAAGTAATAA
ATATATATGGTTTTTAAAAATCAAATAGTTTAGAAGAACTTCTAATGAAGAATAAAAAGC
CTCCACCTGTACATTATAAATTTGTACAAATGCACAGAATGTACACCACCAAGAGTGACC
TGTAATGTAAACATGGACTTTGGGTGATAATAATGTGTCTATGTAGGTTCTTCAGTAGTA
ACAAATGTATCTCTCTAGTGGGGACGTTGATAATGGTGGAGGCTGTGCATGCAGGGGCT
GTATGGGGAATCTTTGTACCTTCCTCTCAATTTTGCTGCAAACCTATAACTGGTCTAAAA
ATAAAGTCTATTTTTAAAAAAGCCTTTTCCACCTCACCTCTCCCAACCTCAGTCCACTTG
CCAAAGGTAGCCATTGCTAGTTTTAATTCTTTGGAATACCTATAAATAATGTTATTTATA
TGTTATATAAATAATAATGTGTTTGCTACTATTTCTGGGCTCATCACCCATAGACGTTAA
TTATCACCTTTCCTCTCTTGAGATTTTCTCTCTCCTGTATCTGCAGGTCAGTGGGGAATT
GGCCGAGCTGGCTGGGCTTGGCTGGCTGGACTGGCTCCAAGCTGTGGGTCCAGCTAGGCA
TGTCTCCTTCGTAGGTCAGGCTCAGGTCTGCTCTGGATTCCCCCTGGGGTCTAAGATGAA
```

-continued

Sequence listing

```
GGGACAGGGAAGCTCTTGTCACAATAATGGCAAAGCCACAAGAGGGAAGGCTCAGCTGCA
CAAGTGCATTTCAAACCTTTGCTAACATCTCATTGGCCAAAGCACGTCACATGGCCACAG
TCAGGAGTGAAGAAGTGCACTGTCTCTAGTAGCAGGCACTGCAAAGTCACATAGTCAAGG
GCCTGGATATAGACAGAAGTGAAGAACTGGGACCTTTTATTCAATCTACCATATTTCTCA
TAATTCTGTTTTCTTATAGACTTCTCTGTAACAGTATTTTAGCTCAAATAATACAACACA
GCTTTGCCCAATGGTTGGCCTCTTTTAAGTGGCTGATAGATACTTGATGAGTTTCTTAAA
TCTCAACATTCCCACAGGTTTCTGAGAAGGAATTTTGTTAGATAGTTTAGGCTTGGCGGA
TGAAGAAAGTTTGGGTGTGGGTTCTTCAAAGTCAGTCTGGCTGGAAACACCTTGTTCTCC
CCTTCCCTTCTATGAAGTGAAGAGTGTCTCCAGATGGTGTATAGACAGCGAGTTGCTACG
GAAACATCATTTGATCTCCCCAGAAGATTACTACACCGATACAGTGCCGTTTCACTCTGC
ACCTAAAGGTAATGCTTCTGTGCTCTCAAGGCCTCTGATACCATTTGGGGGAAGTTCAGT
AGGGCCACGTTGGCCACCTCTGCTGCCATTTCCTTGCTCAGAGGTTTTTTTCACCTTTTC
TTTAATTTCGATGGTGACTGTTGGGAAAGTCAAATCTGAGCATCTGAGCATGCCAATTTC
TTGCTAGTGCTCCCCCGCCTGTATGACTGAAGTCCAGGCTTCTCCATGTGGACTATGATG
CCCACATCTGCTGCCCAATACCAAGAATTATGTAAGTGCTTGGAGTTGCAGTTGAACCAA
GAGAAGGAAAAACTGAAGACATAGAAAAGCAAGGGAGCGTGTACCTGATGAGTTGGAGCA
GGGACTTATGGGTTTTCCCATGCAGGAAAAGAGCAGCTTCTCATCCTTTCAGAATGGAGG
GAAGCCTGGGTAGAGAGGCAGAGAGGGTGTGTACATGTATGTGACATTGGGCCAGTTTCC
TGTGATATGGGAGGCAAGATATTCTGAGAATGAGTGGGGTGGGAGGCTGTGATGTGGGCT
TAAGCAGCGAGTTAGACTTATGGAAGAGTCCACACGTGGACAGGGAGGAGAAGTCCCTGTGTG
GATTCTGTGGCCAGTTATCGGGATTGCCTAGCATGCTGGGCTCAGAAGACAAGCTCTCCC
ATAGCTCCAGTTGAGGGACTGTTTGATTCTCTGGGGCTTGGGAGCTGAGAAGGTGTTTGG
GGTGGGAGGATTGGGATCTAGAAAATTGAGGGTGCTCCTGGGGAGAGTTCCACTGATGGT
CTGAGCTACGTAGGGAAGTAAGGCAAGAAAGAGGTAGCAGAATCAAGTGTCATGGAGTAC
TAAGCCACTTAGTATTTTTTTTTTTTTGAGGCAGAGTTTCACTTTTGTTGTCCAGGCTAG
AGTGCAATGGCACGATCTTGGCTCACCACAACCTCCATCTCCCAGGTTCAAGCAATTCTC
CTTCCTCAGCCTCCCAAGTAGCTGGGATTACAGGCGTGTGCCACCACACCTGGCTAATTT
TGTATTTTTAGTAGAGAGGGGGTTTCTCCATGTTGGTCTCAAACTCCTGACCTCAGGTGA
TCCACCCACCTCAGCCTCCCAAAGTGCTGGGATTACAGGCATGAGCCACCGCACCCGGCC
ACCACTTAGTATTTTAAAGTTAGTTGGAAACTCAGTATCTTATGCAGGTCAATAAGAATG
GGGCTAACATGTATTGAGAGTTAACCAGGCATTGTGCTAAGAGATTTGTGATGGTATCCA
TTTGATTGCATTCTTGCTAGCAATGAATGTTCTCATTTAACCTTTGGAGGGATGGTTTTC
TTGTTTGTTTGTTTGTTTGTTTTTTCTTGAGACAGAGTCTCGCTTTGTCACCCAGG
CCAGAGTACAGTGGTGTGATCTACTGCAACCTCTGCCTCCTGGGTTCAAGCGTTTCTCCT
GCTTCAGCCTCAGCCTCCTGAGTAGCTGGGATTAAAGGCGCCTGCCATCATGCCTGGATA
ATTTTTTTGTATTTTTAGTAGAGACAGGGTTTCACCATGTTGGCCAGGCTGGTTTCCAAC
TCCTGACCTCAAGTGATCCGCCGGCCTCAGCCTCCCAAATTGCCAGGATTACAGGCATGA
GCCACTGCGCTTGGCCAGGGGGTGGGGATGATCTTAACAGTGTAAAAGCTCATACAAA
CTTTCATTCCTTCTGTGAGCTCTTCAGAAAGCATGCTCATGTATGGGGTATGTGTACAGG
CATGTGTGTGTGACAGTGGTCTACTCATGTTCTTTGACCATGTTGGAAAATATTTTAACA
CTCTAGTCCTAAATTTTGTTGTTGTTTGTTTGTTTTTGAGACCGGGTCTTGCTTTG
TTGCCCAGGCTGGAGTGCAGAAGCACAACCATAACTCACTACAACCTTGACCTCCTGTGC
TGAAGTAATTCTCCCCACTCAGCCTCCTGAGCATCTGGGACCACAGGCATGCACTACCAC
ACCCAGCAAATTTTTAAATTTATTTTTGTAGAGATAGGGTCTCACTCTCACTATGTTGC
CAAGGCTGGTGTCAACTCCTGGGCTTAAGTGATGCTCCCACCTTGGCCTCCCAAAGTGCT
GGGATGATAGGTGTGAGCCACCACACATGGCCATTTGAATACATAGAATAAGTTCCAGG
AGTAATTCATATGTTGAAGAGCAATTATAGCTGGTGTGGTAAATATGAAAGTTTAGGAGA
AAGATCAAGCTAACTGTGGCTTTGGTGGTTTTATTTGGTCATCTTAGGAATGCCCACCTC
CTCACCTTGTTGCAGTGATTCAGTTTGTTTCCTTGATGCTGTAGGCATCTCCCTACCTGG
ATGTTCAAAACTGACATTTAGCTGTGAGAAGCGTTCCGTCCAGAAGAAAGAGCTGAACAA
GAAGCTTGAAGATTCATGCAGGAAGAAGCTTGCTGAGTTCGAAGATGAGTTAGACCACAC
TGTGGACAGCCTGACATGGAATTTAACTCCTAAGGCCAAAGAAAGGACCAGAGAACCTCT
CAAGGTCAGTTTGGAAGGCTGTGCAGAGCAGTGTTTGGGGGGACAGAGAGGCAGTGAAGG
GGAAGGCATTCAGATGACATGAGAAGCTGTGATGAATCCATCGCAAAATAGAGTAGAGCT
TGTGTTGGCCATCTATGGGTCATGCAGTTGGTCAAGATGTCAACAAGCACAATCCCTTTG
CCTGTCATTGACTCTATGCTTTTGTATGTTTCAAAGAAAGCAAGTCAACCAAGGAATAAA
AACTGGATGAACCACTTACGTGTGCCACAGAGAGAGCTAGACAGACTTCTGCTTGCCAGA
ATGGAGAGTCGGAACCACTTCCTAAAAAATCCCCGTTTTTTTCCTCCTAACACTCGATAT
GGAGGCAAGTCTCTTGTTTTTCCTCCAAAGAAGCCAGCACCGATAGGAGAATTCCAGAGT
ACAGAGCCAGAACAGAGGTATGTCTTTCTCTGGCTTGAACTCTCAGAAAACCTGGCCCAT
GAGAGTTAACCTAGATGGTCCTCCGTTTGGTCTGGCTGTAGAGGTTCCCTAGACTTGTGGG
GCAGGGTAGCAGTATCAGAACAGAGCAGGGCTGCAGGGTCACCCACTGGTGTGGCCTTTG
AACCTTCCCCAGAGTCCTGGGTTTATGCTTTTCTGACCTGCCAGGGGTCTTGAGAAATAG
GGGTTGGTGTTGGCCCTTTATTTACATTGGAGCAATCTGGGTCAAATGGAAGCAATCCCG
TTAGAGACATAGGTCTTGAGTAATAACAGCATTTGAAATTTGATTGATTATAAATAATTA
GTGTAAACTGTGATTTTTCTTTAAGAGTGCCTTTGCCTATATATCAGTAACTGTCCTTAT
GAAAGTAATGAGTTGCTTCATGGGTTCATAATTTTAGTAAGCCTAAAACTATTAACATTT
CTTTATTAGACAACTAATATTTTTTATTAAGAAAAATTAGATACAAAAACTAGCTGGGTA
TGGTGGCATGCACCTGTGATCCCAGCCACTTGGGAGGCGGAAGTGGAAGGATCACCTGAG
CACAGGGGTGTCGAGGCTGCAGTGAGCCAAGATTGTGCCACTGCACTCCAGCCTAGGTGA
CAGAGTGAGACCCTGTCAAAAAGAAAATAGAAGAGAAGAGAAGAGAGGAGAAGAG
AAAGAAAAGAAAGAAAGATTAGAAAAGACTAATATTTGAGATACCTATATTAAAAACCCA
CTTACTTATTGGTGTTTAAACATGTAGAGTTTTTCCTATGCATATTGAAAATGAAATATG
TAGCTACTTATGTCTTCACAAAGATTGGATCATACTGTAAAATTATTTTATAACCTGCAT
TAACAATAAGATCCAAAAACCCCCCAACAAATGGTATATTGTGAATATCTTTGATGGTCT
TTATGTATTTATTTTTACATTAATCAGTCACTGCCTACTATTTCATTGTATGGATGAAAC
TAACAGCCTTTCTCCCCCTCTTTTTTCATCCCACAGTTGTGCTGATACTCCAGTGTTTCT
```

```
AGCTAAGCCACCAATTGGGTTTTTCACAGATTATGAAATTGGTCCAGTTTATGAGGTAGA
CATCTTGTTTCTTTACAGCTCCCACCCCATCTGCTTTCTTATTTTTAAAAAGTCTTTATT
ATGGAAATTTTCTTTTTTTTTTCTTTTTTTTTTTTTTTAGTATTTATTGATCATTCTT
GGGTGTTTCTCGGAGAGGGGGATTTGGCAGGGTCTAGGACAATAGTGAAGGGAAGGTCAG
CAGATAAACATGTGAACAAAGGTCTCTGGTTTTCCTAGGCAGAGGGCCCTGCCGCCTTCC
GCAGTGTTTGTGTCCCTGGGTACTTGAGATTAGGGAGTGGTGATGACTCTTAACGAGCAT
GCTGCCTTCAAGCATCTGTTTAAACAAAGCACATCTTGCACCGCCCTTATTCATTTAACC
CTGAGTGGACAGAGCACATGTTTCAGAGAGCACGGGGTTGGGGGTAAGGTTATAGATTAA
CACCATCCCAAGGCAGAAGAATTTTTCTTAGTACAGAACAAAATGGAGTCTCCTATGTCT
ACTTCTTTCTATACAGACACAGTAAAAATCTGATCTCTCTTTCTTTTCCCCACATTTCCC
CCTTTTCTATTTGACAAAACCGCCATCGGCATCATGGCCCGTTCTCCATGAGCTATTGGG
TACACCTCCCAGACGGGGTGGCGGCCGGGCAGAGGGGCTCCTCACTTCCCGGACGGGGCG
GCCGGGCAGAGGCTCCCCCACCACCTCCCGGGAAGGGCGGCTAGCCGGGCGGGGGCTGCC
CCCCACCTCCCGGACGGGGTGGCTGCGGGCAGAGACACTCCTCAGTTCCCAGACGGGGT
CGCGGCCGGGCAGAGGCGCTCCTCACATCTCAGACGGGGCGGCGGGGCAGAGGCGCTCCC
CACATCCCAGACGATGGGCGGCCGGGCAGAGACGCTCCTCACTTCCTAGATGGGATGACG
GCCAGGAAGAGGCGCTCCTCACTTCCCAGACTGGGCGGCCGGGCAGAGGGGCTCCTCACA
TCCCAGACGATGGGCGGCCAGGCAGAGACGCTCCTCACTTCCTAGATGGGGTGGCGGCCG
GGCAGAGGCTGCAAACTCAGCACTTTGGGAGGCCAAGGCAGGCGGCTGGGAGGTGGAGGT
TGTAGCGAGCCGAGATCATGCCACTGCACTCCAGCCTGGGCAACATTGAGCACTGAGTGA
GCGAGACTCCGTCTGCAATCCCGGCACCTCGGGAGGCTGAGGCTGGCAGATCACTCGTGG
TCAGGAGCTGGAGACCAGCCCGGCCAGCACAGCGAAACCCCGTCTCCACCAAAAAACACG
AAAACCAGTCATGCGTGGCGGCGCACGCCTGCAATCGCAGGCACTCGGCAGGCTGAGGCA
GGAGAATCAGGCAGGGAGGTTGTAGTGAGTCGAGATGGCGGCAGTACAGTCCAGCCTCCG
CTCGGCATCAGAGGGAGACCGTGCAGAGGGAGAGGGAGAGGGAGGAGAGGGAGACTGTGC
AGAGGGAGAGGGAGAGGGAGAGGGAGGAGAGGAAGACCGTGCAGAGGGAAAGGGAGAGGG
AGAGGGCGGAAATTTTTAACTGTACACAAAACTAGGGAAAAGACTATAACTACTCCTCAT
GTGCCCAATATGCAGCTTCAACAGTTATCTACATTTTGCCAATCTGGTTTTGTCTATTAC
TCCTACAACCTCTTCATGTACACATCTATATGCACATGTATGTGCTGGAGTCATAGAAGG
AAAATATGATATCATGTCATTCTTCAGTTAATACATCAATTAGTATCTCAACAGATAAG
GGTTTTAAAAAGTAACCATAGTACCACTGTCACACCCAGCCATATTAATAATGATTCCTT
AATATCAACTAATACCCATCTATGTCTGATCTTCATTTGTTTTAAAAAAAAGTCCATTTA
TATTTGGTTTCTTTGCATCAGAATCTAAACATTGCATTTGATTAAAGTATCTCTTAATTC
TCCTTTAGTTGATAATAATTCCTCTCCCACCTCCTGCTTTTTAAAAATGCCATTTATTTG
TTGAAGAAACTGCAATTTCGTACACCCTGGATTTGGCTAATTGCGTTATTGTGGTGACAT
TAAACGTGTTCTTTTATCTTCCATATTTTCCACAAACTGGTCATTAGATATAGAGATTTG
ATGAGATTCAAGTTCCATTTTTCCTCTTTTTTGACAAGAATACTTCCTTGGTGGTACTGT
GTATTTCTTATTGCAATCCATCAGGAGGAAGCATGGGATCTGGGTTTCCCATGATCAGTT
ATGAATGGCATCAGGTGTTGAAATTCTGATTCATTCTCTATAAAGTTCTTATCAAACTTT
CACTTAATAGTTAACAGCCTAGATGACTGCCAGATGACTATTGTCCAGATCCATTTTTC
TTCAATCAGGGCTTACAAAATGGTAATTTCTAATTCTATTATTCCATCTACATTTATTAG
CTTGATTTTCCATTTAAAAAACAGAATAAAACTTTCCCTCTAACTTTGATTCCTGCCTCC
TCCTCTTTCTTGTACTCTCCTGATATCTATAGGTAACTATTTCTATTAGTTTGCATTCTT
CCATTGTTTCTTTTTGAACCATAAGCAAATATGTATATATAGTTGAACCCCCCTTTCCTTC
TTACTGTCCTCTACATCTTAACAGTATATCCAGTAATTCCTGCAAGAGCAGAGGCTTTCC
TCATTCCTTTTTCCCAGCTTCTTTCTTTTAGAAGCTTCCCACCTTCTTGGGGAATCAGGT
CAAGACCAAGCTTAGCAGTCACCAACTCTGCTCACCAGGTACAAAGACAACTAGGCCTAA
TGATAGCAATCCCTTCACATGCACATGGATTGCATTTTATAGTTTAAAGAGCACTTGCCT
ATCCATAATTCTTGAGGAATGTCTCAACCACTCATGGCAAAAAGCAGACCAATATGGTAG
CTCTATATGCTGAACATTAGAGGAAGCATTTTGCTTACTCCCTGGACTTAACAGTAATGT
GTTGTCTTTTGTACTTCTGTGTCTGGGACTTCTGTGTCTGGCCATCACGTTTTAAGGACA
GTTGTAGAAGCTGGCAAACACCCAGAGGAAAGGAGCTAAAATCATGTCAGTTAGGGAATA
GAATAGGGAAAAGGGAGAGCTGCTGATGGACTTATGGAAGATATTCTTCTTCAGGGCTTT
CAGATGCCTGCTGTGGAAGCCTGTGCTCAGAGCCTGGAGATCCTGAGGCTGTAGATGAGG
TAGACATAGACTGCTATGGAACAGTCTTTCCTCTGATCTTTGCCTACTTGTCTAATTCTC
ATCCCTTTGATGTTCATAACAGTTGTTTACCCGGCTAAACTATAAAGTGTAAGGATAAAA
ACAGTTCAAATTTTCAGTCTTTAAAAATTTATGTCCCATGTACCCTTTCTCTGAAACCTC
CCAGGGAACATGCTTCTTTAATAGAAATGAGGAAACCAATGAAGAGGAAGGCATGGAATG
TGGTACCAAGAGATCCAACATAGGGGAGAGGTGAAGGAAATCTCCAGGTTAATAACTCTT
AAGAGATTTTGCAGTTAATATTGCTGCAAAGCAAAATTTCCCAAAGCTCAGCAACTTAAA
ACAATCATTTTATCATGCTTACAAATTCTTTGGGTGAAAAATTCAGAGAGAGCACAATGG
GAATGACTTGTTCCACAATGTCTGAGGCCATTGCTGGAAAGAGTCAGTGCTTAGGGGTGA
CATAAAAGTTGGGGTTGATGCTGTTGATGCTGTTGTAGATAGAGAGCTGAGGCTGTCTAC
CAGAATGTCTACACCACATAGCTTCTCTATGTGGGCTGTGCTTCCTTACAGTATGGCAAT
CTCAGGTTAATCAGACTTTTACATGACAATGCAAGTGAGTATCTGCACTTTTTTTTTTT
TTTTTTGAGATGGAATCTTGCTCTATTACCCAAGCTGGAGTGCAGTTGGCAGGATCTTGGC
TCACTGCAACCTCTGCCTCTTGGGTTCAAGCAATTCTCCCACTTCAGCCTCCTGTGTAAC
TGGGATTACAGGTACGCACCACCACGCCTGGCTAATTTTTTATATTTTTGGTAGAGAGAG
GGTTTTGCCATGTTGGCCATGCTGGTCTCGAACTCCTGACCTCAGATGATTCACTCGCCT
TGGCCTCCCAAAGTCCTGGGATTACAGGCGTGAGCCATTGTACCTGGCCAAGTATCTGCA
CTTCTAAGTGAGTATCCTAGCAAGCAAGAAGGAGATTGCATCACATTTTATGACCTAATC
TTGTAAGTTGCACAGCACTACATCCTCTGCATGCCGTAGATTACAAACAAGTCACTAAGG
TTCATCCAGATTCAAGGGAAGATATGTAGACTTCATTTCTTTTTTTTTTAAAACCTTTTT
TTTGAAATAAGGTCTGGCTCTGTCGCCCAGGCTGGAGTGCAGTGGCATGATCTTGGCTCA
CTGCAACCTCTGCCTCCTGGGCTCAAGCAACTCCTCCCAACTCAGCTTCCCAAGAAGCTG
GGGCTACAGGTGCAGGCCACCACACCTGGCTAATTTTTGTATTTTTTGTATAGACGGGTT
TTTGCTATGTTGCCCAGGCTGGTTTCAAACTCCTGAGCTCAAGCAACCCACCCGCCTCGG
```

-continued

Sequence listing

```
CTTCCTAAAGTGCTAGGATTACAGGCGTGAGCCAGTGTCCAGCCTAGACTTCATCTCTAA
TGAGAACAGTGTCAAAGAACTTATGGATGTGTCTTAAAACTGCTCTAGGAGTTATCCTAT
ATGATAGCAGTAGGTGTAGTGGGCAACTAGCCCAGATTAGAAGAGGCCAGAAAGCTCTAG
GAGAGAGGTTGATTTATGGAGATGACATTGAGAAGAGTCCCTGATACACCTGGACATATGGG
GGAGAGATTTGTAGGGTGGTGGAGAAGGATTGAATTATTGATAAGCACAAAGCAAACAAA
ATAATTAGTTGATTATTCACTCCAGGAAAACCAAAAATTGTACAAGGCAGGGAAAGGAAT
CACCTCATGCTCAGCTGTGAATAGCAATTACTTAGTAACTTGAATATAACATGAATTACT
AATCTAACCAGTAGTATGATATAACTATATTGGAAACATGGGGGATAGGAAGGGCGTGTC
ATATGGTGAGTCAGATATGGGAGAGGGAAGAGGGAATATCCATATCCTCCATCTATAATT
AATACCTAAAACTGAACAAAAGTAGTATACTATTTGGAGACATGGAAATAAATACCAAAA
TAATCAGCTAAAGGATGAAAAAGTGTTTATCTTTGGGGAGTGGGAAATGGCAGGATGGGG
CCAGGGGAAGAGGGCAGTATTCTATTTTCAAAACCTTGTCGAACTCTGACTCTTTAAACC
ATGTGGCTGTCCAACTTAGAAGAAAACAATTTAAAAAAACCCAAAACTTTCCACAAAAAG
AAACACCAGGCCCAGATCATTTTGCAGGCACAGATTATGAAACATTCGAGCTATTCCCTA
TTTTATGAAACTATTTCAGAGACTAGAAAAAGAGGGAATGTACCATCATTATTAGGTAAT
AAGCCTAATTACCTTGACACCAAATAAAAATATATACCAGTCTTAAGAACATAGGTGCAG
AAATACTAGGTAAAAAACAGCAAACCAAACCAAACAGTAAGGAACAACACACACACACAC
ACACGCAGCCAATTCTTTGAAACCCAGGAACGCAGGGAATGTCTTCACAGCAGGCCTTGA
GTTGGCAGTTGGCTCTGCTGAGCCTATTATTTTTTCCTCCAAAGCTTCCAGTGCTGTTA
AGGAAAGCCAGTCCATGCCACAGTCCTTATAATGATCACTATCCCAAACCTTGCAGCCAC
CACAGCTACCATGTTTCACTCCCTGGCCTTCCACCTGCACCTCATTTCAGTTGACCACTA
GTGAAAGCCTTGGTAATTGTGACAATACCATCCCATGGTGCTCACACCCTAGTTCCCACC
AGCTGTTTCACAGATGGATTGGTGTAATATGTAGTGTTGGCCAAAAATTGATGTAAATGC
TGATTTAGGAATACAAATCTATAAATAAAAATAGGAAGACATACTTCATATTTATGTCAA
TTTTTATCTGGTGGGGGGCTGGTAGAGGATTTCAACTTTATCTGTAATGTTTTATTTCTT
AAGCTGGGTGATGGAAACATGGCTTCTGTCATGTTATAATTTATACATTGTTTTCTAGTG
TAACATTTCACAAAATATTAACAAAAGATGTGTACCTGTATTGATGTGCTACACACTGTG
CTGGGTGCAGTTGGAGGATTAGGTCTAGACCTTGCCCTTGGGGGTCTCCCAATCTGGGGT
GGCAGAAAAGAAAGTGGGGCTTAAAGGGGGTGAGTGGGTTGCGTAAGAGGCCCAATTACA
TCCTGACATAGAGGTGCCATAACACTCTTTGTGTCCATGGGAAGAATGGTTCAGAGATAC
GTGTTGAGGAAGACAGTAAGTAAGAGGTGAGGTGAGCAAAACTTTGAAACCAGATATCCT
AGGCTCAAACCTAACTGGTGCCTCTTTGAACTCCAGTTTCTTCAGCTGTGAGATAGAAAC
AGTTCCCACCTTTCCTGGTTGTTGCGAGGTTGAGGAGGTACAGAGCAGATGCTCATAAAT
AGTAATTGTTATTTTAAACAATAGGTCAGTTTCATGCACGTCCGTGTGAAGAGACTGCTA
AACAAGCTTTGTGTGAGCAATAAAAGCTTTTAATCACCTGGGTGCAGGCGAGCTGCGTCC
ACAAAGAGAGTCAGTGAAAAGAGATGGGGTGGGTCCATTTTATAAGATTTGGTGGGTAA
AGGAAAATTGCAGTCAAAGGGGGTTTGTTCTCTGGCGGGCAGGAGTGGGAGTCGCAAGGT
GCTCAGTGGGGGAGCTTTTTGAGCCAGGAAAAGGACTTTCACAAGGTAATGTCATCACTT
AAGGCAAGGACCGGCCATTTTCACTTCTTTTGTGGTGGAATGTCATCAGTTAAGGCGGGG
CAGGGCATTTTCACTTCTTTTGTGATTCTTTAGTTACTTCAGGCCATCTGGGCATATAGG
TGCAAGTCACAGGAGATGCGATGGCTTGCCTTGGGCTCAGAGGCCTGACATTCCTGCCTT
CTTATATTAATAAGAAAATGAAACAAATAGTGTTGAAGTGTTGGGGTGGCGAAAATTT
TTGGGGGATGGTATGGAGAGAGAGAATGGGCGATGTTTCTTAGGGCTGCTTCAAGCGGGA
TTGGGCAGCGTGGGAACCTAGAGTGGGAGAGAGAAAGCTGAAGGGAGATCTTGTGGTAA
GTGGTGATATCGTGGGGTTGTTAGAAGAAACATTTGTTGTATAGAATGATTGGTGATGGC
CTGGATATGGTTTTGGATGAATTGAGAAACTAAACGGAAGATACAAGGTCTGAATAAAAG
AAGGAGAAAATGGGTATTAAAGGACTAAGAATTGGGAGGACCTAGGATATTTAATTAGA
GAGTGCCTAAGGGGGTTCAGCGCAATTACTTGCTTGGTTTAGAAGTGATCTCCTTGAGGA
TAGATTTCCATGATGGAAAGGAAATGAGAGGTTCTAAGAGACGGGCTAGCGGCTTGTAAC
CTACATGGAAGAGGTTATGAAATGACGACAGAATAGAATGGGCCTGTGAGGCTGGAAGGA
GGTATTTTCCTTGGTCTAAGAACTATTTGCCTTGTGTGGGAAGAGATTGATAGGTGGAAA
TTTCAGCGGGGAAGTAGGTGGGAGTGACCGATGTGAAGGAGAAAAACTGGCCCTGAGGGA
CAGAAGTTGGAGAGCTAGCTGCTTGTCTAGCCACCTTATCAGCATAAGCGTTGCTTAGAG
CAATGGGATCTGACGCCTTTTGATGCCTCTTGCAGTGAATGACCTTAGCCTCCTTTGGAA
GTAAGGGGCCTTGAGTAGAGTTTTTATTAAAGAGGCATTAATGATGGAGGACCCTTGTG
TAGTGAGGGAGCCTCTTTCAGCCTATATGACCACATGGTGGTGCAGAATATGAAAGGCAT
ATTTAGAATCAGTGTAGATATTGACGCATAGTCCTTTTCCAAGAGTGAGGGCTTGAGTTA
AGGCAACTAGTCTGGCTTGCTGAGAGGTAGTGGAGGGGGCAGAGTGGTAGCCTCAATGA
TAGATGTGGAAGATACTATAGCATAGCCTGCCTTTGCTGGTGAGTGGCAATTAGGCCTGG
TGGAACTGCCATCAATAAACCAAGTGTGATTAGGGTGAGAAACAAGGAAGAAGGAAATGT
GGGGAAATGGGGTGAACATCAGGTGGATCAGAGAGATGCAGTCATGAGGGTCAGGTGTGG
TATCTGGAATAATGTGGGAGGCCAGATTGAAGTCCAGGCCAGGAACAATGGTAACTGTGG
GAGATTCAACGAAGAGTGAGTGTAGCTGAAGGAGCCGGGGAGCAGAAAGTATATGCGTCA
GGTGTGAGGAAGAAAATAGATTTTGGAAATTATGAGAGCTGTAGAGAGTGAGTTGAGCAT
AGTTTGTGATTTTGAGGGCCTCTAAAAGTATTAGGGCGGCAGCAGCCACTGCACGGAGAC
ATGATGGCCAGCCTAAAACAGTAAGGTCAAGTTGTTTGGACAAAAAGGCTACAGGACGCG
ATCCTGGTCCTTGTGTAAGAATTCTGACTGCACAGCCCTGCACTTCGGCTGTGTGTAATG
AAAAGAGTTGGGATGAGTCAGGGAGAGCTAGAGTGGGGGCAGTCTCTAAAGCTGTCTTCA
AGGAACAGAAAGAGGAGTGGGGAAAGGATTTAGGATCTATGGGTCAACTAGGTTTCCTT
TTGTGAGTTTATATAATGGTTTTGTTAGGATGGCAAAACCAGGTATCTAAAGGCGAAAAT
ATCTAACCATGCCTAGGAAGGAAAGGAGTTGTTGTTTTGTAGAAGGGGTTGGGGTTTGAG
AGATTAGTCGGGCACGATTGGCAGGGAGAGCACGTGTGTTTTTATGAAGAATTATGCCGA
GGTAGGTAATGGATGGAGAAGACATTTGAGTTTTGGAGGGAGATACCTGATATCCTTTGG
AGAATAAATGTTGAAGGAGCAGAAGTGTGTCTTGTTGAGAAGATTCAAAGGAGGGGCTAC
AAAGAAGAAGGTCATCAATATATTGAATAAGGTGAGAAGCGGAGGGGTGGAAAGAAAGTA
AATCACGAGAAAGAGCTTGGCTGAAGTAATGAGGGCTGTCCCTGAAACCTTGCGGCAGCA
CAGCCCAGGTAAGCTGCTGGGACTGATGGGTGACAGGGTCAGTCCAGGTGAAAGCAAAGA
```

```
Sequence listing

GAGGCTGGGATGAGGAGTGCAGGGGAATAGTGAAAAAAGCATCTTTAAGATCGAGAACAG
AACACTGAGTTGTGGAGGAAGGTATTGAGGACAAAAGAGTGTATGGGTTGGGCACCACAG
GATGGATGGCAAAACAATTTGGTTGATAAGGTGCAGATCCTGAACTAATCTGTAAGACTT
GTCTGGTTTTTGGACAGGTAAAGTGGGGGAATTGTAAGGAGAGTTTTTAGGTTTTAGAAG
CCCATGCTGTAGCAGGCGAGTGATAACAGGCTTTAATCCTTTTAAAGTGTGCTGTGGGAT
GGGATATTGGCATTGAGTGGGGTAAGGGTGATTAGGTTTTAATGGGATGGTAATAGGCAT
GTGATCAGTTGCCAGGGAAGGAGTAGAGATGTCTTATACTTGTGGGTTAAGGTGGGGGGA
TACGAGAGGAAGACACAAAGGAGGCTTTGGGTTGGGGAGAAGAGCGGCAATGAGATGCGG
CTATAGTAGTCAGGGAAGCAGATAATTTGGTTAAAATATCTCGGCCTAATAAGGGAACTG
GGCAGGTGGGGATAACTGAAAAAGAGTGCATAAAAGAGTGTTGCCCAAGTTGGCACCAGA
GTGGGGGAGTTTTCAGGGGTTTTGAAGCTTGGCCGTCAGTACCTACAACAGTTATTGGGG
CTAGGGAAACAGGCCTTTGAAAAGAAGGCAACATGGAGTGGGTAGCCCCTGTGTCGATTA
AACAGGGGATGGACTTACTCTCCACTGTGAGAGTTACCTGAAGCTCAGCATCTGTGATGG
TCTAGGGGATTCTGAGGTGATCGGGCAGCATCAATCTTCAGTCGCTAAGCTGAGCAGAT
CTGGGAAGGAGTCGGTCAGAGAGCCTTGGGCTAGAGCTTTAGGGGCTCTAGGAGTGGCTG
CTGGGCGAGCTGGGCAGTCTGCCTTCCAGTGGGTCCTTACACAGATGGGACATGGCTTGG
AAGGAATCCTGGGCTGCAGGCATTCCTTGGCCTAGTGGCCAGATTTCTGGCACTTGAAGC
AGGATCCTGATGGAGGAAGTCTTGTAGGAATGCTTGACTGCTGCAGCTTAGGCATTTTGA
AGTTCTTGTATGCTGGAGGTGTGGCTGAGTTTTGTCTCACAGCAGAGGCAAGTAATTGTA
ACTCAGAAATGCGTTGCCATCTGGCTGCTTCCTCTCTATTATTGTACACCTTGAAGGTGA
GGTTGATTAATTCCTGTTTGTGGGGTTTGAGGGCCAGATTCTAATTTTTGAAGTTTTTTC
CTAATGTCAGGAGTGGATTGGGTGATAAAATGCATATTGAGAATAAGGCGGCCTTCTGGC
CCCTCTGGGTCTAGGGCGGTAAAGCGTCTAAGGGTTGCTGCTTAAGCGGGCCATGAACTG
GGCTGGGTTTTCGTCTTTACCTTGGGTAGTTTCTTTAAGCTTGTCAGAATTAACAGCTTT
GTAAGCTGCCTTTTTAAGCCTTTCAACTAGGCAGGAAATCATGTAATCTTGCCTAGCTAT
ACCTGGGGAATTTGTCTGGTAGTTCCATTGGGGATCCTCTTGGGGAACTGCTCTAATGCC
TTCCTGGAGGTCAGGTTCATGAAGCCGGCGGTTATCAGCATGAGATTGGGCTAGAGAAAA
AACTCTTTCCTGTTCATCTGGGGAGAGGGTAGAAGTCAGGATGACATTTAAGTCACTCCA
GGTTAAATTGTAGGACAGAGTTAGATATCAGAATTCCTGTATATATTTAGTGGGGTCTGA
TGAGAAAGAGCCTAAACGCTGACTGATTTGAGAGAGGTCTGATAGAGAAAAAGGTACATG
TACCCTGACTATGCCTTTAGCTCCAGCCACCTCTCTAAGAGGAAATTGTTGGGCGGGTGG
GGAAAAGCTAGTCGCAGAACTAAACTGTAAGCCGGACCGGGTGTGAGGAGGGGAGGTGGT
AGAAGGATTATAGGATGGAAGAGCGGAGGCTGAGGAAGAATTGGGACTTAGCTCAACCTG
GCCATGAGCAGCCTGAGGAGGAGGGAAAGGTCAGATGGGCCTGTAGAAGGAAGACTGGA
AAGATTCAACGACGCTTGGGGTTGGGACTGAGGGGGCAGGCGGGAAGGAAAGAAGGAGGA
TTTGGGAGGAATCGCATTGGGAACAGAGACTAGGGAGGGAACAAAGTGTGAAAAGTGCCT
GGACGTAAGGCACCTCAGACCATTTGCCTATTTTTTGACAAAAATTATTTAGGTCTTGTA
GGATGGAGAAATTGAAAGTGCCATTTTCTGGCCATTTAGAGCCATTGTCAAGTTTGTATT
GGGGCCAAGCAGTGTTGCAGAAGAAAATAAGGCATTTAGGTTTTAGGTCAGATGTGAGTT
GAAGAGGTTTTAAGTTCTTGAGAACACAGGCTAAGGGAGAAGAAGGAGGAATGGAGGGTG
GAAGGTTGCCCATAGTGAAGGAGGCAAGCCCAGAGAAAAGAGAGTAGAGACACGGAGG
GAAGGGGTTCGGGGGTTCTTACCCTCCAGAAAAGTGGGAAAGGGGTCGGGGCGTGGAAAT
AAGGGGTTGGGGCACAGAGATAAGAGGTCAGGGCATGGAAATAAGGGATCGGGGTGCAGA
GATAAGAGGTCGGGGCACAGAAATAAGGGATTGGGGCACAGGGATAAGAGGTTGGGGCAT
GGAAATAAGGGATTGGGGTTCTTGCCCCCTAGAAAAGCGGGACTTGCCACTAAGGGTGA
AGGAGAAGGGGTTGAGGGGTTCTTGCCTCTCCCCTAGAAAACAGAGAAGGGGTAGAGAC
TCAGAGAGAAGGGGTTGGGGTACTTGCCCCTCCCCTAGAAAAGCGGGACTTGCCACTAAG
GGTGAAAGACCAAGGCAGGTGTCCTTGTGTGGTCTGACACCTCTGAAACGTGGGTGAATA
ATCAGAGAGGCATCCCTGCAATGATTAAACATCAAGGGAAGGCTGCCTTCCTAGTCTGTG
ACCGGCACCGGAGTTTTGGGTCCACGGATAAAACATGTCTCCTTTGTCTCTACCAGAAAA
TGAAAGGAATTGAAATTAAGAGAAGGGAGAGATTGAAGGGTGGCGCCAAGATTGAAGGA
GAAAGAGGTTGAGGGATAGTGAGGGAGGTTGGAGAAGAGAGTAAAAAGAGGCCGCTTACC
AGATTTGAAATTGGTGAGATGTTTCTTGGGCTCATCGGTCTGAGGACCTGAGGTCGTAGG
TGGTTTCATGTGCGTCCGTGTGAAGAGACCACCAAACAGGCTTTGTGTGAGCAATAAAGC
TGTTTATTTCACCTGGGTACAAGTGGGCTGAGTCTGAAAAGAGAGTCAGTGAAGGGAGAT
GGGGTGGGGCTGTTTTATAAGATTTGGGTGGGTAAAGGAAAATTACAGTCAAAGGGGGTT
TGTTCTCTGGCAGGCAGGAGTGGGGGTCGCAAAGTACTCAGTGGGGGAGCTTTTTGAGCC
AGGATGAGCCAGGAAAAGGACTTTCACAAGGTAATGTCATCACTCAAGGCAAGGACCGGC
CATTTACACTTCTTTTGTGGTGGAATGTCATCAGTTAAGGTGGGCAGGGCATATTCACT
TCTTTTGTGATTCTTCAGTTACTTCAGGCCATCTGGGCATATACATGCAAGTCACAGGGG
ATGCAATGTCTTGGCTTGGGCTCAGAGGCCTGACATTCCTGCCTTCTTATATTAATAAGA
AAAATAAAACAAAATAGTGGTAAAGTGTTGGGACAGCAAAAATTTTGGGGGATGGTATGG
AGCGATAATGGGCGATGTTTCTCAGGGCTGCTTTGATCAGGATTAGGGGCAGCGTGGGAA
CCTAGAGTGGGAGAGATTAAGCTGAAGGAAGATTCTGTGGTAAGGGGTGATATTGTGGGG
TTGTTAGAAGAAACATTTGTTGTGTAGAATTATTGGTGATGGCCTGGATACAGTTTTGTA
TGAATTGAAAAACTAAATGGAATAAGAGAAGGAGAAAAACAGATATAAAAGGTCTAAGAA
CTGGGAGGACCTAGGACATCTGATTAGAGAGTGCCTAAGGAGATTCAGCATAGTCCTGCC
AGCAAAGATTATTTATTTACTTCAAGAGTTAAGAATGGCAGTTTGGGGATAGCACGAGGA
GATATCAGCTGTGATGCTTGGAGAAACAGTGTAAACCGGCAGTGTAAACAAGAGCAGGG
CATGTATGAGTAGTTGAGAATGGAGAATAGGAGTATGACTAGACAGAAAATAGTAGGGAT
GACAAGTGTTTTTGGGGCACAGTCTAAGTTGGTCCAGTGTCTGGAATGAGACTGGGACCT
AATAAAAAGGAGCTCAAATGGGCTGTACCTTGTAGCATTCCGAGGACAGGTCTGATTTCT
GAGAAGGGAAAGTGGTGAAAGTATTGTCCAGTCCTTTTTAAGTTGGTGGCTGAGCTTGGT
GAGGTTTGTTTTTAAAAGACCTTTAGTCTGTTCTACTTTTCTTGAAGACAGAGGACCGTA
AGGGATATAAAGGTTTCCTGAAAAACTGCTTGGCTGATTTGACAAATAAAGGCTGGTCTG
TTATCAGATTGTATAGAGGTGGGAAGGCTAAACTGAGGAATTATGTCTGACAGAAGGGAA
GAAATTACTGGGATGGCCTTCTCAGACCCTGTAGGAAAGGCCTCTACTTATCTAGTGAAA
```

```
GTGTCTACTTAGACTAAGAGGTATTTTAGTTATCTGACTCAGGGCATGTTGAGTAAAGCT
AATTTGCCAGTCCTGGGTGGGGGCAAATCTTCAAGCTTGATGTGTAGGGAAGGGAGGGGG
CCTGAATAATCCCTGAGGAGTAGTAGAATAGCAGATGGAACACTGAGAAGTTATTTCCTC
GAGGATAGATTTCCACAATGGAAAGGAAATGAGAGGTTCTAAGAGGCGGGCTAGTGGCTT
GTACTATAGCATAGCCTGCCTTTGCTGGTGTGTGGCGATTAGGCCTGGTGGAACTGCCAT
CAATAAATCAAGCATGATCAGGGTGAGGGACAGGAAAGAAGGAAATATGGGGAAATGGGG
TGAATGTCAGGTGGATCAGAGAGATACAGTCATGGGGGTCAGGTGTGTTATCAGGAATAA
TGTGAGAGGCCAGATTGAGGTCCGGGCCAGGAACAATGGTAACTGTGGGACTTAACAAAG
AGTGAGTACAGCTGAAGGAGCCGGGGAGCAGAAAGTATATGCGTCAGGTATGAGGAAGAA
AATAGATTTTGGAAGTTATGAGAAATGTAGAGAGTGAGTTGAGCATAATTTGTGATTTTT
AGGGCTTCTAAAAGTATTAAAGCAGCAGCAGCCGCTGCACGCAGACATGAGGGCTAGGCT
AAAACAGTAAGGTCAAGTTGTTTGGACAGAAAGGCTACAGGGTGCGGTCCTGGCTCTTGT
GTAAGAAATCCGACTGCACTAACCATGCCTAGGAAGGAAAGGAGTTGTTGTTTTGTAACA
GATTGAGGTTTGGGAGATTAATTGGGCACAATCAGCAGGGAGAGCACGTGTGTTTTTATG
AGAATTATGCCGAGATAGGTAACAGATGAGGACGAAATTTGGGCTTGACTGAAGTAATGG
GGTCTATCTGTGAAGTCTTGCGGCAGTACAGCCCAGGTAATTTGCTGAGCCTAATGGGTG
TCAGGGTCAGTCTAAGTGAAAGCAAAGAGAGGCTGGGATGAAGGGTGCAAAGGAATAGTA
AAGAAAGCATGTTTGAGATCCAGAACAGAATAATGGGTAGTAGAGGGAGGTATTGAGGAC
AGGAGAGTATATGGGTTTGACACCATGGGGTGGATAGGCAAAACAATTTGGTTGATAAGG
CATAGATCCTGAACTAACTTGTAAGGCTTGTCTGGTTTTAGGACAGGTAAAATGGAGGAA
TTGTAAGGAGAGTTTATAGGCTTTAAAAGGCCATGCTGTAGCAGGCGAGTGATAACAGGC
TTTAATCCTTTCAAAACATGCTGTGGGATGGGATATTGGCATTGAGCGGGGTAAGGGTGA
TTAGGTTTTAATGAGATGGTAAGGGGTGCATGATCGGTCGCCAAGGAGGGAGTAGAGGTA
TCTTATACTTGTGGGTTAAGGTGGGGAATACAAGAGGAGGGCCCAAAGGAGGCTTTGGA
TTGGGAAGAAGGGCAGCAATGAGATGTAGCTGTAATCCAGGAATAGTCAGGGAAGCAGAT
AATTTAGTTAAAGTGTCTCGGCCTAATAAGGGAACTGGGCAGGTGGGGATAACTAAAAGG
AGTGCTTAAAAGAGTATTGTCTAAGTTAGCACCAGAGTTGGGGAGTTTTAAGAGGTTTAG
AAGCCTGGCTGTCAATACCCACAACAGTTATGGAGGCAAGGGAAACAGGCCCTTGAAAAT
AAGGTAATGTGGAGTGGGTAGCCTCCGTATTGATTAAGAAGGGGACAGACTTACCTTCCA
CTGTGAGAGTTACCCAAAGCTCGGTGTCCGTGATGGTCTAGGGGCTTTGGAGGCGATCG
GGCAGCATCAGTCTTCAGGCACTAAGCCAAGAAGACCTGGGAAGGAGTCAGTCAGAGAGC
CTTGGGCCAGAGTTCCAGGGGCTCTGGGAGTGGCTGCCAGGTGAGTTGGACAGTCCGATT
TCCAGTGGGGTCCCACACAGATGGGACGTGGCTTAGGAGAAATCCCGGGTTGCAGGCATT
CCTTGGCCTGGTGGTCAGATTTCTGGCACTCGTAGCAAGCTCCTGGGGGAGGAGGTTCTG
GAGGAATGCCTGGCTGCTGCGGTTCAGGCGTTTGGAAGTTCTCGTGTGCTGGAGATGTGG
CTGGGGTTTGTCTCACAGTGGAGGCAAGGAATTGCAACTTTTTTCTATTATTGTACACCT
TGAAGGTGAGGCTAATTAAGTCCTGTTGTGGGGTTTGAGGGCTGGAATTTAATTTTTGGA
GTTGTATTTAATGTCAGGAGCGGATTGGGTAATAAAATGTATATTGAGAATAAGATAGCC
CTTTGACCTTTTAGGGTCTAGGGCTGTAAAGCGTCTCAGGGTTGCTGCTGAAGGAGCCAT
GAACTGGGCTGGGTTTTTATATTTGATGAAAAAGCCTAAATGCTGTCTGATTTGGGATAA
AGAAAAAGGAGCATTAACCTTGACTATGCCTTTAGCTCCAGCCACCTTTTTAAGAGTAAA
TTGCTGGGCAGGTGGGGAGGGCTAGTCACGGAACGAAACTGTAAGCCGGACCAGGTGTG
AGGAGGGGAGGTGATAAAAGGATTATAGGGTGGAGGAGCAGAGGCTGAAGAAGAATTGGG
ACCTAGCTTGGCCTGGTGAGGAGGGGAGAGGTCAGATGGGTCTGTAGAAAAGGAAGATTA
GAAAGACTCAATGATGCTTGGGGTTGGGACTGAGGGGACAGGCGGGAGGGAAAGAAGGAA
GATTTGGGACGAGTTGCATTGGGCACAGAGACTAGGAAGGGACTGATGTGTAAAAGAATG
CCTGGACATCAGGCACCTCAGACCGTTTGCCTATTTTATGACAATTATTTAGATCTTGTA
GGATGGAAAAATTGAAAGTGCCGTTTTCCAGCTATTTGGAACTACTGTCGAGTTTGTATT
GGGGCCAAGCGGTGTTGCAGAAGAAAACAAGGCATTTAGGTTTTAGGTCAGGTGTGAGTT
GAAGAGCTTTTAAGTTCTTGAGAACACAGGCTAAGGGAGGAGAAGGAGGAATGGAGGGTG
GAAGGTTGCCCATAGTGAAGGAGGCAAACACAGAGAGAAGAGAGCGTAGAGACACGGAGG
GAAGGGGTTCGGGTGTTCTTTTTTTTTTTTTTTTAATTTATTTTTTATTGATAATT
CTTGGGTGTTTCTCACAGAGGGGATTTGGCAGGGTCATGGGACAATAGTGGAGGGAAGG
TCAGCAGATAAACAAGTGAACAAAGGTCTCTGGTTTTCCTAGGCAGAGGACCCTGCGGCC
TTCCGCAGTGTTTGTGTCCCTGATTACTTGAGATTAGGGATTGGTGATGACTCTTAACGA
GCATGCTGCCTTCAAGCGTCTGTTTAACAAAGCACATCTTGCACCGCCCTTAATCCATTT
AACCCTGAGTGGACACAGCACATGTTTCAGAGAGCACAGGGTTGGGGGCAAGGTCACGA
TCAACAGGATCCCAAGGCAGAGGAATTTTTCTTAGTGCAGAACAAAATGAAAAGTCTCCC
ATGTCTACTTCTTTCTACACAGACACGGCAACCATCCGATTTCTCAATCTTTTCCCCACC
TTTCCCGCCTTTCTATTCCACAAAGCAGCCATTGTCATCCTGGCCCGTTCTCAATGAGCT
GTTGGGCACACCTCCCAGACGGGGTGGTGGCCGGGCAGAGGGGTCCTCACTTCCCAGTA
GGGGCGGCCGGGCAGAGGCGCCCCTCACCTCCCGGACGGGGCGGCTGGCCGGGCGGGGGG
CTGACCCCCAACCTCCCTCCCGGACGGGGCGGCTGGCCGGGCAGAGGGGCTCCTCACTT
CCCAGTAGGGGCGGCCGGGCAGAGGCGCCCCTCACCTCCCGGATGGGGCGGCTGGCCGGG
CAGGGGGCTGAGCCCCTCACCTCCCGACGGGGCGGCTGGCCGGGCGGAGGGCTGACCCC
CCCACCTCCCTCCCGGACGGGGCGGCTGGCCGGTGGGGGGCTGACCCCCCCCATCTCCC
TCCCGGACGGGGTGGCTGGCCGGGCTGAGGGGCTCCTCACTTCCCAGTAGGGGCGGCCGG
GCAGAGGCGCCCCTCACCTCCCGGACGGGGCGGCTGGCCGGGCGGGGGCTGACCCCCCC
ACCTCCCTCCCGGACGGCACGGCTGGCCAGGCGGGGGCTGACCCCCCCACCTCCCTCCC
GGATGGGGCGGCTGGCCGGGCGGGGGCTGACCCCCCCCACCTCCCTCCCGGACGGGGT
GGCTGCCGGGCGGAGATGCTCCTCACTTCCCAGATGGGGTGGCTGCCGGGCGGAGAGGCT
CCTCACTTCTCAGACGGGGCAGCTGCCGGGCGGAGGGGCTCCTCACTTCTCAGACGGGGT
GGTTGCCAGGCAGAGGGTCTCCTCACTTCTCAGACGGGGCGGCCGGGCAGAGACCCTCCT
CACCTCCCAGACGGGGTCTCGGCCAGGCAGAGGCGCTCCTCACATCCCAGATGGGGCGGC
GGGGCAGAGGCGCTCCCCACATCTCAGACGATGGGCGGCCGGGCAGAGACGCTCCTCACT
TCCTAGATGTGATGGCGGCTGGGAAGAGGCTCTCCTCACTTCCTAGATGGGGATGGCGGCC
GGGCGGAGACGCTCCTCACTTTCCAGACTGGGCAGCCAGGCAGAGGGGCTCCTCACATCC
```

```
CAGACGATGGGCGGCCAGGCAGAGACACTCCTCACTTCCCAGACGGGGTGGCGGCCGGGC
AGAGGCTGCAATCTCGGCACTTTGGGAGGCCAAGGCAGGCGGCTGCTCCTTGCCCTCGGG
CCCCGCGGGGCCCGTCCCGGTTCGGGTGTTCTTAACCCTCCAGAAAAGTGGGAAAGGGGT
CAGGGCACGGAAATAAGGGATTGGGGCACAGAGATAAGAGGTTGGGGTGTGAAATAAGG
GATTGGGGGTTCTTGCCCCTAGAAAAGCGGGACTTGCCGCTAAGGGTGAAGGAGAAGGG
GTTGAGGGGTACTTGCCCCTCCCCCAGAAAAGCAGAGAAGGGGTAGAGACTCAGAAGGGG
TTGGGGTACTTGCCCCTCCCCCAGAAAAGCAGAGAAGGGGTAGAGACATGGAGAGAAGGG
GTTGGGGTACTTGCCCCTCCCCCAGAAAAGCGGGACTTGCCGCTAAGGGTGAAGGACCAA
GGCAGGCCTCCCTGCGTGGTCTGACACCTTTGAAACGTGGGTGAATGATCAGAGAGGTGT
CCCTGCAATGATTAAACACTACGGGAAGGCTGCCTTCCCAGTCCGTGACCGGCGCCGGAG
TTTTGGGTCCACAAATAAAACGTGTCTCCTTTGTCTCTACCAGAAAATGAAAGGAATTGA
AATTAAGAGAAGGGAGAGATTGAAGGGTGGCACCAAGATTGAAAGGAGAAAGAGGTTGAG
GGATAGTGAGGGAGGTTGGAGAAGAGAGTAAAAAGAGGCCGCTTACCGGATTTGAAATTG
GTGAGATGTTTCTTGGGCTCATCGGTCTGAGGACCTGAGGTCGTAGGTGGTTTCATGTGC
GTCCGTGTGAAGAGACCACCAAACAGGCTTTGTGTGAGCAATAAAGCTGTTTATTTCACC
TGGGTACAAGTGGGCTGAGTCTGAAAAGAGAGTCAGCGAAGGGAGATGGGGTGGGGCTGT
TTTATAAGATTTGGGTGGGTAAAGGAAAATTACAGTCAAAGGGGGTTTGTTCTCTGGCAG
GCAGGAGTGGGGGTTGCAAAGTACTCAGTGGGGGAGCTTTTTGAGCCAGGATTGGCCAGG
AAAAGGACTTTCATAAGGTCACATCATCACTTAAGGCAAGGATGGGCCATTTTCACTTCT
TTTGTGGTGGAATGTCATCAGTTAAGGCAAGGACCAGCCATTTACACTTCTTTTGTGGTG
GAATGTCATCAGTTAAGGCAAGGACCAGCCATTTACACTTCTTTTGTGGTGGAATGTCAT
CAGTTAAGGTGGGGCAGGGCATTTTCACTTCTTTTGTGATTCTTCAGTTACTTCAGGCCA
TCTGGGCATATACCTGCAAGTCACAGGGGATGCAATGGCTTAGCTTAGGCTCAGAGTTCT
GACAGATCTATTCCTGCCTTCATTTTTACCTTGTATTTTATTTATTTGTTTTTAAAATTT
TAAACTAATTTTTTTGTTTTTTTTTTGGTAGAGAGAGTCTCTTCATGTTGTCCAGGCAG
GTCTCAAACTTCTGACCTCAAGTGATCCGCCTGCCCCAGCCTCCCAAAGTGCCGGGATTA
CAGGCGTGAGCCACCACACCTGGCCTGTATTTTATTTTTTACTATGGAAACTTCCCAAAA
CAAACAAAAGTACATAGGATGGCATAATGAATCCCCATGTACCCCTCAGCCAGCTTCGAC
AGTTACCAACATGTGGCCAAGCCTATTTCATTTCTACCTCTACCCCCTTCTCATATTAGA
GTAAATCCTGGACATCGTATCATTTCGTCTATAAGTGTTGCTGTCTAAAAGAGATCATCT
TACCTTTCAACAGATGGTAATTGCGCTGCAGAACACCACCACGACCAGCCGCTACCTGCG
AGTCCTCCCGCCTTCCACGCCATACTTCGCTCTGGGACTGGGTAAGTTCAGTATTTGTAA
GTTCATTAGTAGTAGTGGTAATAGTAGTGGTGGTATTAGTAGTAATAGTAGTAGTGGTGG
TAGTAATGGTAGCAATGATAGTAGTAGTGGTGGTGGTAGTAGTAGTAGTGATGGTGGTAG
TAGTGGTAGTAGTAGTAGTGGTGGTGGTAGTAGTAGTGGTAGTAGTAGTAGTGGTGGTGG
TGGTGGTGGTAGTAATAGTAGTGGTGGTGGTGGTAGTAGTGGTGGTGGTAGTAGTAGTGG
TAGTAGTAGTGGTAGTAGTAGTAGTGGTGGTGGTAGTAGTAGTGGTAGTAGTAGTGG
TAGTAGTAGTAGTGGGGGGGTGGTAGTAGTAGTAGTAGCAGTAGCAGTAGCAGTACTGCT
ACTACTTTGAGGATTGCCTCAAAGTCACTTGCTGGGCTTGCTGCCAGTTGCTGACTCCCG
CCCTGAGTCTACAGCCTGGGCCTGGACTCCCCCCCATCAGCAGTCCTTGAGGGCTCCTCAT
GCTCCACCAGCAATGTGTCCTCAGAGCCTTGACAGCTCCTTTCTCCTGACCGCCTCCACC
CAGGCACTGGTCCTGCTATCTCCCCACTCCTCGTGCTGCCATTCTCCTCAATCAGGCCCT
CTCTATTCCTCACTTAAGCCTCAGCAGCAGCCCCCAGCCAGCCTTCCTACTTTAGTGTC
ACAGTATTTGTCTTAAGAACAACTCTGATCATGTCACCCCGTTCAGAAATCTCAAAAGTT
TCTCTGCTATCCACCAAAGAAATTCTAAGCCATAGGGCAGGCATGGCCCCACCTGACCT
TTCTGGATGGATGGTGTCATTTCCCCCCAGGCTCTGGCATGCTTACCTGGAGTCGCCACC
CTTGCAGCCTGCTCCCCTCGCATGCCCTTTTCCTGCCATCAGCGTGGCTTTGGCCCAGAA
GGCACTTACAGAGCCAGCCCTGGCAGGGCTGGGTCTGTACCAGCTGAGCTCAAGCCCTG
GTGGCTGGCTGCTCTCCAGGATCCTCACTTGTCACTTTTGTCATGCACAGGGATGTTCCCA
GGAAAAGGTGGAATGGTGGCTCCTGGAATGACCTGCCAGTACATTGTCCAGTTTTTTCCC
GACTGCCTTGGGGATTTTGATGATTTTATTTTAGTGGAGACCCAGTCAGCCCACACACTT
CTGATCCCCCTGCAGGCCCGGAGGCCGCCCCCCGTGCTGACATGTGAGTGTGCACCGTAG
CTTCCCACAGATTCAGTTAAGGTTGGAGAGTCCCCATAAGGACTGCCTGCCTCTCAGGTT
CCCTTTGTATCAGCACACAGCTTGGCTCTCTTGGGCAGGGCCGTGGGTCCTGCAGAGGA
AACTGCTAGCAGCTTCTGTAGCCATCCACAGTGTCAAGCCATGATTGTTCTGCTTGCTTT
TGGGTTTTCTCAGTGGAGGTTGACTCACAGCAGGGGATGAGGCCAACAGTCCAGCTAACC
CCACCATAGGTTTTGCTGGCTTATGAACATCCCTGAGGGGACCTGCTGCCACGTGGGCAA
GGAAGAAGTGCCTGTGCACCCTGAGGAGTCCTAACAGGTCGTCGTTGTCCTCGTGGCTGT
GGGGGTAGGAGTCCTTAGCAAAGCTGGCTTCAGCTGGGCTCCCTCAGCGACAAGCTTCTA
CAGCTGGGCATAGGCTGGAATTTGGGACCGTGATCCCCCTTACTTCTGCCATAGCCCCCA
AGGACCATGCTGGGTGGCCCTGGCTGAGCATGAATCCACAATGGGCACTGACTTCTGCTG
CTCTAGCCAGGAGTGAATAGAGTCCCATGGCACTATTGCCATGTGGCCAGCAGCAGCCTG
GGCAGAGCCCAAGTGGGTGTAGGGTCAGGACATGTCCCCACTCATCCTCTCTGCATAGGG
TGCTGGGCTGGGACCAGCTGTCCTGATCTCTGGCTGTACCTCAGGAGAAGCATGACAGTA
GGGCCTATTAAGAGTGACCTGTTGTTTCTCTTGCACATGTTCTCCTGTGGCTACAGTGTC
ACCGGTGTTGGACTGTGGTTACTGCCTCATTGGGGGAGTCAAGATGACCAGATTCATCTG
CAAAAATGTGGGTTTCAGTGTTGGCAGGTTCTGCATTATGCCCAAAACAAGCTGGCCACC
ACTAAGTTTCAAGGTGAGTGATCACAGGTTGCTAACTGGAAAAATTACAAGTCCATCAAA
GGAAATAACCCCCAGAGGAACTTACTAGAGTATACCTATGATTGGAAACACACAGAACGC
AGAGTGTTGTAAACTCTCTATGCAACTGCCACAACCCGAATGAGAATGGATGTATAAGGG
TCCAGTGTTGTAGTTCTGGTTATGTCACTAATACCTGTACCATGCTGGGCAAGCGGTATC
ACCTCTCTTATCCTTCAAGCCCTGGCTCAAATGTGACTGCATTCACTCATTCAGTCCTTC
TTTATTGTAGCAAATGACTGAATAGTTCAGAGGTTACAAATTGGCTGCCCTTTGGCCAAA
TTCTGCTGGTATTTGTTTGGCACAGCACTTAACATTTTCTGAGCCAACATTTAAAAATAA
GGAGATTTGGCCAGGCGCAGTGGCTCACACATGTAATCCCAGCACTTTGGGAGGCTGAGG
CAGGCAGATTACCTGAGGTCAGGGGTTTGAGACCAGCCTGGCCAATATGATGAAACACCG
TCTCTACTAAAAATAAAAAATTAGCCGGGTGTGGTGGCATGTGCCTGTAGTCCCAGCTAC
```

```
TCAGGAGGCTGAGGAAGGAGAATCACTTGAACCCGGGAGGTGGAGGTTGCAGTGAGCCGA
GATCGCACCACTACACTCCAGCCTGGGCGACAGAGTGAGACTCCATCTCAAAAAAAAAAA
AAAAATGGAGATTTTATATAAAGTTCTACATTTCCAGTCCTTTGAAAAACTGGAAGATAT
GAAGGCCAGGGCCAGGATTCACTGTGAGCCTGTTGGCCAGGGCTGGGGGCAGGCCCTGTG
TACCTTGTCCTGAGTGCCCAGCTCCACCAGTCCCAAGAGCATCCCAGCACTGACACCATC
CATCAGCATGCTCACACCATCCATCAGCACTGACACCATCCATCAGCACTGACACCATCC
ATCAGCATGCTCACACCATCCATCAGCACTGACACCATCCATCAGCACTGACACCATCCA
TCAGCATGCTCACACCATCCATCAGCACTGACACCATCCATTAGCACTGACACCATCCAT
CAGCATGCTCACACCATCCATCAGCACTGACACCATCCATCAGCATGCTCACACCATCCA
TCAGCACTGACACCATCCATCAGCACTGACACCATCCATCAGCATGCTCACACCATCCAT
CAGCACTGACACCATCCATCAGCATGCTCACACCATCCATCAGCACTGACACCATCCATT
AGCATGCTCACACCATTATTTTTCTCATAGCAAAGATATTTATTTGTACCCAGAAAACAA
GGGATACATCTAGAGGATGACATTTCAAGATGTTCCAAGAAAGACATTTCACTCATTTCT
GTTACTGACCAGGGTCTTGTAGGCATGGGTTTGTGTCCCTGGCATGCTAAGTGACTTCTT
GTGTAGGCACTGGGGCTGCAGCTCTCGTGCCTCAGGAGCTTGTAGCCAGGGGTGGGTCAG
GGTTGGAGGCAGACACATATGCTAGCACCTGTGACACTGGGTGTTACTGTAGGAAAAGGA
CAATGTGCTTTGGGAGCCCAGGGGAGGGCCCACTCAGCTCACCTCCTGAGTGAGACCTTC
TCACACGCTTGTCACTTTGTGTCCCAATCACTTGGTGATGGTGTTCCTTGTACCTCCTGT
CAGTAGTCAGCTCTTCACAGATGTTCTAAGACTTACTCTCCTTAACCTTCAGAACCTCAC
CTGGTACCTGGTGATGGCTGAGTAAATGCCTGCTGAATGAATAAGCCTCAGTTTTTTCAT
TACCATGTGACTGGATGATCCTTAAGTTCCTTCACATTGCAAAATGGATGTTTGAAGGAG
AGAAGTTTGCAATCTGAATACTGGCTTTTACAATGTCTTCCACACTGTTGGGTAATCTGC
TTTTCTTTAAGGCCATTGCAACCGTCGGCTTTGTTGAACAACCTCCTTTTGGAATCCTGC
CTTCGGTGTTTGAGCTGGCCCCGGGACATGCTATATTAGTGGAGGTAGGTAATCAGACAT
TGGCATGTATTTCCTCAACTGCTTGCATGCTTGCATTTGTCTCTGTTTTCATGACTCAAG
TGTCCAGTCCCATCCCATATCACAGCCTTAGTGACTTCTGGGTAGACGCATATTCTTGCA
TTCTGTAGGGTGATGTCAGATGTCATTTGACTGTCTTATGAGCATTTTCACAAAGCAAAT
GCAGATAGCCCTAGCATCACATCACAAACCTGAGCCTTGCTAGTCCACACCTTTAGTCTG
GGAGCTACCTCCACCAATGTCCAAGCTGCCTCCAAGATCTTCGCTTGGTTCTTCAGTCTC
TCTTGGGTCTTCCCTCCCCAGGCCCTCTATCATCTGGTACCTGATTATTGCGGTTATT
GTGGCTTTGTTCTCACTTTCCTGCTTCATCCTCAGTTTGTATAGTCAGCAAGGCCCAACT
CCGTTACGCCTCATCCTGAACCTCTGCAGAAGCTCTCAGTGGTCTGCCCCTGGCTGTGGG
CGTCTCCTTTCCTAACTGGCCCCTTTTGCTGCCCCCTTCAGCTGATCACACCTGCTTGCT
GGTCCCCAGAGGTGCCCATGAGAAATGGTGATACTTCCTGTCCCTGTTGCAGCACACTGC
CACTCTCCCCGACTCCTGGTCTAGGAGTCTGACTCCACTTCATGTGACTGGGTGTGGGCT
GCTACAGACATGCTTGGCCTTTCACACTAGCCTGCCGAGGGAGGCCCCTGACATTCAGGA
GCAAAAACCGTCTGGCTTCTGGGGGTGGATTTGGCCTGTGCCATATCACCAGGTAGTGAG
ATCCAGCAGCCCTTATTCTTAAACTCAGCTGCACATTGCAATCACCTGAGAGACCTGGAA
ACAACACCAAGGCCCTATCCCTGAGGTTCTGAGTTCACTAGACTGGGCTGTGGCCTGGGT
GCCGGACTTCTAAAGTCCCCCAGGGAATGCTGGTGTGCAGCCAAGTTGGAGTTCAACTGC
CACAGCGACTCTGCCATGCTGTCAGGAAGGGCTTCCTCTTATCAGCTGCTTTCTAGTTTC
AAGTGCCCAGTAGGTTCTGCAGCCCTAGGATGTGGCTCTCTTATTCATGTCCCTGCTCAT
CTGATCCCTGATGAGAAACTAGTTCTTGGGATTGAGACTGAGCCAGTTCAGGGGCTTTGT
CAGGCCTCATCTACTGCTGAGGGGCAGGTTGGGTCTACAAGGCCCATACACAGGCCAGGT
TCTCTGTTCTCTTGGTGTAGTCCAGGACTTGTCACAGGCTCATCGAAGCTTTAAGGAATT
GGAGCTGCTCTGCCCTGGACATCCCCCTCATCCCATCCTCCTGGGATCTCCAAGTAAAGG
AAGAGGGTAGCAGCAGGACTCTTAGGGGAGCAGTGAGGGAGCTGGGGAAGGCTTTCCCCT
TGGCATTTCTTGCGTATTTTGTTTACTGATTGTTTGGGGTTTGTCTGTTCCAAAATGTA
TTCATAGTTCCAAATAAGAAATACATTTGCATGATTAAAAATTCAAAAGAGACTGGTT
GCAGTGGCTCAGGTCTGTACTCCTAGCACTTTGGGAGGCTAAAGCAAGAGAACTGCTGAG
TCTGGGAGTTAAAGACCAGCCTGGGCAACATAGTGATATACTGTCTGTATAGACAATTTT
TAAAGTAAAAATAAATTCAAAAGAGCCAGGTGTAGTGGCTCACACCTATAATCTCAACA
CTTTGGGAGGTCAAGATAGGAGGATCACTTGAGGCCAGGAGTTTGAGTTTACAGTGAACT
GTGATTGAGCCACTGTACTCCAGCCTGGGCAACAGAGTGAAACCCTGTCCTAAAAATAAA
TAAATAAAAATAAAACATTCAAAAGATGTAAACAGGTAAACAGTGAAATGCTCCCTTTCA
CCCCAGTTCCTCAGCCATCCAGAGGCCATACCTGGCCAGTTTTCTGAATGCCCTTCCAGA
GATAGTCTATGCCCAAATAAGCAACTGCACATGTTTTTACCCCCATTTTTTCTTCACAC
ACAAAGTTGCCCACTCTATACTCTGTTCTTTGCCTTGTGTTTTCTACTTAACTCTATATC
TTAGAGATCATTCTCATATGTTTTAGTAACTGCATAGTATCCTACTGTGTGAATGGACCA
TAATTTAGTTCAGCAGTCTCCTGCTGATTGACCTGAAGATTTTTTCTGATCTCTGGCTA
CAAATTATGTATAAATTATACATACATCACTCTGTCCAAGGATGAGTCTACCCACAGGAT
ACAGTCCTTGAAGTAGATTTGCTGATCCAGCGCTTTGTGCCCTCATAATTGTAAGGCATG
TTGCCAAAATCCTTACCATGCGGATTGTACCAATTTATACTTTCAACAGCAGTATGTAAG
GGTGTCTGTTTCTTTACACCTTTGCCAATACAGTATATTATAAAACTTAGAAACTGTTCA
TGGACGTTGTATATAAAACATATACAAAATAGAGAGAATAATGATCATCCATGTATTC
ATTACTCATCTTCAACAATTATCAACCCTTGGCCAATCTTATTACATCTATACCCCTCCA
TTTCCCTCAGACATTCCCCACCCTGCTCTTCTAGATTATTTTGAACAAAATCAAGACAAA
ATATCATTGCATTTAACAGAATGAAACTAGACCTGTGTCTCTCACCATATACAAAAATTA
ACTTATTAATAAAATGGATTAAAGATTTAAATATAAGACTTGAAAATGTAAAACTACTAG
AAGAAAATGGTGGAAATCTGTATGACATTGGTCTGGGCAATGATTTTTTGCATATGATCT
CAAAAGCACTGGCAACAAAAGTGAAAATAGGGGCCAGGTGCGGTGGCTCAGCACTTTGGG
AGGCTGAGGTGGGAGGATTCTTGAGCCCAGGAGTTTGAGACCAGCCTGGGCAACATAAG
GAGACCCCATCTCTATAAAAAATTTAAAAAACTAGCCGGGTGTGGTGGCATGCACCTGTG
GTCTCAGCTACTTGGGAGCTGAAGTGGGAGGATCGCTTGAGCTCAGGTGTTAGAGGCTGC
AGTGAGAAATGATCACACCACTGCACTCCAGCCTGGGTGACAGAGCAAGATCCTGTCTCA
AAAAGCAAACAAACAAATGAACAAACAAAAAACAAACATGAATAGACAAATGGGATTA
CCTCAAACGAAAAGCTTCTACACAGCAAAGGAAACAAGCAACAGAGTGAAGAGACAATC
```

-continued

Sequence listing

```
TGTGAAATGGGAGAAAATACTATCACATCTGAGGAGGGGTTAACTCCAAAAATATATAAG
GAACTTAATGCAATAGCAAGAAAACAACCTGCTTTTTTTAATGGGCCAAAGACCAATTAG
ACATTCCTCAAAAGAAGACATATAAATGGTCAATGAGTATATGAAAACATTCTCAACATC
ATTAATCATCAGGGAAATGCAAATTAAAACCACAGTGAGCTCCCACCTGACACCCGTTAG
AATGGCTATTATCAGAAAGATGAAAGGTAAGTGTTGGCGAGGATGTAGAGAAAAGGGAAT
CCTTGCCCGCTGTTGATGGGAATGTAAATTACTACAGCCGTTATGGAAAATAATATGGAG
TTCCTTCAAAAAATTAAAAATGGAACTACCATATGATTCAGCAGTCCTACTACTAGGTAT
ATATACAAATGAAATCTGGCTGGAGTGCAGTGATGTGATCATTGCTCACTGCATCCTCTA
ACTCCTGGGCTCAAAAGATACCATTTAAAAGATATCCGCACTCTTATGTTCATTGTGTCA
TTCACAATAGGCAAGCTATGGAATCACCCTAAGTGTCTATTGATAGAGGATAAAGAAAAT
GAGGTATATGTACACAATGGAATAACAGCCCTGCAAAAGAAGGAAATCCTGTCGTTTGCG
ACAACATGGATAAGTCTGGAGGACATTATGTGAAGCCAAGCACAGAAAGACAAATACTGC
ATGATTGCACCTATATGTTGGACCTTAAATAATTGAACTCATAAAAGCAGAGAATAGAAT
GGTGATTACCAGGGTTGGGGGTTGGGGGAATTGGGGAAAAAATAGAAAACAAATCATTGC
ATTTATGACAGCTCACCTTCTGCTCTTTGCCAGTATGAGTGGTAAAAAGCCGTTCTTCTG
GATGGTTTTCATTGACATTTCTCTTATTATGAATGAGGGTATGTGTTGTCATTCATTTAA
GGGCCATTTGTATTTTGGTCTCTGTGAACTTTATCTTCATATCCTTTTAGCTTGCTCCCT
GCTTTTCTCTGGGGTGGAGCTAGGGTAAAACACTTGGCCTTAGGAGTAAGGTGGGAGGTG
GCAGGGAGGGGAACAGAGAGTGAAGAGCAAAGAAAGGGGTGTGTGTCCGAGAGGAGGAGG
GTGGGAGGCGGGGAGGGTGGAAGCCCTTTAATGGGAGGTAACGGAACAACCCTTCTCTCC
CCCAGGTCTTGTTTTCCCCAAAGAGCCTAGGAAAGGCAGAGCAGACCTTCATCATCATGT
GCGACAACTGCCAGATAAAGGAGCTGGTGACCATAGGTGGGCTTGAGTGTACTCCCAGGG
GCAAGGCTGGAGAGGCTGCCCCAGCTCCAGGGGCACTGACCACAGTAGCATTAGCGGCA
GCCCACCTGTTTCCTGTGTGTCAGGAGCGCACATTAAGAATGCTGCAGCCTCCAGGTG
CCAGAGTCTCGTTTCAGGCCCATTGCTCTGGTCTGACTTTGGAGACCAAGCCAGTGTGGC
CTCCAAGACAGTCCAAGGAGCCTTCTAGCAAGAGACAGCTGGAAACCTGGGGTGAAATCT
TTCATTGTTTCATTTTGAAACTCACTTTGATCTCCTTTGGGGAATTGCCAGTGGCTCACA
CATAAACAGCCAGAGCCACCTCTAGATTTCTGCAGGGTTAGAAGAGGCATCCTAGGAATC
GTGACAAGATGCCCCTGGCCGCCCCTCCCTCTCTTCCTCCCTCCCTCCTTCCTTCCCTCT
TTTCCTCCTTCCCTCCCTCCTTTTCTCCCTTCTTCTCTCCCTTCCTCATTAATTGAGTGT
CTGCTATATGCTAGGTTCTCAAAATCACCTCCTTTTGGTCTTCAAAGATGTGAGAACATT
AACCTGTGGGCGGATATCCCCCTTTTCCCTCCAGTGTGAGCTTGCAGGAATCATGGTCAA
GGCCAGCTGCATGTGGATGGCGGCATGGGTCCTGCAGCAGCCTTGGCCTGATTTCAGCCC
TAGTGAGCCTTCACTGACTTCACTTACTCTACTTTGGCAGGAATTGGGCAGCTGATTGCT
TTGGATCTGATCTATATTTCTGGTGAAAAAAGCCAGCCAGACCCTGGAGAGCTCACAGAC
TTAACAGCCCAGCACTTCATCGATTTGAGCCTGAAAACCTTCGGTCCACGGCTAGGAAG
CAGCTGATTATTAGAAATGCTACGTGGGTAACCCCTGTGTGTGCCCCAATACCCAACCCT
TCTTCTTGCTTACCTGGCCCTCAGTCCCAGTGAGACAGGAGGTCCTTCCAAGGGCCTGGG
GAAGACTGGGCACAGAATGGATATCCAAATTCAATTGAGGGATCCAGATTGACCCAGTCT
ATCATGGAAACCAGTAGCCACTCTTGGCTACTTAAATTTAAATCAATTAACATTAAATTA
AGAGCTCACTTCCTCAGTGGCACCAGCCACATGTAGCTAGTGGCTGTCATATTGGACAGT
GCAGATCTGTAAGATCTCCATCCCTTCAGGAAGTTATGTTAGATAGTGCTGCCCCAAATC
ATCCTGGACCATCCCTAGCCAGCCCCAGCTTTCCAGAGAGGACATACCATGCCTGTGTAG
GGGAAGCCATCCAAGTCCCAGGGGCAGACAGACTATAGTCTGTGGGTTTCATTCTCCTTG
CCATTTATTTCCTGACCCGCCTCTGAGCACTACCATGAAACCAGGACAAATCTCAGGGAG
CCTCCCAACCAGGGCTGCCCTGGGGACCCCAGACATTACACAGGACTCTGTCATCTCTCC
CCCGGGATAGCTGCAAGTCCTGCCCCTCCTATGCTATGGAGTTGCCACTGTTCCTGTTGG
CAGCCAGTAGGCACATATCTTTCTGGACACAGCTCTCCTGGGAGCCCATAACAGGAAAGG
CAGAGGGCAGGAATGGGGTTGATGTGGCAAACCTTGGAAACTCATGTGGTGAGAGACATT
GCAGAAGATCTTCCCAATATTAGGGGGTGATGTATAGCCTCTTCCACTTTAATGATTGGA
ACATGAGTTCCTGACTTACCATGTCCCTGAGTCATGGTAGGTCCAACCTCCAGCTGCCA
TGGCTGGGAAGCGAGGAGCTCTCTTACATAGTCTCTGTCTTAGACTCCCTCGCCCACTTG
CTGCCCCTCCTCCATTGGAGGGTCCTCCATTGGAAGGGTGTGAAGGCTGACCTGGTTTCT
TCCTGTTCCTAGGTCCTTTCCTGCTCCCTCTTGGAGCAGGGCAGGGAGGCATGGGGTGGA
GGGACCTGGTCCCAGCAGAACTGGGACATGGCCTTGGATGCGTTGCCCCCACAGGCACGT
GGAGCTGGCCTTCTACTGGCAGATCATGAAGCCCAACCTGCAGCCCCTCATGCCTGGAGA
AACCTTCAGCATGGACAGCATCAAGTGCTACCCCGACAAGGAGACTGCCTTCTCCATCAT
GCCCAGAAAGGGGGTTCTAAGCCCCCACACAGACCACGAGTTCATCCTGAGCTTTTCTCC
TCATGAGGTTCAGATGGTGTCATCTCAGTAGCCACACATGGTTGGATCATGTATTTAGAC
CCCCCACCTGTGTTCCTCAATCACACTGAAGCCACAGCTGGGCCCACCGAGGTGCTATCC
TGCCCAGGCCAGCACTTGGCTGAGTTGGGTTGGAGTACACACCTGGTGTGCAGGGTGAAG
CAGCTCATTTTGTCTGGTCCTGATCCCAGACTCACCCCATCTGCAGCAAGACCCTTGGCT
GGCTTCCTCCGCTCTGGGTGTCTCCCACATGTCTACTATGGCAAAAACATTACCATCCC
CACCCATACCACAGCATCCCCTAGAGAGAGTGAGGTGCAGGGACCCGAGGGCCAGGTTAG
CACAGCGCTGGCCCCAGCATGGAGGGAAGCCCTGTGGGCCACGGTAGGCTAGAAGGGAAT
TCGAGCTGGGCATGAAAAGGATGCTCCGGGGCCATTGTTAGTGGGTTTGGGGCTGAGATG
AGTGATCCTGCCTCTGGTCCCAGCATCCAGCTGCCTCGTTGTCTATCCTGGGAGGGTGTG
GTGCTTCGGACACGTTGAGGGGCTTTGTCAGCATCAGGAAGGCCTTTGCTTCTTGCACCC
AGGCCCAGCTGAGACAGGCCCCTGAGTCCTGGCTCATGTTCTGGCAGCAACTTCACTTTT
CCTAAGGAGGGGAGGAGGCAGCAGGGAAGCAACCCTGGGTTTTCAGAAGGTCCTTCTGAT
GGCTAGGCTAAGGGGAGGAAGAATTCCTGCCATGCCCCAGCCTTCTCCAGGACAACCTGC
TGGAACGCAGTGGTGTTTTCAGGGCACTGTGTTTGCCTTGCAGCTGAGGGATTTTCACAG
TGTGCTCCAGATGGTGCTAGAGGAAGTCCCAGAGCCTGTAAGGTGAGAGAAACTGGGCCC
TGGATGAGAAGTGGGCAGCTGGGCCTTCCCCACCTTGGGGGTTCTCCTGGGGAAGGTAT
CAGGTGAGGGGAGTGGGCAGCCTGGTCCCCGCAGGCTTTGGGGAGTGAGAGCATTTTTT
TTGCCCTTGCCCTGGCAACCCAGCCCTGCAATGGGCTGAGCACACTAAGCTCGCTAAACTC
ACTATGAGGCCACCCCAGGAACTTTGGAGCTGTGCCCCAGGCCCATTGTTGCTCTTGGGG
```

```
AGCCAAACTGGGGGGCCCTCGGTGGTGGTGAGTGTGGAGGAAAAGCTTTGCCCCCATGGT
GTAAACCTTCAGGCTGGGGCTCCAGGCAGCCCAGTGCAGAGATCCCAGGCTGGAGGGCTG
CAGATGGTCCCTGGAGGCAGCAGGGCAATGCCCCGTCCCAGTCCTTATGCTAAACCACTG
TCACAGCCATCGGTGCTTATCACCTTTCAGGCACTGGCTAATGCCTTTGATTTAGGGGGC
TCAGGAGCTGTGGGTTAGGCAGTGTTTTTTTTTTCACAAGGCCAAACGTGGGACAGAGGC
AGGGACACTCTAGGATGTGCTTCCAGGTGTGCCGGCTCCTAGCTAACGGTGGGTTTGTGT
TTAGTTCAGAAGCGGAGAGCCTGGGGCACTCCTCCTACTCTGTGGATGATGTGATTGTCC
TGGAAATCGAGGTGAAAGGCTCAGTAGAACCTTTCCAGGTTCTCTTAGAGCCATATGCCC
TCATCATCCCAGGGGAGAACTACATTGGGATAAATGTGAAGAAGGCTTTTAAGGTAGGTC
ATTGTCTCTCCCTGCCTAGGCTGGCCGAGGCAGTGTTGACATGAGTGCAAGTGTAGGGA
GGATATAGCAGGAGGGGCAGATGGTAGCAGCCACTGCATGGAGGCTGAGGCCATTCCCAG
GGCTTTGAACCCAACTTGACTTGCACAGATGCATAGGCCAGGCATGGCTGTCTTCTTTTA
TCAGCCTCCCAGAATCCTCTGAAAGTTAGGGCTATGGAACCTATTCCCGTCCTTGGCAGA
GTATGTCAGCCACAGGCACTGCAGTGTGGAGGGAGGGTGCTTTTGGGTTGGGAGGCCCAT
GGCTTTGGGTGGCCAGGAATTAGCCGGGAAGTGTCATATGGACTCTTTACGAGCCCACAA
TCCTACAGTCCTTCAGCAGGTACAGAATTGACATGAAGGGGCAGTAAATGGGCAGCCTGG
TCTCGGGTGTCTTTCAGATGTGGAACAACAGCAAGTCACCCATCAGATACCTGTGGGGGA
AGATCAGCGACTGCCACATCATTGAAGTGGAGCCCGGCACAGGGGTCATAGGTACCTTGG
GGACTGCAGGAGGGGTTGTGACCTGCCTGGGGCTGGCTCAGGAAGAAATCTTCAGAGTTA
AAGGGGCTTATGCAGGGCTCTTGGTGTCCTGTGACTGCTCTGGCTGAGGCCTGGGATGTG
AGGGAGATGAGAAGTCTGTGCAAGCCAGATGTCTGGGCCCAATCATAGGAGGAAACTGCC
TCTGCTTCTCCTCTCCACCTCTCCCTTTCCCTCTCTTCTCAGAGCCCAGTGAGGTCGGGG
ATTTTGAGTTGAACTTTACTGGGGGTGTCCCTGGCCCCACAAGCCAGGACCTGCTGTGTG
AAATCGAAGACTCGCCCTCGCCAGTGGTGTTACACATTGAGGCTGTCTTTAAGGTGCTGC
AGGTGGAGCTGGGCAGTGGGGTGGGCCCAGAGAGGTGGCAGGGCTGGGACACTGAGCCAT
CCCCAGGTGGCCCAGTGACAGGCCCTCTGGGTGTCTCAGGGGCCTGCCCTCATCATCAAC
GTCTCAGCCCTTCAGTTTGGTCTGCTCCGCCTGGGGCAGAAAGCCACAAACTCCATCCAG
ATCCGGAACGTCAGCCAGCTCCCAGCCACATGGCGCATGAAGGAGAGCCCAGTCTCCCTC
CAGGAAAGGCCTGAGGATGTAAGTCAGGCACTGCTGGTTCCTCTGGTGCCCCCACAATGA
GCCCGTTTAGCTTGCCCTGGTGAAACTTGCCCTGGTGTGTTTAGATCAGAGCTTCGAGGC
TGGTGGAGGAAAAGCCTGCCTGGTGACTTCGGCCTGGCGGTGCCTCCTGTTCTCCCCATC
GCTGAGGCAGCTCAGCTCCTCTCTACAGCCAAATGTAATCCCCCATCAGCATTTCCTGTG
CCTTTCACTACCATCGGATTTAGAAATAGGGCGTGGGTTTCTCCCTCAGAGCCGTCTGAG
GCAGGAAGAGATGGGCAGCTAGGTTGGGCAGGAAGCCTCCAAGGCTGCTGCTGCTCCAGC
CGCATTCCCACCTCCTCCCCACTCTCTGGAAGGTTCAGATCCTCCCAGGGATCTGCTACC
AGATGGCATCTGGTCACAGGCTGGCAGCCCAAACCCAAGGCTCCAAAAAGAAAATTCAAG
ATTTATTTCGACTCAAATGGCACTTTTCACTATAAAAGTAGGAAAAAAAGCAGCTAAGTA
TTATCATAATCATATTTAAATGCAGTGGGCGATCTGGAACAAGACAAAGTCACACAAATC
ACCAGCTACTCGCAAAATGCCCGCAGTGAGTCGTACATCACCGCCCCTTCACCACGGCAT
GGCTGCAGCTCCCTGGTGGACTGCACATGTGAGACCCTGGCCATGTCTGGTGACCACACT
CTCCTTCTGGCTGCTTCCCACCGAGGTCCCCATCCTGCTTGCCCACTTGCCCTCCGAGTC
AGAACACCGCACACTTTTCCTTCTGTATTAAGGAGCCCAGGGAAGACAATCCAAGCCATG
CATATACCTTATTTTGCTAGTGTGCATTCCCTTTCTGCAGGAAAGTGGGCTTTCCTTTCT
ATTCCAGGGAGGCCTCGCTCCTTTACCTGATGGCCTATAGCTGGGCACTCTGAAACCTAG
AAGTTATGACAGTGTGCATCAAATTGCCAACGCCATTGCCAAGTACCTGTTACACAGGCT
TGGAGTTCAATACTTTCCCTCCCAGGGCTCATCCATCTCCCACCATGGATCCTGAAACCA
CAAAAGACTAAGGCTGGCGCTTGGGCTGGGATGGGGCTGGGGGCAGGGTGGCATCAGTAT
CTTTAGTGTCCACATTATGTTTAGCCAAGAACCCTTTCTTCAAATGAAACTTTATGCAAA
AGCCCAGAACATAGAATAAACTGTGACTGCTCCAGCCACCCAGAGACCCCCTTGTTAGGC
ACCTCTGCCCCATCCTGCTTCTCCCCACATTCCAGTCCCCTGCACTTCTAGGGATTTCCT
GGGATTTTCCAGAGCACAGTTAGAAGCTTACAGACCTCAGCCAGCCTCCTCATTTGATAG
AGGAGAGACTGGAAGGGGCAGGGCTTCCCCAAGGTCATACGGCTGATGGGTAGCGGCATC
ACATCTGATCCCTCTTGTCTAGTTTTCAGTCTGTGGTGTTCTCCCACTGTGAAGAATAAC
TATGTTTTATAATGGAAATAATTGCCAATGTTATAGTATTGTAAGATAATTCCCTCTCTA
CAGTTCTCTGCACTCTATTCTTTTGAGCTCTCAAAAATAATGTTGGGATTTGGGGTTTGT
TAGATGGTCTCAGATTAGGGGACGCAGAGCTGCTGAAACCCAACCCTAGACTACAGCCAC
CCCCAGAGCTCCAAGGGAGATGCACATGAGCAACAAAGACAAAATAAAGCAAAGTGGCTC
CTTACAGGGACAAGTGTCCTCTCTCAGTCAGGGCAGGAAGAATGGAATGTAAAGAGCCCT
CCCCAGATGGGGACACTTTTCTTCCTGCTCTTTCCCTTCCCCTCTCCCTTTGTGTGTGTG
CCTGGCATGGGAGGAGGAGCAGACCGGGGCGGGGTGGGGGTGGGGCGGGTAAATGAGG
CTGAGCCTGCAGTAGGGGACAGAAGGAAGGGGTGGGGGAAAGACCACGTGGGTGCAAAGG
AGAAATCTGGCCACAATAGACTCTCCCCTCCCCTAATCTAGTGACCTGGTGGCTTTCCTC
AGTTGAAGCTGCTCAGAGGGCTACCCCCCTAGTTTGGCTCACCAGCTCTCCTCTGGCTCC
CCAGCTCTCCCCATTTTCCCTGGAGCACCTCCCTCCGCCTTCTATCTCTCAGATCTGGGC
CAGGGCATGGGGCCCTCTGACTTATGTATTCCTTTACTTGGGAGACTCAGTTTCTATGCTC
TTAATCCTGAGACTCTTGTGGCTGTGGTCCCCCACCTGCTTGCCTGTTTCTGGATCCCAG
ATGGCTCTTGGAAGAGCTGGGGCAGCTTAGGAGTGACTTTGGTTAGGCATGGCCAGCCCC
CAGTTCCTCTGCAATTCCAAGTGTCCTCAGTGCTCATCCTCCTGAGTGTTCTCCGGGGCA
GGTGTCTCCCTTCGACATTGAGCCTTCGAGTGGCCAGCTTCACTCTCTGGGGGAGTGCAG
GGTGGACATCACCTTGGAGGCCCTGCACTGCCAGCATCTGGAGACCGTCCTGGAGCTGGA
GGTGGAAAATGGTGCCTGGAGGTAAGGGTGCCGTGGGAAGAGCCACTACAACAAACTATG
CATATTCGTGATGTATTTATCTATATTATATATTTATCTAGAGATGTTCTGGATTTAAAA
CTATTGAATCCAGAAAATTAGTATTCTATAAAATTTGTAAATTACAGAAAAGAAACTCAA
AATGACGCATAATCCATTCCCTAGGGATGATCCACTGATAATATTATGTATATATCTTTC
TAGGGTGTGTGTATTAAAGAGATGTAAATTAGTATAACTACTTTCGAAACTACGTTAGCA
TCAGCTAGTGTTTGCCCTTCTGAGTATACTCCCAGGGAAATCCTTATACATGCACAGTGG
GAGATGTGTGCTCATGTTGGAATGCTCAGACTGGACTGTTCCTACAGGAAAAACTAGAAA
```

```
AAACCACTGTCTGTCAACAGGAGAATGGACATTTAAAAAGTGTGACATATTTAAATAAGC
ACATACCATTGTATTCTGGGAGGAACATGCTAGAGGTTTCAAAGGTATTGGTAGTATTCC
TTTTTTTCTTCTTCATTCTCCCTCCGCTCCCCCACTTCCCTCCTTTTCTTTCTTTCTAGT
GGAAAACTTCTCATATATATAAAAACAGAAAGAATAGTATAATAAACCTCCACATACTCT
TTCCTCCCTTCAATAATTGTCAACTCACTGCAAGTACTGTTTCATCCATATCCCCTATCT
CCTTCTCCCCACTCCTTCCCAAATTATTTTCAAATAAAATATTCATTTTCCTGCTGGGCA
TGGTGGCTCACGCCTGTAATCCCAGCACTTTGGGAGGCCGAGGCAGGCAAATCACGAGGT
CAGGAGTTCGAGATCAGCCTGGCAACATGGTGAAACCCCGTCTTTACTAAAAATACAAAA
ATTAGCCAGGTATGGTGGTGCTCGCCTGTAGTCCCAGCTACTTAGGAGGCTGAGGCAGAA
GAATCACTTGAATCCTGGAGGCAGAGGTTGCAGTGAATGAATATATATATATATTCATTT
TCTTAAGCTGGCTGGTGATAATATTTTGTTTCTAAAGTTGTGTGGAGGTAGTACATAGAT
GTTGTTTTATTATTCGTTAAACTATATATATGTTTAAACTGTATATATGTTTTATACTCA
TTTTTGCATATATTTGGTGTTTCATTGTAAAAACATTTAAATGCTCATTTAAATCTCTGT
GGATGCTCTTGAATTATCCTCCAAAAAGACTGTGTCATTTTATACTTCTGCCTACAGTGT
GTGAGACTAGCCATTACCCCACACTTTCACCATGACAAATGTTGTTGGACTTTGTATACT
TGACCATCTGACAGTTGTTCAAATGTCCCCTCCTGTGATAACAAATACAGGTCTAGGTAT
GAGTCTTTGCATTGGTCCTTCAGGGCAATTTGCGGGCATTAGATGTGAAGGCTAAGTCTG
CCTGCAGCTCAGGGGAAGGGCTTTCTATTAAGTCTGTGCTTATTTCCTTTCCTTTTCTGT
CTCTGTTCTTTCTCCTGAAAGGACCTTGTATTATCAGAATGTTTACAGTAGCAGGTGATG
GAAACACAGACATTACCAACTTAGGCAAAAAAGAGGAAGCATTGGCTCACGTAACTGGGC
ATTCCCACCTTGCTGAATCCAAGGGCCCAACACTTTTCCCTTTGTCTGGTCTTCTGCTTC
CTCTCTTTCTCTACCCTCTTTCCCCCTTCTCTACCTCCATCCCAGCCCCAACCCATCTAC
TGCTCTTTTTTTGTGGGCCCTTCTCTCCCTATTGACAAGGGCCCTTCGCACTCTGCCTT
GGGGAGAGGCCACTTAGAGCTCCAGGCTCACACACTCCCACCTTAACAATCTCTGAGAGC
CAATCTGGCTCTTTGCAGAGATAGGCCCTGATTGCTCTTGCTCTTGTGTGGGTCATGTAC
CCGCCCCTTCCCCTGCTGGGTGACAGGGAGGATCTGTCTCCAGAAGAGGCAATCATGTTT
CGAAATTTCAAGCTTTGTTGTTCTTGCGTCTTTCCTTTTCTATAGTAATCTGTTATAGTC
TTATCAATGCAACAGCCTCTCAGATTCCCCCAAGAAAATGAATTTCTGTTTTCCCAGATG
TTGGAGTTCTTCTTTACTTTTTGAGTTTTCTTCTGCTTCTAGTAATCTTTGCCTGTCCAG
TCCTGTTTTTGAATGGAGGAGGAAGTTGATTTGCATAAGGAGCTGGTGTTGTAAGTTTCT
TCTGAGTAAAAGGGGGTAGATGTGGAGAGCACCCCTATTCTAAGGGATGAAGTACATGTG
AGTCACCACCCTCAGAGCACACAGCTAGCCTGAATCCATCAGAGAAAGGGACCTTTGGGG
AAAACAGCCCTAAACAAACAGTGGAGAAAACCCATACTGGGCAGCTACACAAATCAATTC
GTGCCTTCATTCATAAATAAGAATGAAGGAATAGCATCTTTCTGGTTGTTTCCTCCTCAT
GACAGTTGAGAGGTCCAGTGTTACTGCAGGCTCTGCCCTGGCCTCTCTCAGCGTGATAC
CCACAGTCTTCAGTGGGGGCAAATACTGTGGCAGCCCAGTCTTTTTCTTTTTTCTTAATTTTCAATT
TTAATTTTTATTATTTGTACAAATTTATGGGGTACATGTGCAATTGTGTTATGTGCGTAG
ATTATATAGTGGTCAAGTCAGGGCTTTAGGGTATCCATCACCCAAATAGCATACATTGTA
CTCATGAACTAATTTCTCATCACCCATTTCCCTCCTATGCCCTCACCCTTCCGAGTCTCC
GTTGTCTATCATTCCAATCTCTATGTCCATATGTACACGTTTTTAGCACCCACTTGAGTG
AGATCATGTGATATTTGACTTCTGTGCCTGGGGCAGCCCACTCTTCCATGTGTTGCTCTG
AGCTCTGGGGCTGGAGCCCTGACCTGGCTAAGCCAATGGATCTTCAGCAGTGCTTTGCTC
AGCTCCCCCGCCCTTTGATGCCCTCATTCCATCATTAAGGATTGCATTGCACGTAACCTG
TGCAGGGATTTCAAGCAGCAGTTTTGTTCTCCTCTGTTTTATCAGTTAACCTGATCACAT
TATTTCTTTCTCCTATTTTCTTTTCCTTGTTTGCATAACATTTTATTTGCTTTATTATCT
TTTACTTCAAAATTTTCACAAATAGGGCATTTGCTAGATATTACATTTCTTTGCATTCAC
AATTTGTCTGTTTGGCACAAAGCTAGCTTTCTGCCTGTGTCAGCTTTGAATGTGCCTTCC
TCACTAAGCTTAATCATTTTTTAGCTTAATCATTTTGATTTAAAGTGAGATACGTACGAC
TCTTCTTTTCACTTGAAGACTTAGAGGCTATTGTAGGGTTATCGTTTGGTCTAATTTCAA
TATTGTTGTGTCTCAAGGAATAGGGAGGCCTGAGGAGGGAGAGAGACGGAAATGACCA
GTAAGTAGAGCAGTCAAATGCACACAGCATTTACCAGTTGAGCCCATTATCGTATATGA
TTGCTGTTTATGGCACCCCAAAACAATTACAGTAGTAACATCAAAGATCACTAATCACAG
GTTACCATAACAGCTATAGCAAAAAAGTTTGCAAGACATGACACAGAGACATGAAATGAG
GACATGCAATTGGAAAAATGACATTGATAGGCTTGCTCAATGCAGCGTTGTCACAAACCT
TCGATTTGTAAAAATCACAGTATCTGTGAAGTACAATAAAGCAGAGCATAATAACATGAG
GTATGTTTGTAACTGAATTTCTTATATAGGTCAATTTAGACTTTTTTCTTGGCCAGGCAC
AGTGGCTCATGACTGTAATCCCAGCACTTTGGGAGGCTGAGGTGGACGGATCACCTAAGG
TCAGGAGTACGAGACCAGGCTAGCCAACATGGTGAAACCCCATTTCTACTAAAAATACAA
AAATTAGCCGGGTGTGGTGGTGCACACCTGTAATCCCAGCTACTCGGGAGGCTGAGGCAT
GAGAATAGCTTGAACGTGGGAGGCAGAGGCTGCAGTGAGCCGAGATTGTGCCACTGCACT
CCAGCCTGGGCAACAGAGCAAGACTCTGTATGCCCCACCCCATCCCCCCAAAAAAGATT
TTTTTTTTTTTCTCAGTTTTGGTAGTTTGCATCACTCTAGGAATTTAGGAATTTGTCCAT
TTTATCTGTGATGTAATTTGTTGGTACATAGTTGTTAGTGGTATTCTCTGATAATTATTT
TTATTTCTGTATGATCAGTAGTGATGTCCCCACTTTCATTCCTGATTTCTCTAATTTGAA
TCTTCAGCAAATTTTCTTGGTCAGTCTAGTCTAGCTAAAGGTTTATCAATGTTGGTGAT
ATTTTCAAAGAACCAGCTTTTGCTTTTGTTGATTTTCTGTAATGTTTTTCTATTTTCTAT
TTCATTTATCTCTGCTTTCTAGTCTTTATTATTTCTGTCCTTCCACTTGCTTTGGGTTTA
GTTTGCTCTTCTCTTTCTAGTTTCTTAAGGTAAAAGCTGAGGTTTTTGATTTGCAATCTT
TCTTTTTTGTTTGTTTAAAGAAAATTGTATTTACAAATATAAATTTTCCTCTAACCACTC
CCTTAGTTGCATCCTATAACTTTTCATATATCATGTTTTCATTTTCATTGATATAAAGT
ATTTTCTAATTTTTCTTGTGGTTTCTTATTTGACTTGTTTATGAATGTGTTATTTAATTT
GCACATATTTTGTTTCACAAATTTCTTTCTGTTGTTGATTTCTAATTTGATTCTATTGTT
GTTGGAGAACCCACTTTATATAATTATAGTCGTTTAAAACTTATTGAGACTTGTTTTATG
GGCTATTCTGGAGAATATTCCTTGTGCACTCGAGAAAATAATGTATTCTGCTGTTATTG
TGTAGAGTGTTGCCTGTTCTGTTTGGTTTATAGTGCTGTTTAAATCTTCTATTTCAATGT
TTATCTTCTGGTTAGTTGTTTTTCCATTATTAAAAATGGGCTGTTGAAGTCTCCAACCAT
TATTGTTGAATTGCTGATCTCTCCTTCAATTCTGTCAGTTTTTGCTTCATGTATTTTGTG
```

```
GTGCTGTTGTTAGATACATACATGTTTATAATTGTTATATCTTTCTAATTTATCTTTTTA
TAATTATAAAATATCCTTCATTGTCTCTAATAACCATTTTTGTCTTAAAGCCTATTTTAT
CTAACATTCATATATCTCCTGGAGCTCTCTTTTGGGTACTGTTTGCATGATATATATTTT
TCCATCCTTTTTCTTTGAAACTATTTGTGTCTTTGAATCTAAAGTGTCTCTTGTAAACAG
CATATACTTGGATCATTTTTTTAAAATCCATTTTGCTAATCTCTGCCTTTTGATTGGATT
GTTTAATCCCTTTATATTTAATGTAAATACTGATAAAGTAGAACTTCATCTCCCGTTTTG
CTATTTGTTTTCTGTATGTATTTTGTGTTTCCTGCATTCCTTGTGTTTCCTGCATTCCTC
CATTATTGCCTTCTTCTTTGTTAGATAGGTAGTTTCTAGTATGCCATTTTAATTTCCATG
TTTCTTTTACTTTTTAAAAAGTTATTTTCTTACTGGTTGTCCAGGGCTTTATAGTATATC
TTAATTTCAAAACAGTCTGGTTTAGATTAACACCAACTTAATTTCAGTAGTCTGAAATGT
TACTGTAATATAGCTCAGCTCTATTCTCTCCCCTTCCTTTGTACTATTATTGTCATACAA
ATTACATATTTATACATTATAGGTTTATCAAGACAGTTTTACAGTTATTGGTTTGTATAG
TTGCCCTTTAAATCAGATAGAAAAGTAAGCAAAAATACATTTATTCTGTCTTTGTATTTA
CATATGAATTTATCTTGATATGGTTATATCAGTCAAGGCTTAATATTTATTTCTTAATAA
CCTATTAAGACATTTATTACAAAGAATCAGGTTACACAACTATAGGGACTAGCTAGGCAA
GCCTAAAATCTGTAGGGCAGGTTTTCAGGAAGGGCATGCTGGCATTTTTGGGGACAAGAT
GAAGATGTTATAAACACATGGAATTTCTTTGTCTGGGTAAGCCCATTTCTGCTTTTAAGA
CCTTTTAGTGGCCAGGCATGGTAGCTCACCTTTGTAATCCCAGCACTTTGGGAGGCCAAG
GTGGGAGGATCACCTGAGGTCAGGAGTTTGAGACCAACCTGGCCAACACACTGAAACCTC
ATCTCTACTAAAAATACAAAAACTTGCCTGGCATGGTGGCACATGCCTGTAGTCCCAGCT
ACTCGGAGGCTGAGGCAGTAGAATTTCTTGAACCCAGGAGGCAGAGGTTGCAGTGAGCC
AAGATCGCACCACTGCACCCCAGCCTGGGTGACAGAGTGAGACTCTATCTCAAAAAAAA
AAAAAAAAAAAAAAAGACCTTTCAACTAATTGAATTAGGCCCATCTAGATTATCTAGGAT
AATCTCCTTTACTTAAACTTAACTGATTATGAACATTAATCATACCTACAAAATACCTTC
AGCCGTTCAGACATGTAAAGAGCTTGCCCATCAAGCTCCTGCTCTCACAACAAGGAAAGA
CTGAACAAACTGAAACAATGATTTTTCTTAGATCTATCAGAGAGTTGAGGTTGCAGGACA
AGTGGCCACCCCAAAAGCTGGAGATATAGGCAAATACTGAGAATACAGATCAGTTTACCT
GAAGCAGAAGAACACTTAAATGGTAGTTTCAACAAATTCCTGGTGGCTAAGTGTAGGCTA
GCTTAAGAGTTTAAAAATCCTGGGGGCTCAGTAGGTTCTCATGGTGAAAACTGGAAAAAA
AATTCTCTCTTGTTTAGCCAGGGTGGGATGGGGAGGGGAAGTAACCATTCTGAAATACGC
CCAGAGGAAAAGTGAAATAAGCCACTTTGAAATAAGCCCAGAGTGTTCTTGCAACAATTT
CTCTTACACCCGAGATTTCTACTTTTTGAGCAATTATAAATGGTACTATATTTTAAATTT
CGATTTCCACATGTTTGTTGTTAGTATATAAAAATGTGATTCATTTTTGTATATTGATCT
TATATCCTGAAACTTTGCCGAACCCACTCATTAATTCTAGAGTTTCTAAAAATATAGATA
CCTTGGGATTTTCTACATAGACTGCATGTCATCTAGAAATAGGGACAGCTTTACTTCTTC
TTTTCTAATCAGTATGCCTTTTGTTTCCTCGTGTTCCAGCTACCTTCCTGTGTATGCTGA
GGTACAGAAGCCCCATGTGTACCTACAGAGCAGCCAGGTGGAGGTTAGAAATCTCTACCT
GGGTGTGCCCACGAAGACAACCATCACACTTATCAATGGCACGCTCCTGCCTACCCAGTT
CCACTGGGGCAAGGTGAGTGAGCCCACAGCATCAGGCAGCAGTCTGCAGCCCTCAGCCAC
AGAGGCCCACATAGAGGGGGGCATTGTCCCCCAAATATCCTCACAGAACAGAGATACTCA
GCCTCCCTCCCACAGCCTGTCCCTTGCTCGTAGTGTGCATAAAAGCTCCTCAAAGGAGCA
GCATATCTGGTCCAGCTTTTTCTTGCCCTGCCTCTAGGGAATTCCAGTTCCCTGACCAAG
AAGGAGTTTCTGGTGAACATAGCTAGAGCCTCCCAGCCAACATAGCCCATGACTGGCCCA
GGTAGCTGTTGGAGCCCAGTTGTGGTGCTGCTCCTGCCCGTGGCTGACTGGGGAGCTCTG
AGTGTCATGGGACATAAGGCCACATCCATGTGCACCAGAAGCATCTGCCCTCTGCTCCCC
ATCCCTCGGGGCCTTCAAGGGCAGTTTCTTTTGTCCAGATAACCTCCCAACAAGTGGTAA
AGTCCATCCAGGGTTGGGGAGGAGAGGAGAAGGGACCCGTGGTTTATCCCCAGAAGTGAG
CACCCAGCCCTGTCGGTTTTGCTGTGGGCCCCAGTCTGCCAGTCTCCAGCATTGCATGCA
GCAGTGCTGAGCACTCTCTGGATACTGGTCCATTCTGGGAGCCCAGTAAGTGACAACAGG
CTCACTCATGTGTCTGCCAGCTCCTCGGACACCAAGCAGAATTCTGCATGGTGACAGTCT
CCCCCAAACATGGCCTGCTGGGCCCAAGTGAGGAGTGCCAGCTCAAGTTGGAGTTGACTG
CTCATACCCAGGTGAGTAAGGCAATGTAGGGCCTGAGTGACCGGAAGGCACCCTGCCAA
CCATACGCACCTGTGCCACCAGGGAGGCCCTAGCTTAGGCCACATTGCTGGTTCTTGTGG
GTGGGAAGAGATTTCTTGCATTTGGGTCTGGGGTCCCCATTCCTGCTGGGTCTGCTCCC
TAGGGACACATGGTCAGAGAGCCTGGAGTAGGCCTGGGGATGTGCCCTGAGACCCACTGG
CCATGCCTGGCCTTTGGCATGAGTTTTTGCCCTCCCCAGGCCATTCTCTGTGGCCGCAGG
TGGGCCCAGCTTTCTGATTTGCCCAGAGATCCAGAGCAGAGCTGTTGCTCACAGCAGGCA
CTGTGCCAGGTACTACCCAGGGAGGCTAACTGGTACCTAGGTTTCCCGCTGGAGGCCACC
AGGGTGGAATATGCTCAGTCATAGGGCCGTTCCTAGCTGTCCCTTTGTGGTTCTTGTGGG
AAAAGAAACTTCCTCCTTACAGAGACTTGCAAACTCAGGTCTCAGCTCCCCCTGGCAAAT
ATGGGGATGGCCGGCCTGAGCTCTGGGACGACAGACAGGCAGGCCCAGGTGTGGAACAGA
TCTTGCTCAGGGAGGGTTTGATTTCTAGGGTAGCAGCTTCATCAGAGGAAGTGCGCAGCT
TCTCCAGAGGCCCTCTCTGAGGGGTCTCCCTTCACGTGGGCATGCCCAGATATTTGGGGC
AGACTCAGACAGCCATAAGGCCTGAGGAAAGGGCCAGGCTTCCTGGGGCTGAGGGCGGGT
CGACTGGCTGGGCTCACTGGAGGGACTGGAGATGAGCCTGGCCAGAGGTCAAGGCTCCAC
AGCAATCCCCTGTGCTGCGGAAGACCATCTGGGCTCATCTTCAGAGGCCCCAGGCCTGGT
CTGACCCCTGGATGGGCTTTCTTATAGGAAGAGCTGACCCATCTGGCCCTCCCTTGTCAC
GTGTCAGGCATGAAGAAGCCACTGGTTCTAGGCATTTCTGGGAAGCCCCAGGGACTGCAA
GTGGCCATTACCATCTCTAAGGAGAGCTCTGATTGCAGGTGAGCCCAGGGTTGGTGGTCT
GGGGGTGGCAGTGGACTGAGGAATGAGGCAGCCGCGCCCAGGACCAGCACGGCACTGTGG
TATCAGTCTGCGCCCATCTGATTCCTGCAGGCAGGAAAACGCCACAGTGTTATTGCGGCC
ACTCACCACTCCTGTGGGGACAGCTCCCTTTACCCCATCCCTGCCCTCTGTGTGGTCTCC
CCACACACACTTGGAGGCGTGGTGCCCTGGCAGGCAGGAGATGGCAGGGGACAGGGCTGT
AGGTACCCTGGGCTTGCCCACATGAGGCCCAGCAACTGGGAGCCATGCCAGCATGCCGCT
GGCCAGGGACGGTTTGTGCAGAGTTTGAGGCCTCTCTCAGCATCATGGGTGGCAGGAAA
GGTGGGTCTGTGGTTGGCAGCTCAATGAAACAGGAGTCTGAGGATGAAGCCTGGTGTCTG
GGCAGCTTCTGCATGCCCACCCAAGATGGCTCCCTGGGCAGGGCCAAGGGTGGTGTGTTA
```

-continued

Sequence listing

```
CATAGTACCAATGGGCACAGGACAGTGTTTTCAGCACAGAGCAGTGGCCAGGCCACCCAA
AGGAGCTCCGCCTGGACTTTGGCTCAGCGGTGCCACTGAGGACCCGTGTGACTCGCCAGC
TCATTCTCACCAATCGCTCCCCAATACGGACCCGTTTCTCCCTCAAGTTTGAGTATTTCG
GGAGCCCCCAAAACAGCCTGAGCAAAAAGACCAGCCTGTAAGTCTTGCTTCTTTCACTTC
CCAGGGCAGATGAAGCTGGATGGGGTGTACCCTGTTGAGCCTCTGTGTGGCTTAGGTGGC
CAGTGGCTGGTCGGTGTGAGAGATGGGAGTGTGTGTTTTTACAGGTAGACATGGGGACAG
GCAGAGAGGAAATGGCTCCTGCTGTCCACCTCCCGGGCCCTGAGTGGGCGTGTGGGAGAG
GCTGGGATTGCGGCCCCTTTTCCTCAGCCTGGCCTGCTGGAGTGGAGGCTTCTGATGGAC
CAGGCAGATGGGCCTGTAGTGAGGGAGAGGTTACTGTAGACAGAAGGAACTGTGCAGGCC
AAAGGGTGGGAGGAATAGTTCAGGAGTAGGGAGTCTTCAGGGACCACTGATAGCGTGCCT
GGGCTGACATGTGGAGAGTGAGATGGGGTGCCCCATAGATCAGACAGTGATCAGCAAAGC
TACTATGTGTAAGGACAGAGGCAAGATCTAGAGTGCTGCTTACACAGACACACACACACA
CACACACGTACATATACACACACATGCATACACACATACATATACACATGCATACACACA
TACACACATGCATATACACATATACATACACATGCATAGACACAAATATACACACATACA
CATATGTATACACATATACACATGCACACACACATATACATAAACATACATACATATGCA
CATACATACATGCTCATATACACACACACCCACATACACACATACACACATAGGTGTGCCAG
AACCAGCTAGCACTGGTTCAGGAGAACTGATTGTTAAATATTCAGGAATTTTGCAAATCT
CTAACTTGAAATCAAACATTATAATTTAGGACTTTTTTTTTCTGGAATCTCCACTGTGTG
GACACCTCACCACCTAATCTAGTGAAGCAAGAGGGCCCAACTTAGAAACCACGGCTATGG
GTGGAAGGCGACCCATGAACAGTTTATAAGGCATTAACTTTCTATTGTGGAAAGCTAGTG
TGTACCCAATGCTGGACAGATGTCAGCAGGAAAAACTGGAAATGGGCCTGTTGCAGAATT
CTGGGCTAGAGATGGGGAGTCTGGGCTGGGTTTGTGTCCAGGAGTAACCATGGCACAGAG
CCTGTGGGCAGGGAGTCCTGCTTCAGAGCCCGCCTGGGTTTCTGGGGAGGTAATCCCTGC
AGCTGGCGGGTGGCCCGCAGCTGGGGATGTTTGAATGGTAGGGGTACAGTGGGAGCAAAG
ACCAGAGAAGGAGGTAAAGGAAAGAACTGACCAGCTCTCCCCTGGGAAGAGCAGGCAGGG
CCACCTTCCTCTGCTGGGCACCTGGTAGAATGCTGGTTGCTCTAGAACCTGGCTCAGGTC
TTGGGACAGGCTTGTCTGACTTGATACTATTTCTGTGTCTCCACTTGTAAAGTCCCAACA
TGCCTCCTGCCCTGCTAAAGACAGTGCGGATGCAAGAGCACCTGGCCAAGCGAGAGCAGC
TGGGTAAGCGCCACCAGGGTGGGGCTTCGGGGCCCAGGCCACGGCCAGAGCCACAGCCTT
CTGTGGATGTGGGCTGGCAGCTGCCAGGGAGCGGGACCAGGACCAGAGACTGCTCTCAGA
TGGCCAAGGCGCTCCACCTGACAATGCCTCTTCCTGTTGAGGCCACTTCCCTTCTAGGGC
ACAGGCTCATGCACAGGGCCTGGACTCCATTTGGGATGGGAGTGGCTCATGAGGGAGGGC
TCCCATGGGGACCCAGCCTCTCAGGGAGTAGAGAGGCTGACCACGCAGGACCCTGAGTAG
CTTGCCTCTGGATTCCAGGCTCCCAGGAGGAGGGCACATGTAGCCTGACCAAGGAGAGGC
TGGAGGGTGGCTTATCGGGACAGTGCTTTGCTCACACACGAGGGTTTGGACCTCACTCC
CAACCCCAGGCCCGTGAATCCCCCACAGTCGCGGTTCTTTCCCAGATTTTATGGAGAGCA
TGCTATCCCACGGGAAAGGAGCTGCTTTCTTCCCTCACTTTTCCCAGGGCATGCTGGGGC
CCTACCAGCAGCTGTGCATTGACATCACAGGCTGTGCCAACATGTGGGGCGAGTACTGGG
ACAACCTCATCTGCACGGTAAGGGTACACAAGAGGGCAGTGGCCTGGGGGTGGAGAGTC
TGCCCAGCCCTCGCCTTCAGCCTCTCTCCCCTCCAACACCTGGCCCTCAGACTCTCAAAC
CTCACCAGGTTGAAACGCGATGCCCACCGAGCTTGGGATGGGCATTCGTGTCTGAGGCAG
CCTCTGGGGTTCTGGCTGAGGCATTTCAGGCAGGAGGGGTCCTCATAAGCAGTAGAACTT
TCCACACCTTTTCCCAGGAGATGCAGGGCTGGGGCCATATCGAGGAGGGAAGAGGAGACA
GTAGGCTGCTGCCTGGGCCAGGACCCAAGACTTGGAGTAGGGAGTGTGGAGTGGAGGGAC
AGTAGCAGCCTCCCAGAGCCAGGTCCTTGCCCCGCCCTTGGTGGGGCTCACCCAGGGGTC
CATTTAATTGCTCCAGCACTCAGCATAAATGGAGTATCTACTGTGTGTGGGTTCCTGTGT
GGGCCGCTGTAGTGTGGAGGATACAGGGATGAATAAGGTAACCAGCAAGGCACCCCTAGT
TTAGTCTGGAGGGATGAAACCTGCATACGTTATCCTACCGTTAAGTTGTTAAATAGAAGA
TTTTCATGAACTATTTAGTAAATTGAACAGATTAATTATAGTAGATATTTGCTTTAAATT
GTGTGTGTTCTGTATGACAAAGAATTGATCATGTTAATATAAAAAGGGATCTTAAGTAAC
AGGAAGCTGGGGAAGAGTATCCCAAGTGGGCAAGGTTTGAATAAACAACTCCAAGAAAGA
CAAATACAGACAGACGGCCAATAAACATATTAAAATCTGTCACCACCACTGATAATTAAA
GAAATGCAAAATAAAAGAGCCACAAAATACTGGTTTTGACACATTAGCAGGTTTAAAAG
TTGTTGGTGAAGATACAGGGGAAAGGGTGCTTTGAGCCCCCTTCTCCACGTCTGTCAGTA
GAGGAGTGGATACAGACATTGGGCCACATCCCTAAGGGAATTCTGCACAGCCTGTTATAT
GATGCTGTAAACTCTTTATTAGTAAAAATTAATCCTATATTGTTCGCTGGGTGCAGTGGT
TCATGCCTGTAATCCCAGCACTTAGGGAGGCTGAGGTGGGTGGATGTCTTGAGCTCAGGA
GTTTGAGAGCAGCCTGGGCAACATGGCAAAACCCCTTCTCTACAAAAAATACAAAAATTA
GCTGGGCGTGATGGCATATGTCTCTGGTCCCAGCTATTCAGGAGGCTGAGGTGGGAGGAT
CACTTGTGCCCAGGAGTTAGAGGTTGCAGTCAGCCGAGATCATGCCACTGCACTCCAGCC
TGAGCGATGGAGCAAGACTCTGTCTCAATAATAATAATAATAATAATAATCCTATATTGT
TAAAAGAAAAGATTATTAAAGGCATGTGCAGCATGCTCCCCATTTATATCTGGGTCTTCA
CAAAAGAAGTGTAGACACTTGTACACTGAAATGCTAACAGTAAGTCATGCTGCAGAGGTA
GGATTGGAGGTGATTATCACACTCTTATATTTTCTAAAAATAAGATTTATTACTTTTGAT
TAGCAGAGAAAGTAATAAAGTTCTTTTCATTTAAAAGACAGAAATTTGATCAAAGGGAC
TACCAGAGGCCGAAGACCTCAGGCTTGCCAGGTGCAGTGGCTCACACTTGTAGATCCAA
CACTTTAGGAGGCTGAGGCAGGAAGATTGCTTGAGGCCAGTAGTTTGAGACCAGCCTGAG
CAACATAGTAAGACCCTGTGTCTACTAAAAAAAAAAAAAAAAAAAAAGTCCTCAGGCTG
GGAGCTTTGTGCAGGCTGCCTGGCTGGGAGGGAGAGTGGAGATGGCGGAAGTGGGAGAG
AAGACAGAGTGGTACACAGTGAGGCTGGGACCAAACTGTGGGGCCCCTGGGCTGGCTGGA
CAAGTGGAGGCCTTGCCCAGAGGGGATGTGGTCGCAACCGGTGACAGGAGTGACAAAGGG
CTGGGGTGTGTTTGCAGGTGGGAGACCTGCTGCCGGAAGTCATCCCAGTGCACATGGCAG
CGGTGGGCTGCCCCATCAGCTCCCTGAGGACCACCTCCTACACTATTGACCAGGCCCAGA
AGGAACCAGCCATGAGGTGCTCCATGCTCAGCCTGAGCCTCTGCTCCCTGGTAGCCCCTG
AAACCCTCCGGCCTCCGGGCTGGGCTGCCCACGTTGGCTTGTTATTCTCCAGCTGGCCTA
GGGCCATTGGTGCCACTACAAGAAGGTTCCAGGCCAGGGTTTCCCTGGGGAAGGTGGC
CTCAGGGGACGTGGCCACCACCTGGACATCTCTGAGGGATTTTGTGGGGCAGAAGTGGCG
```

-continued

Sequence listing

```
AGTAGTCAGTGTGGTCCGAGGTCAGCACCAGCCCTGGGGCCCCTGGCACAGTTGAACTGG
AATCAGCATAGTCTGCTCAGGGCAGGTGGGTGGGTTGCCAGGGCACAGGGCAGCCCCAGA
GCCCAGCTCACCTGGTGCCGCCTGGGGAAGGCACCAGCCCCAGGTCTCATTAATTCTCGA
GTGAGGCCAGACCACTGTGGTATTTCCCCCTGCCTGAGCCCCCAGTCCCAGCCCTCCTCC
CTACCTGCAAGGTGTACGCTGGCTGTGGCTGTACTGAGTCCAGTCTGTCCCCCTCCAGGT
TCGGCACCCAGGTCTCCGGAGGAGACACAGTTACCCGAACCCTTCGCCTGAATAACTCCA
GCCCCTGTGGTAAGACATGCATGAGAGAAGTCAGTGTTCTTGCCACAGGCTGTGCCTTGT
GGTGAGCCAGGCTGGGAGGGAAGGTGGGAGGGAAGCCGATGGCCCATGAACAGGACCCAG
GTGTCCAGGGGGCCTGTGGTTACGGAAGTGTGGATGGGCCCACAGATGCCCTGCTCTCAT
CAGGGTTGCTGTTTGGAGGAACAGACAATAAGAGGGGATCCCTTTCTCATTCCTCCAGCC
GGCAGGACCTGACCTGCCTGAGAGCTGCTGGGGATACAGCGGGGACAGGACAGCAGGGTT
TCTGCCGAGGGGCTTCCCTCCTGATGGGTGGGACAGATGTGACTGTGGACTGCAGTGTGT
GGAGTGTGTGGCATACAACTGAAGGGAAGGCCGGAGTGCTGGGGGAACGTGTTGAAGGGC
CAGGCTCCCCTGTGGAGGGGAGGCAGAGTGTAGGCTGAGTCTAAGAGGAAGGGTAAGCCG
ATGTGGGCCAGGGGAGCATGTGGGGGCAAAGAGTGCTCTGGGCCTGAGAAAGGGTTAGGA
GAGGAAGCTGGTGACACTGAAGAGGGGGCCCTGGCCATGCCTGCCCCTGAGGAGAGCTGC
GAGCAGGACTGAAGGCAGGAGGGGAGGGGAAGATGGGTTCGATGCAGGCAGATGTCTAGG
TTTGGGACAGGACTTTGGGGACTTCTCAGCTTGGGGCTTCTGGGAGATGAGGTGGGGCT
ACCGGCTGGGTGTGGGAAGGCAGATGGAGGTGTCAGAGGAGGGCAGGGACAGCTTGACAT
TGTCATGGTGCAGGCTGGAGAGAGAGCAATGGGGAGCCCCAGCTTAGGTTGGGGACAGAT
TGATGGGGGTGGCAATCTGTTCAGCTGGGGGACTTCCCCCAGTGGTACTCAGAGGGACGG
CACAGTTCAGTTCTTTCAGGGTTAGGTGTTGCCAGGTGGGTGCAAAGGGAGATACGAGGA
TGCTGGCAAGACAGAGGTGGACATGGCGGCCCCCAAAGACTAGTCTGCCTGGGGAAGGAC
GTGAAAGCTGACATAGGCTGATGGATAGATGGGGAGAAGGAAGGGCATGTGGGGGTTAGA
GAGCCCAGCCTGCCCACAAACAGGCCGGAAGGAGAAGCAGCTGTGGGAGAGAGCAGAGCA
CCTGCATTCAGGCATCTGGACATGGAGACCTGGTCTTGTGACCATGAGGACTTCAGGTGA
TAGAGCCAAACGGCATAAGCCTGTAAAGCCTTTTTAAAATTTTAAATGAGAATTGCCTGG
AAGTGGCATTAGAGAGGCAGAGAGGCACCCCCTCCACCTGGGTATGGGAGAATAGGTCAT
CTCTGTCTGGGGGTATGAGGAGGAGGGGGCCCCGGGGGGTTGTCTGCTCCTCCCTTATTC
CTCACCCTGCTCCACACATCTGCCCCAGACATCCGCCTGGATTGGGAGACCTATGTTCCA
GAAGACAAGGAAGACCGGCTGGTGGAGCTGCTGGTGTTTTATGGGCCACCTTTCCCGCTG
CGGGACCAAGCCGGGAATGAGCTTGTGTGCCCTGATACCCCTGAGGGTGGCTGCCTCCTC
TGGTCCCCAGGCCCCTCCAGTTCATCGGAATTCAGCCATGAAACTGACTCATCAGTGAGC
AGGGGTGGAGGGGCGGGCAGGCTGGCCACTGAGGGCCACTGAGGTGTGGCCAGTAGGCT
AGTTGAACCTCAGTGACTGCGTGAACCTCAGTGATTCCTTGGTGACAGGTTGAGGGCAGC
TCCAGTGCCAGCAATAGGGTGGCACAGAAGCTCATCTCAGTCATCCTGCAGGCACATGAG
GGGGTGCCCTCCGGCCACCTGTACTGTATCAGCCCCAAGCAGGTGGTGAGTTGGGGTATG
GGCTGGGAGCTGTCTGCATTGGCCGGCCAGTGGGCATGGGACAGTGCTAAGGCTGCTGTG
TCTATGCCAGGTGGTCCCTGCTGGGGGCAGCAGTACCATCTACATCTCCTTCACCCCTAT
GGTGCTCAGCCCTGAGATCCTGCACAAGGTGGAGTGTACTGGCTACGCCCTGGGTTTCAT
GAGCTTGGACAGCAAGGTGAGCTCTTCCGGCCTGGGGTGGGGGCCGCAGCCACTGCTCCC
TCCTGGGTAGCATGCTGCCTACTCAGCCCAGGGATCAGCTGTGATCAGACTTGGGCTCAG
TAGGTGGAAAGGGAGATTCAGGGAAGAGGCATCGCCTGCAGGACTTTGCGGTGGGACCC
CTGAAACTGGACCTGCATAGCTACGTGAGGCCTGCACAGTGAGTCAGCTGGGGTGCCCCA
TCTCCTTTCATCCCCATGGGGTGCACCCTCACCAGGCACTGGTGGAGCCAGGCAGGGTTC
TCAGAGCAAAAGGACGGGCATGGGTGGAGAAGTCAGCAGAGGAGCCCAGGGAAAGGCTGG
CCCGAGGCTGGATGAGCAGAGTGGGGCAGCCAGAAGGCCCCAGGCGCCCGGCTTGCCCC
AACAATGCCTATTGCTGGGCAGGCTAAGTGTGGAGCTGGACTACGGCGGCAGTATGGAAT
TCCAGTGCCAGGCCAGTGACCTCATTCCCGAGCAGCCCTGCTCTGGGGTGAGTGTGCTGC
CACCCTCTGGCCCTGCCAGCTTACCTGGACCTCAGATGTCTCTGTGTGCCCTTGTGGGAC
TCAGGCCTTATAGTCTGAGCCCAAATCCCCTCCCCCAGCCCTCCCAGCCCTACCCTAGAG
CCATGGGGTTGAAGAGAGAGACAAGATGCATTCCCTGCCTCCTACCTCTGTGGCTGCCCA
GGTGCTGAGTGAGCTGGTGACCACCCACCACCTGAAGCTGACCAACACTACAGAGATCCC
ACACTACTTCCGGCTTATGGTCTCCAGGCCCTTCTCCGTTTCTCAAGATGGGGCGAGCCA
GGACCACAGAGCTCCTGGCCCTGGCCAGAAGCAGGAGTGTGAGGAGGAGACAGCCTCAGC
GGACAAGCAGCTGGTGCTCCAAGCACAGGAGAACATGCTGGTCAGTGGGGGAGTCTGCAG
CCCTTGCCTCGATGGCACACCCTCACATGTGTACAGACAGCACCCCTGCACGCCACCCTC
AGGTGCTTGTACCCAGACGCAAACTGCATGCCTGACCCTGCCATACCCTGCATGAACACT
CGGGGGTGCACTCCACCAGAGACACCACATTCAGCACCTCTGCACAAGTGGCTCACATG
GGCATGGCCACACCAGACGTTGTGTTCACATACATGCATGCACGTGCTCCATAAATGTCC
CCAGACTTCCCTTTCCCTCTTAGTCCCCACTGCTGAGATGCTGGTGGAGGCTGATGCATT
CCTGTGAGCACCTCCCCTTCCCACACACACAGACTCCGTCCTCCTGTGCAAGCTCAGGGT
TTGTGTCCCAGCTCAGGTGAGCCCATGGGGTTGCCATAATTGTAAGACACTCCAGGTTCT
AACGTAAAATTTCCTCTTCTGACTTATTCTCAGTGACAATTGGATCCTGGATTTTCAGAG
TTGGTTAGGTAGGGAAGGTCTTGGGAATGTCAGGACCTCACTGGAAACCATCAACTTCC
TCTGGTCTCTGAGGCAACTGGAATGAGGCTGAGTGTGCGCACACCCATATCTGCACAGTG
GGCTTCCAGGGTGTGCAGAGGCAGGCTGAGGGTAGACAGCGCCGCCCTGTCTCCTACTTC
CCCTCCTGCTTCAGAGGCCCTCTTTCTTCTTCTCGGAGGGCTTCCCTTTATGCTGTGCTC
CCTTGAGCTCTGCCAGGTCCTAGCCTCACTCTGCACATTTCTGGGTTGTCTCATCCATTT
CCAGAGCCTCAGTGAACAGCCATATTATTTCTATCCAATGTATACTCCACTGTGTAGCGA
GGGCTGCTGTGTACTAGATGCTGTGCTAGGTGATGTACTCCCCGAGGACCTCATCATG
GAGGTCAGGGACACACACGGATCTGCAGAAGACAGAATGGCACCCTTGACCCACTTTGCG
TTTGCTCCCTTCAACGAGCTAAATGGATGGGAAGGCCCAGAGCACAGCCAGAGGTTCCAT
TCCACCAGAGCTTCCAAGGAGACACGGCGGTTAGCCACCAGGCATTTAAAAGTCCTTGGC
AGCTCTGGGGAAGCCCAAAAGTTCCAGAAAAAGGACATCACATAATTAATGGTGCTGCAT
CTCACCCTCCATGCGCTAACAATGCTCAGGCTTCTGGCTCCTGGCCAGAATTATCTCCCA
GGCTCTAGAGCCAAACTCAATCTGTCCAAAGTGAACTCCCCATCCCCTCCCCACCTTGTC
```

```
CTGCCCCACATCTGTGCCTCCTTTTTGTGGTGGCATTTTGTCTCAGCAAATACCAACCCC
AGCCCCCTTGCTCATGCCCAGAGCTCTGGCACCCCTTGTCCTAGACCCATCTCTGACCAA
GCCACCAAGCCCTGCGGATGCCCCCTCCTAAAGTTCTCCCAACACTATTCTCTTTTCTTC
ATCCCTACACCCATATCTTGGTTTAGGACAGCAGTTTCTAAGCCTGGCAATAGATCAGTG
GCCTTTTTTTTTTTAGATTGGGTCTTGCTGTGTCACCTAGGCCGGAGTGCAGTGGCGTGA
TCATGGTTCACTGAAGCCTCGACTGCCTGGGGGGTTCAAGCAATTCTCCCACCTCGGCCT
CCCAAGTAGCTGGGACCACAGGTGCATGCCACCATGCCCAGCTATTATTTGCAGAGATAA
GGTCTCATTATATTGCCCAGGCTGGTCTTGAACTCCTGGGCTCAAGCGATCCTCCCAACT
CAGCCTCCCAAAGTGCTGGGATTACAGATGTAAGCCACTGCTCCCAGCAAATTAGTACCC
TTGACAAAGCTTGTTAAGGCAGCAGCTCCCAGACCCCACCTCCAGACATGTGAAGGTCTG
GGTGAGGCGCAAGAATTTATATTTTTAACAAGTGCCTCACCGTTGATTCTGAGAAGCTTG
TACCAAGGACCTGTGCTGGGAGCCAGGAGTCCAAGCTTCATCCTGTCCAGCCTCAGTTAC
AGCCTCAGCCCCTGGTCTGGCATCATCACACTCATGTGTGGTCTGCAGCCCACCTCCCCA
CCAGGTCAGTGACCTGTCAGAGGCTCCTCACTATCCTCAGCACACAGACCAAGTCCTTCC
TCTGCCTCTGAGCCCAACCACAGCCCTGGGCATTTGAAGCTGTAAAGGGCAACTTGCTCA
TGTCCCTTCCCTTCTAGCCTCTGACCTCTGAGGGCAGACATGACTTGTCCCTGACACTAG
CAGGGTGCTGGGCAGAGTAGGTGCTGGGCAGCGCTTGTGGAATGAAAGCACCAGGTTGGG
GAGCTGCTGGGCTGTTGGCTGGGCAAGGCTGGGCCTGGGAGGAAAGGAGGATGGAGCTCC
AGGTGGGGAAGTGGCCACCTGCCCTCTGCAGCCGGAGTTGACACCATGTCCACATCTGCT
CAGGTGAACGTGTCCTTCTCACTCTCCCTGGAGCTGCTCTCCTATCAGAAGCTCCCAGCT
GACCAGACACTGCCTGGGGTGGACATTCAGCAGAGTGCGAGTGGAGAGAGAGAGATGGTG
TTTACTCAGAACCTGCTCCTGGAGTACACCAACCAGACCACTCAGGCACGCCCCAGGCCC
ACCTACATGTGGAGGAGGGTGGAAGTGGGCTGGGCTGTGTTCTGCTGGGGCAGAGGAGG
AAAGACCTAGCAGGGCCCTCAGAAATAAGGAGCCCCTGCCCCTGTCCTGGGGCTCAGTCT
CCCCTAGAAGAGGCCCTGTGTGCAGAGAGATGAGGGCCATCCAACCTCACCTGCCTCATG
AGCTCAAAACCAGGTGAGGGGCCAGAGTGTGGGAAATCAGGGAAGGCTCCCTGCGGGAGG
AAGGACATGAAGCCTGAACACCATTTAATCAAGGAAGGGAAACACGTTGACAGCCAGGCC
AAAAGAAAGGCCTGATGGGTGGGACAGAGCACCTGAAGCAGCTGCGAAGGACAGCCCTGG
GGCTTGCCAGGCTTCAAGCACCAGGGCGAGCACCATGGACCAGGTCACCAGGCCGTAGTG
TGGAGGCTAAGCAGGGGCTGCTAGTAAGGAGTGTGAAGGAGTGGCCTGGGGAAGACTCTA
GAGAGGCCGGGGGCAGGAGGCTGAGCAGTGGAGCCGAGGCGCTCTAGCCTGGCACCTGGG
CAGCTGCTGGGGCTGAGGCTGTGGGATGGTGCATGGCAGTGCCTGAGTGTGATGCAGGGG
CTGCCAGGAGATAGAGGAGGGCACAGGTGGGGCCTGCGGCCAAGGAACACAGACAAATGG
TCCACGGCTGAGAGGAGCTGAGGGCTGGGCCTTGGGGGCCACCACAGGAGGAGCAGTGAA
GGAGGGCAGAGCCCAACCAGCCAGGGTGCAGGGACTGAAGCTTTATGAGTTAGGGAGGCA
GGGACAGCGGGGGAATGGATGGCATCACCCTGGCCCTTTCCCTGTGCAGACTCCCAGTAG
CAGCCTGTGGCCTTTTAAGGTGGCGCTGGTCCCCTGCCAACTTCTGGGAGCTTCCCGTTT
TCTTCAGGAGCATCAGCACTTGGGGTCAGCAGGGTTCTGTGTGTCCCAGAGGCCCTGGCT
CAGAGCCCACCCAGAATGGACAAGGTTGCCTGGTCTCCCACAGGTGGTGCCCCTGCGGGC
TGTGGTGGCCGTGCCTGAGCTGCAGCTCTCCACCAGCTGGGTGGACTTTGGGACCTGCTT
TGTGAGCCAGCAGCGAGTCCGGGAGGTCTACCTGATGAACCTGAGCGGGTGCCGAAGCTA
CTGGACTATGCTGATGGGTATGTCCTACCCTGCCACCTACCCACCGTTCCCCTACAGGGC
TGTGCCAAGAGAAGACCCCCCAGGAAGGGGCCCCTGTGCGCCGTCCCTGCATGCTGGCTC
CCAGGGCAGGCACCACTTGGAATTTCTGCAGAGCAGCCAGTCCCCCAATCCCACATGATC
TCAGGGTTGCCCTGCCCTGCAGTGCTGAGCAAGACCAGAGGTACAGGCCCGGGGGTGGGT
AAAGTCTTCCTGTGGGAGTACATGGGGCTGCCTGCACTCATGTGTCTTCCCTTCCCTTTG
GTGCAGGCCAGCAGGAGCCAGCCAAGGCCGCTGTGGCCTTCAGGGTCTCCCCAAACAGTG
GGCTGCTAGAAGCACGATCCGCCAATGCACCCCCAACCTCCATCGCCTTGCAGGTTTTCT
TCACTGCCAGGTGCAGCCCCTTCCAACCTTCCCAAACTGCCCACAGAGCCTGGACCCCCT
TGCCCAGGTGCCTCCTAACCTCAGCCCCCACATGCTCCCCACAGGAGTAGTGAGCTGTAC
GAGTCCACGATGGTGGTGGAAGGTGTGCTCGGTGAGAAGTCCTGCACCCTGCGGCTCCGG
GGCCAAGGCTCCTATGATGAGAGATACATGTTGCCTCACCAGCCCTGAGGCTCCGCCCCA
GCCCTCAGCCCCAGGCCCCAGCTGGAGAAAAAACATTGCCCAGGGATTAGGAGCAGCTCT
TCAGCACAAAGACACAGACTTGGGGACCTGGGGACCTCTGGGCAGCTCCTGGAATGGAAG
AACCCCCTTCCACAATGGTCTCAGCCTAGGCCCTCATGATATGTCCTCAGAGCTAACATA
AAGGACAGGCCACACCACAGCAGAGACCACCACATTGAGATCACTACTCAGTGCATAGCG
AAGACCAGTATGGCAAAATTAGTCTTGGAAAAAAACCACAGCCACTAAGATAAATTCATG
CACTTTTACTATGCCCATTGCACTTCTCATCCATGGATTTGCCTTGCCTTAAGAATTAAC
CATGGCCTTGTGGCCTGGGTGACCCAGGCTGCTTTTATCTTGCACAGCTAAAGAGGGTCT
GATGGGTGGCTCAACACCCCACCCACTCCTATACCATGTCATCAGTGTTCACATTTTCCA
AATGAGTTGAAGTGCCTTGATCTGTCCACTGCCACCACCACCAGTGCTGAGTTTTCCCAT
GTGGTTTTGCTTTTGTGGTGTTACTGCCTTGCTGCTAGAGCAGCAGGACTGTCTGCGTAG
CGCCTCCAGCCTGGGACCTCACTCAGTTCCCAGGGTATTCAAAGACGGCAGCGGCTCCCA
TTCCAGTCCCGATGCACATGGACACCACTCCGTATGCCCTGTGAAAACAAAACTTAATTG
GCTGGGCAAAGGCACCCACCCAAATTACCTCCAGACCAGGCTGACCCAGAAGGACGTCATG
GACAAGTAGGATGCAAAACCATCAGACCAGATCTGTGGGCAAGCGGTACCCTGGCCTCCC
ACTTGGGCACACACACGGTGACAGATGCCCACTGCAGGCTAGTATCCCTTTCAAGGCTGG
CCCTTAAGGAAAACAGGGATCATGCCCCTACATCCTAAGTTCAGGGTGTTTCTGTGTGCA
TGTTCCCCTCCCCAGGGATCGATCATAATCCCAAAAGACACAATCCCAAACACAATCATC
CCAAATGTTGAAATCCTGGAAGAACAAAATCCCTAAAGTCTAAAATCCTGAAAATCACAA
TCCTAAAAGATCAAAATCCTGAAAATATAATTCTGGAAAAAATAATTTGGAAGCCTGGCC
TGGTGGCATCTACTTGTAGTCCCAGCTATTCAGCAGGCTGAGGCAAGAGGATCACTTGTG
CCTAGGAGTTCAAGACCAGCCTAGGCAATATAGCAAGACCCCATCTTAGAAAAAAACTTT
TTTAAAAGATTGATTTAAAAGATATTTACATTTTTAGGCCAGGTGTGGTGGCTCAAACCT
GTAATCCCAACACTTTGGGAGGCCGAGGCGGGAGGATCACGAGGTCAGGAGTTCAAGACC
AGCCTCGCCAACATGGTGAAACCCTGTCTCCACCAAAAATACAAAAATTAGCTGGGTGTG
GTGGCAGACACCTATAATCCCAGATACTCGGGAGGCTGAGGCTGAGGCAGGAAAATTGCT
```

```
TGAACCCAAAAGGCAGAGGTTGCAGTGAGCCGAGATCACACCACTGCACTCCAGCCAGCC
TGGACAACGGAGTGAGATTCCATGTCAAAAAAAAAAAAAAATGTACATTTTTAAAAGGGG
ATTTATTTGAGAAACAAAAACAACAGAACACTTCACAGGCTACTTTACACAATAAAATAG
AAAATAATTACAAATTTCTGCAAGCATAAACACTCAGGTATGCTAACAATAGTCACAGGA
TTATAACAATTATAAACAGACAAACTGTATTCATAAATAGGTTAAAAGCAAACTGTATAA
ATTGCTGGTAATCATGTGCACCCAGCTTTATAACTGCAGTCATATGAATACCATGATGGA
CAACCTACGTCTTTTGATGAGATTGATCAAAAACTGATAGAGCCAGGCACTGTGGCTCAC
ACCTGTAATCCCAGCACTTTGGAAGCTAAGGTGGGAAGATCACTTGAACCCAGGAGTTCC
AGACCAGCCTGGGCAACATAGCAAACCCTGTCTCTACAAAAAATACGAAAAATTAGCTG
GGTGTGGTGGCACCCACGTGTAGTCTCAGCTACTCAGGAGGCTGAGGTGGGAGGATTGCT
TGAGTCAGGGAAGCAGAGGTTGCAGTGAGCCAAGATGGAGCCACTCCACTCCAGCCTGGG
CGCCTGAGTAAGACCCTGTCTCAACAAACCAACCTGTGATG

SEQ ID NO: 2 (cDNA sequence corresponding to a human wild-type
DLEC1 Mrna, GenBank Accession No. NM_007335.3)
GTTAGCGGCGTCTCGGTTGCCATGGAGACCAGGAGCTCCAAAACGCGGAGGTCTTTAGCGTCCCGGACCA
ACGAGTGCCAGGGGACAATGTGGGCGCCAACTTCGCCACCAGCCGGGTCCAGCAGCCCCAGCCAGCCCAC
CTGGAAGTCCTCCTTGTATTCCTCCCTCGCCTACTCTGAGGCCTTCCACTACAGCTTCGCAGCCCGGCCC
CGCCGCCTCACGCAGCTTGCGCTGGCGCAGCGTCCCGAGCCTCAGCTGCTTCGTCTGCGCCCTCCTCGC
TGCGCACCCAAGATATCTCGCACTTGCTCACCGGCGTCTTCCGCAACTTGTACTCAGCCGAGGTCATCGG
CGACGAAGTGAGCGCAAGCTTGATCAAGGCCCGCGGCAGCGAGAATGAGCGCCACGAGGAGTTCGTGGAC
CAGCTGCAGCAGATTCGGGAGCTCTATAAGCAGCGGCTGGATGAGTTTGAAATGTTGGAGAGACATATCA
CTCAGGCCCAAGCACGGGCTATTGCGAAAATGAGCGGGTCATGAGCCAGGCTGGAGTACAGGACCTCGA
GAGCCTTGTCAGGTTGCCTCCAGTGAAGAGTGTCTCCAGATGGTGTATAGACAGCGAGTTGCTACGGAAA
CATCATTTGATCTCCCCAGAAGATTACTACACCGATACAGTGCCGTTTCACTCTGCACCTAAAGGCATCT
CCCTACCTGGATGTTCAAAACTGACATTTAGCTGTGAGAAGCGTTCCGTCCAGAAGAAAGAGCTGAACAA
GAAGCTTGAAGATTCATGCAGGAAGAAGCTTGCTGAGTTCGAAGATGAGTTAGACCACACTGTGGACAGC
CTGACATGGAATTTAACTCCTAAGGCCAAAGAAAGGACCAGAGAACCTCTCAAGAAAGCAAGTCAACCAA
GGAATAAAAACTGGATGAACCACTTACGTGTGCCACAGAGAGAGCTAGACAGACTTCTGCTTGCCAGAAT
GGGAGAGTCGGAACCACTTCCTAAAAAATCCCCGTTTTTTTCCTCCTAACACTCGATATGGAGGCAAGTCT
CTTGTTTTTCCTCCAAAGAAGCCAGCACCGATAGGAGAATTCCAGAGTACAGAGCCAGAACAGAGTTGTG
CTGATACTCCAGTGTTTCTAGCTAAGCCACCAATTGGGTTTTTCACAGATTATGAAATTGGTCCAGTTTA
TGAGATGGTAATTGCGCTGCAGAACACCACCACGACCAGCCGCTACCTGCGAGTCCTCCCGCCTTCCACG
CCATACTTCGCTCTGGGACTGGGGATGTTCCCAGGAAAAGGTGGAATGGTGGCTCCTGGAATGACCTGCC
AGTACATTGTCCAGTTTTTTCCCGACTGCCTTGGGGATTTTGATGATTTATTTTAGTGGAGACCCAGTC
AGCCCACACACTTCTGATCCCCCTGCAGGCCCGGAGGCCCCCCGTGCTGACATTGTCACCGGTGTTG
GACTGTGGTTACTGCCTCATTGGGGGAGTCAAGATGACCAGATTCATCTGCAAAAATGTGGGTTTCAGTG
TTGGCAGGTTCTGCATTATGCCCAAAACAAGCTGGCCACCACTAAGTTTCAAGGCCATTGCAACCGTCGG
CTTTGTTGAACAACCTCCTTTTGGAATCCTGCCTTCGGTGTTTGAGCTGGCCCCGGGACATGCTATATTA
GTGGAGGTCTTGTTTTCCCCAAAGAGCCTAGGAAAGGCAGAGCAGACCTTCATCATCATGTGCAACACT
GCCAGATAAAGGAGCTGGTGACCATAGGAATTGGGCAGCTGATTGCTTTGGATCTGATCTATATTTCTGG
TGAAAAAAGCCAGCCAGACCCTGGAGAGCTCACAGACTTAACAGCCCAGCACTTCATACGATTTGAGCCT
GAAAACCTTCGGTCCACGGCTAGGAAGCAGCTGATTATTAGAAATGCTACGCACGTGGAGCTGGCCTTCT
ACTGGCAGATCATGAAGCCCAACCTGCAGCCCCTCATGCCTGGAGAAACCTTCAGCATGGACAGCATCAA
GTGCTACCCCGACAAGGAGACTGCCTTCTCCATCATGCCCAGAAAGGGGGTTCTAAGCCCCCACACAGAC
CACGAGTTCATCCTGAGCTTTTCTCCTCATGAGCTGAGGGATTTTCACAGTGTGCTCCAGATGGTGCTAG
AGGAAGTCCCAGAGCCTGTAAGTTCAGAAGCGGAGAGCCTGGGGCACTCCTCCTACTCTGTGGATGATGT
GATTGTCCTGGAAATCGAGGTGAAAGGCTCAGTAGAACCTTTCCAGGTTCTCTTAGAGCCATATGCCCTC
ATCATCCCAGGGGAGAACTACATTGGGATAAATGTGAAGAAGGCTTTTAAGATGTGGAACAACAGCAAGT
CACCCATCAGATACCTGTGGGGGAAGATCAGCGACTGCCACATCATTGAAGTGGAGCCCGGCACAGGGGT
CATAGAGCCCAGTGAGGTCGGGGATTTTGAGTTGAACTTTACTGGGGGTGTCCCTGGCCCCACAAGCCAG
GACCTGCTGTGTGAAATCGAAGACTCGCCCTCGCCAGTGGTGTTACACATTGAGGCTGTCTTTAAGGGGC
CTGCCCTCATCATCAACGTCTCAGCCCTTCAGTTTGGTCTGCTCCGCTGGGGCAGAAAGCCACAAACTC
CATCCAGATCCGGAACGTCAGCCAGCTCCCAGCCACATGGCCATGAAGGAGAGCCCAGTCTCCCTCCAG
GAAAGGCCTGAGGATGTGTCTCCCTTCGACATTGAGCCTTCGAGTGGCCAGCTTCACTCTCTGGGGGAGT
GCAGGGTGGACATCACCTTGGAGGCCCTGCACTGCCAGCATCTGGAGACCGTCCTGGAGCTGGAGGTGGA
AAATGGTGCCTGGAGCTACCTTCCTGTGTATGCTGAGGTACAGAAGCCCCATGTGTACCTACAGAGCAGC
CAGGTGGAGGTTAGAAATCTCTACCTGGGTGTGCCCACGAAGACAACCATCACACTTATCAATGGCACGC
TCCTGCCTACCCAGTTCCACTGGGCAAGCTCCTCGGACACCAAGCAGAATTCTGCATGGTGACAGTCTC
CCCCAAACATGGCCTGCTGGGCCCAAGTGAGGAGTGCCAGCTCAAGTGGAGTTGACTGCTCATACCCAG
GAAGAGCTGACCCATCTGGCCCTCCCTTGTCACGTGTCAGGCATGCAGTGATGAAGAAGCCACTGGTTCTAGGCATTT
CTGGGAAGCCCCAGGGACTGCAAGTGGCCATTACCATCTCTAAGGAGAGCTCTGATTGCAGCACAGAGCA
GTGGCCAGGGCACCCAAAGGAGCTCCGCCTGGACTTTGGCTCAGCGGTGCCACTGAGGACCCGTGTGACT
CGCCAGCTCATTCTCACCAATCGCTCCCCAATACGGACCCGTTTCTCCCTCAAGTTTGAGTATTTCGGGA
GCCCCCAAAACAGCCTGAGCAAAAAGACCAGCCTTCCCAACATGCCTCCTGCCCTGCTAAAGACAGTGCG
GATGCAAGAGCACCTGGCCAAGCGAGAGCAGCTGGATTTTATGGAGAAGCATGCTATCCCACGGGAAAGA
GCTGCTTTCTTCCCTCACTTTTCCCAGGGCATGCTGGGGCCCTACCAGCAGCTGTGCATTGACATCACAG
GCTGTGCCAACATGTGGGGCGAGTACTGGGACAACCTCATCTGCACGGTGGGAGACCTGCTGCCGGAAGT
CATCCCAGTGCACATGGCAGCGGTGGGCTGCCCCATCAGCTCCCTGAGGACCACCTCCTACACTATTGAC
CAGGCCCAGAAGGAACCAGCCATGAGGTTCGGCACCCAGGTCTCCGGAGGAGACACAGTTACCCGAACCC
TTCGCCTGAATAACTCCAGCCCCTGTGACATCCGCCTGGATTGGGAGACCTATGTTCCAGAAGACAAGGA
AGACCGGCTGGTGAGCTGCTGGTGTTTTATGGGCCACCTTTCCCGCTGCGGGACCAAGCCGGAATGAG
CTTGTGTGCCCTGATACCCCTGAGGGTGGCTGCCTCCTCTGGTCCCCAGGCCCCTCCAGTTCATCGGAAT
TCAGCCATGAAACTGACTCATCAGTTGAGGGCAGCTCCAGTGCCAGCAATAGGGTGGCACAGAAGCTCAT
CTCAGTCATCCTGCAGGCACATGAGGGGGTGCCCTCCGGCCACCTGTACTGTATCAGCCCCAAGCAGGTG
GTGGTCCCTGCTGGGGGCAGCAGTACCATCTACATCTCCTTCACCCCTATGGTGCTCAGCCCTGAGATCC
TGCACAAGGTGGAGTGTACTGGCTACGCCCTGGGTTTCATGAGCTTGGACAGCAAGGTGGAAAGGGAGAT
```

```
TCCAGGGAAGAGGCATCGCCTGCAGGACTTTGCGGTGGGACCCCTGAAACTGGACCTGCATAGCTACGTG
AGGCCTGCACAGCTAAGTGTGGAGCTGGACTACGGCGGCAGTATGGAATTCCAGTGCCAGGCCAGTGACC
TCATTCCCGAGCAGCCCTGCTCTGGGGTGCTGAGTGAGCTGGTGACCACCCACCCACCTGAAGCTGACCAA
CACTACAGAGATCCCACACTACTTCCGGCTTATGGTCTCCAGGCCCTTCTCCGTTTCTCAAGATGGGGCG
AGCCAGGACCACAGAGCTCCTGGCCCTGGCCAGAAGCAGGAGTGTGAGGAGGAGACAGCCTCAGCGGACA
AGCAGCTGGTGCTCCAAGCACAGGAGAACATGCTGGTGAACGTGTCCTTCTCACTCTCCCTGGAGCTGCT
CTCCTATCAGAAGCTCCCAGCTGACCAGACACTGCCTGGGGTGGACATTCAGCAGAGTGCGAGTGGAGAG
AGAGAGATGGTGTTTACTCAGAACCTGCTCCTGGAGTACACCAACCAGACCACTCAGGTGGTGCCCCTGC
GGGCTGTGGTGGCCGTGCCTGAGCTGCAGCTCTCCACCAGCTGGGTGGACTTTGGGACCTGCTTTGTGAG
CCAGCAGCGAGTCCGGGAGGTCTACCTGATGAACCTGAGCGGGTGCCGAAGCTACTGGACTATGCTGATG
GGCCAGCAGGAGCCAGCCAAGGCCGCTGTGGCCTTCAGGGTCTCCCCAAACAGTGGGCTGCTAGAAGCAC
GATCCGCCAATGCACCCCCAACCTCCATCGCCTTGCAGGTTTTCTTCACTGCCAGGAGTAGTGAGCTGTA
CGAGTCCACGATGGTGGTGGAAGGTGTGCTCGGTGAGAAGTCCTGCACCCTGCGGCTCCGGGGCAAGGC
TCCTATGATGAGAGATACATGTTGCCTCACCAGCCCTGAGGCTCCGCCCCAGCCCTCAGCCCCAGGCCCC
AGCTGGAGAAAAAACATTGCCCAGGGATTAGGAGCAGCTCTTCAGCACAAAGACACAGACTTGGGGACCT
GGGGACCTCTGGGCAGCTCCTGGAATGGAAGAACCCCCTTCCACAATGGTCTCAGCCTAGGCCCTCATGA
TATGTCCTCAGAGCTAACATAAAGGACAGGCCACACCACAGCAGAGACCACCACATTGAGATCACTACTC
AGTGCATAGCGAAGACCAGTATGGCAAAATTAGTCTTGGAAAAAAACCACAGCCACTAAGATAAATTCAT
GCACTTTTACTATGCCCATTGCACTTCTCATCCATGGATTTGCCTTGCCTTAAGAATTAACCATGGCCTT
GTGGCCTGGGTGACCCAGGCTGCTTTTATCTTGCACAGCTAAAGAGGGTCTGATGGGTGGCTCAACACCC
CACCCACTCCTATACCATGTCATCAGTGTTCACATTTTCCAAATGAGTTGAAGTGCCTTGATCTGTCCAC
TGCCACCACCACCAGTGCTGAGTTTTCCCATGTGGTTTTGCTTTTGTGGTGTTACTGCCTTGCTGCTAGA
GCAGCAGGACTGTCTGCGTAGCGCCTCCAGCCTGGGACCTCACTCAGTTCCCAGGGTATTCAAAGACGGC
AGCGGCTCCCATTCCAGTCCCGATGCACATGGACACCAACTCCGTATGCCCTGTGAAAACAAAACTTAATT
GGCTGGGCAAAGGCACCCACCCAAATTACCTCCAGACCAGGCTGACCCAGAAGGACGTCATGGACAAGTAG
GATGCAAAACCATCAGACCAGATCTGTGGGCAAGCGGTACCCTGGCCTCCCACTTGGGCACACACACGGT
GACAGATGCCCACTGCAGGCTAGTATCCCTTTCAAGGCTGGCCCTTAAGGAAAACAGGGATCATGCCCCT
ACATCCTAAGTTCAGGGTGTTTCTGTGTGCATGTTCCCCTCCCCAGGGATCGATCATAATCCCAAAGAC
ACAATCCCAAACACAATCATCCCAAATGTTGAAATCCTGGAAGAACAAAATCCCTAAAGTCTAAAATCCT
GAAAATCACAATCCTAAAAGATCAAAATCCTGAAAATATAATTCTGAAAAAATAA

SEQ ID NO: 3 (polynucleotide coding sequence for DLEC1 protein)
ATGGAGACCAGGAGCTCCAAAACGCGGAGGTCTTTAGCGTCCCGGACCAACGAGTGCCAGGGGACAATGT
GGGCGCCAACTTCGCCACCAGCCGGGTCCAGCAGCCCCAGCCAGCCCACCTGGAAGTCCTCCTTGTATTC
CTCCCTCGCCTACTCTGAGGCCTTCCACTACAGCTTCGCAGCCCGGCCCCGCCGCCTCACGCAGCTTGCG
CTGGCGCAGCGTCCCGAGCCTCAGCTGCTTCGTCTGCGCCCCCTCCTCGCTGCGCACCCAAGATATCTCGC
ACTTGCTCACCGGCGTCTTCCGCAACTTGTACTCAGCCGAGGTCATCGGCGACGAAGTGAGCGCAAGCTT
GATCAAGGCCCGCGGCAGCGAGAATGAGCGCCACGAGGAGTTCGTGGACCAGCTGCAGCAGATTCGGGAG
CTCTATAAGCAGCGGCTGGATGAGTTTGAAATGTTGGAGAGACATATCACTCAGGCCCAAGCACGGGCTA
TTGCGGAAAATGAGCGGGTCATGAGCCAGGCTGGAGTACAGGACCTCGAGAGCCTTGTCAGGTTGCCTCC
AGTGAAGAGTGTCTCCAGATGGTGTATAGACAGCGAGTTGCTACGGAAACATCATTTGATCTCCCCAGAA
GATTACTACACCGATACAGTGCCGTTTCACTCTGCACCTAAAGGCATCTCCCTACCTGGATGTTCAAAAC
TGACATTTAGCTGTGAGAAGCGTTCCGTCCAGAAGAAAGAGCTGAACAAGAAGCTTGAAGATTCATGCAG
GAAGAAGCTTGCTGAGTTCGAAGATGAGTTAGACCACACTGTGGACAGCCTGACATGGAATTTAACTCCT
AAGGCCAAAGAAAAGGACCAGAGAACCTCTCAAGAAAGCAAGTCAACCAAGGAATAAAAACTGGATGAACC
ACTTACGTGTGCCACAGAGAGAGCTAGACAGACTTCTGCTTGCCAGAATGGAGAGTCGGAACCACTTCCT
AAAAAAATCCCCGTTTTTTTCCTCCTAACACTCGATATGGAGGCAAGTCTCTTGTTTTTCCTCCAAAGAAG
CCAGCACCGATAGGAGAATTCCAGAGTACAGAGCCAGAACAGAGTTGTGCTGATACTCCAGTGTTTCTAG
CTAAGCCACCAATTGGGTTTTTCACAGATTATGAAATTGCTCCAGTTTTATGAGATGGTAATTGCGCTGCA
GAACACCACCACGACCAGCCGCTACCTGCGAGTCCTCCCGCCTTCCACGCCATACTTCGCTCTGGGACTG
GGGATGTTCCCAGGAAAGGTGGAATGGTGGCTCCTGGAATGACCTGCCAGTACATTGTCCAGTTTTTC
CCGACTGCCTTGGGGATTTTGATGATTTTATTTTAGTGGAGACCCAGTCAGCCCACACACTTCTGATCCC
CCTGCAGGCCCGGAGGCCGCCCCCCGTGCTGACATTGTCACCGGTGTTGGACTGTGGTTACTGCCTCATT
GGGGGAGTCAAGATGACCAGATTCATCTGCAAAAATGTGGGTTTCAGTGTTGGCAGGTTCTGCATTATGC
CCAAAACAAGCTGGCCACCACTAAGTTTCAAGGCCATTGCAACCGTCGGCTTTGTTGAACAACCTCCTTT
TGGAATCCTGCCTTCGGTGTTTGAGCTGGCCCCGGGACATGCTATATTAGTGGAGGTCTTGTTTTCCCCA
AAGAGCCTAGGAAAGGCAGAGCAGACCTTCATCATCATGTGCAACAAGCTGCAGATAAGGAGCTGGTGA
CCATAGGAATTGGGCAGCTGATTGCTTTGGATCTGATCTATATTTCGGTGAAAAAAGCCAGCCAGACCC
TGGAGAGCTCACAGACTTAACAGCCCAGCACTTCATACGATTTGAGCCTGAAAACCTTCGGTCCACGGCT
AGGAAGCAGCTGATTATTAGAAATGCTACGCACGTGGAGCTGGCCTTCTACTGGCAGATCATGAAGCCCA
ACCTGCAGCCCCTCATGCCTGGAGAAACCTTCAGCATGGACAGCATCAAGTGCTACCCCCGACAAGGAGAC
TGCCTTCTCCATCATGCCCAGAAAGGGGGTTCTAAGCCCCCACACAGACCACGAGTTCATCCTGAGCTTT
TCTCCTCATGAGCTGAGGGATTTTCACAGTGTGCTCCAGATGGTGCTAGAGGAAGTCCCAGAGCCTGTAA
GTTCAGAPGCGGAGAGCCTGGGGCACTCCTCCTACTCTGTGGATGATGTGATTGTCCTGGAPATCGAGGT
GAAAGGCTCAGTAGAACCTTTCCAGGTTCTCTTAGAGCCATATGCCCTCATCATCCCAGGGGAGAACTAC
ATTGGGATAAATGTGAAGAAGGCTTTTAAGATGTGGAACAAGCAAGTCACCCATCAGATACCTGTGGG
GGAAGATCAGCGACTGCCACATCATTGAAGTGGAGCCCGGCACAGGGGTCATAGAGCCCAGTGAGGTCGG
GGATTTTGAGTTGAACTTTACTGGGGGTGTCCCTGGCCCCACAAGCCAGGACCTGCTGTGTGAAATCGAA
GACTCGCCCTCGCCAGTGGTGTTACACATTGAGGCTGTCTTTAAGGGGCCTGCCCTCATCATCAACGTCT
CAGCCCTTCAGTTTGGTCTGCTCCGCCTGGGGCAGAAAGCCACAAACTCCATCCAGATCCGGAACGTCAG
CCAGCTCCCAGCCACATGCGCATGAAGGAGAGCCCAGTCTCCCTCCCCTCAGGAAAGCCTGAGGATGTGTCT
CCCTTCGACATTGAGCCTTCGAGTGGCCAGCTTCACTCTCTGGGGGAGTGCAGGGTGGACATCACCTTGG
AGGCCCTGCACTGCCAGCATCTGGAGACCGTCCTGGAGCTGGAGGTGGAAAATGGTGCCTGGAGCTACCT
TCCTGTGTATGCTGAGGTACGAAGCCCCATGTGTACCTACAGAGCAGCCAGGTGGAGGTTAGAAATCTC
TACCTGGGTGTGCCCACGAAGACAACCATCACACTTATCAATGGCACGCTCCTGCCTACCCAGTTCCACT
GGGGCAAGCTCCTCGGACACCAAGCAGAATTCTGCATGGTGACAGTCTCCCCCAAACATGGCCTGCTGGG
CCCAAGTGAGGAGTGCCAGCTCAAGTTGGAGTTGACTGCTCATACCCAGGAAGAGCTGACCCATCTGGCC
```

| Sequence listing |
|---|
| CTCCCTTGTCACGTGTCAGGCATGAAGAAGCCACTGGTTCTAGGCATTTCTGGGAAGCCCCAGGGACTGC
AAGTGGCCATTACCATCTCTAAGGAGAGCTCTGATTGCAGCACAGAGCAGTGGCCAGGCCACCCAAAGGA
GCTCCGCCTGGACTTTGGCTCAGCGGTGCCACTGAGGACCCGTGTGACTCGCCAGCTCATTCTCACCAAT
CGCTCCCCAATACGGACCCGTTTCTCCCTCAAGTTTGAGTATTTCGGGAGCCCCCAAAACAGCCTGAGCA
AAAAGACCAGCCTTCCCAACATGCCTCCTGCCCTGCTAAAGACAGTGCGGATGCAAGAGCACCTGGCCAA
GCGAGAGCAGCTGGATTTTATGGAGAGCATGCTATCCCACGGGAAAGGAGCTGCTTTCTTCCCTCACTTT
TCCCAGGGCATGCTGGGGCCCTACCAGCAGCTGTGCATTGACATCACCAGGCTGTGCCAACATGTGGGGCG
AGTACTGGGACAACCTCATCTGCACGGTGGGAGACCTGCTGCCGGAAGTCATCCCAGTGCACATGGCAGC
GGTGGGCTGCCCCATCAGCTCCCTGAGGACCACCTCCTACACTATTGACCAGGCCCAGAAGGAACCAGCC
ATGAGGTTCGGCACCCAGGTCTCCGGAGGAGACACAGTTACCCGAACCCTTCGCCTGAATAACTCCAGCC
CCTGTGACATCCGCCTGGATTGGGAGACCTATGTTCCAGAAGACAAGGAAGACCGGCTGGTGGAGCTGCT
GGTGTTTTATGGGCCACCTTTCCCGCTGCGGGACCAAGCCGGGAATGAGCTTGTGTGCCCTGATACCCCT
GAGGGTGGCTGCCTCCTCTGGTCCCAGGCCCCTCCAGTTCATCGGAATTCAGCCATGAAACTGACTCAT
CAGTTGAGGGCAGCTCCAGTGCCAGCAATAGGGTGGCACAGAAGCTCATCTCAGTCATCCTGCAGGCACA
TGAGGGGGTGCCCTCCGGCCACCTGTACTGTATCAGCCCCAAGCAGGTGGTGGTCCCTGCTGGGGGCAGC
AGTACCATCTACATCTCCTTCACCCCTATGGTGCTCAGCCCTGAGATCCTGCACAAGGTGGAGTGTACTG
GCTACGCCCTGGGTTTCATGAGCTTGGACAGCAAGGTGGAAAGGGAGATTCCAGGGAAGAGGCATCGCCT
GCAGGACTTTGCGGTGGGACCCCTGAAACTGGACCTGCATAGCTACGTGAGGCCTGCACAGCTAAGTGTG
GAGCTGGACTACGGCGGCAGTATGGAATTCCAGTGCCAGGCCAGTGACCTCATTCCCGAGCAGCCCTGCT
CTGGGGTGCTGAGTGAGCTGGTGACCACCCACCACCTGAAGCTGACCAACATCTACAGAGATCCCACACTA
CTTCCGGCTTATGGTCTCCAGGCCCTTCTCCGTTTCTCAAGATGGGGCGAGCCAGGACCACAGAGCTCCT
GGCCCTGGCCAGAAGCAGGAGTGTGAGGAGGAGACAGCCTCAGCGGACAAGCAGCTGGTGCTCCAAGCAC
AGGAGAACATGCTGGTAACGTGTCCTTCTCACTCTCCCTGGAGCTGCTCTCCTATCAGAAGCTCCCAGC
TGACCAGACACTGCCTGGGGTGGACATTCAGCAGAGTGCAGTGGAGAGAGAGATGGTGTTTACTCAG
AACCTGCTCCTGGAGTACACCAACCAGACCACTCAGGTGGTGCCCCTGCGGGCTGTGGTGGCCGTGCCTG
AGCTGCAGCTCTCCACCAGCTGGGTGGACTTTGGGACCTGCTTTGTGAGCCAGCAGCGAGTCCGGGAGGT
CTACCTGATGAACCTGAGCGGGTGCCGAAGCTACTGGACTATGCTGATGGGCCAGCAGGAGCCAGCCAAG
GCCGCTGTGGCCTTCAGGGTCTCCCCAAACAGTGGGCTGCTAGAAGCACGATCCGCCAATGCACCCCCAA
CCTCCATCGCCTTGCAGGTTTTCTTCACTGCCAGGAGTAGTGAGCTGTACGAGTCCACGATGGTGGTGGA
AGGTGTGCTCGGTGAGAAGTCCTGCACCCTGCGGCTCCGGGGCCAAGGCTCCTATGATGAGAGATACATG
TTGCCTCACCAGCCCTGA |

SEQ ID NO: 4 (amino acid sequence for DLEC1 protein, GenBank Accession
No. NP_031361)
METRSSKTRRSLASRTNECQGTMWAPTSPPAGSSSPSQPTWKSSLYSSLAYSEAFHYSFAARPRRLTQLA
LAQRPEPQLLRLRPSSLRTQDISHLLTGVFRNLYSAEVIGDEVSASLIKARGSENERHEEFVDQLQQIRE
LYKQRLDEFEMLERHITQAQARAIAENERVMSQAGVQDLESLVRLPPVKSVSRWCIDSELLRKHHLISPE
DYYTDTVPFHSAPKGISLPGCSKLTFSCEKRSVQKKELNKKLEDSCRKKLAEFEDELDHTVDSLTWNLTP
KAKERTREPLKKASQPRNKNWMNHLRVPQRELDRLLLARMESRNHFLKNPRFFPPNTRYGGKSLVFPPKK
PAPIGEFQSTEPEQSCADTPVFLAKPPIGFFTDYEIGPVYEMVIALQNITTTSRYLRVLPPSTPYFALGL
GMFPGKGGMVAPGMTCQYIVQFFPDCLGDFDDFILVETQSAHTLLIPLQARRPPPVLTLSPVLDCGYCLI
GGVKMTRFICKNVGFSVGRFCIMPKTSWPPLSFKAIATVGFVEQPPFGILPSVFELAPGHAILVEVLFSP
KSLGKAEQTFIIMCDNCQIKELVTIGIGQLIALDLIYISGEKSQPDPGELTDLTAQHFIRFEPENLRSTA
RKQLIIRNATHVELAFYWQIMKPNLQPLMPGETFSMDSIKCYPDKETAFSIMPRKGVLSPHTDHEFILSF
SPHELRDFHSVLQMVLEEVPEPVSSEAESLGHSSYSVDDVIVLEIEVKGSVEPFQVLLEPYALIIPGENY
IGINVKKAFKMWNNSKSPIRYLWGKISDCHIIEVEPGTGVIEPSEVGFDELNFTGGVPGPTSQDLLCEIE
DSPSPVVLHIEAVFKGPALIINVSALQFGLLRLGQKATNSIQIRNVSQLPATWRMKESPVSLQERPEDVS
PFDIEPSSGQLHSLGECRVDITLEALHCQHLETVLELEVENGAWSYLPVYAEVQKPHVYLQSSQVEVRNL
YLGVPTKTTITLINGTLLPTQFHWGKLLGHQAEFCMVTVSPKHGLLGPSEECQLKELTAHTQEELTHLA
LPCHVSGMKKPLVLGISGKPQGLQVAITISKESSDCSTEQWPGHPKELRLDFGSAVPLRTRVTRQLILTN
RSPIRTRFSLKFEYFGSPQNSLSKKTSLPNMPPALLKTVRMQEHLAKREQLDFMESMLSHGKGAAFFPHF
SQGMLGPYQQLCIDITGCANMWGEYWDNLICTVGDLLPEVIPVHMAAVGCPISSLRTTSYTIDQAQKEPA
MRFGTQVSGGDTVIRTLRLNNSSPCDIRLDWETYVPEDKEDRLVELLVFYGPPFPLRDQAGNELVCPDTP
EGGCLLWSPGPSSSSEFSHETDSSVEGSSSASNRVAQKLISVILQAHEGVPSGHLYCISPKQVVVPAGGS
STIYISFTPMVLSPEILHKVECTGYALGFMSLDSKVEREIPGKRHRLQDFAVGPLKLDLHSYVRPAQLSV
ELDYGGSMEFQCQASDLIPEQPCSGVLSELVITHHLKLINTTEIPHYFRLMVSRPFSVSQDGASQDHRAP
GPGQKQECEEETASADKQLVLQAQENMLVNVSFSLSLELLSYQKLPADQTLPGVDIQQSASGEREMVFTQ
NLLLEYTNQTTQVVPLRAVVAVPELQLSTSWVDFGTCFVSQQRVREVYLMNLSGCRSYWTMLMGQQEPAK
AAVAFRVSPNSGLLEARSANAPPTSIALQVFFTARSSELYESTMVVEGVLGEKSCTLRLRGQGSYDERYM
LPHQP SEQ ID NO: 5 (Genomic DNA sequence for MSP region shown in FIG. 12)
GCTTCGCAGCCCGGCCCCGCCGCCTCACGCAGCTTGCGCTGGCGCAGCGTCCCGAGC
CTCAGCTGCTTCGTCTGCGCCCCTCCTCGCTGCGCACCCAAGATATCTCG SEQ ID NO: 6 (Genomic DNA sequence for BGS region shown in FIG. 12)
GAAGACACAAATGTTTACAATGACCACAGCGATGACGGGATCCGAGAGAAAGGCA
AGGCGGAAGGGGTGAGGCCGGAAGCCGAAGTGCCGCAGGGAGTTAGCGGCGTCTC
GGTTGCCATGGAGACCAGGAGCTCCAAAACGCGGAGGTCTTTAGCGTCCCGGACCA
ACGAGTGCCAGGGGACAATGTGGGCGCCAACTTCGCCACCAGCCGGGTCCAGCAGC
CCCAGCCAGCCCACCTGGAAGTCCTCCTTGTATTCCTCCCTCGCCTACTCTGAGGCCT
TCCACTACAGCCACTTCGCAGCCCGGCCCCGCCGCCTCACGCAGCTTGCGCTGGCGCAGC
GTCCCGAGCCTCAGCTGCTTCGTCTGCGCCCCTCCTCGCTGCGCACCCAAGATATCT
CGCACTTGCTCACCGGCGTCTTCCGCAACTTGTACTCAGCCGAGGTCATCGGCGACG
AAGTGAGCGCAAGCTTGATCAAGGCCCGCGGCAGCGAGAATGAGCGCCACGAGGA
GTTCGTGGACCAGCTGCAGCAGGTAACGTGGCGGTGGCGTCGCGTCTGCGGACGGT

Sequence listing

```
GCCGGGGTCTCAGCGCTCGGCACGCGTCAGCACCTGCCAGGTGCCAGGCGCTGTTCC
AGGATCTGGGGCTGCAGTT
```

REFERENCES

1. Naylor S L, Johnson B E, Minna J D, Sakaguchi A Y. Loss of heterozygosity of chromosome 3p markers in small-cell lung cancer. Nature. 1987; 329: 451-4.
2. Kovacs G, Erlandsson R, Boldog F, Ingvarsson S, Muller-Brechlin R, Klein G, et al. Consistent chromosome 3p deletion and loss of heterozygosity in renal cell carcinoma. Proc Natl Acad Sci USA. 1988; 85: 1571-5.
3. Ogasawara S, Maesawa C, Tamura G, Satodate R. Frequent microsatellite alterations on chromosome 3p in esophageal squamous cell carcinoma. Cancer Res. 1995; 55: 891-4.
4. Sato T, Akiyama F, Sakamoto G, Kasumi F, Nakamura Y. Accumulation of genetic alterations and progression of primary breast cancer. Cancer Res. 1991; 51: 5794-9.
5. Huang D P, Lo K W, Choi P H, Ng A Y, Tsao S Y, Yiu G K, et al. Loss of heterozygosity on the short arm of chromosome 3 in nasopharyngeal carcinoma. Cancer Genet Cytogenet. 1991; 54: 91-9.
6. Hesson L B, Cooper W N, Latif F. Evaluation of the 3p21.3 tumour-suppressor gene cluster. Oncogene. 2007; 26: 7283-301.
7. Dammann R, Li C, Yoon J H, Chin P L, Bates S, Pfeifer G P. Epigenetic inactivation of a RAS association domain family protein from the lung tumour suppressor locus 3p21.3. Nat Genet. 2000; 25: 315-9.
8. Agathanggelou A, Dallol A, Zochbauer-Muller S, Morrissey C, Honorio S, Hesson L, et al. Epigenetic inactivation of the candidate 3p21.3 suppressor gene BLU in human cancers. Oncogene. 2003; 22: 1580-8.
9. Chow L S, Lo K W, Kwong J, To K F, Tsang K S, Lam C W, et al. RASSF1A is a target tumor suppressor from 3p21.3 in nasopharyngeal carcinoma. Int J Cancer. 2004; 109: 839-47.
10. Qiu G H, Tan L K, Loh K S, Lim C Y, Srivastava G, Tsai S T, et al. The candidate tumor suppressor gene BLU, located at the commonly deleted region 3p21.3, is an E2F-regulated, stress-responsive gene and inactivated by both epigenetic and genetic mechanisms in nasopharyngeal carcinoma. Oncogene. 2004; 23: 4793-806.
11. Hu X T, Zhang F B, Fan Y C, Shu X S, Wong A H, Zhou W, et al. Phospholipase C delta 1 is a novel 3p22.3 tumor suppressor involved in cytoskeleton organization, with its epigenetic silencing correlated with high-stage gastric cancer. Oncogene. 2009; 28: 2466-75.
12. Daigo Y, Nishiwaki T, Kawasoe T, Tamari M, Tsuchiya E, Nakamura Y. Molecular cloning of a candidate tumor suppressor gene, DLC1, from chromosome 3p21.3. Cancer Res. 1999; 59: 1966-72.
13. Ying J, Poon F F, Yu J, Geng H, Wong A H, Qiu G H, et al. DLEC1 is a functional 3p22.3 tumour suppressor silenced by promoter CpG methylation in colon and gastric cancers. Br J Cancer. 2009; 100: 663-9.
14. Qiu G H, Salto-Tellez M, Ross J A, Yeo W, Cui Y, Wheelhouse N, et al. The tumor suppressor gene DLEC1 is frequently silenced by DNA methylation in hepatocellular carcinoma and induces G1 arrest in cell cycle. J Hepatol. 2008; 48: 433-41.
15. Zhang L, Zhang Q, Li L, Wang Z, Ying J, Fan Y, et al. DLEC1, a 3p tumor suppressor, represses NF-kappaB signaling and is methylated in prostate cancer. J Mol Med (Berl). 2015; 93: 691-701.
16. Wang Z, Li L, Su X, Gao Z, Srivastava G, Murray P G, et al. Epigenetic silencing of the 3p22 tumor suppressor DLEC1 by promoter CpG methylation in non-Hodgkin and Hodgkin lymphomas. J Transl Med. 2012; 10: 209.
17. Kwong J, Chow L S, Wong A Y, Hung W K, Chung G T, To K F, et al. Epigenetic inactivation of the deleted in lung and esophageal cancer 1 gene in nasopharyngeal carcinoma. Genes Chromosomes Cancer. 2007; 46: 171-80.
18. Seng T J, Currey N, Cooper W A, Lee C S, Chan C, Horvath L, et al. DLEC1 and MLH1 promoter methylation are associated with poor prognosis in non-small cell lung carcinoma. Br J Cancer. 2008; 99: 375-82.
19. Sasaki H, Hikosaka Y, Kawano O, Moriyama S, Yano M, Fujii Y. Methylation of the DLEC1 gene correlates with poor prognosis in Japanese lung cancer patients. Oncol Lett. 2010; 1: 283-7.
20. Al Sarakbi W, Reefy S, Jiang W G, Roberts T, Newbold R F, Mokbel K. Evidence of a tumour suppressor function for DLEC1 in human breast cancer. Anticancer Res. 2010; 30: 1079-82.
21. Kwong J, Lee J Y, Wong K K, Zhou X, Wong D T, Lo K W, et al. Candidate tumor-suppressor gene DLEC1 is frequently downregulated by promoter hypermethylation and histone hypoacetylation in human epithelial ovarian cancer. Neoplasia. 2006; 8: 268-78.
22. Rauch T, Li H, Wu X, Pfeifer G P. MIRA-assisted microarray analysis, a new technology for the determination of DNA methylation patterns, identifies frequent methylation of homeodomain-containing genes in lung cancer cells. Cancer Res. 2006; 66: 7939-47.
23. Bromberg J F, Wrzeszczynska M H, Devgan G, Zhao Y, Pestell R G, Albanese C, et al. Stat3 as an oncogene. Cell. 1999; 98: 295-303.
24. Yue P, Turkson J. Targeting STAT3 in cancer: how successful are we? Expert Opin Investig Drugs. 2009; 18: 45-56.
25. Ho Y, Tsao S W, Zeng M, Lui V W. STAT3 as a therapeutic target for Epstein-Barr virus (EBV): associated nasopharyngeal carcinoma. Cancer Lett. 2013; 330: 141-9.
26. Timme S, Ihde S, Fichter C D, Waehle V, Bogatyreva L, Atanasov K, et al. STAT3 expression, activity and functional consequences of STAT3 inhibition in esophageal squamous cell carcinomas and Barrett's adenocarcinomas. Oncogene. 2014; 33: 3256-66.
27. Harada D, Takigawa N, Kiura K. The Role of STAT3 in Non-Small Cell Lung Cancer. Cancers (Basel). 2014; 6: 708-22.
28. Yu H, Lee H, Herrmann A, Buettner R, Jove R. Revisiting STAT3 signalling in cancer: new and unexpected biological functions. Nat Rev Cancer. 2014; 14: 736-46.
29. Stahl N, Farruggella T J, Boulton T G, Zhong Z, Darnell J E, Jr., Yancopoulos G D. Choice of STATs and other substrates specified by modular tyrosine-based motifs in cytokine receptors. Science. 1995; 267: 1349-53.
30. Tan Q, Wang G, Huang J, Ding Z, Luo Q, Mok T, et al. Epigenomic analysis of lung adenocarcinoma reveals novel DNA methylation patterns associated with smoking. Onco Targets Ther. 2013; 6: 1471-9.
31. Ying J, Shan L, Li J, Zhong L, Xue L, Zhao H, et al. Genome-wide screening for genetic alterations in esophageal cancer by aCGH identifies 11q13 amplification oncogenes associated with nodal metastasis. PLoS One. 2012; 7: e39797.
32. Pierce B G, Wiehe K, Hwang H, Kim B H, Vreven T, Weng Z. ZDOCK server: interactive docking prediction of protein-protein complexes and symmetric multimers. Bioinformatics. 2014; 30: 1771-3.
33. Pastuszak-Lewandoska D, Kordiak J, Migdalska-Sek M, Czarnecka K H, Antczak A, Gorski P, et al. Quantitative analysis of mRNA expression levels and DNA methylation profiles of three neighboring genes: FUS1, NPRL2/G21 and RASSF1A in non-small cell lung cancer patients. Respir Res. 2015; 16: 76.
34. Kashuba V I, Li J, Wang F, Senchenko V N, Protopopov A, Malyukova A, et al. RBSP3 (HYA22) is a tumor suppressor gene implicated in major epithelial malignancies. Proc Natl Acad Sci USA. 2004; 101: 4906-11.
35. Li J, Wang F, Haraldson K, Protopopov A, Duh F M, Geil L, et al. Functional characterization of the candidate tumor suppressor gene NPRL2/G21 located in 3p21.3C. Cancer Res. 2004; 64: 6438-43.
36. Zabarovsky E R, Lerman M I, Minna J D. Tumor suppressor genes on chromosome 3p involved in the pathogenesis of lung and other cancers. Oncogene. 2002; 21: 6915-35.
37. Zhang Q, Ying J, Li J, Fan Y, Poon F F, Ng K M, et al. Aberrant promoter methylation of DLEC1, a critical 3p22 tumor suppressor for renal cell carcinoma, is associated with more advanced tumor stage. J Urol. 2010; 184: 731-7.
38. Bocchini C E, Kasembeli M M, Roh S H, Tweardy D J. Contribution of chaperones to STAT pathway signaling. JAKSTAT. 2014; 3: e970459.
39. Sehgal P B. Plasma membrane rafts and chaperones in cytokine/STAT signaling. Acta Biochim Pol. 2003; 50: 583-94.
40. Chen X, Ying Z, Lin X, Lin H, Wu J, Li M, et al. Acylglycerol kinase augments JAK2/STAT3 signaling in esophageal squamous cells. J Clin Invest. 2013; 123: 2576-89.
41. Chen H, Hutt-Fletcher L, Cao L, Hayward S D. A positive autoregulatory loop of LMP1 expression and STAT activation in epithelial cells latently infected with Epstein-Barr virus. J Virol. 2003; 77: 4139-48.
42. Zhang G, Tsang C M, Deng W, Yip Y L, Lui V W, Wong S C, et al. Enhanced IL-6/IL-6R signaling promotes growth and malignant properties in EBV-infected premalignant and cancerous nasopharyngeal epithelial cells. PLoS One. 2013; 8: e62284.
43. Gao S P, Mark K G, Leslie K, Pao W, Motoi N, Gerald W L, et al. Mutations in the EGFR kinase domain mediate STAT3 activation via IL-6 production in human lung adenocarcinomas. J Clin Invest. 2007; 117: 3846-56.
44. Ye X, Feng G, Jiao N, Pu C, Zhao G, Sun G. Methylation of DLEC1 promoter is a predictor for recurrence in Chinese patients with gastric cancer. Dis Markers. 2014; 2014: 804023.
45. Chan W H, Chang K P, Yang S W, Yao T C, Ko T Y, Lee Y S, et al. Transcriptional repression of DLEC1 associates with the depth of tumor invasion in oral squamous cell carcinoma. Oral Oncol. 2010; 46: 874-9.
46. Jin H, Wang X, Ying J, Wong A H, Cui Y, Srivastava G, et al. Epigenetic silencing of a Ca(2+)-regulated Ras GTPase-activating protein RASAL defines a new mechanism of Ras activation in human cancers. Proc Natl Acad Sci USA. 2007; 104: 12353-8.
47. Ying J, Li H, Seng T J, Langford C, Srivastava G, Tsao S W, et al. Functional epigenetics identifies a protocadherin PCDH10 as a candidate tumor suppressor for nasopharyngeal, esophageal and multiple other carcinomas with frequent methylation. Oncogene. 2006; 25: 1070-80.
48. Li L, Tao Q, Jin H, van Hasselt A, Poon F F, Wang X, et al. The tumor suppressor UCHL1 forms a complex with p53/MDM2/ARF to promote p53 signaling and is frequently silenced in nasopharyngeal carcinoma. Clin Cancer Res. 2010; 16: 2949-58.
49. Li L, Ying J, Tong X, Zhong L, Su X, Xiang T, et al. Epigenetic identification of receptor tyrosine kinase-like orphan receptor 2 as a functional tumor suppressor inhibiting beta-catenin and AKT signaling but frequently methylated in common carcinomas. Cell Mol Life Sci. 2014; 71: 2179-92.
50. Li L, Li C, Mao H, Du Z, Chan W Y, Murray P, et al. Epigenetic inactivation of the CpG demethylase TET1 as a DNA methylation feedback loop in human cancers. Sci Rep. 2016; 6: 26591.
51. Li L, Zhang Y, Fan Y, Sun K, Su X, Du Z, et al. Characterization of the nasopharyngeal carcinoma methylome identifies aberrant disruption of key signaling pathways and methylated tumor suppressor genes. Epigenomics. 2015; 7: 155-73.

What is claimed is:

1. A method for diagnosing and treating esophageal squamous cell carcinoma (ESCC) in a subject, comprising the steps of:
   (a) treating DNA from an esophageal epithelial tissue sample taken from the subject with an agent that differentially modifies methylated and unmethylated DNA;
   (b) determining number of methylated CpGs in a genomic sequence, which is SEQ ID NO:5 or 6 or a fragment thereof comprising at least 10 CpGs;
   (c) comparing the number of methylated CpGs from step (b) with the number of methylated CpGs in the genomic sequence from a non-ESCC sample and processed through steps (a) and (b);
   (d) determining the subject, whose sample contains more methylated CpGs in the genomic sequence determined in step (b) compared to the number of methylated CpGs with the number of methylated CpGs in the genomic sequence from a non-ESCC sample and processed through steps (1) to (3), as having an increased risk for ESCC compared with a healthy subject not diagnosed with ESCC;
   (e) administering X-ray or CT scan to the subject who is determined to have an increased risk for ESCC in step (d) and confirming the presence of ESCC in the subject; and
   (f) administering to the subject confirmed to have ESCC in step (e) surgery, chemotherapy, radiotherapy, immunotherapy, photodynamic therapy, or any combination thereof.

2. The method of claim 1, wherein the genomic sequence is SEQ ID NO:5.

3. The method of claim 1, wherein the genomic sequence is SEQ ID NO:6.

4. The method of claim 1, wherein the agent that differentially modifies methylated DNA and unmethylated DNA is an enzyme that preferentially cleaves methylated DNA, an enzyme that preferentially cleaves unmethylated DNA, or a bisulfite.

5. The method of claim 1, wherein step (b) comprises an amplification reaction.

6. The method of claim 5, wherein the amplification reaction is a polymerase chain reaction (PCR).

* * * * *